United States Patent
Xie et al.

(10) Patent No.: US 10,159,662 B2
(45) Date of Patent: Dec. 25, 2018

(54) AZETIDINE DERIVATIVE, PREPARATION METHOD THEREFOR, AND USE THEREOF

(71) Applicant: SICHUAN KELUN-BIOTECH BIOPHARMACEUTICAL CO., LTD., Chengdu (CN)

(72) Inventors: Yinong Xie, Chengdu (CN); Zejin You, Chengdu (CN); Zhiwen Deng, Chengdu (CN); Jun Zhu, Chengdu (CN); Ao Wang, Chengdu (CN); Yan Feng, Chengdu (CN); Dong Long, Chengdu (CN); Hong Zeng, Chengdu (CN); Hongmei Song, Chengdu (CN); Qijun Ye, Chengdu (CN); Wei Qi, Chengdu (CN); Donghai Su, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Chengdu (CN)

( * ) Notice: Subject to any disclaimer, the term of this patent is extended or adjusted under 35 U.S.C. 154(b) by 0 days.

(21) Appl. No.: 15/767,508

(22) PCT Filed: Dec. 8, 2016

(86) PCT No.: PCT/CN2016/109036
§ 371 (c)(1),
(2) Date: Apr. 11, 2018

(87) PCT Pub. No.: WO2017/097224
PCT Pub. Date: Jun. 15, 2017

(65) Prior Publication Data
US 2018/0289680 A1    Oct. 11, 2018

(30) Foreign Application Priority Data

Dec. 11, 2015 (CN) .......................... 2015 1 0924946

(51) Int. Cl.
| | | |
|---|---|---|
| *A61K 31/437* | (2006.01) | |
| *A61P 19/02* | (2006.01) | |
| *A61P 29/00* | (2006.01) | |
| *A61P 35/00* | (2006.01) | |
| *A61P 37/00* | (2006.01) | |
| *A61K 39/00* | (2006.01) | |
| *A61K 31/343* | (2006.01) | |
| *A61K 38/17* | (2006.01) | |
| *A61K 31/519* | (2006.01) | |

(52) U.S. Cl.
CPC ............ *A61K 31/437* (2013.01); *A61P 19/02* (2018.01); *A61P 29/00* (2018.01); *A61P 35/00* (2018.01); *A61P 37/00* (2018.01); *A61K 31/343* (2013.01); *A61K 31/519* (2013.01); *A61K 38/1793* (2013.01); *A61K 2039/505* (2013.01); *A61K 2300/00* (2013.01)

(58) Field of Classification Search
None
See application file for complete search history.

(56) References Cited

U.S. PATENT DOCUMENTS 8,420,629 B2    4/2013    Rodgers et al.

FOREIGN PATENT DOCUMENTS

| CN | 102026999 | * | 4/2011 |
|----|-----------|---|--------|
| CN | 102026999 A |  | 4/2011 |
| RU | 2601410 | * | 11/2016 |
| RU | 2601410 C1 |  | 11/2016 |
| WO | 2010/039939 A1 |  | 4/2010 |
| WO | 2013/173506 A2 |  | 11/2013 |

OTHER PUBLICATIONS

International Search Report; PCT/CN2016/109036, dated Mar. 6, 2017.

* cited by examiner

*Primary Examiner* — Karl J Puttlitz
(74) *Attorney, Agent, or Firm* — Kilpatrick Townsend and Stockton LLP

(57) ABSTRACT

The present invention relates to an azetidine derivative for use as a Janus kinase (JAK) inhibitor, a drug composition comprising same, a preparation method therefor, and a use thereof in the treatment of JAK-related diseases comprising, for example, inflammatory diseases, autoimmune diseases, and cancers.

33 Claims, No Drawings

AZETIDINE DERIVATIVE, PREPARATION METHOD THEREFOR, AND USE THEREOF

CROSS-REFERENCE TO RELATED APPLICATIONS

This application is a National Phase Entry of PCT/CN2016/109036, filed Dec. 8, 2016, which application claims priority to CN 201510924946.1, filed Dec. 11, 2015, the teachings of which are hereby incorporated by reference in their entireties for all purposes.

FIELD OF THE INVENTION

The present invention relates to an azetidine derivative for use as a Janus kinase (JAK) inhibitor, a drug composition comprising same, a preparation method therefor, and a use thereof in the treatment of JAK-related diseases comprising, for example, inflammatory diseases, autoimmune diseases, and cancers.

BACKGROUND OF THE INVENTION

Protein kinases are a series of structurally related enzymes that are responsible for the control of signal transduction processes within the cell. They exert their physiological functions through catalyzing the phosphorylation of proteins (or substrates) and thereby modulating the cellular activity of the substrates, including modulating various important biological processes, such as cell growth, survival and differentiation, organ formation and morphogenesis, neovascularization, tissue repair and regeneration. Many diseases are associated with abnormal cellular responses triggered by protein kinase-mediated events.

JAK is a non-receptor type tyrosine kinase, and belongs to the family of protein kinases. The molecular weight of JAK is about 120 kDa to 140 kDa. In mammals, there are four members in the JAK family: JAK1 (also known as Janus kinase-1), JAK2 (also known as Janus kinase-2), JAK3 (also known as Janus kinase-3) and TYK2 (also known as protein-tyrosine kinase 2). These kinases exert their functions through interaction of cytokines and cytokine receptors (see Rodig S., et al., "Disruption of the Jak1 gene demonstrates obligatory and nonredundant roles of the Jaks in cytokine-induced biologic responses", Cell, 1998, 93 (3), 373-83).

JAK plays a key role in the signal transduction of cytokines. The downstream substrates of the JAK family of kinases include the signal transducer and activator of transcription (STAT) proteins. Many diseases are associated with abnormal JAK/STAT signal transduction, such as immune system diseases (e.g., organ transplant rejection), autoimmune diseases (e.g., multiple sclerosis, rheumatoid arthritis, juvenile arthritis, psoriatic arthritis, type-I diabetes, lupus, psoriasis), allergic conditions (e.g., asthma, food allergy, atopic dermatitis and rhinitis), skin diseases (e.g., psoriasis, atopic dermatitis, rash), solid and hematologic malignancies (e.g., prostate cancer, kidney cancer, liver cancer, pancreatic cancer, gastric cancer, breast cancer, lung cancer, head and neck cancer, thyroid cancer, glioblastoma, leukemia, lymphoma, multiple myeloma), and myeloproliferative disorders (including erythrocytosis, idiopathic thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome or systematic mast cell disease.

Blocking signal transduction at the level of the JAK kinases is believed to hold promises for developing new treatments for JAK-related diseases such as inflammatory diseases, autoimmune diseases, myeloproliferative disorders and cancers, to name a few. JAK inhibition is also anticipated to have therapeutic benefits in patients with skin immune disorders (such as psoriasis and skin sensitization). Therefore, it is desired to develop novel JAK inhibitors, so as to more effectively treat JAK-related diseases.

For example, the expression levels of interleukin IL-6, IL-15, interferon (IFN), granulocyte-macrophage colony stimulating factor (GM-CSF) and the like are significantly elevated in the rheumatoid arthritis synovial tissue, which plays a crucial role in the occurrence and development of disorders. All the above-mentioned cytokines exert their functions via the JAK-STAT signaling pathway. Therefore, targeted blocking of the JAK-STAT pathway can achieve the purpose of improving the pathophysiological process of rheumatoid arthritis (see Joel M. K. et al., Arthritis Rheum. 2009, 60, 1859-1905).

For JAK inhibitors, some studies have been performed (see, e.g., Peter Norman, "Selective JAK inhibitors in development for rheumatoid arthritis", Expert Opin. Investig. Drugs, 2014, 23 (8), 1067-77). Among them, Baricitinib is a drug candidate for the treatment of rheumatoid arthritis, and multiple Phase III clinical studies are ongoing in the United States (see CN102026999). Tofacitinib is currently the only JAK1 and JAK3 selective inhibitor approved by FDA in the United States for the treatment of rheumatoid arthritis (see Kremer, J., et al., "The safety and efficacy of a JAK inhibitor in patients with active rheumatoid arthritis: Results of a double-blind, placebo-controlled phase IIa trial of three dosage levels of CP-690, 550 versus placebo", Arthritis & Rheumatism, 2009, 60 (7), 1895-1905). However, several adverse effects are reported for patients taking Tofacitinib, such as potential serious infections, and the increased risk of cancer and heart failure (Tofacitinib is labeled with a black box warning of serious infections and cancer risks by FDA regulation). These adverse reactions may be due to its inhibition of the JAK3 enzyme. In addition, Tofacitinib has a short half-life in human, and thus twice daily administration is required. Moreover, Tofacitinib cannot be co-administered with a disease modifying anti-rheumatic drug (DMARD) (e.g., methotrexate). Therefore, it is desired to develop JAK inhibitors having improved JAK selectivity and pharmacokinetic properties and being able to be co-administered with a DMARD (e.g., methotrexate), so as to provide patients with better therapeutic effects and reduced adverse reactions.

SUMMARY OF THE INVENTION

In one aspect, the present invention provides a compound of Formula I or a pharmaceutically acceptable salt, stereoisomer, polymorph, solvate, metabolite or prodrug thereof, as a JAK inhibitor:

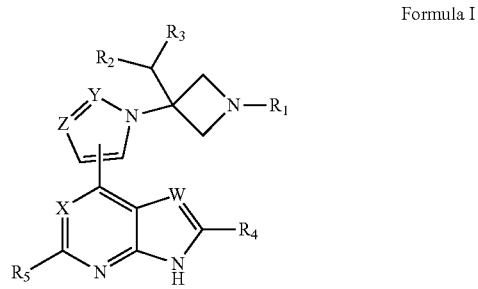

Formula I wherein:

R$_1$ is selected from the group consisting of C$_{1-6}$ alkyl, C$_{3-10}$ cycloalkyl, 3- to 10-membered heterocyclyl, C$_{6-14}$ aryl, 5- to 14-membered heteroaryl, C$_{7-20}$ aralkyl, C(O)R$_{10}$, and S(O)$_2$R$_{11}$;

R$_2$ and R$_3$ are each independently selected from the group consisting of H, CN, halogen, and C$_{1-6}$ alkyl;

R$_4$ and R$_5$ are each independently selected from the group consisting of H, halogen, and CN;

X is selected from the group consisting of N and CR$_6$;
Y is selected from the group consisting of N and CR$_9$;
Z is selected from the group consisting of N and CR$_7$;
W is selected from the group consisting of N and CR$_8$;

R$_6$, R$_7$, R$_8$ and R$_9$ are each independently selected from the group consisting of H, halogen, CN, C$_{1-6}$ alkyl, C$_{1-6}$ alkoxyl, and C(O)NR$_{12}$R$_{13}$;

R$_{10}$ and R$_{11}$ are each independently selected from the group consisting of C$_{1-6}$ alkyl, C$_{3-10}$ cycloalkyl, 3- to 10-membered heterocyclyl, C$_{6-14}$ aryl, 5- to 14-membered heteroaryl, C$_{7-20}$ aralkyl, and NR$_{12}$R$_{13}$;

R$_{12}$ and R$_{13}$ are each independently selected from the group consisting of H and C$_{1-6}$ alkyl;

wherein the above alkyl, cycloalkyl, heterocyclyl, aryl, terocyclyl, aryl, heteroaryl and aralkyl are each optionally substituted with 1, 2 or 3 substituents independently selected from the group consisting of halogen, CN, and C$_{1-4}$ alkyl.

In another aspect, the present invention provides a pharmaceutical composition comprising the compound of the present invention or a pharmaceutically acceptable salt, stereoisomer, polymorph, solvate, metabolite or prodrug thereof and one or more pharmaceutically acceptable carriers, and optionally further comprising one or more additional drugs for the treatment of a JAK-related disease.

In another aspect, the present invention provides a method for the treatment of a JAK-related disease, comprising administering to a subject in need thereof a therapeutically effective amount of the compound of the present invention or a pharmaceutically acceptable salt, stereoisomer, polymorph, solvate, metabolite or prodrug thereof or the pharmaceutical composition, and optionally further comprising administering to a subject in need thereof an additional drug for the treatment of a JAK-related disease.

In another aspect, the present invention provides use of the compound of the present invention or a pharmaceutically acceptable salt, stereoisomer, polymorph, solvate, metabolite or prodrug thereof or the pharmaceutical composition in the manufacture of a medicament for the treatment of a JAK-related disease.

In another aspect, the present invention provides the compound of the present invention or a pharmaceutically acceptable salt, stereoisomer, polymorph, solvate, metabolite or prodrug thereof or the pharmaceutical composition for the treatment of a JAK-related disease.

In another aspect, the present invention provides a method for the preparation of a compound of the present invention, the method comprises:

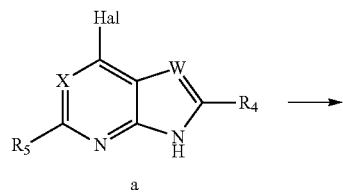

a

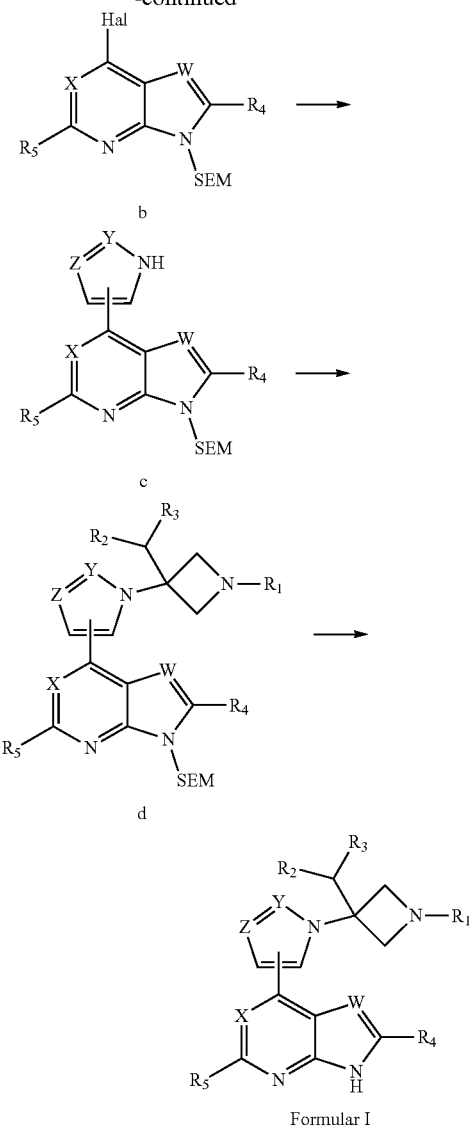

wherein Hal is selected from the group consisting of fluorine, chlorine, bromine, and iodine, and the remaining groups and substituents are each as defined above;

wherein:

compound a is reacted with SEMCl in the presence of a base in a polar aprotic solvent, to afford compound b;

compound b is reacted with a suitable regent in the presence of a base, under the catalysis of a palladium catalyst, to afford compound c;

compound c is reacted with a suitable regent in the presence of a base, to afford compound d; and compound d is reacted under the catalysis of a Lewis acid, to afford a compound of Formula I; alternatively, compound d is first reacted under the catalysis of an acid, and the resulting product is then reacted, after treatment, in the presence of a base, to afford a compound of Formula I.

In another aspect, the present invention provides a method for the preparation of a compound of the present invention, the method comprises:

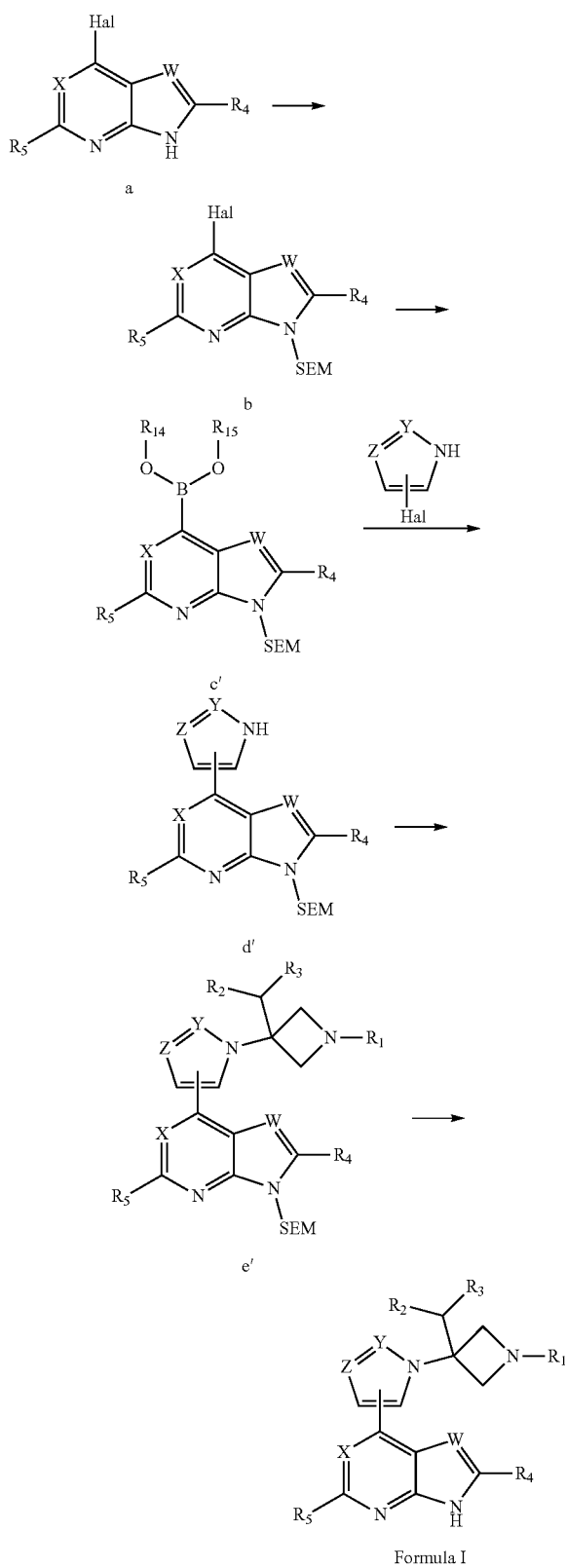

wherein Hal is selected from the group consisting of fluorine, chlorine, bromine, and iodine;

R$_{14}$ and R$_{15}$ are each independently selected from the group consisting of H and C$_{1-6}$ alkyl; or R$_{14}$ and R$_{15}$ together with the atoms to which they are attached form a 5- or 6-membered ring system; and the remaining groups and substituents are each as defined above;

wherein:

compound a is reacted with SEMCl in the presence of a base in a polar aprotic solvent, to afford compound b;

compound b is reacted with a suitable regent in the presence of a base, under the catalysis of a palladium catalyst, to afford compound c';

compound c' is reacted with a suitable regent in the presence of a base, under the catalysis of a palladium catalyst, to afford compound d';

compound d' is reacted with a suitable regent in the presence of a base, to afford compound e'; and compound e' is reacted under the catalysis of a Lewis acid, to afford a compound of Formula I; alternatively, compound e' is first reacted under the catalysis of an acid, and the resulting product is then reacted, after treatment, in the presence of a base, to afford a compound of Formula I.

Compared with JAK inhibitors in the prior art, the compound of the present invention has many advantages, including excellent JAK kinase inhibitory activity, better selectivity towards JAK1 and JAK2, more favorable pharmacokinetic properties, good patient compliance, capability of being combined with other drugs, and better safety, etc.

DETAILED DESCRIPTION OF THE INVENTION

Compound and Preparation Method Therefor

In one embodiment, the present invention provides a compound of Formula I or a pharmaceutically acceptable salt, stereoisomer, polymorph, solvate, metabolite or prodrug thereof:

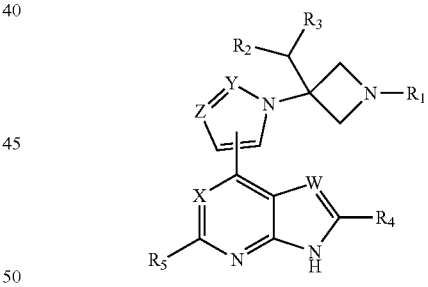

Formula I wherein:

R$_1$ is selected from the group consisting of C$_{1-6}$ alkyl, C$_{3-10}$ cycloalkyl, 3- to 10-membered heterocyclyl, C$_{6-14}$ aryl, 5- to 14-membered heteroaryl, C$_{7-20}$ aralkyl, C(O)R$_{10}$, and S(O)$_2$R$_{11}$;

R$_2$ and R$_3$ are each independently selected from the group consisting of H, CN, halogen, and C$_{1-6}$ alkyl;

R$_4$ and R$_5$ are each independently selected from the group consisting of H, halogen, and CN;

X is selected from the group consisting of N and CR$_6$;

Y is selected from the group consisting of N and CR$_9$;

Z is selected from the group consisting of N and CR$_7$;

W is selected from the group consisting of N and CR$_8$;

R$_6$, R$_7$, R$_8$ and R$_9$ are each independently selected from the group consisting of H, halogen, CN, C$_{1-6}$ alkyl, C$_{1-6}$ alkoxyl, and C(O)NR$_{12}$R$_{13}$;

$R_{10}$ and $R_{11}$ are each independently selected from the group consisting of $C_{1-6}$ alkyl, $C_{3-10}$ cycloalkyl, 3- to 10-membered heterocyclyl, $C_{6-14}$ aryl, 5- to 14-membered heteroaryl, $C_{7-20}$ aralkyl, and $NR_{12}R_{13}$;

$R_{12}$ and $R_{13}$ are each independently selected from the group consisting of H and $C_{1-6}$ alkyl;

wherein the above alkyl, cycloalkyl, heterocyclyl, aryl, heteroaryl and aralkyl are each optionally substituted with 1, 2 or 3 substituents independently selected from the group consisting of halogen, CN, and $C_{1-4}$ alkyl.

In a preferred embodiment, $R_1$ is selected from the group consisting of $C(O)R_{10}$ and $S(O)_2R_{11}$.

In a preferred embodiment, $R_2$ and $R_3$ are each independently selected from the group consisting of H, CN, F, and methyl.

In a preferred embodiment, $R_4$ and $R_5$ are each independently selected from the group consisting of H, F, Cl, and CN.

In a preferred embodiment, X, Y, Z or W is each independently selected from the group consisting of N and CH.

In a preferred embodiment, $R_6$, $R_7$, $R_8$ and $R_9$ are each independently selected from the group consisting of H, F, Cl, CN, methyl, ethyl, methoxy, and $C(O)NH_2$.

In a preferred embodiment, $R_{10}$ and $R_{11}$ are each independently selected from the group consisting of methyl, ethyl, n-propyl, isopropyl, cyclopropyl, n-butyl, isobutyl, tert-butyl, aziridinyl, pyrrolidinyl, phenyl, benzyl, and $N(CH_3)_2$, wherein the above groups are each optionally substituted with 1, 2 or 3 substituents independently selected from the group consisting of F, CN, and methyl.

In a preferred embodiment, $R_{12}$ and $R_{13}$ are each independently selected from the group consisting of H, methyl, and ethyl.

A compound of Formula I obtained by any combination of the above preferred groups is encompassed by the present invention.

In a preferred embodiment, the compound of Formula I or a pharmaceutically acceptable salt, stereoisomer, polymorph, solvate, metabolite or prodrug thereof is a compound of Formula II or a pharmaceutically acceptable salt, stereoisomer, polymorph, solvate, metabolite or prodrug thereof:

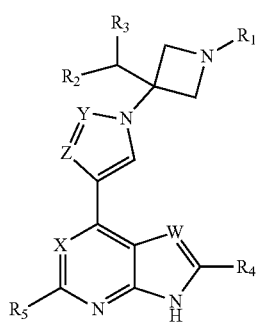

Formula II wherein the groups and substituents are each as defined above for Formula I.

In a preferred embodiment, the compound of Formula II or a pharmaceutically acceptable salt, stereoisomer, polymorph, solvate, metabolite or prodrug thereof is a compound of Formula III or a pharmaceutically acceptable salt, stereoisomer, polymorph, solvate, metabolite or prodrug thereof:

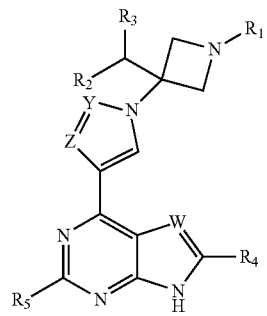

Formula III wherein:

one of W and Z is N;

alternatively, W is $CR_8$, Z is $CR_7$, and $R_2$, $R_4$, $R_5$, and $R_8$ are not H at the same time.

In a preferred embodiment, the compound of Formula II or a pharmaceutically acceptable salt, stereoisomer, polymorph, solvate, metabolite or prodrug thereof is a compound of Formula IV or a pharmaceutically acceptable salt, stereoisomer, polymorph, solvate, metabolite or prodrug thereof:

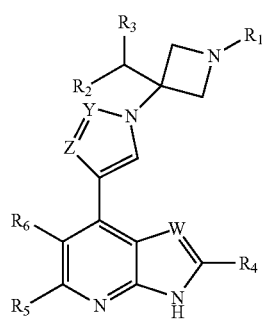

Formula IV wherein:

$R_1$ is selected from the group consisting of $C(O)R_{10}$ and $S(O)_2R_{11}$;

$R_{10}$ and $R_{11}$ are each independently selected from the group consisting of $C_{1-6}$ alkyl, $C_{3-10}$ cycloalkyl, 3- to 10-membered heterocyclyl, $C_{6-14}$ aryl, 5- to 14-membered heteroaryl, $C_{7-20}$ aralkyl, and $NR_{12}R_{13}$, wherein the alkyl, cycloalkyl, heterocyclyl, aryl, heteroaryl and aralkyl are each optionally substituted with 1, 2 or 3 substituents independently selected from the group consisting of halogen, CN, and $C_{1-4}$ alkyl.

In a preferred embodiment, the compound of Formula IV or a pharmaceutically acceptable salt, stereoisomer, polymorph, solvate, metabolite or prodrug thereof is a compound of Formula V or a pharmaceutically acceptable salt, stereoisomer, polymorph, solvate, metabolite or prodrug thereof:

Formula V

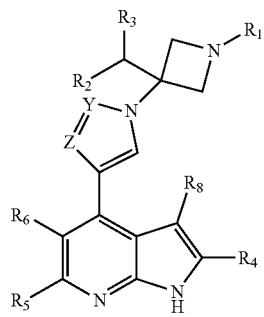

wherein the groups and substituents are each as defined above for Formula I.

In a preferred embodiment, the compound of Formula V or a pharmaceutically acceptable salt, stereoisomer, polymorph, solvate, metabolite or prodrug thereof is a compound of Formula VI or a pharmaceutically acceptable salt, stereoisomer, polymorph, solvate, metabolite or prodrug thereof:

Formula VI

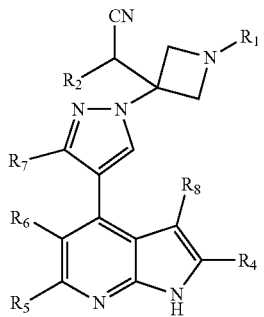

wherein the groups and substituents are each as defined above for Formula I.

In a preferred embodiment, the present invention provides a compound or a pharmaceutically acceptable salt, stereoisomer, polymorph, solvate, metabolite or prodrug thereof, wherein the compound of the present invention is selected from the group consisting of:

1

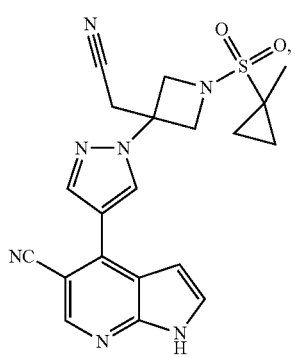

2

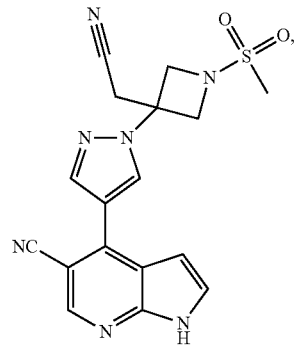

3

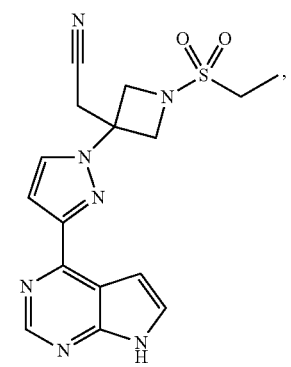

4

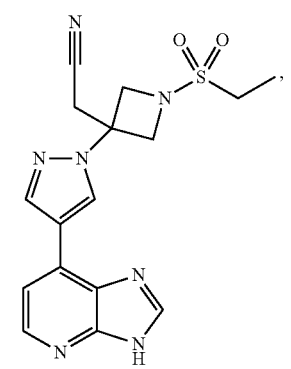

5

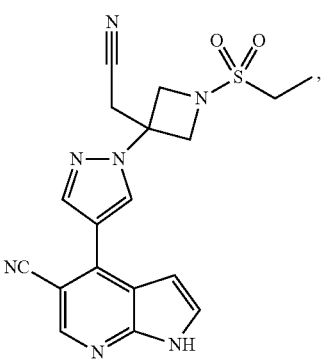

-continued

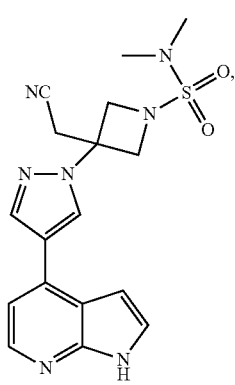 14
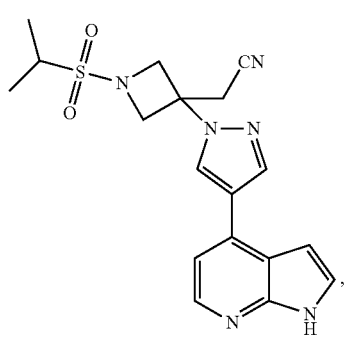 18
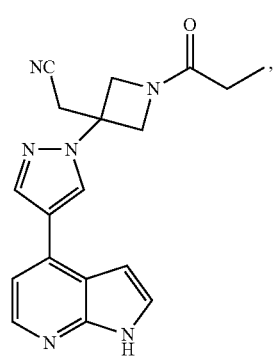 15
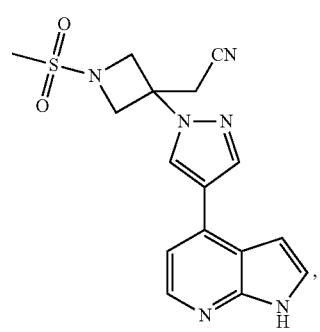 19
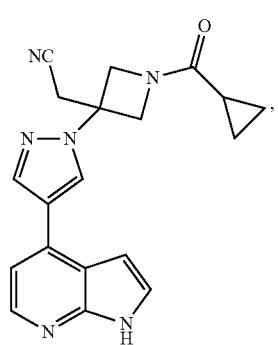 16
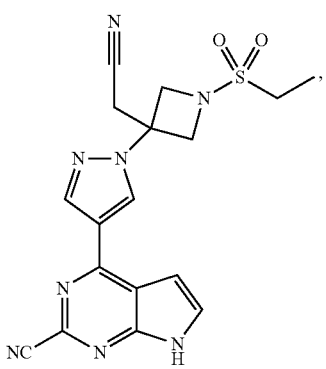 20
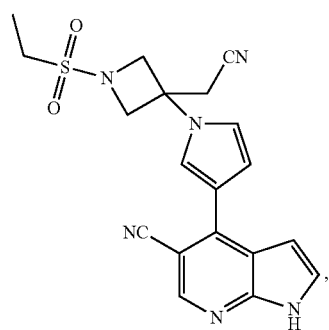 17
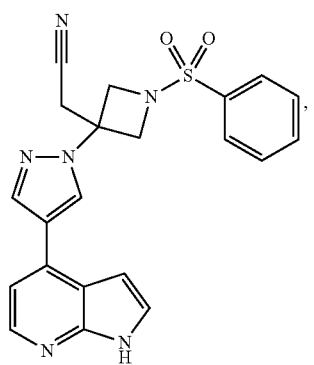 21

22 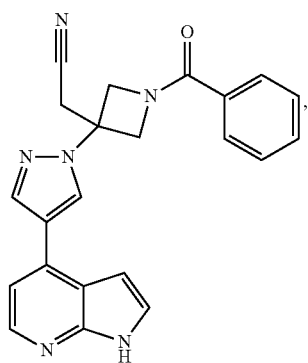
23 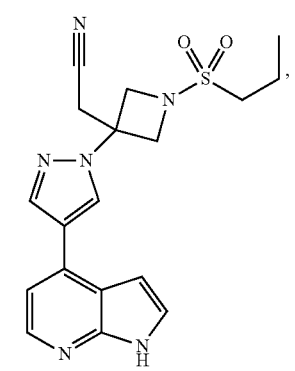
24 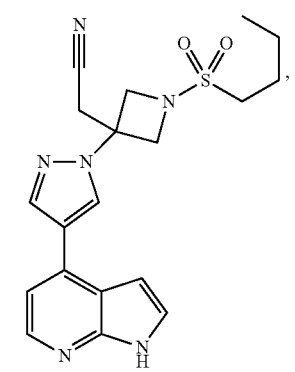
25 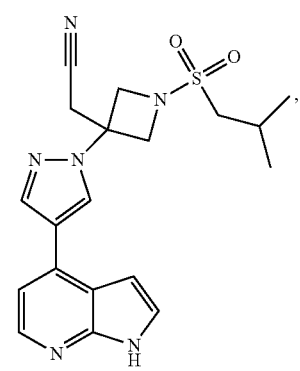
26 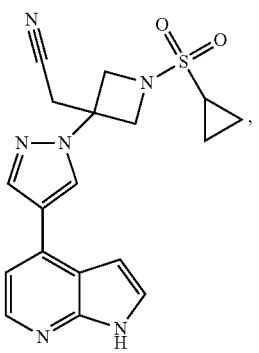
27 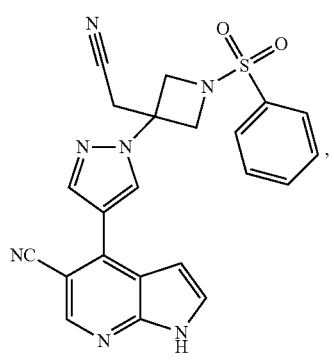
28 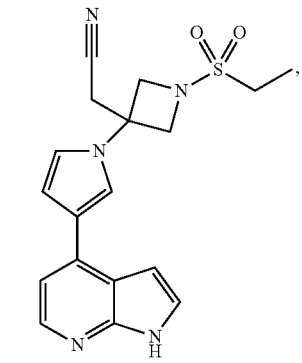
29 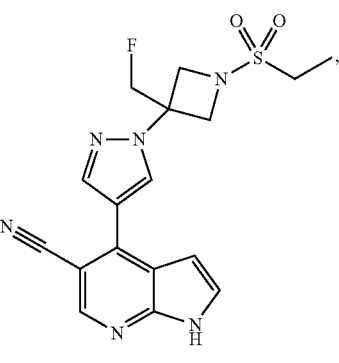

-continued
30
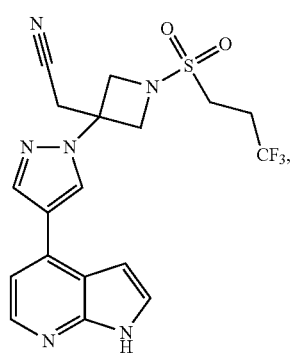
31
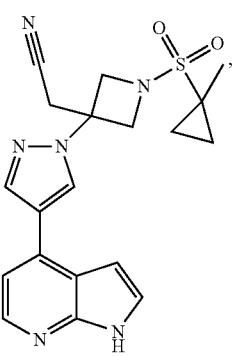
32
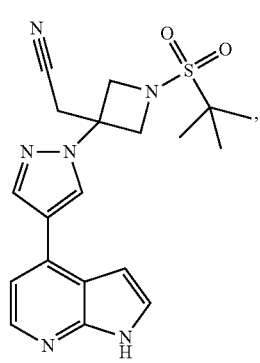
33
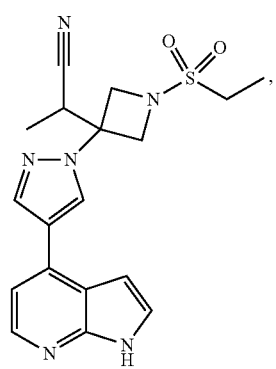
-continued
34
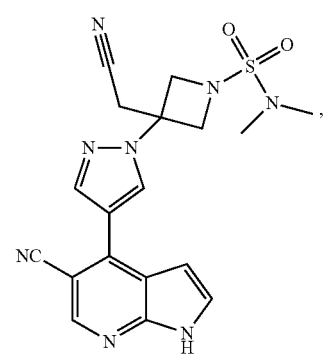
35
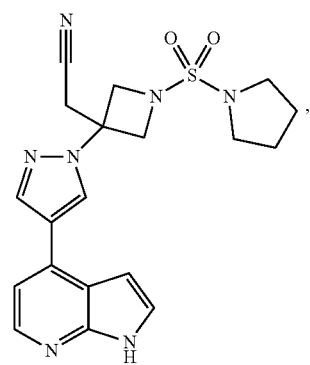
36
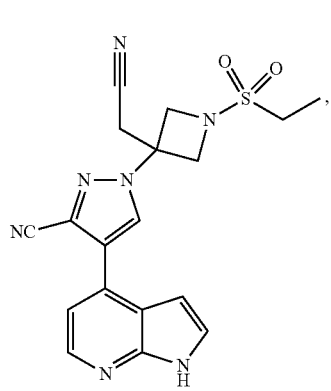
37
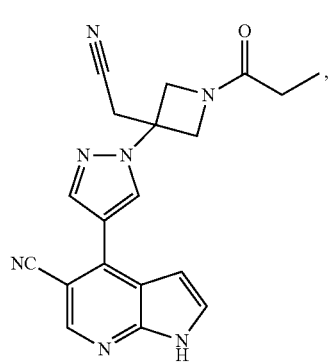

38
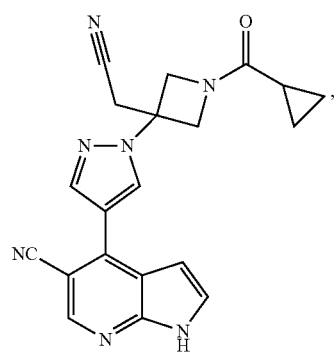
39
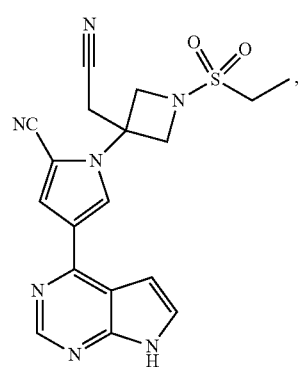
40
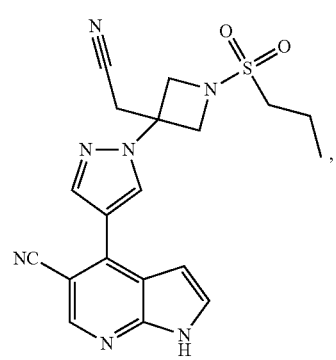
43
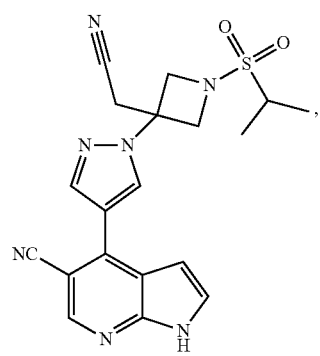
44
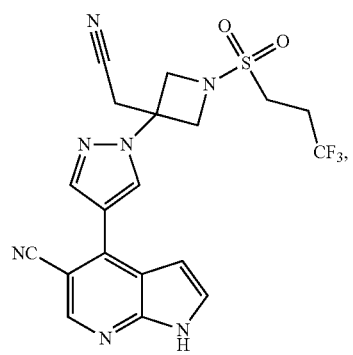
45
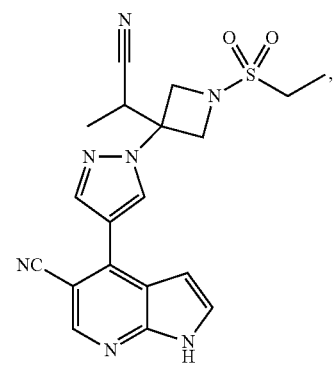
48
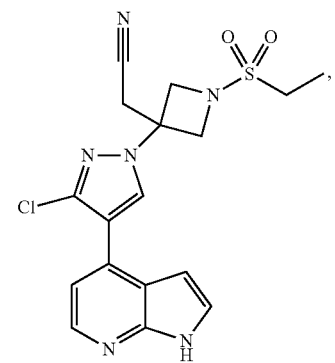
49
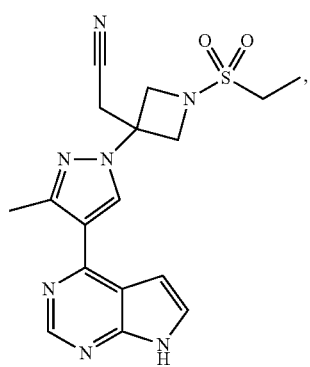

-continued
50
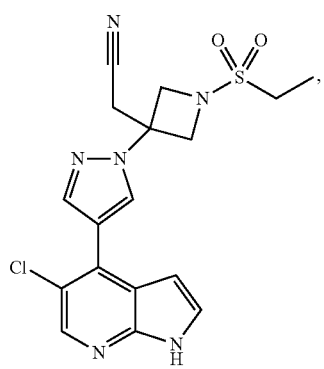
51
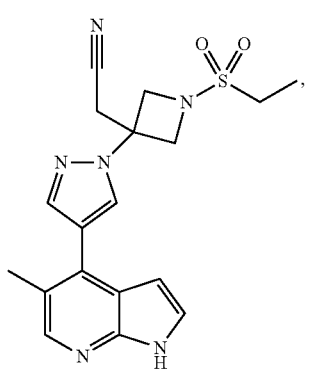
52
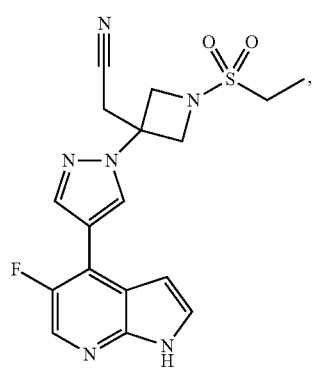
56
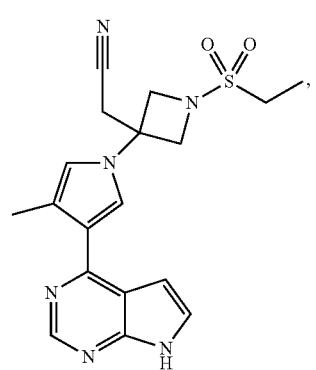
-continued
59
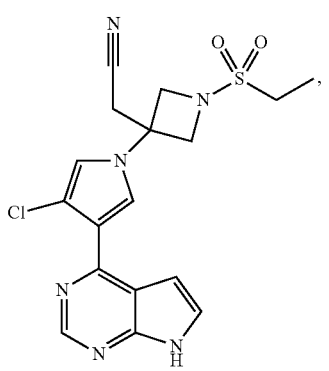
60
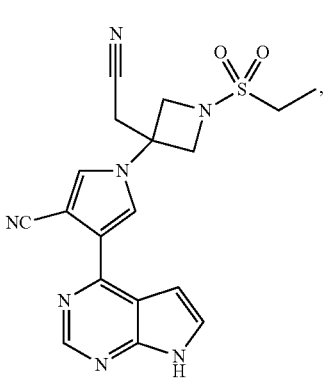
61
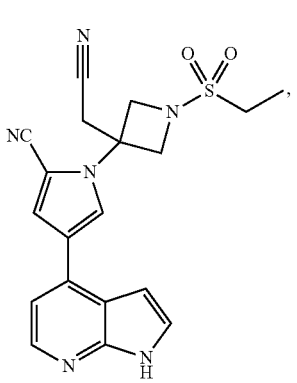
62
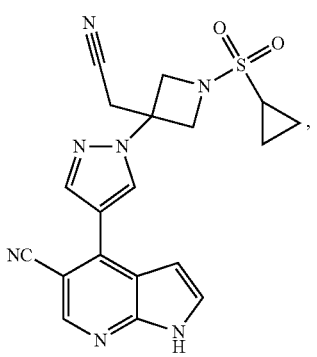

63
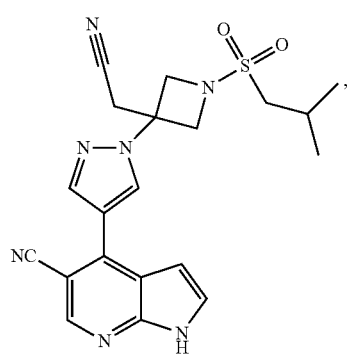
64
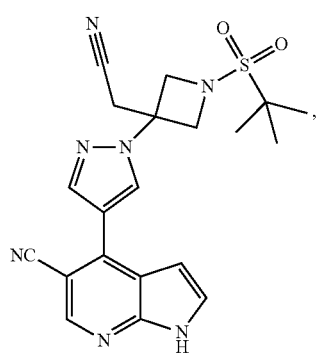
65
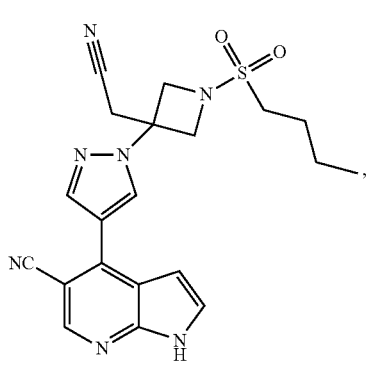
66
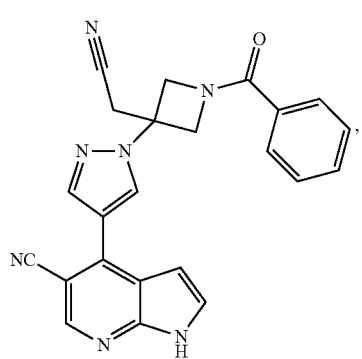
67
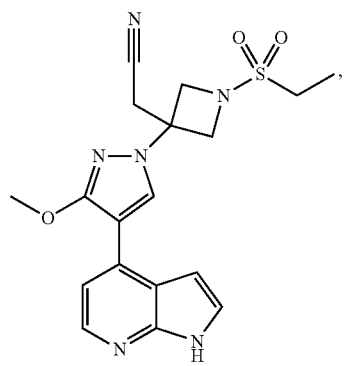
68
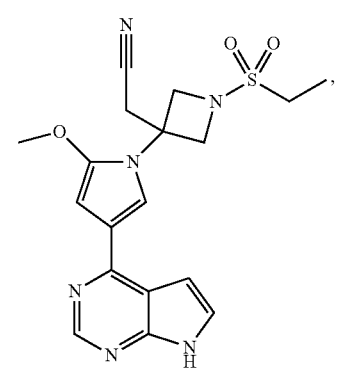
69
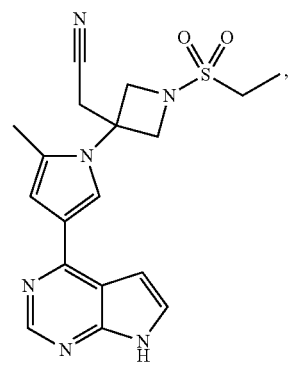
70
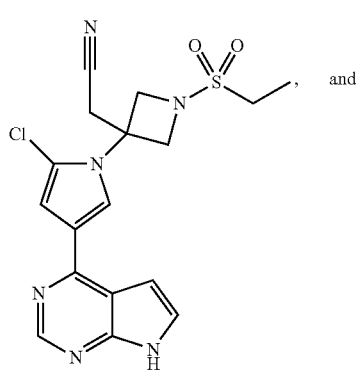, and -continued

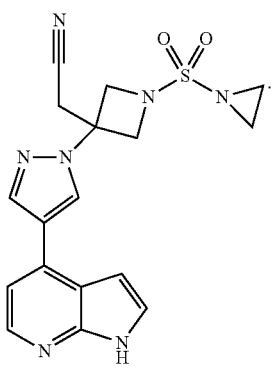

71

In a preferred embodiment, the present invention relates to a method for the preparation of a compound of the present invention, wherein the method comprises:

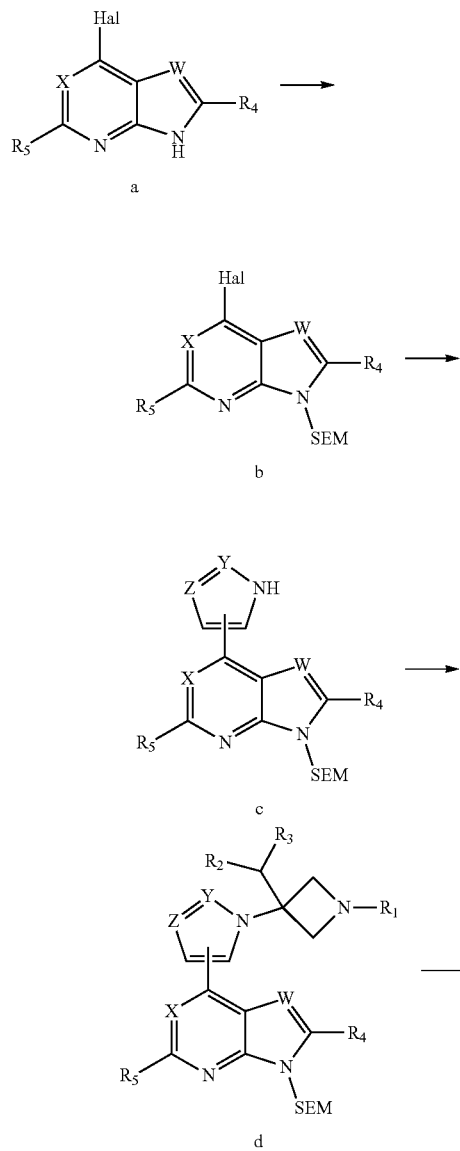

-continued

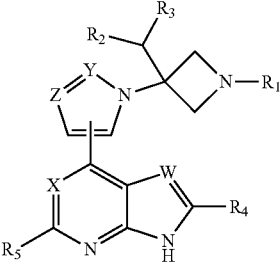

Formular I wherein Hal is selected from the group consisting of fluorine, chlorine, bromine, and iodine, and the remaining groups and substituents are each as defined above;

wherein:

compound a is reacted with SEMCl in the presence of a base (e.g., NaH or LDA) in a polar aprotic solvent (e.g., DMF or DMSO) at 0° C. to room temperature for 3-24 h, to afford compound b;

compound b is reacted with a borate compound in the presence of a base (e.g., sodium carbonate, potassium carbonate, potassium phosphate, or potassium acetate), under the catalysis of a palladium catalyst (e.g., Pd(PPh$_3$)$_4$, Pd(dppf)Cl$_2$ or Pd(OAc)$_2$), under the protection of an inert gas at room temperature to 100° C. for 5-24 h, to afford compound c, and the reaction can be carried out in a solvent (e.g., a mixed solvent of dioxane and water);

compound c is reacted with an acrylonitrile compound in the presence of a base (e.g., DBU, DMAP, potassium carbonate, or triethylamine) at 0° C. to room temperature for 18-24 h, to afford compound d, and the reaction can be carried out in a solvent (e.g., acetonitrile, acetone, N,N-dimethylformamide or dichloromethane); and compound d is reacted under the catalysis of a Lewis acid (e.g., lithium tetrafluoroborate) at room temperature to 100° C. for 18-24 h, to afford a compound of Formula I, and the reaction can be carried out in a solvent (e.g., acetonitrile); alternatively, compound d is first reacted under the catalysis of an acid (e.g., trifluoroacetic acid or a Lewis acid (e.g., boron trifluoride etherate)) (e.g., in a solvent such as dichloromethane) at 0° C. to room temperature for 3-8 h, and the resulting product is then reacted, after treatment, in the presence of a base (e.g., sodium hydroxide, aqueous ammonia or sodium carbonate) optionally in a solvent (e.g., tetrahydrofuran, methanol or ethanol) at 0° C. to room temperature for 10-24 h, to afford a compound of Formula I.

In a preferred embodiment, the present invention relates to a method for the preparation of a compound of the present invention, wherein the method comprises:

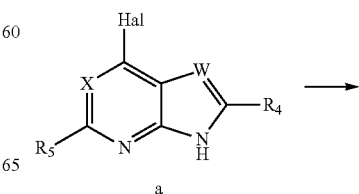

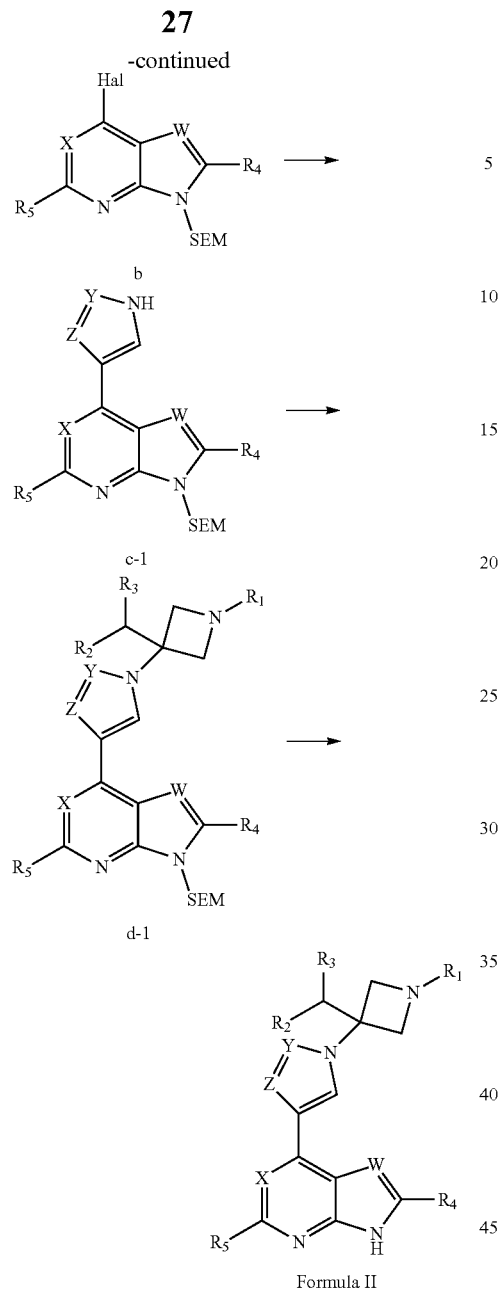

wherein Hal is selected from the group consisting of fluorine, chlorine, bromine, and iodine, the remaining groups and substituents are each as defined above, and the reaction conditions are the same as those described above.

In a preferred embodiment, the present invention relates to a method for the preparation of a compound of the present invention, wherein the method comprises:

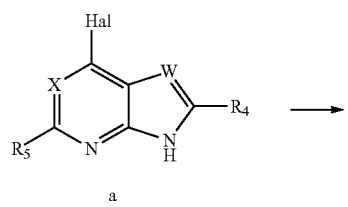

wherein Hal is selected from the group consisting of fluorine, chlorine, bromine, and iodine;

$R_{14}$ and $R_{15}$ are each independently selected from the group consisting of H and $C_{1-6}$ alkyl; or $R_{14}$ and $R_{15}$ together with the atoms to which they are attached form a 5- or 6-membered ring system, preferably, $R_{14}$ and $R_{15}$ together with the atoms to which they are attached form the following group:

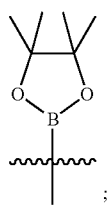

and
the remaining groups and substituents are each as defined above;
wherein:
compound a is reacted with SEMCl in the presence of a base (e.g., NaH or LDA) in a polar aprotic solvent (e.g., DMF or DMSO) at 0° C. to room temperature for 3-24 h, to afford compound b;
compound b is reacted with a borate compound in the presence of a base (e.g., sodium carbonate, potassium carbonate, potassium phosphate, or potassium acetate), under the catalysis of a palladium catalyst (e.g., Pd(PPh$_3$)$_4$, Pd(dppf)Cl$_2$ or Pd(OAc)$_2$), under the protection of an inert gas at room temperature to 100° C. for 5-24 h, to afford compound c', and the reaction can be carried out in a solvent (e.g., dioxane, water, or a mixed solvent thereof);
compound c' is reacted with a borate compound in the presence of a base (e.g., sodium carbonate, potassium carbonate, potassium phosphate, or potassium acetate), under the catalysis of a palladium catalyst (e.g., Pd(PPh$_3$)$_4$, Pd(dppf)Cl$_2$ or Pd(OAc)$_2$), under the protection of an inert gas at room temperature to 100° C. for 5-24 h, to afford compound d', and the reaction can be carried out in a solvent (e.g., a mixed solvent of dioxane and water);
compound d' is reacted with an acrylonitrile compound in the presence of a base (e.g., DBU, DMAP, potassium carbonate, or triethylamine) at 0° C. to room temperature for 18-24 h, to afford compound e', and the reaction can be carried out in a solvent (e.g., acetonitrile, acetone, N,N-dimethylformamide or dichloromethane); and
compound e' is reacted under the catalysis of a Lewis acid (e.g., lithium tetrafluoroborate) at room temperature to 100° C. for 18-24 h, to afford a compound of Formula I, and the reaction can be carried out in a solvent (e.g., acetonitrile); alternatively, compound e' is first reacted under the catalysis of an acid (e.g., trifluoroacetic acid or a Lewis acid (e.g., boron trifluoride etherate)) (e.g., in a solvent such as dichloromethane) at 0° C. to room temperature for 3-8 h, and the resulting product is then reacted, after treatment, in the presence of a base (e.g., sodium hydroxide, aqueous ammonia or sodium carbonate) optionally in a solvent (e.g., tetrahydrofuran, methanol or ethanol) at 0° C. to room temperature for 10-24 h, to afford a compound of Formula I.
In a preferred embodiment, the present invention relates to a method for the preparation of a compound of the present invention, wherein the method comprises:

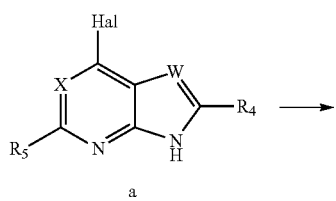

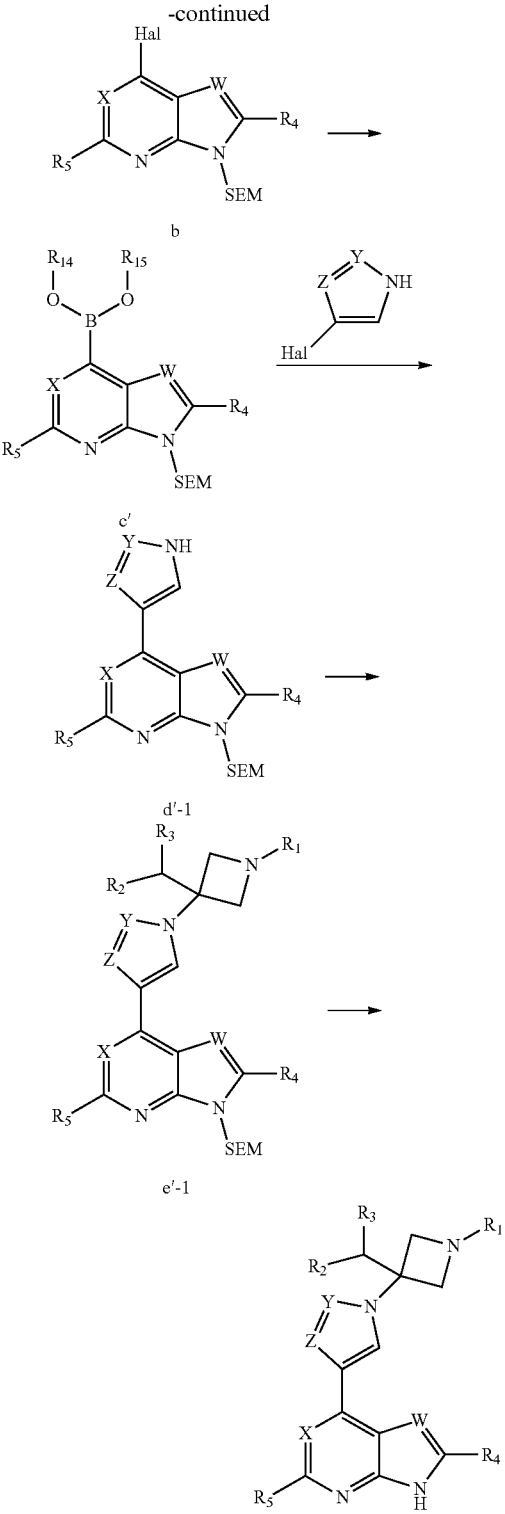

wherein Hal is selected from the group consisting of fluorine, chlorine, bromine, and iodine, the remaining groups and substituents are each as defined above, and the reaction conditions are the same as those described above.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkyl" is defined to include saturated aliphatic hydrocarbon comprising straight and branched chains. In some embodiments, alkyl has 1-6, e.g., 1-4, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, or n-hexyl), which is optionally substituted with one or more (e.g., 1 to 3) suitable substituents such as halogen (e.g., $CF_3$, $C_2F_5$, $CHF_2$, $CH_2F$, $CH_2CF_3$, $CH_2Cl$ or $-CH_2CH_2CF_3$, etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkoxy" refers to a linear, branched or cyclic, saturated monovalent hydrocarbon residue represented by a formula of —O-alkyl, wherein the term "alkyl" is as defined above or refers to a "cycloalkyl" as defined below, such as methoxy, ethoxy, n-propoxy, isopropoxy, cyclopropyloxy, n-butoxy, isobutoxy, tert-butoxy, sec-butoxy, cyclobutoxy, pentoxy, iso-pentoxy or n-hexyloxy group, or isomers thereof.

As used herein, the term "cycloalkyl" refers to a saturated or unsaturated, non-aromatic monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, decahydronaphthalene, etc.)), which is optionally substituted with one or more (e.g., 1 to 3) suitable substituents. The cycloalkyl has 3 to 15 carbon atoms. For example, the term "$C_{3-10}$ cycloalkyl" refers to a saturated or unsaturated, non-aromatic monocyclic or polycyclic (e.g., bicyclic) hydrocarbon ring having 3 to 10 ring forming carbon atoms (e.g., cyclopropyl, cyclobutyl, cyclopentyl, cyclohexyl or bicyclo[1.1.1]pentyl), which is optionally substituted with one or more (e.g., 1 to 3) suitable substituents, e.g., methyl substituted cyclopropyl.

As used herein, the term "heterocyclyl" refers to a saturated or unsaturated, monovalent, monocyclic or bicyclic residue having 2, 3, 4, 5, 6, 7, 8 or 9 carbon atoms and one or more (e.g., 1, 2, 3 or 4) heteroatom-containing groups selected from the group consisting of C(=O), O, S, S(=O), S(=O)$_2$, and NR$^a$ wherein R$^a$ represents a hydrogen atom, $C_{1-6}$ alkyl, or $C_{1-6}$ haloalkyl group, in the ring. A heterocycloalkyl may be linked to the rest of a molecule through any one of the carbon atoms or a nitrogen atom (if present). In particular, 3- to 10-membered heterocyclyl refers to a group having 3 to 10 carbon atoms and heteroatom(s) in the ring, such as, but are not limited to, oxiranyl, aziridinyl, azetidinyl, oxetanyl, tetrahydrofuranyl, dioxolinyl, pyrrolidinyl, pyrrolidinonyl, imidazolidinyl, pyrazolidinyl, pyrrolinyl, tetrahydropyranyl, piperidinyl, morpholinyl, dithianyl, thiomorpholinyl, piperazinyl or trithianyl.

As used herein, the term "aryl" refers to an all-carbon monocyclic or fused-ring polycyclic aromatic group having a conjugated π electron system. For example, as used herein, the term "$C_{6-14}$ aryl" refers to an aromatic group containing 6 to 14 carbon atoms, such as phenyl or naphthyl. Aryl is optionally substituted with one or more (such as 1 to 3) suitable substituents.

As used herein, the term "heteroaryl" refers to a monovalent monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same or different. Moreover, in each case, it can be benzo-fused. In particular, heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, thiadiazolyl etc., and benzo derivatives thereof; or pyridinyl, pyridazinyl, pyrimidinyl, pyrazinyl, triazinyl, etc., and benzo derivatives thereof.

The term "aralkyl" preferably means aryl substituted alkyl, wherein aryl and alkyl are as defined herein. Normally, the aryl group may have 6-14 carbon atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" is defined to include F, Cl, Br, or I.

The term "substituted" means that one or more (e.g., one, two, three, or four) hydrogens on a designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means that a compound is optionally substituted with a specified group, radical or moiety.

When a bond to a substituent is shown to cross a bond connecting two atoms in a ring, then such substituent may be bonded to any of the ring-forming atoms in that ring that are substitutable.

The compound of the present invention may also contain one or more (e.g., 1, 2, 3, or 4) isotopes. For example, in the compound of the present invention, hydrogen or H may be in any isotopic form, including $^1$H, $^2$H (D or deuterium) and $^3$H (T or tritium); carbon or C may be in any isotopic form, including $^{12}$C, $^{13}$C and $^{14}$C; and oxygen or O may be in any isotopic form, including $^{16}$O and $^{18}$O, etc.

The term "stereoisomer" refers to isomers formed due to the presence of at least one asymmetric center. A compound having one or more (e.g., one, two, three or four) asymmetric centers can give rise to a racemate, racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitrosooxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, solvate, metabolite or prodrug, which can directly or indirectly provide the compound of the present invention or a metabolite or residue thereof after being administered to a patient in need thereof.

A pharmaceutically acceptable salt of the compound of the present invention includes an acid addition salt and a base addition salt thereof.

A suitable acid addition salt is formed from an acid which forms a non-toxic salt. Specific examples include aspartate, bicarbonate/carbonate, bisulfate, borate, camphorsulfonate, citrate, cyclamate, edisylate, esylate, fumarate, gluceptate, gluconate, glucuronate, hexafluorophosphate, hydroiodide/iodide, isethionate, lactate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, tannate, and xinofoate salts.

A suitable base addition salt is formed from a base which forms a non-toxic salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Hand book of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

The compound of the present invention may exist in the form of a hydrate or a solvate, wherein the compound of the present invention contains a polar solvent, in particular water, methanol or ethanol, for example, as a structural element of the crystal lattice of the compound. Polar solvents, in particular water, may exist in a stoichiometric or non-stoichiometric amount.

The present invention further encompasses a metabolite of the compound of the present invention, i.e., a compound generated in vivo upon administration of a drug.

Prodrugs of the compound of the present invention can be formed through replacing suitable functional groups in the compound of Formula I with those known in the art (for example, the "pro-moieties" described in "*Design of Prodrugs*" by H. Bundgaard (Elsevier, 1985)).

Pharmaceutical Composition and Therapeutic Method

Another aspect of the present invention provides a pharmaceutical composition comprising a therapeutically effective amount of the compound of the present invention or a pharmaceutically acceptable salt, stereoisomer, polymorph, solvate, metabolite or prodrug thereof and one or more pharmaceutically acceptable carriers, and optionally further comprising one or more additional drugs for the treatment of a JAK-related disease.

Another aspect of the present invention provides a method for the treatment of a JAK-related disease, comprising administering to a subject in need thereof a therapeutically effective amount of the compound of the present invention or a pharmaceutically acceptable salt, stereoisomer, polymorph, solvate, metabolite or prodrug thereof or the pharmaceutical composition.

The pharmaceutical composition and method of the present invention can be used for the treatment of a JAK-related disease, such as, but is not limited to, an immune system disease (e.g., organ transplant rejection), autoimmune disease (e.g., multiple sclerosis, rheumatoid arthritis, juvenile arthritis, psoriatic arthritis, type-I diabetes, lupus, psoriasis), allergic condition (e.g., asthma, food allergy, atopic dermatitis and rhinitis), skin disease (e.g., psoriasis, atopic dermatitis, rash), solid and hematologic malignancy (e.g., prostate cancer, kidney cancer, liver cancer, pancreatic cancer, gastric cancer, breast cancer, lung cancer, head and neck cancer, thyroid cancer, glioblastoma, leukemia, lymphoma, multiple myeloma), and myeloproliferative disorder (including erythrocytosis, idiopathic thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome or systematic mast cell disease.

Particularly, the compound of the present invention is for the treatment of a JAK-related disease including e.g., inflammatory disease, autoimmune disease, and cancer. More particularly, the compound of the present invention is for the treatment of rheumatoid arthritis.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to, sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g., Remington's Pharmaceutical Sciences (1990).

The pharmaceutical composition of the present invention can act systemically and/or topically. To this end, it can be administered through a suitable route, such as through injection, intravenous, intraarterial, subcutaneous, intraperitoneal, intramuscular or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "therapeutically effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic or prophylactic agents, including, but are not limited to, chemotherapeutic agents or anti-proliferative agents, anti-inflammatory agents, immunomodulators or immunosuppressive agents, neurotrophic factors, agents for treating cardiovascular diseases, agents for treating destructive bone disorders, agents for treating liver diseases, antiviral agents, and agents for treating blood diseases, diabetes, or immune deficiency diseases. In particular, the one or more additional therapeutic or prophylactic agents are selected from the group consisting of efalizumab, mycophenolate sodium, etanercept, and methotrexate, etc.

EXAMPLES

The present invention is further described with reference to the following examples, which are not provided to limit the scope of the present invention.

The abbreviations as used in the present invention have the following meanings:

| Abbreviation | Meaning |
| --- | --- |
| ACN | acetonitrile |
| $BF_3C_4H_{10}O$ | boron trifluoride etherate |
| n-BuOH | n-butanol |
| $CDCl_3$ | deuterated chloroform |
| $CD_3OD$ | deuterated methanol |
| $CH_3CN$ | acetonitrile |
| m-CPBA | 3-chloroperbenzoic acid |
| DAST | diethylaminosulfur trifluoride |
| DBU | 1,8-diazabicycloundec-7-ene |
| DCM | dichloromethane |
| DIEA/DIPEA | N,N-diisopropylethylamine |
| DMAP | 4-dimethylaminopyridine |
| DMF | N,N-dimethylformamide |
| DMSO | dimethyl sulfoxide |
| EA | ethyl acetate |
| EtOH | ethanol |
| h | hour |
| HCl | hydrochloric acid |
| $H_2O$ | water |
| $H_2O_2$ | hydrogen peroxide |
| HPLC, LC | high performance liquid chromatography |
| $K_2CO_3$ | potassium carbonate |
| KOH | potassium hydroxide |
| LDA | lithium diisopropylamide |
| LHMDS | lithium bis(trimethylsilyl)amide |
| $LiBF_4$ | lithium tetrafluoroborate |
| MeOH | methanol |
| min | minute |
| MS | mass spectrometry |
| NaH | sodium hydride |
| $Na_2CO_3$ | sodium carbonate |
| NaOH | sodium hydroxide |
| NCS | N-chlorosuccinimide |
| $NH_4OH$ | ammonia |
| NMP | N-methyl pyrrolidone |
| NMR | nuclear magnetic resonance |
| PE | petroleum ether |
| $Pd(dppf)Cl_2$ | 1,1-bis(diphenylphosphino)ferrocene]dichloropalladium(II) |
| $Pd(PPh_3)_4$ | tetrakis(triphenylphosphine)palladium |
| $Pd(OAc)_2$ | palladium acetate |
| rt | room temperature |
| $R_t$ | retention time |
| SEM- | [2-(trimethylsilyl)ethoxy]methyl- |
| SEMCl | [2-(trimethylsilyl)ethoxy]methyl chloride |
| TBAF | tetrabutylammonium fluoride |
| TFA | trifluoroacetic acid |
| THF | tetrahydrofuran |
| TLC | thin-layer chromatography |

The structures of compounds were confirmed by NMR spectroscopy ($^1$H NMR) or mass spectrometry (MS).

The reactions were monitored by thin-layer chromatography (TLC) or LC-MS. The developing solvent systems employed include: dichloromethane-methanol system, n-hexane-ethyl acetate system, and petroleum ether-ethyl acetate system.

Microwave reactions were conducted using the Biotage-Initiator+microwave reactor.

Silica gel of 200 to 300 mesh (Qingdao Ocean) was generally used as the stationary phase in column chromatography. Eluent systems included: dichloromethane-methanol system and n-hexane-ethyl acetate system.

In the following examples, the reaction temperature was generally room temperature (20° C.~30° C.), unless otherwise specified.

The reagents used in this application were purchased from Acros Organics, Aldrich Chemical Company or Topbiochem, etc.

Example 1: 4-(1-(3-(cyanomethyl)-1-((1-methylcyclopropyl)sulfonyl)azetidin-3-yl)-1H-pyrazol-4-yl)-1H-pyrrolo[2,3-b]pyridine-5-carbonitrile (1)

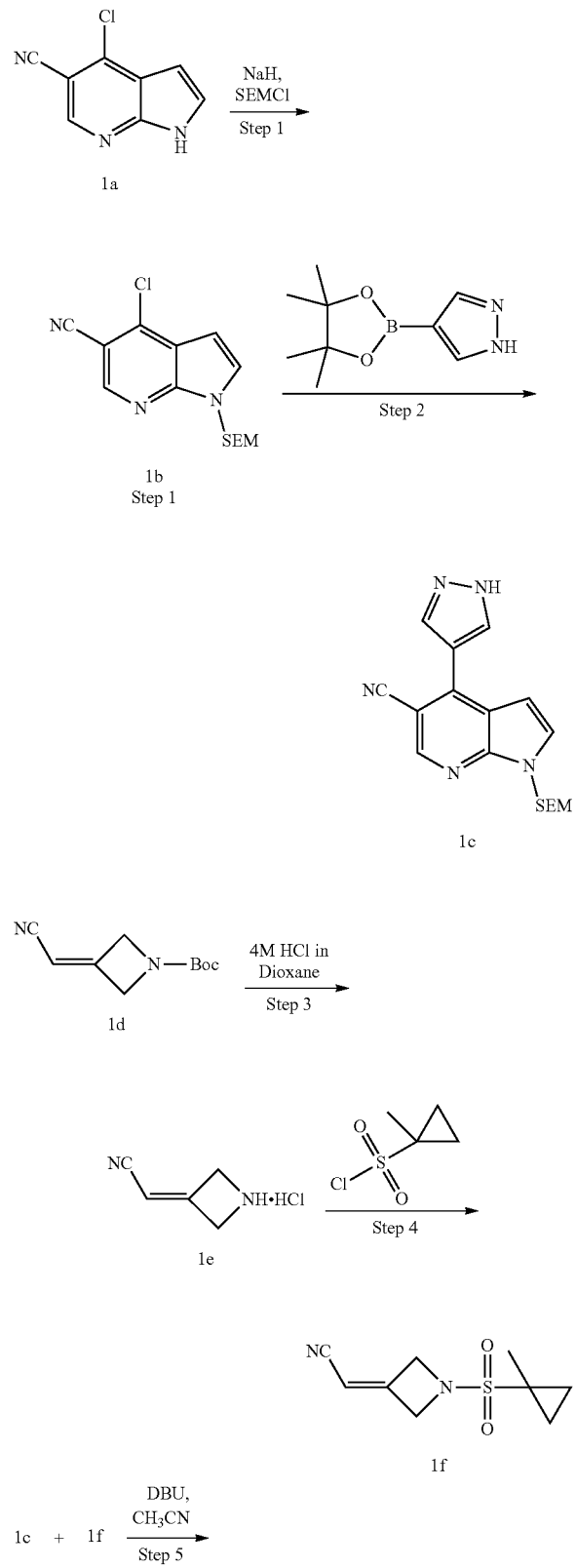

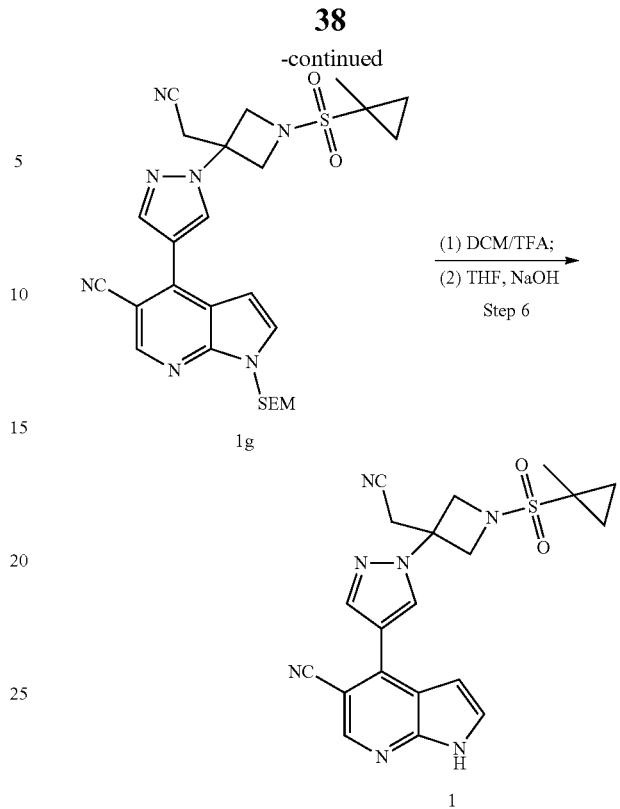

Step 1: 4-chloro-5-cyano-1-((2-(trimethylsilyl)ethoxy)methyl)-1H-pyrrolo[2,3-b]pyridine (1b)

At room temperature, 4-chloro-5-cyano-7-azaindole (1a) (1.92 g, 10.76 mmol) and DMF (22 mL) were added to a 100 mL three-necked flask, and nitrogen atmosphere protection was applied. The mixture was cooled to below 5° C. in an ice-salt bath, and after the reaction solution was stirred until homogeneous, sodium hydride (60 wt %, 560 mg, 13.98 mmol) was added to the flask in portions while keeping the temperature of the system no higher than 10° C. After being stirred for 1 h, the system was slowly added with [2-(trimethylsilyl)ethoxy]methyl chloride (2.33 g, 13.98 mmol) dropwise while keeping the temperature of the system no higher than 5° C. and the stir was continued for 2 h. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford 4-chloro-5-cyano-1-((2-(trimethylsilyl)ethoxy)methyl)-1H-pyrrolo[2,3-b]pyridine (1b) (4.30 g, yield: 86%, white solid). MS (ESI, m/z): 308.1 [M+H]+.

Step 2: 4-(1H-pyrazol-4-yl)-5-cyano-1-((2-(trimethylsilyl)ethoxy)methyl)-1H-pyrrolo[2,3-b]pyridine (1c)

At room temperature, compound 1b (200 mg, 0.65 mmol), 4-pyrazoleboronic acid pinacol ester (189 mg, 0.98 mmol), a potassium carbonate (225 mg, 1.63 mmol) solution (2 mL) and 1,4-dioxane (8 mL) were sequentially added to a 50 mL reaction flask, and nitrogen atmosphere protection was applied. After the reaction solution was stirred until homogeneous, Pd(dppf)Cl$_2$ (50 mg, 0.065 mmol) was added under nitrogen atmosphere protection. The reaction system was heated to 95° C., and refluxed overnight. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford 4-(1H-pyrazol-4-yl)-5-cyano-1-((2-(trimethylsilyl)ethoxy) methyl)-1H-pyrrolo[2,3-b]pyridine (1c) (134 mg, yield: 61%, yellow solid). MS (ESI, m/z): 340.2 [M+H]+.

Step 3: 2-(azetidin-3-ylidene)acetonitrile hydrochloride salt (1e)

Compound 1d (1.0 g, 5.15 mmol) and a 4M solution of HCl in dioxane (10 mL) were added to a 50 mL reaction flask, argon atmosphere protection was applied, and the reaction was stirred in an ice bath for 2.5 h, while white solid gradually precipitated. The reaction was monitored by thin layer chromatography. After the reaction was complete, the reaction solution was filtered with suction, and the filter cake was washed with anhydrous ether and dried, to afford 2-(azetidin-3-ylidene) acetonitrile hydrochloride salt (1e) (600 mg, yield: 90.0%, white solid), which was used directly in the next reaction.

Step 4: 2-(1-((1-methylcyclopropyl)sulfonyl)azetidin-3-ylidene)acetonitrile (1f)

Under cooling with an ice bath, compound 1e (200 mg, 1.54 mmol), dichloromethane (10 mL), triethylamine (1.3 mL, 9.24 mmol) and DMAP (3.8 mg, 0.03 mmol) were sequentially added to a 50 mL reaction flask, and after the reaction was stirred until homogeneous, a solution of 1-methylcyclopropane-1-sulfonyl chloride (357 mg, 2.31 mmol) in dichloromethane (10 mL) was slowly dropwise added to the reaction system. After the addition, the reaction solution was stirred for 1 h, quenched with water, and extracted with dichloromethane. The organic phase was washed with water, a solution of citric acid and saturated brine, dried over anhydrous sodium sulfate, and concentrated under reduced pressure, to afford 2-(1-((1-methylcyclopropyl)sulfonyl)azetidin-3-ylidene) acetonitrile (1f) (272 mg, yield: 83.4%, brown solid). MS (ESI, m/z): 213.1 [M+H]+.

Step 5: 4-(1-(3-(cyanomethyl)-1-((1-methylcyclopropyl)sulfonyl)azetidin-3-yl)-1H-pyrazol-4-yl)-1-((2-(trimethylsilyl)ethoxy)methyl)-1H-pyrrolo[2,3-b]pyridine-5-carbonitrile (1g)

Compound 1f (150 mg, 0.71 mmol), compound 1c (235 mg, 0.70 mmol) and acetonitrile (25 mL) were added to a 50 mL reaction flask, DBU (130 mg, 0.85 mmol) was added after the reaction solution was stirred until homogeneous. The reaction was performed at room temperature for 1 h, and monitored by thin layer chromatography. After the reaction was complete, the reaction solution was quenched with water, concentrated under reduced pressure, and purified by column chromatography on silica gel, to afford 4-(1-(3-(cyanomethyl)-1-((1-methylcyclopropyl)sulfonyl)azetidin-3-yl)-1H-pyrazol-4-yl)-1-((2-(trimethylsilyl)ethoxy) methyl)-1H-pyrrolo[2,3-b]pyridine-5-carbonitrile (1g) (179 mg, yield: 46.5%, white foamy solid). MS (ESI, m/z): 552.2 [M+H]+.

Step 6: 4-(1-(3-(cyanomethyl)-1-((1-methylcyclopropyl)sulfonyl)azetidin-3-yl)-1H-pyrazol-4-yl)-1H-pyrrolo[2,3-b]pyridine-5-carbonitrile (1)

At room temperature, compound 1g (179 mg, 0.33 mmol) and a mixed solution of TFA/DCM (V:V=1:2, 8.5 mL) were added to a 50 mL reaction flask, argon atmosphere protection was applied, and the reaction was stirred at room temperature for 3 h. After LC-MS indicated the reaction was complete, the reaction solution was quenched with water, extracted with dichloromethane, dried over anhydrous sodium sulfate, concentrated under reduced pressure, and purified by column chromatography on silica gel, to afford a hydroxymethyl intermediate (92 mg), which was then placed in a 250 mL reaction flask, and tetrahydrofuran (15 mL) was added to completely dissolve the sample. 1M NaOH was added to adjust the pH to 10-11, and the reaction was stirred at room temperature for 24 h. After the reaction was complete, tetrahydrofuran in the system was distilled off, and off-white solid precipitated, which was filtered with suction. The filter cake was washed with water, and dried under vacuum, to afford 4-(1-(3-(cyanomethyl)-1-((1-methylcyclopropyl)sulfonyl)azetidin-3-yl)-1H-pyrazol-4-yl)-1H-pyrrolo[2,3-b]pyridine-5-carbonitrile (1) (70 mg, yield: 40.1%, off-white solid). $^1$H NMR (400 MHz, DMSO-$d_6$) δ: 8.83 (s, 1H), 8.65 (s, 1H), 8.34 (s, 1H), 7.78 (d, J=3.48 Hz, 1H), 6.89 (d, J=3.44 Hz, 1H), 4.59 (d, J=8.92 Hz, 2H), 4.27 (d, J=8.92 Hz, 2H), 3.73 (s, 2H), 1.49 (s, 3H), 1.22 (t, 2H), 0.93 (t, 2H). MS (ESI, m/z): 422.1 [M+H]+.

Example 2: 4-(1-(3-(cyanomethyl)-1-(methylsulfonyl)azetidin-3-yl)-1H-pyrazol-4-yl)-1H-pyrrolo[2,3-b]pyridine-5-carbonitrile (2)

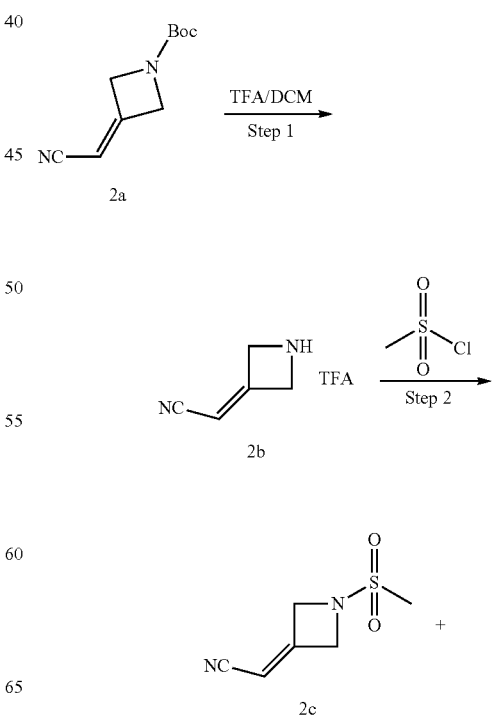

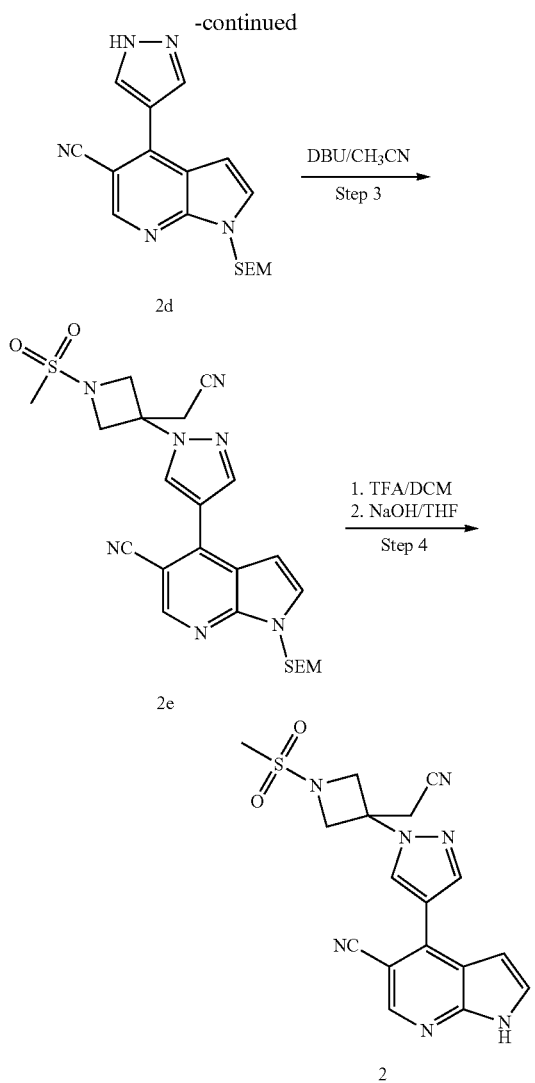

Step 1: 2-(azetidin-3-ylidene)acetonitrile trifluoroacetate salt (2b)

Tert-butyl 3-(cyanomethylene)azetidine-1-carboxylate (2a) (583 mg, 3 mmol) was dissolved in a mixed solution of dichloromethane (18 mL) and trifluoroacetic acid (6 mL), and stirred at room temperature for 30 min. The reaction was rotary evaporated to dryness, to afford a transparent oil, which was used directly in the next reaction.

Step 2: 2-(1-(methylsulfonyl)azetidin-3-ylidene) acetonitrile (2c)

The transparent oil obtained in step 1 was dissolved in dichloromethane (10 mL), the reaction system was placed in an ice bath, and triethylamine was slowly added until the pH reached 9. DMAP (8 mg, 0.06 mmol) was then added, and the reaction solution was stirred in an ice bath for 5 min. Methanesulfonyl chloride (0.3 mL, 3.9 mmol) was dissolved in dichloromethane (2 mL), and then slowly dropwise added to the reaction system. The reaction solution was performed in an ice bath for 30 min, extracted with ethyl acetate, and the organic phase was washed with an aqueous solution of citric acid, dried over anhydrous sodium sulfate, and rotary evaporated to dryness, to afford a solid, which was triturated in petroleum ether, to afford 2-(1-(methylsulfonyl)azetidin-3-ylidene)acetonitrile (2c) (423 mg, white solid, yield: 82%), MS (ESI, m/z): 173 [M+H]$^+$.

Step 3: 4-(1-(3-(cyanomethyl)-1-(methylsulfonyl) azetidin-3-yl)-1H-pyrazol-4-yl)-1-((2-(trimethylsilyl) ethoxy)methyl)-1H-pyrrolo[2,3-b]pyridine-5-carbonitrile (2e)

4-(1H-pyrazol-4-yl)-1-((2-(trimethylsilyl)ethoxy) methyl)-1H-pyrrolo[2,3-b]pyridine-5-carbonitrile (2d) (200 mg, 0.58 mmol) and 2-(1-(methylsulfonyl)azetidin-3-ylidene)acetonitrile (2c) (150 mg, 0.87 mmol) were dissolved in acetonitrile (10 mL), the reaction system was added with DBU (0.16 mL), and then stirred at room temperature overnight. After the reaction was complete, the reaction was rotary evaporated to dryness, and purified by column chromatography on silica gel, to afford 4-(1-(3-(cyanomethyl)-1-(methylsulfonyl)azetidin-3-yl)-1H-pyrazol-4-yl)-1-((2-(trimethylsilyl)ethoxy)methyl)-1H-pyrrolo [2,3-b]pyridine-5-carbonitrile (2e) (270 mg, white solid, yield: 89.5%). MS (ESI, m/z): 512 [M+H]$^+$.

Step 4: 4-(1-(3-(cyanomethyl)-1-(methylsulfonyl) azetidin-3-yl)-1H-pyrazol-4-yl)-1H-pyrrolo[2,3-b] pyridine-5-carbonitrile (2)

4-(1-(3-(cyanomethyl)-1-(methylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (2e) (270 mg, 0.52 mmol) was dissolved in dichloromethane (7 mL), the reaction system was placed in an ice bath, and added with trifluoroacetic acid (7 mL). The temperature was kept below 10° C. during the whole reaction process. After TLC indicated the reaction was complete, the reaction solution was rotary evaporated to dryness, tetrahydrofuran (10 mL) was added, and the pH of the system was adjusted to 10 with 1N NaOH. After the reaction was complete, the reaction solution was rotary evaporated to dryness, and purified by TLC, to afford 4-(1-(3-(cyanomethyl)-1-(methylsulfonyl)azetidin-3-yl)-1H-pyrazol-4-yl)-1H-pyrrolo[2,3-b]pyridine-5-carbonitrile (2) (84 mg, white solid, yield: 43%). $^1$H NMR (400 MHz, DMSO-d$_6$) δ: 12.42 (s, 1H), 8.82 (s, 1H), 8.63 (s, 1H), 8.32 (s, 1H), 7.76 (d, 1H, J=3.6 Hz), 6.89 (d, 1H, J=3.6 Hz), 4.61 (d, 2H, J=9.2 Hz), 4.29 (d, 2H, J=9.2 Hz), 3.70 (s, 2H), 3.14 (s, 3H). MS (ESI, m/z): 382 [M+H]$^+$.

Example 3: 2-(3-(3-(7H-pyrrolo[2,3-d]pyrimidin-4-yl)-1H-pyrazol-1-yl)-1-(ethylsulfonyl)azetidin-3-yl) acetonitrile (3)

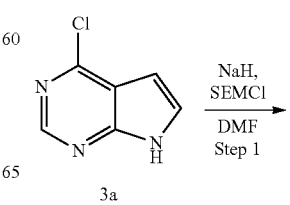

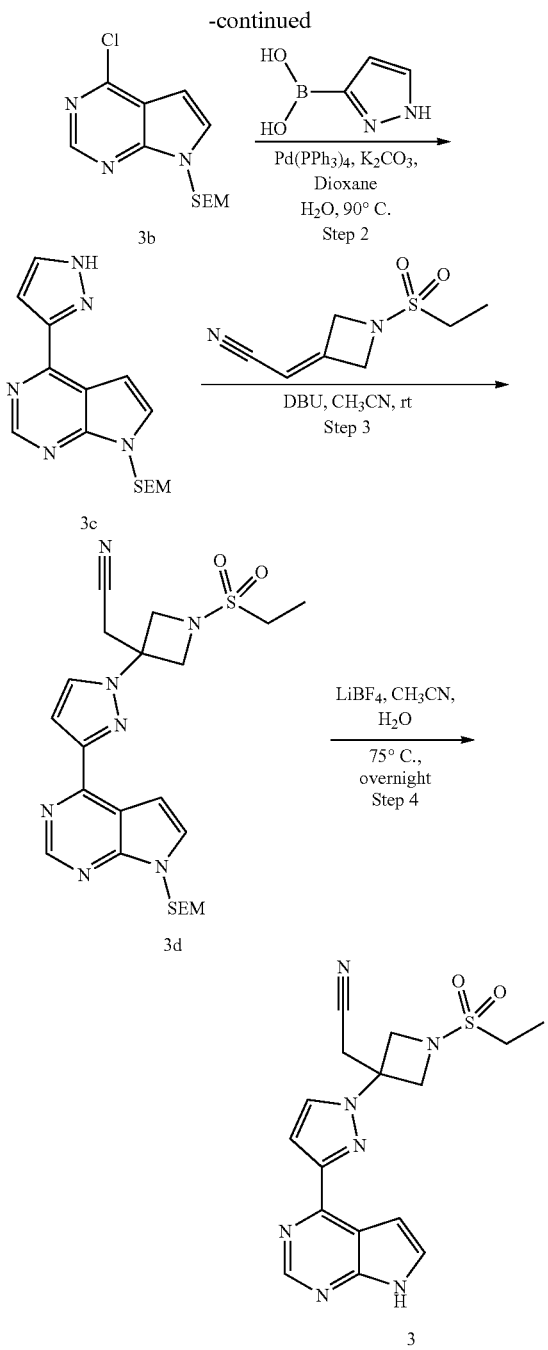

Step 1: 4-chloro-7-((2-(trimethylsilyl)ethoxy)methyl)-7H-pyrrolo[2,3-d]pyrimidine (3b)

Under cooling with an ice-salt bath, sodium hydride (340 mg, 60%) was added in two portions to a solution of 4-chloropyrrolopyrimidine (3a) (1.0 g, 6.5 mmol) in DMF (15 mL) while keeping the temperature of the reactants no higher than 10° C., and the reaction was stirred under nitrogen atmosphere protection for 1 h. SEMCl (1.4 g, 8.5 mmol) was slowly added via a syringe while keeping the temperature no higher than 10° C. The reaction was warmed to room temperature, and stirred overnight. The reaction was quenched with water, extracted with EA, dried over anhydrous sodium sulfate, and the organic phase was concentrated, and purified by preparative flash chromatography (PE:EA=19:1), to afford 4-chloro-7-((2-(trimethylsilyl)ethoxy)methyl)-7H-pyrrolo[2,3-d]pyrimidine (3b) (1.834 g, oil product), yield: 97%. MS (ESI, m/z): 284 [M+H]$^+$.

Step 2: 4-(1H-pyrazol-3-yl)-7-((2-(trimethylsilyl)ethoxy)methyl)-7H-pyrrolo[2,3-d]pyrimidine (3c)

At room temperature, under protection of nitrogen, 4-chloro-7-((2-(trimethylsilyl)ethoxy)methyl)-7H-pyrrolo[2,3-d]pyrimidine (3b) (500 mg) and 1H-pyrazol-3-boronic acid (135 mg) were dissolved in dioxane (10 mL), water (5 mL) and potassium carbonate (414 mg) were then added, and the reaction was stirred at room temperature for 10 min. Under protection of nitrogen, Pd(PPh$_3$)$_4$ (116 mg) was added. The reaction system was placed in an oil bath at 95° C., and stirred overnight. TLC indicated starting materials substantially disappeared. The reaction was quenched with water, extracted with EA, and the organic phase was dried over anhydrous sodium sulfate, and purified by preparative flash chromatography (PE:EA=1:1), to afford 4-(1H-pyrazol-3-yl)-7-((2-(trimethylsilyl)ethoxy)methyl)-7H-pyrrolo[2,3-d]pyrimidine (3c) (50 mg, solid), yield: 9%. MS (ESI, m/z): 316 [M+H]$^+$.

Step 3: 2-(1-(ethylsulfonyl)-3-(3-(7-((2-(trimethylsilyl)ethoxy)methyl)-7H-pyrrolo[2,3-d]pyrimidin-4-yl)-1H-pyrazol-1-yl)azetidin-3-yl)acetonitrile (3d)

At room temperature, acetonitrile (2 mL) was added to a mixture of 4-(1H-pyrazol-3-yl)-7-((2-(trimethylsilyl)ethoxy)methyl)-7H-pyrrolo[2,3-d]pyrimidin (3c) (45 mg) and 2-[1-(ethylsulfonyl)-3-azetidinylidene]acetonitrile (35 mg) to obtain a reaction solution, DBU (25 mg) was then added, and the reaction was stirred at room temperature overnight. The reaction was concentrated, and purified on a preparative silica gel plate, to afford 2-(1-(ethylsulfonyl)-3-(3-(7-((2-(trimethylsilyl)ethoxy)methyl)-7H-pyrrolo[2,3-d]pyrimidin-4-yl)-1H-pyrazol-1-yl)azetidin-3-yl)acetonitrile (3d) (75 mg, brown solid), yield: 105% (containing some solvents). MS (ESI, m/z): 502 [M+H]$^+$.

Step 4: 2-(3-(3-(7H-pyrrolo[2,3-d]pyrimidin-4-yl)-1H-pyrazol-1-yl)-1-(ethylsulfonyl)azetidin-3-yl)acetonitrile (3)

At room temperature, 2-(1-(ethylsulfonyl)-3-(3-(7-((2-(trimethylsilyl)ethoxy)methyl)-7H-pyrrolo[2,3-d]pyrimidin-4-yl)-1H-pyrazol-1-yl)azetidin-3-yl)acetonitrile (3d) (75 mg, 0.15 mmol) was dissolved in acetonitrile (2.5 mL), water (0.5 mL) and lithium tetrafluoroborate (140 mg) were added, and then the reaction system was placed in an oil bath at 80° C. and stirred overnight. The reaction was quenched with water, extracted with EA, and dried over anhydrous sodium sulfate. The organic phase was concentrated, and purified on a preparative silica gel plate (EA:MeOH=15:1), to afford 2-(3-(3-(7H-pyrrolo[2,3-d]pyrimidin-4-yl)-1H-pyrazol-1-yl)-1-(ethylsulfonyl)azetidin-3-yl)acetonitrile (3) (40 mg, white solid), yield: 73%. MS (ESI, m/z): 372 [M+H]$^+$. $^1$H NMR (DMSO-d6, 400 MHz) δ 12.12 (s, 1H), 8.76 (s, 1H), 8.27 (d, J=2.8 Hz, 1H), 7.58-7.60 (m, 1H), 7.17 (d, J=2.4 Hz, 2H), 4.57 (d, J=8.8 Hz, 2H), 4.26 (d, J=9.2 Hz, 2H), 3.72 (s, 2H), 3.21-3.26 (m, 2H), 1.21-1.25 (m, 3H).

Example 4: 2-(3-(4-(3H-imidazo[4,5-b]pyridin-7-yl)-1H-pyrazol-1-yl)-1-(ethylsulfonyl)azetidin-3-yl)acetonitrile (4)

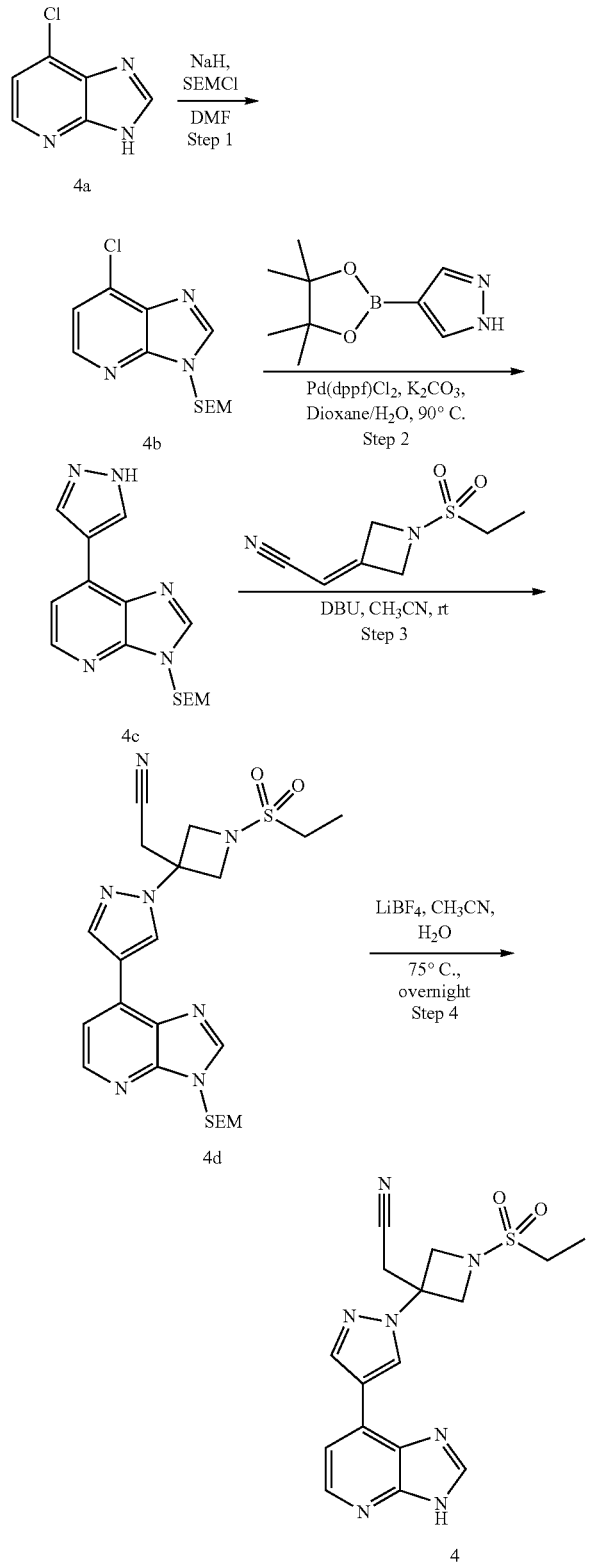

Step 1: 7-chloro-3-((2-(trimethylsilyl)ethoxy)methyl)-3H-imidazo[4,5-b]pyridine (4b)

Under cooling with an ice-salt bath, sodium hydride (340 mg, 60%) was added in two portions to a solution of 7-chloro-3H-imidazo[4,5-b]pyridine (4a) (1.0 g, 6.5 mmol) in DMF (15 mL) while keeping the temperature of the reaction no higher than 10° C., and the reaction was stirred under nitrogen atmosphere protection for 1 h. SEMCl (1.4 g, 8.5 mmol) was slowly added via a syringe while keeping the temperature no higher than 10° C. The reaction was warmed to room temperature, and stirred overnight. The reaction solution was quenched with water, extracted with EA, and dried over anhydrous sodium sulfate. The organic phase was concentrated, and purified by preparative flash chromatography (PE:EA=4:1), to afford 7-chloro-3-((2-(trimethylsilyl)ethoxy)methyl)-3H-imidazo[4,5-b]pyridine (4b) (1.01 g, oil product), yield: 55%. MS (ESI, m/z): 284 [M+H]$^+$.

Step 2: 7-(1H-pyrazol-4-yl)-3-((2-(trimethylsilyl)ethoxy)methyl)-3H-imidazo[4,5-b]pyridine (4c)

At room temperature under protection of nitrogen, 7-chloro-3-((2-(trimethylsilyl)ethoxy)methyl)-3H-imidazo[4,5-b]pyridine (4b) (400 mg) and 4-pyrazoleboronic acid pinacol ester (383 mg) were dissolved in dioxane (14 mL), water (4 mL) and potassium carbonate (390 mg) were then added, and the reaction was stirred at room temperature for 10 min. Pd(dppf)Cl$_2$ (103 mg) was added under protection of nitrogen. The reaction system was placed in an oil bath at 95° C., and stirred overnight. After TLC detected substantial disappearance of a substrate, the reaction was quenched with water, extracted with EA, and the organic phase was dried over anhydrous sodium sulfate. The residue was purified by preparative flash chromatography (PE:EA=3:7), to afford 7-(1H-pyrazol-4-yl)-3-((2-(trimethylsilyl)ethoxy)methyl)-3H-imidazo[4,5-b]pyridine (4c) (175 mg, brown solid), yield: 39%. MS (ESI, m/z): 316 [M+H]$^+$.

Step 3: 2-(1-(ethylsulfonyl)-3-(4-(3-((2-(trimethylsilyl)ethoxy)methyl)-3H-imidazo[4,5-b]pyridin-7-yl)-1H-pyrazol-1-yl)azetidin-3-yl)acetonitrile (4d)

At room temperature, acetonitrile (6 mL) was added to a mixture of 7-(1H-pyrazol-4-yl)-3-((2-(trimethylsilyl)ethoxy)methyl)-3H-imidazo[4,5-b]pyridine (4c) (175 mg) and 2-[1-(ethylsulfonyl)-3-azetidinylidene]acetonitrile (103 mg) to obtain a reaction solution. DBU (100 mg) was then added, and the reaction was stirred at room temperature overnight. The reaction was concentrated, and purified on a preparative silica gel plate (DCM:MeOH=20:1), to afford 2-(1-(ethylsulfonyl)-3-(4-(3-((2-(trimethylsilyl)ethoxy)methyl)-3H-imidazo[4,5-b]pyridin-7-yl)-1H-pyrazol-1-yl)azetidin-3-yl)acetonitrile (4d) (214 mg, oil), yield: 77%. MS (ESI, m/z): 502 [M+H]$^+$.

Step 4: 2-(3-(4-(3H-imidazo[4,5-b]pyridin-7-yl)-1H-pyrazol-1-yl)-1-(ethylsulfonyl)azetidin-3-yl)acetonitrile (4)

At room temperature, 2-(1-(ethylsulfonyl)-3-(4-(3-((2-(trimethylsilyl)ethoxy)methyl)-3H-imidazo[4,5-b]pyridin-7-yl)-1H-pyrazol-1-yl)azetidin-3-yl)acetonitrile (4d) (210 mg, 0.40 mmol) was dissolved in acetonitrile (8 mL), water (1 mL) and lithium tetrafluoroborate (373 mg) were added, and then the reaction system was placed in an oil bath at 80° C. and stirred overnight. The reaction was quenched with water, extracted with EA, and dried over anhydrous sodium sulfate. The organic phase was concentrated, and purified on a preparative silica gel plate, to afford 2-(3-(4-(3H-imidazo[4,5-b]pyridin-7-yl)-1H-pyrazol-1-yl)-1-(ethylsulfonyl)azetidin-3-yl)acetonitrile (4) (110 mg, white solid), yield: 71%. MS (ESI, m/z): 372 [M+H]$^+$. $^1$H NMR (DMSO-d6, 400 MHz) δ 13.15 (s, 1H), 9.06 (s, 1H), 8.64 (s, 1H), 8.47 (s, 1H), 8.31 (d, J=4.4 Hz, 1H), 7.57 (d, J=5.2 Hz, 1H), 4.52 (d, J=9.2 Hz, 2H), 4.26 (d, J=9.2 Hz, 2H), 3.68 (s, 2H), 3.22-3.28 (m, 2H), 1.23-1.27 (m, 3H).

Example 5: 4-(1-(3-(cyanomethyl)-1-(ethylsulfonyl)azetidin-3-yl)-1H-pyrazol-4-yl)-1H-pyrrolo[2,3-b]pyridine-5-carbonitrile (5)

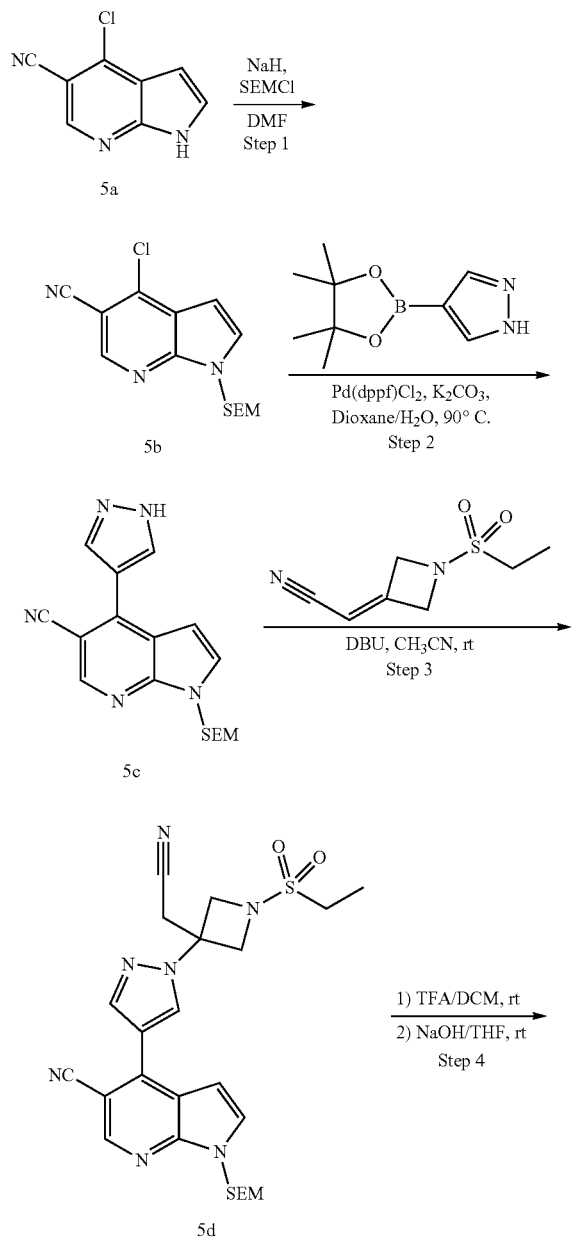

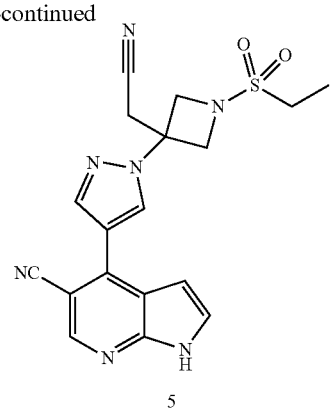

Step 1: 4-chloro-5-cyano-1-((2-(trimethylsilyl)ethoxy)methyl)-1H-pyrrolo[2,3-b]pyridine (5b)

At room temperature, 4-chloro-5-cyano-7-azaindole (5a) (1.92 g, 10.76 mmol) and DMF (22 mL) were added to a 100 mL three-necked flask, and nitrogen atmosphere protection was applied. The mixture was cooled to below 5° C. in an ice-salt bath, and after the reaction solution was stirred until homogeneous, sodium hydride (60 wt %, 560 mg, 13.98 mmol) was added to the flask in portions while keeping the temperature of the reaction no higher than 10° C. After being stirred for 1 h, the system was slowly added with 2-(trimethylsilyl)ethoxymethyl chloride (2.33 g, 13.98 mmol) dropwise while keeping the temperature no higher than 5° C. and the stir was continued for 2 h. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford 4-chloro-5-cyano-1-((2-(trimethylsilyl)ethoxy)methyl)-1H-pyrrolo[2,3-b]pyridine (5b) (4.30 g, yield: 86%, white solid). MS (ESI, m/z): 308 [M+H]$^+$.

Step 2: 4-(1H-pyrazol-4-yl)-5-cyano-1-((2-(trimethylsilyl)ethoxy)methyl)-1H-pyrrolo[2,3-b]pyridine (5c)

At room temperature, 4-chloro-5-cyano-1-((2-(trimethylsilyl)ethoxy)methyl)-1H-pyrrolo[2,3-b]pyridine (5b) (200 mg, 0.65 mmol), 4-pyrazoleboronic acid pinacol ester (189 mg, 0.98 mmol), a potassium carbonate (225 mg, 1.63 mmol) solution (2 mL) and dioxane (8 mL) were sequentially added to a 50 mL reaction flask, and nitrogen atmosphere protection was applied. After the reaction solution was stirred until homogeneous, Pd(dppf)Cl$_2$ (50 mg, 0.065 mmol) was added under nitrogen atmosphere protection. The reaction system was heated to 95° C., and refluxed overnight. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford 4-(1H-pyrazol-4-yl)-5-cyano-1-((2-(trimethylsilyl)ethoxy)methyl)-1H-pyrrolo[2,3-b]pyridine (5c) (134 mg, yield: 61%, yellow solid). MS (ESI, m/z): 340 [M+H]$^+$.

Step 3: 4-(1-(3-(cyanomethyl)-1-(ethylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (5d)

4-(1H-pyrazol-4-yl)-5-cyano-1-((2-(trimethylsilyl)ethoxy)methyl)-1H-pyrrolo[2,3-b]pyridine (5c) (259 mg, 0.76 mmol), 2-[1-(ethylsulfonyl)-3-azetidinylidene]acetonitrile (155 mg, 0.84 mmol) and acetonitrile (10 mL) were sequentially added to a 50 mL reaction flask, and DBU (119 mg, 0.84 mmol) was then added. The reaction was performed at room temperature for 2 h, and monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford 4-(1-(3-(cyanomethyl)-1-(ethylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (5d) (305 mg, yield: 76%, white solid). MS (ESI, m/z): 526 [M+H]$^+$.

Step 4: 4-(1-(3-(cyanomethyl)-1-(ethylsulfonyl)azetidin-3-yl)-1H-pyrazol-4-yl)-1H-pyrrolo[2,3-b]pyridine-5-carbonitrile (5)

At room temperature, a mixed solution of 4-(1-(3-(cyanomethyl)-1-(ethylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (5d) (260 mg, 0.49 mmol) and TFA/DCM (1:1) (8 mL) were added to a 50 mL reaction flask, and the reaction was performed under argon atmosphere protection for 2.5 h. After thin lay chromatography indicated the reaction was complete, the reaction was concentrated under reduced pressure to obtain a yellow oil, which was then directly dissolved in tetrahydrofuran (10 mL), and stirred until homogenous. A 1M solution of sodium hydroxide was added to adjust the pH of the reaction to 10, and the reaction was performed for 0.5 h. After thin lay chromatography indicated the reaction was complete, the reaction was extracted with ethyl acetate, dried over anhydrous sodium sulfate, concentrated under reduced pressure, and purified by column chromatography on silica gel, to afford the target product, 4-(1-(3-(cyanomethyl)-1-(ethylsulfonyl)azetidin-3-yl)-1H-pyrazol-4-yl)-1H-pyrrolo[2,3-b]pyridine-5-carbonitrile (5) (65 mg, yield: 35%, white solid). $^1$H NMR (400 MHz, DMSO-d$_6$) δ 12.41 (s, 1H), 8.82 (d, J=0.8 Hz, 1H), 8.63 (s, 1H), 8.32 (d, J=0.8 Hz, 1H), 7.76 (dd, J=3.6, 2.2 Hz, 1H), 6.88 (dd, J=3.7, 1.5 Hz, 1H), 4.59 (d, J=9.1 Hz, 2H), 4.27 (d, J=9.1 Hz, 2H), 3.70 (s, 2H), 3.25 (q, J=7.3 Hz, 2H), 1.25 (t, J=7.3 Hz, 3H) ppm. MS (ESI, m/z): 396 [M+H]$^+$.

Example 6: 2-(3-(4-(9H-purin-6-yl)-1H-pyrazol-1-yl)-1-(ethylsulfonyl)azetidin-3-yl)acetonitrile (6)

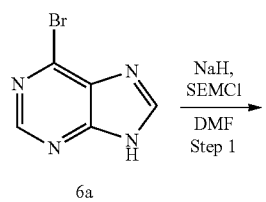

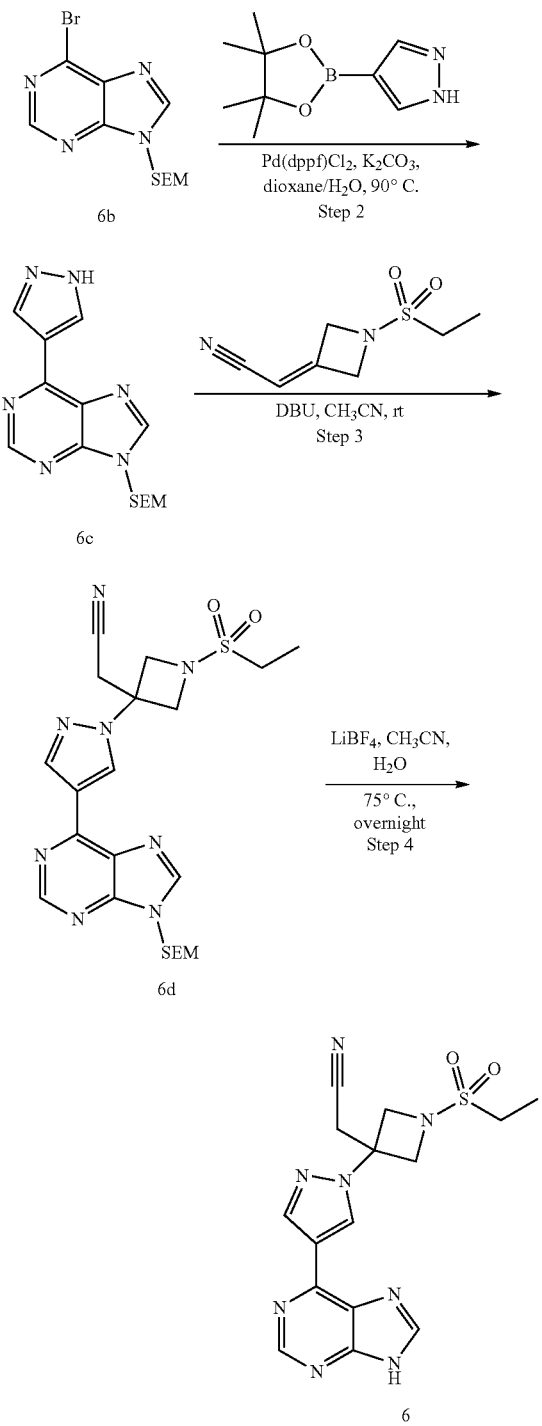

Step 1: 6-bromo-9-((2-(trimethylsilyl)ethoxy)methyl)-9H-purine (6b)

Under cooling with an ice-salt bath, sodium hydride (522 mg, 60%) was added in three portions to a solution of 6-bromopurine (6a) (2.0 g, 10.0 mmol) in DMF (15 mL) while keeping the temperature of the reaction no higher than 10° C., and the reaction was stirred under nitrogen atmosphere protection for 1 h. SEMCl (2.2 g, 13.0 mmol) was slowly added while keeping the temperature no higher than 10° C. The reaction was warmed to room temperature, and stirred overnight. The reaction was quenched with water, extracted with EA, and dried over anhydrous sodium sulfate. The organic phase was concentrated, and purified by preparative flash chromatography (PE:EA=17:1), to afford 6-bromo-9-((2-(trimethylsilyl)ethoxy)methyl)-9H-purine (6b) (1.9 g, solid), yield: 58%. MS m/z: 329 [M+1]$^+$.

Step 2: 6-(1H-pyrazol-4-yl)-9-((2-(trimethylsilyl)ethoxy)methyl)-9H-purine (6c)

At room temperature, 6-bromo-9-((2-(trimethylsilyl)ethoxy)methyl)-9H-purine (6b) (990 mg) and 4-pyrazoleboronic acid pinacol ester (780 mg) were dissolved in dioxane (14 mL), water (4 mL) and potassium carbonate (1.1 g) were then added, and the reaction was stirred at room temperature for 10 min under protection of nitrogen. Pd(dppf)Cl$_2$ (222 mg) was added under protection of nitrogen. The reaction system was placed in an oil bath at 95° C., and stirred overnight. After TLC indicated disappearance of a substrate, the reaction was quenched with water, extracted with EA, and the organic phase was dried over anhydrous sodium sulfate. The residue was purified by preparative flash chromatography (PE:EA=2:3), to afford 6-(1H-pyrazol-4-yl)-9-((2-(trimethylsilyl)ethoxy)methyl)-9H-purine (6c) (400 mg, brown solid), yield: 42%. MS m/z: 317 [M+1]$^+$.

Step 3: 2-(1-(ethylsulfonyl)-3-(4-(9-((2-(trimethylsilyl)ethoxy)methyl)-9H-purin-6-yl)-1H-pyrazol-1-yl)azetidin-3-yl)acetonitrile (6d)

At room temperature, acetonitrile (10 mL) was added to a mixture of 6-(1H-pyrazol-4-yl)-9-((2-(trimethylsilyl)ethoxy)methyl)-9H-purine (6c) (200 mg) and 2-[1-(ethylsulfonyl)-3-azetidinylidene]acetonitrile (118 mg) to obtain a reaction solution. DBU (120 mg) was then added, and the reaction was stirred at room temperature overnight. The reaction was concentrated, and purified on a preparative silica gel plate (DCM:MeOH=10:1), to afford 2-(1-(ethylsulfonyl)-3-(4-(9-((2-(trimethylsilyl)ethoxy)methyl)-9H-purin-6-yl)-1H-pyrazol-1-yl)azetidin-3-yl)acetonitrile (6d) (289 mg, yellow oil), yield: 91%. MS m/z: 503 [M+1]$^+$.

Step 4: 2-(3-(4-(9H-purin-6-yl)-1H-pyrazol-1-yl)-1-(ethylsulfonyl)azetidin-3-yl)acetonitrile (6)

At room temperature, 2-(1-(ethylsulfonyl)-3-(4-(9-((2-(trimethylsilyl)ethoxy)methyl)-9H-purin-6-yl)-1H-pyrazol-1-yl)azetidin-3-yl)acetonitrile (6d) (289 mg, 0.58 mmol) was dissolved in acetonitrile (8 mL), water (1 mL) and lithium tetrafluoroborate (540 mg) were added, and then the reaction system was placed in an oil bath at 80° C. and stirred overnight. The reaction was quenched with water, extracted with EA, and dried over anhydrous sodium sulfate. The organic phase was concentrated, and purified on a preparative silica gel plate, to afford 2-(3-(4-(9H-purin-6-yl)-1H-pyrazol-1-yl)-1-(ethylsulfonyl)azetidin-3-yl)acetonitrile (6) (175 mg, white solid), yield: 81%. MS m/z: 373 [M+1]$^+$. $^1$H NMR (400 MHz, DMSO-d$_6$) δ 13.54 (s, 1H), 9.08 (s, 1H), 8.84 (s, 1H), 8.65 (s, 1H), 8.62 (s, 1H), 4.56 (d, J=9.1 Hz, 2H), 4.26 (d, J=9.0 Hz, 2H), 3.71 (s, 2H), 3.25 (q, J=7.3 Hz, 2H), 1.25 (t, J=7.3 Hz, 3H).

Example 7: 4-(1-(3-(cyanomethyl)-1-(ethylsulfonyl)azetidin-3-yl)-1H-pyrazol-4-yl)-1H-pyrrolo[2,3-b]pyridine-5-carboxamide (7)

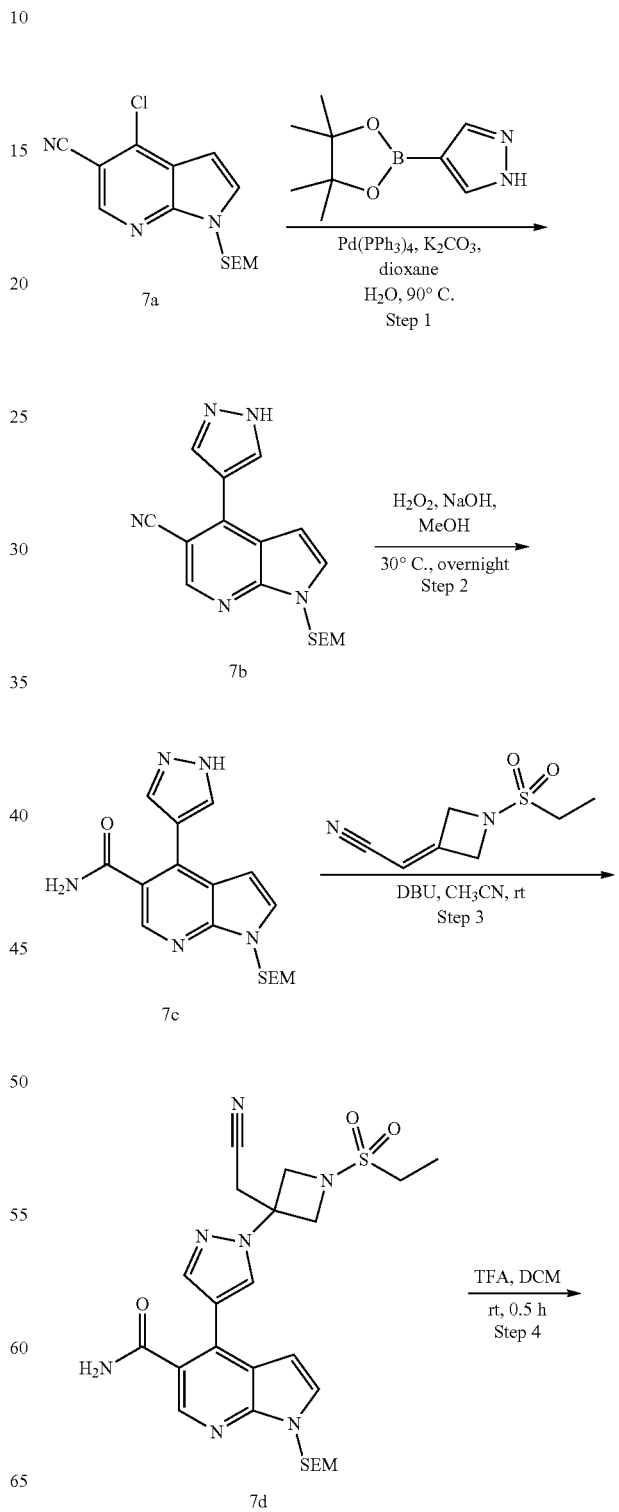

-continued

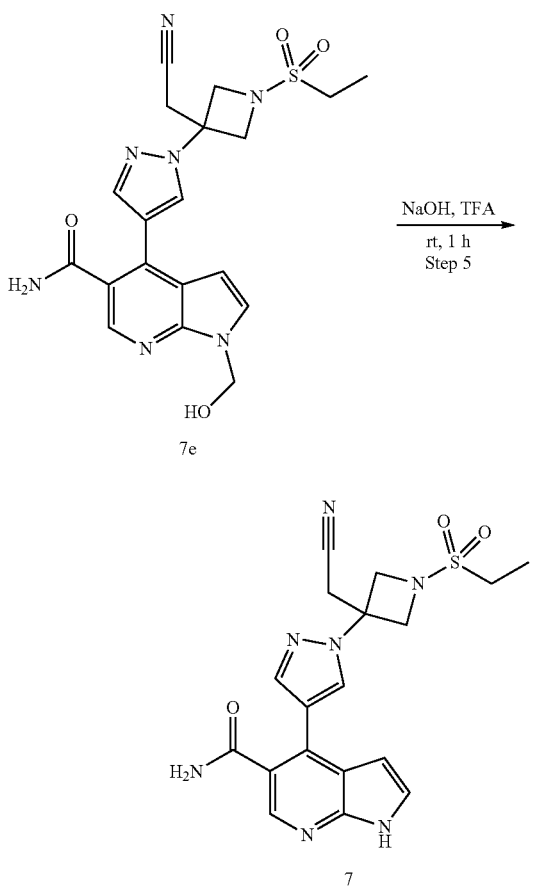

Step 1: 4-(1H-pyrazol-4-yl)-1-((2-(trimethylsilyl)ethoxy)methyl)-1H-pyrrolo[2,3-b]pyridine-5-carbonitrile (7b)

At room temperature under protection of nitrogen, Pd(PPh$_3$)$_4$ (100 mg, 0.176 mmol) was added to a solution of 4-chloro-1-((2-(trimethylsilyl)ethoxy)methyl)-1H-pyrrolo[2,3-b]pyridine-5-carbonitrile (7a) (500 mg, 1.76 mmol), 4-(4,4,5,5-tetramethyl-1,3,2-dioxaborolan-2-yl)-1H-pyrazole (410 mg, 2.1 mmol), and K$_2$CO$_3$ (490 mg, 4.4 mmol) in dioxane:H$_2$O=500 mL:500 mL, argon atmosphere protection was applied, and the reaction was warmed to 100° C., and performed overnight. TLC (PE:EA=1:1) indicated the reaction was complete. The reaction was added with water (500 mL), extracted with ethyl acetate (100 mL*3), and the ethyl acetate layer was combined, washed with saturated brine, dried over anhydrous sodium sulfate, concentrated, and purified by column chromatography, to afford 4-(1H-pyrazol-4-yl)-1-((2-(trimethylsilyl)ethoxy)methyl)-1H-pyrrolo[2,3-b]pyridine-5-carbonitrile (7b) (500 mg, yield: 83%) as a white solid. MS (ESI, m/z): 340 [M+H]$^+$.

Step 2: 4-(1H-pyrazol-4-yl)-1-((2-(trimethylsilyl)ethoxy)methyl)-1H-pyrrolo[2,3-b]pyridine-5-carboxamide (7c)

At room temperature, H$_2$O$_2$ (30%, 1 mL) and an aqueous solution of sodium hydroxide (1M, 1 mL) were sequentially added to a solution of 4-(1H-pyrazol-4-yl)-1-((2-(trimethyl-silyl)ethoxy)methyl)-1H-pyrrolo[2,3-b]pyridine-5-carbonitrile (7b) (200 mg, 0.58 mmol) in methanol (2 mL), and then the reaction was warmed, and performed for 16 h. TLC (PE:EA=1:3) indicated the reaction was complete. The reaction was added with water (500 mL), extracted with ethyl acetate (100 mL*3), and the ethyl acetate layer was combined, washed with saturated brine, dried over anhydrous sodium sulfate, and concentrated, to afford 4-(1H-pyrazol-4-yl)-1-((2-(trimethylsilyl)ethoxy)methyl)-1H-pyrrolo[2,3-b]pyridine-5-carboxamide (7c) (130 mg, yield: 63%) as a white solid. MS (ESI, m/z): 358 [M+H]$^+$.

Step 3: 4-(1-(3-(cyanomethyl)-1-(ethylsulfonyl)azetidin-3-yl)-1H-pyrazol-4-yl)-1-((2-(trimethylsilyl)ethoxy)methyl)-1H-pyrrolo[2,3-b]pyridine-5-carboxamide (7d)

At room temperature, 2-[1-(ethylsulfonyl)-3-azetidinylidene]acetonitrile (71.8 mg, 0.3 mmoL) and DBU (60 mg, 0.39 mmol) were sequentially added to a solution of 4-(1H-pyrazol-4-yl)-1-((2-(trimethylsilyl)ethoxy)methyl)-1H-pyrrolo[2,3-b]pyridine-5-carboxamide (7c) (130 mg, 0.36 mmol) in acetonitrile (3 mL), and the reaction was performed at room temperature for 2 h. TLC indicated the reaction was complete, the reaction was added with water (10 mL), extracted with ethyl acetate (10 mL*3), and the ethyl acetate layer was combined, washed with saturated brine, dried over anhydrous sodium sulfate, and concentrated to afford 4-(1-(3-(cyanomethyl)-1-(ethylsulfonyl)azetidin-3-yl)-1H-pyrazol-4-yl)-1-((2-(trimethylsilyl)ethoxy)methyl)-1H-pyrrolo[2,3-b]pyridine-5-carboxamide (7d) (130 mg, yield: 78%) as a colorless oil. MS (ESI, m/z): 544 [M+H]$^+$.

Step 4: 4-(1-(3-(cyanomethyl)-1-(ethylsulfonyl)azetidin-3-yl)-1H-pyrazol-4-yl)-1-(hydroxymethyl)-1H-pyrrolo[2,3-b]pyridine-5-carboxamide (7e)

At room temperature, TFA (1 mL) was added to a solution of 4-(1-(3-(cyanomethyl)-1-(ethylsulfonyl)azetidin-3-yl)-1H-pyrazol-4-yl)-1-((2-(trimethylsilyl)ethoxy)methyl)-1H-pyrrolo[2,3-b]pyridine-5-carboxamide (7d) (130 mg, 0.23 mmol) in DCM (1 mL), and the reaction was performed at room temperature for 0.5 h. TLC indicated the starting material substantially disappeared. The reaction was directly dried, concentrated, and purified on a preparative silica gel plate, to afford 4-(1-(3-(cyanomethyl)-1-(ethylsulfonyl)azetidin-3-yl)-1H-pyrazol-4-yl)-1-(hydroxymethyl)-1H-pyrrolo[2,3-b]pyridine-5-carboxamide (7e) (60 mg, containing minor de-hydroxymethyl product) as a colorless oil liquid, which was used directly in the next step. MS (ESI, m/z): 444 [M+H]$^+$.

Step 5: 4-(1-(3-(cyanomethyl)-1-(ethylsulfonyl)azetidin-3-yl)-1H-pyrazol-4-yl)-1H-pyrrolo[2,3-b]pyridine-5-carboxamide (7)

At room temperature, an aqueous solution of sodium hydroxide (1M, 1.3 mL) was added to a solution of 4-(1-(3-(cyanomethyl)-1-(ethylsulfonyl)azetidin-3-yl)-1H-pyrazol-4-yl)-1-(hydroxymethyl)-1H-pyrrolo[2,3-b]pyridine-5-carboxamide (7e) (60 mg, 0.135 mmol) in THF (2 mL), and then the reaction was performed at room temperature for 1 h. TLC indicated the starting material substantially disappeared. The reaction was added with water (10 mL), extracted with EA (10 mL*3), and the EA layer was combined, washed with saturated brine, dried over anhydrous sodium sulfate, and concentrated, to afford 4-(1-(3-(cyanomethyl)-1-(ethylsulfonyl)azetidin-3-yl)-1H-pyrazol-4-yl)-1H-pyrrolo[2,3-b]pyridine-5-carboxamide (7) (20 mg, yield: 34%) as a white solid. $^1$H NMR (400 MHz, Chloroform-d) δ 9.39 (s, 1H), 8.00 (d, J=1.5 Hz, 1H), 7.36 (d, J=7.5 Hz, 1H), 7.22 (d, J=1.5 Hz, 1H), 6.68 (s, 2H), 6.50 (d, J=7.5 Hz, 1H), 4.02 (d, J=12.3 Hz, 2H), 3.79 (d, J=12.3 Hz, 2H), 3.45 (q, J=8.0 Hz, 2H), 2.77 (s, 2H), 1.39 (t, J=8.0 Hz, 3H). MS (ESI, m/z): 414 [M+H]$^+$.

Example 8: 2-(3-(4-(1H-pyrrolo[2,3-b]pyridin-4-yl)-1H-pyrazol-1-yl)-1-(ethylsulfonyl)azetidin-3-yl)acetonitrile (8)

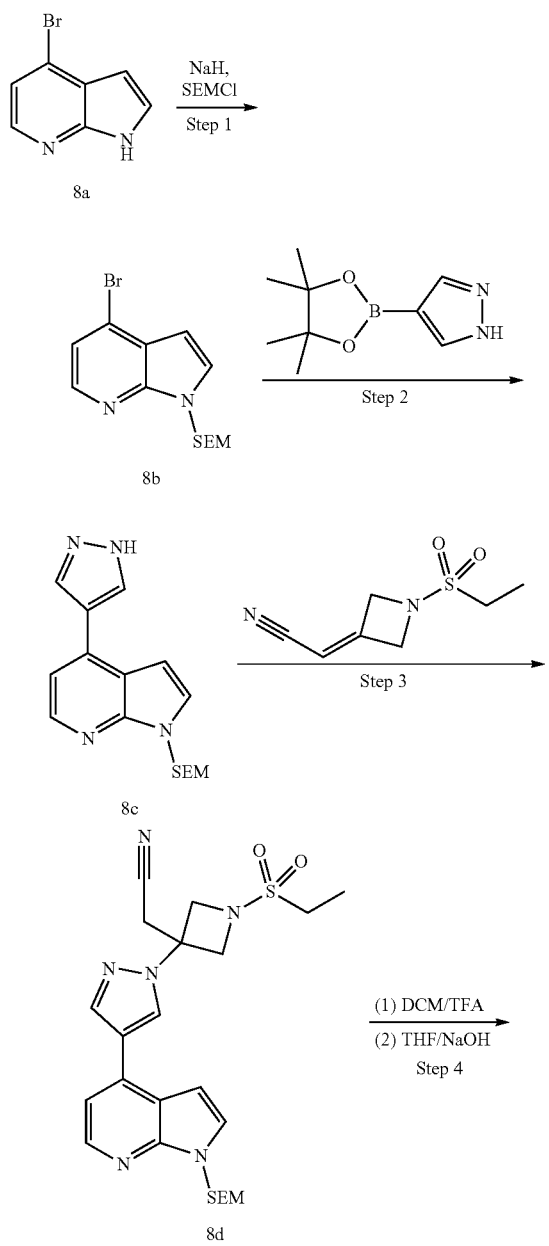

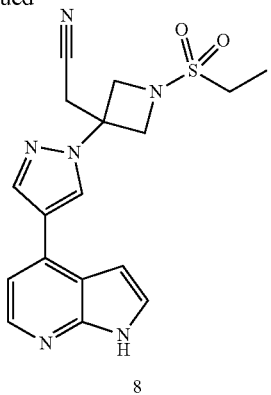

Step 1: 4-bromo-1-((2-(trimethylsilyl)ethoxy)methyl)-1H-pyrrolo[2,3-b]pyridine (8b)

4-bromo-7-azaindole (8a) (10 g, 50.7 mmol) and DMF (100 mL) were added to a 250 mL three-necked flask, the reaction was cooled to below −10° C. in an ice-salt bath, and nitrogen atmosphere protection was applied. After the reaction solution was stirred until homogeneous, sodium hydride (60%, 2.64 g, 54.4 mmol) was added to the reaction in portions within 1 h while keeping the temperature no higher than −5° C. After being stirred for 1 h, the system was added with 2-(trimethylsilyl)ethoxymethyl chloride dropwise while keeping the temperature of the system no higher than 10° C. The addition was complete within about 1.5 h, and the reaction was stirred for 1 h. The reaction was monitored by thin layer chromatography. After the starting material substantially disappeared, the reaction solution was quenched with water, extracted with ethyl acetate, dried over anhydrous sodium sulfate, concentrated under reduced pressure, and purified by column chromatography on silica gel, to afford compound 4-bromo-1-((2-(trimethylsilyl)ethoxy)methyl)-1H-pyrrolo[2,3-b]pyridine (8b) (14.57 g, yield: 88.0%, yellow liquid). MS (ESI, m/z): 326.1 [M+H]$^+$.

Step 2: 4-(1H-pyrazol-4-yl)-1-((2-(trimethylsilyl)ethoxy)methyl)-1H-pyrrolo[2,3-b]pyridine (8c)

Compound 4-bromo-1-((2-(trimethylsilyl)ethoxy)methyl)-1H-pyrrolo[2,3-b]pyridine (8b) (4 g, 12.3 mmol), 4-pyrazoleboronic acid pinacol ester (3.86 g, 19.9 mmol) and dioxane (300 mL) were sequentially added to a 500 mL reaction flask, a potassium carbonate (4.58 g, 33.1 mmol) solution (60 mL) was then added, and the reaction solution was stirred until homogeneous. Pd(dppf)Cl$_2$ (0.97 g, 1.33 mmol) was added, and nitrogen atmosphere protection was applied. The reaction was heated to 95° C., and refluxed overnight. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford compound 4-(1H-pyrazol-4-yl)-1-((2-(trimethylsilyl)ethoxy)methyl)-1H-pyrrolo[2,3-b]pyridine (8c) (1.67 g, yield: 43.5%, yellow solid). MS (ESI, m/z): 314.2 [M+H]$^+$.

Step 3: 2-(1-(ethylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (8d)

Compound 4-(1H-pyrazol-4-yl)-1-((2-(trimethylsilyl)ethoxy)methyl)-1H-pyrrolo[2,3-b]pyridine (8c) (200 mg, 0.64 mmol), 2-[1-(ethylsulfonyl)-3-azetidinylidene]acetonitrile (118 mg, 0.64 mmol) and acetonitrile (15 mL) were added to a 50 mL reaction flask, DBU (116 mg, 0.76 mmol) was added after the reaction solution was stirred until homogeneous. The reaction was performed at room temperature for 1 h, and monitored by thin layer chromatography. After the reaction was complete, the reaction solution was quenched with water, concentrated under reduced pressure, and purified by column chromatography on silica gel, to afford compound 2-(1-(ethylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (8d) (285 mg, yield: 89.1%, yellow solid). MS (ESI, m/z): 500.2 [M+H]$^+$.

Step 4: 2-(3-(4-(1H-pyrrolo[2,3-b]pyridin-4-yl)-1H-pyrazol-1-yl)-1-(ethylsulfonyl)azetidin-3-yl)acetonitrile (8)

At room temperature, compound 2-(1-(ethylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (8d) (345 mg, 0.69 mmol) and a mixed solution of TFA/DCM (1:1) (6 mL) were added to a 50 mL reaction flask, argon atmosphere protection was applied, and the reaction was stirred at room temperature for 1 h. After LC-MS indicated the reaction was complete, the reaction solution was extracted with ethyl acetate, dried over anhydrous sodium sulfate, concentrated under reduced pressure to obtain a yellow oil, which was added with tetrahydrofuran (7.6 mL) at room temperature. The reaction was stirred until homogenous, 1M NaOH solution (7.6 mL) was added, and the reaction was stirred at room temperature for 2 h. After thin lay chromatography indicated the reaction was complete, the reaction was extracted with ethyl acetate, dried over anhydrous sodium sulfate, concentrated under reduced pressure, and purified by TLC, to afford 2-(3-(4-(1H-pyrrolo[2,3-b]pyridin-4-yl)-1H-pyrazol-1-yl)-1-(ethylsulfonyl)azetidin-3-yl)acetonitrile (8) (40 mg, yield: 15.7%, yellow solid). $^1$H NMR (400 MHz, DMSO-d$_6$) δ: 11.72 (s, 1H), 8.78 (s, 1H), 8.35 (s, 1H), 8.21 (d, J=5.00 Hz, 1H), 7.54 (t, J=3.04 Hz, 1H), 7.34 (d, J=5.00 Hz, 1H), 6.90 (dd, J$_1$=3.62 Hz, J$_2$=1.84 Hz, 1H), 4.59 (d, J=9.02 Hz, 2H), 4.24 (d, J=9.02 Hz, 2H), 3.68 (s, 2H), 3.24 (q, 2H), 1.25 (t, J=7.29 Hz, 3H). MS (ESI, m/z): 370.1 [M+H]$^+$.

Example 9: 2-(3-(4-(5-chloro-7H-pyrrolo[2,3-d]pyrimidin-4-yl)-1H-pyrazol-1-yl)-1-(ethylsulfonyl)azetidin-3-yl)acetonitrile (9)

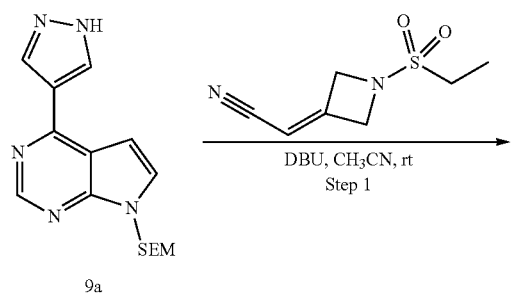

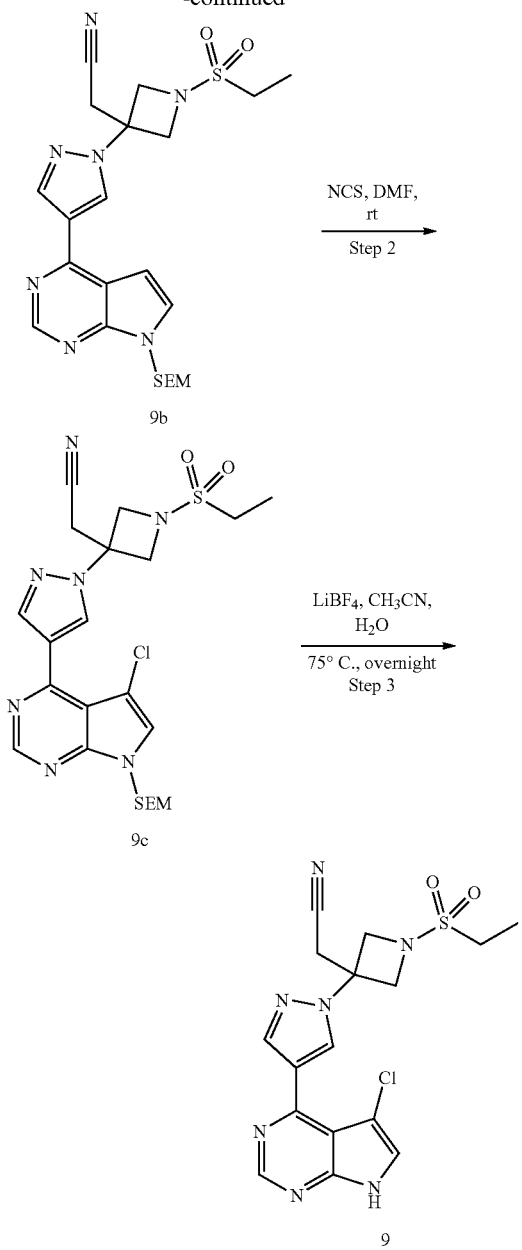

Step 1: 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (9b)

At room temperature, acetonitrile (10 mL) was added to a mixture of 4-(1H-pyrazol-4-yl)-7-((2-(trimethylsilyl)ethoxy)methyl)-7H-pyrrolo[2,3-d]pyrimidine (9a) (214 mg) and 2-[1-(ethylsulfonyl)-3-azetidinylidene]acetonitrile (126 mg) to obtain a reaction solution. DBU (120 mg) was then added, and the reaction was stirred at room temperature overnight. The reaction was concentrated, and purified on a preparative silica gel plate, to afford 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (9b) (327 mg, solid), yield: 77%. MS m/z: 502 [M+1]$^+$.

Step 2: 2-(3-(4-(5-chloro-7-((2-(trimethylsilyl)ethoxy)methyl)-7H-pyrrolo[2,3-d]pyrimidin-4-yl)-1H-pyrazol-1-yl)-1-(ethylsulfonyl)azetidin-3-yl)acetonitrile (9c)

At room temperature, DMF (5 mL) was added to 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)acetonitrile (9b) (200 mg, 0.4 mmol), followed by addition of NCS (70 mg, 0.52 mmol). The reaction was stirred until dissolved, and performed in an oil bath at 30° C. overnight. After TLC indicated the substrate completely disappeared, the reaction was extracted with ethyl acetate, and washed with saturated brine. The organic phase was combined, dried over anhydrous sodium sulfate, concentrated, and purified on a preparative silica gel plate, to afford 2-(3-(4-(5-chloro-7-((2-(trimethylsilyl)ethoxy)methyl)-7H-pyrrolo[2,3-d]pyrimidin-4-yl)-1H-pyrazol-1-yl)-1-(ethylsulfonyl)azetidin-3-yl)acetonitrile (9c) (140 mg, white solid), yield: 65%. MS m/z: 536 [M+1]$^+$.

Step 3: 2-(3-(4-(5-chloro-7H-pyrrolo[2,3-d]pyrimidin-4-yl)-1H-pyrazol-1-yl)-1-(ethylsulfonyl)azetidin-3-yl)acetonitrile (9)

At room temperature, 2-(3-(4-(5-chloro-7-((2-(trimethylsilyl)ethoxy)methyl)-7H-pyrrolo[2,3-d]pyrimidin-4-yl)-1H-pyrazol-1-yl)-1-(ethylsulfonyl)azetidin-3-yl)acetonitrile (9c) (120 mg, 0.23 mmol) was dissolved in acetonitrile (8 mL), water (1 mL) and lithium tetrafluoroborate (210 mg) were added, and then the reaction system was placed in an oil bath at 80° C. and stirred overnight. The reaction was quenched with water, extracted with EA, and dried over anhydrous sodium sulfate. The organic phase was concentrated, and purified on a preparative silica gel plate, to afford 2-(3-(4-(5-chloro-7H-pyrrolo[2,3-d]pyrimidin-4-yl)-1H-pyrazol-1-yl)-1-(ethylsulfonyl)azetidin-3-yl)acetonitrile (9) (57 mg, white solid), yield: 63%. MS m/z: 406 [M+1]$^+$. $^1$H NMR (400 MHz, DMSO-d$_6$) δ 12.58 (s, 1H), 8.78 (d, J=6.1 Hz, 2H), 8.28 (s, 1H), 7.84 (d, J=2.6 Hz, 1H), 4.53 (d, J=9.0 Hz, 2H), 4.24 (d, J=9.0 Hz, 2H), 3.70 (s, 2H), 3.24 (q, J=7.3 Hz, 2H), 1.25 (d, J=7.3 Hz, 3H).

Example 10: 2-(3-(4-(7H-pyrrolo[2,3-d]pyrimidin-4-yl)-1H-imidazol-1-yl)-1-(ethylsulfonyl)azetidin-3-yl)acetonitrile (10)

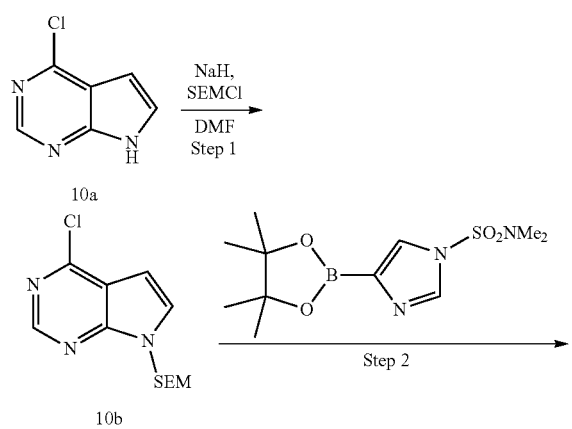

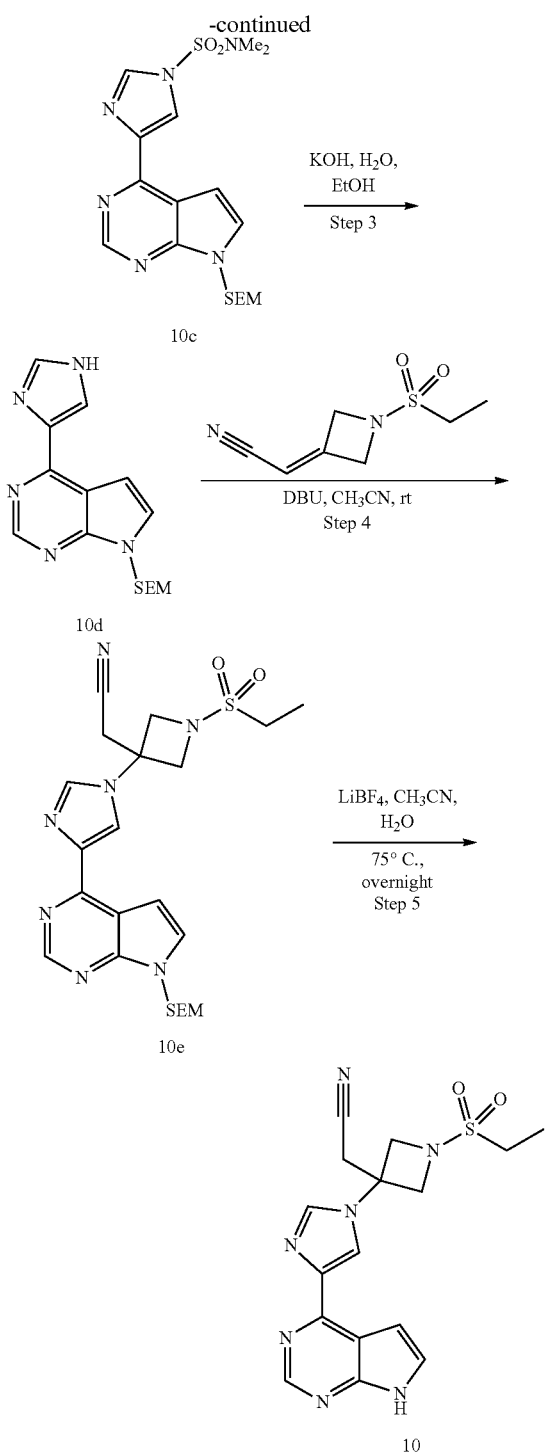

Step 1: 4-chloro-7-((2-(trimethylsilyl)ethoxy)methyl)-7H-pyrrolo[2,3-d]pyrimidine (10b)

Under cooling with an ice-salt bath, sodium hydride (1.1 g, 60%) was added in two portions to a solution of 4-chloropyrrolopyrimidine (10a) (3.0 g, 19.53 mmol) in DMF (15 mL) while keeping the temperature of the reactants no higher than 10° C., and the reaction was stirred under nitrogen atmosphere protection for 1 h. SEMCl (4.2 g, 25.4 mmol) was slowly added via a syringe while keeping the temperature no higher than 10° C. The reaction was warmed to room temperature, and stirred overnight. The reaction was quenched with water, extracted with EA, dried over anhydrous sodium sulfate, and the organic phase was concentrated, and purified by preparative flash chromatography, to afford 4-chloro-7-((2-(trimethylsilyl)ethoxy)methyl)-7H-pyrrolo[2,3-d]pyrimidine (10b) (4.65 g, oil product), yield: 84%. MS (ESI, m/z): 284 [M+H]$^+$.

Step 2: N,N-dimethyl-4-(7-((2-(trimethylsilyl)ethoxy)methyl)-7H-pyrrolo[2,3-d]pyrimidin-4-yl)-1H-imidazole-1-sulfonamide (10c)

At room temperature, 4-chloro-7-((2-(trimethylsilyl)ethoxy)methyl)-7H-pyrrolo[2,3-d]pyrimidine (10b) (150 mg) and 1-N,N-dimethylaminosulfonyl-4-imidazoleboronic acid pinacol ester (210 mg) were dissolved in dioxane (10 mL), water (2 mL) and potassium carbonate (150 mg) were then added, nitrogen atmosphere protection was applied, and the reaction was stirred at room temperature for 10 min. Under protection of nitrogen, Pd(dppf)Cl$_2$ (45 mg) was added. The reaction was placed in an oil bath at 95° C., and stirred overnight. TLC indicated starting materials substantially disappeared. The reaction was quenched with water, extracted with EA, and the organic phase was dried over anhydrous sodium sulfate, and purified by preparative flash chromatography, to afford N,N-dimethyl-4-(7-((2-(trimethylsilyl)ethoxy)methyl)-7H-pyrrolo[2,3-d]pyrimidin-4-yl)-1H-imidazole-1-sulfonamide (10c) (38 mg, brown solid), yield: 17%. MS (ESI, m/z): 423 [M+H]$^+$.

Step 3: 4-(1H-imidazol-4-yl)-7-((2-(trimethylsilyl)ethoxy)methyl)-7H-pyrrolo[2,3-d]pyrimidine (10d)

At room temperature, N,N-dimethyl-4-(7-((2-(trimethylsilyl)ethoxy)methyl)-7H-pyrrolo[2,3-d]pyrimidin-4-yl)-1H-imidazole-1-sulfonamide (10c) (38 mg) was dissolved in ethanol (3 mL), and then an aqueous solution of potassium hydroxide (2%, 12 mL) was added. The reaction was placed in an oil bath at 105° C., and stirred at reflux for 5 h. Then the heating was stopped, and the reaction was allowed to cool naturally, extracted with ethyl acetate, and dried over anhydrous sodium sulfate. The organic phase was rotary evaporated, to afford 4-(1H-imidazol-4-yl)-7-((2-(trimethylsilyl)ethoxy)methyl)-7H-pyrrolo[2,3-d]pyrimidine (10d) (30 mg, purity: 80%) as a crude product, which was used directly in the next reaction without purification. MS (ESI, m/z): 316 [M+H]$^+$.

Step 4: 2-(1-(ethylsulfonyl)-3-(4-(7-((2-(trimethylsilyl)ethoxy)methyl)-7H-pyrrolo[2,3-d]pyrimidin-4-yl)-1H-imidazol-1-yl)azetidin-3-yl)acetonitrile (10e)

At room temperature, acetonitrile (2 mL) was added to a mixture of 4-(1H-imidazol-4-yl)-7-((2-(trimethylsilyl)ethoxy)methyl)-7H-pyrrolo[2,3-d]pyrimidine (10d) (30 mg) and 2-[1-(ethylsulfonyl)-3-azetidinylidene]acetonitrile (20 mg) to obtain a cloudy reaction solution. DBU (20 mg) was then added, and the reaction was stirred at room temperature overnight. The reaction was concentrated, and purified on a preparative silica gel plate, to afford 2-(1-(ethylsulfonyl)-3-(4-(7-((2-(trimethylsilyl)ethoxy)methyl)-7H-pyrrolo[2,3-d]pyrimidin-4-yl)-1H-imidazol-1-yl)azetidin-3-yl)acetonitrile (10e) (13 mg, brown solid). MS (ESI, m/z): 502 [M+H]$^+$.

Step 5: 2-(3-(4-(7H-pyrrolo[2,3-d]pyrimidin-4-yl)-H-imidazol-1-yl)-1-(ethylsulfonyl)azetidin-3-yl)acetonitrile (10)

At room temperature, 2-(1-(ethylsulfonyl)-3-(4-(7-((2-(trimethylsilyl)ethoxy)methyl)-7H-pyrrolo[2,3-d]pyrimidin-4-yl)-1H-imidazol-1-yl)azetidin-3-yl)acetonitrile (10e) (13 mg, 0.003 mmol) was dissolved in acetonitrile (2.5 mL), water (0.5 mL) and lithium tetrafluoroborate (30 mg) were added, and then the reaction system was placed in an oil bath at 80° C. and stirred overnight. The reaction was quenched with water, extracted with EA, and dried over anhydrous sodium sulfate. The organic phase was concentrated, and purified on a preparative silica gel plate, to afford 2-(3-(4-(7H-pyrrolo[2,3-d]pyrimidin-4-yl)-1H-imidazol-1-yl)-1-(ethylsulfonyl)azetidin-3-yl)acetonitrile (10) (8 mg, white solid), yield: 83%. MS (ESI, m/z): 372 [M+H]$^+$. $^1$H NMR (DMSO-d6, 400 MHz) δ 12.01 (s, 1H), 8.67 (s, 1H), 8.33 (d, J=1.2 Hz, 1H), 8.23 (d, J=1.6 Hz, 1H), 7.51-7.53 (m, 1H), 7.21-7.22 (m, 1H), 4.49 (d, J=9.6 Hz, 2H), 4.26 (d, J=9.2 Hz, 2H), 3.67 (s, 2H), 3.21-3.26 (m, 2H), 1.21-1.15 (m, 3H).

Example 11: 2-(3-(4-(6-chloro-7H-pyrrolo[2,3-d]pyrimidin-4-yl)-1H-pyrazol-1-yl)-1-(ethylsulfonyl)azetidin-3-yl)acetonitrile (11)

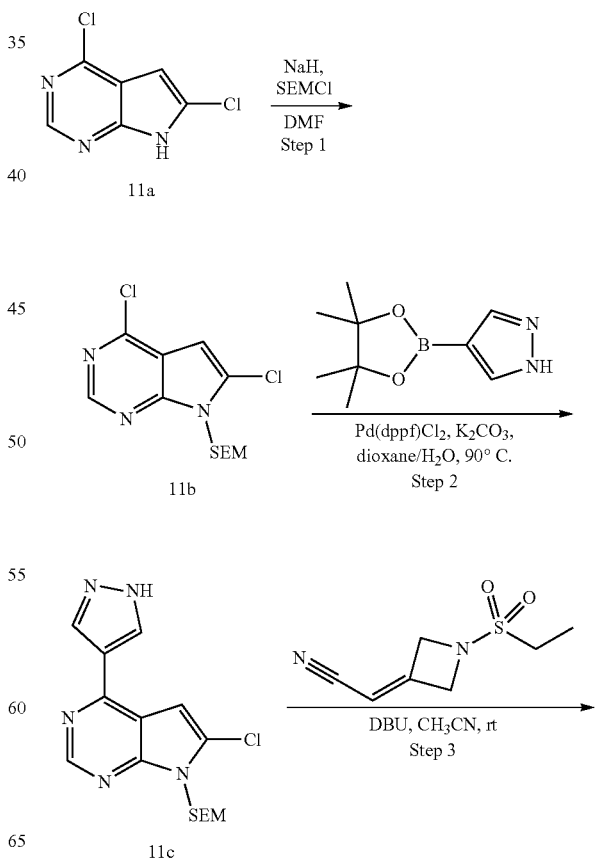

-continued

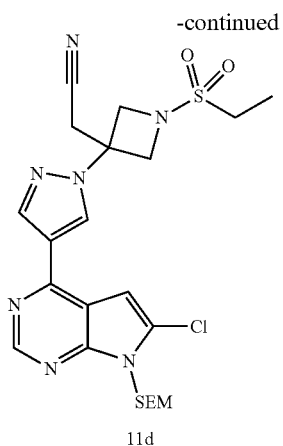

11d

LiBF₄, CH₃CN,
H₂O
───────────→
75° C.,
overnight
Step 4

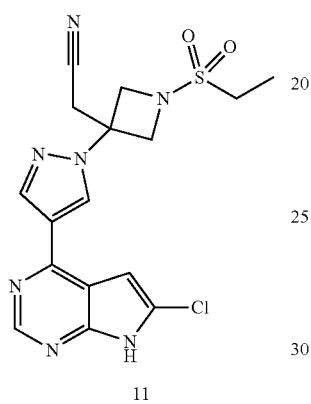

11

Step 1: 4,6-dichloro-7-((2-(trimethylsilyl)ethoxy)methyl)-7H-pyrrolo[2,3-d]pyrimidine (11b)

Under cooling with an ice-salt bath, sodium hydride (213 mg, 60%) was added in two portions to a solution of 4,6-dichloro-7H-pyrrolo[2,3-d]pyrimidine (11a) (1.0 g, 5.32 mmol) in DMF (10 mL) while keeping the temperature of the reactants no higher than 10° C., and the reaction was stirred under nitrogen atmosphere protection for 1 h. SEMCl (1.2 g, 7.20 mmol) was slowly added via a syringe while keeping the temperature no higher than 10° C. The reaction was warmed to room temperature, and stirred overnight. The reaction was quenched with water, extracted with EA, dried over anhydrous sodium sulfate, and the organic phase was concentrated, and purified by preparative flash chromatography, to afford 4,6-dichloro-7-((2-(trimethylsilyl)ethoxy)methyl)-7H-pyrrolo[2,3-d]pyrimidine (11b) (1.0 g, oil product), yield: 60%. MS m/z: 318 [M+1]⁺.

Step 2: 6-chloro-4-(1H-pyrazol-4-yl)-7-((2-(trimethylsilyl)ethoxy)methyl)-7H-pyrrolo[2,3-d]pyrimidine (11c)

At room temperature, 4,6-dichloro-7-((2-(trimethylsilyl)ethoxy)methyl)-7H-pyrrolo[2,3-d]pyrimidine (11b) (358 mg) and 4-pyrazoleboronic acid pinacol ester (327 mg) were dissolved in dioxane (10 mL), water (2 mL) and potassium carbonate (150 mg) were then added, nitrogen atmosphere protection was applied, and the reaction was stirred at room temperature for 10 min. Under protection of nitrogen, Pd(dppf)Cl₂ (82 mg) was added. The reaction was placed in an oil bath at 95° C., and stirred overnight. TLC indicated starting materials substantially disappeared. The reaction was quenched with water, extracted with EA, and the organic phase was dried over anhydrous sodium sulfate, and purified by preparative flash chromatography, to afford 6-chloro-4-(1H-pyrazol-4-yl)-7-((2-(trimethylsilyl)ethoxy)methyl)-7H-pyrrolo[2,3-d]pyrimidine (11c) (161 mg, yellow oil), yield: 41%. MS m/z: 350 [M+1]⁺.

Step 3: 2-(3-(4-(6-chloro-7-((2-(trimethylsilyl)ethoxy)methyl)-7H-pyrrolo[2,3-d]pyrimidin-4-yl)-1H-pyrazol-1-yl)-1-(ethylsulfonyl)azetidin-3-yl)acetonitrile (11d)

At room temperature, acetonitrile (10 mL) was added to a mixture of 6-chloro-4-(1H-pyrazol-4-yl)-7-((2-(trimethylsilyl)ethoxy)methyl)-7H-pyrrolo[2,3-d]pyrimidine (11c) (160 mg) and 2-[1-(ethylsulfonyl)-3-azetidinylidene]acetonitrile (85 mg) to obtain a reaction solution. DBU (100 mg) was then added, and the reaction was stirred at room temperature overnight. The reaction was concentrated, and purified by preparative flash chromatography, to afford 2-(3-(4-(6-chloro-7-((2-(trimethylsilyl)ethoxy)methyl)-7H-pyrrolo[2,3-d]pyrimidin-4-yl)-1H-pyrazol-1-yl)-1-(ethylsulfonyl)azetidin-3-yl)acetonitrile (11d) (177 mg, solid product). MS m/z: 536 [M+1]⁺.

Step 4: 2-(3-(4-(6-chloro-7H-pyrrolo[2,3-d]pyrimidin-4-yl)-1H-pyrazol-1-yl)-1-(ethylsulfonyl)azetidin-3-yl)acetonitrile (11)

At room temperature, 2-(3-(4-(6-chloro-7-((2-(trimethylsilyl)ethoxy)methyl)-7H-pyrrolo[2,3-d]pyrimidin-4-yl)-1H-pyrazol-1-yl)-1-(ethylsulfonyl)azetidin-3-yl)acetonitrile (11d) (177 mg, 0.33 mmol) was dissolved in acetonitrile (10 mL), water (1 mL) and lithium tetrafluoroborate (310 mg) were added, and then the reaction system was placed in an oil bath at 80° C. and stirred overnight. The reaction was quenched with water, extracted with EA, and dried over anhydrous sodium sulfate. The organic phase was concentrated, and purified on a preparative silica gel plate (DCM:MeOH=10:1), to afford 2-(3-(4-(6-chloro-7H-pyrrolo[2,3-d]pyrimidin-4-yl)-1H-pyrazol-1-yl)-1-(ethylsulfonyl)azetidin-3-yl)acetonitrile (11) (70 mg, white solid), yield: 53%. MS m/z: 406 [M+1]⁺. ¹H NMR (400 MHz, DMSO-d₆) δ 13.04 (s, 1H), 8.93 (s, 1H), 8.72 (s, 1H), 8.47 (s, 1H), 7.22 (s, 1H), 4.60 (d, J=9.1 Hz, 2H), 4.24 (d, J=9.1 Hz, 2H), 3.69 (s, 2H), 3.24 (q, J=7.3 Hz, 2H), 1.25 (d, J=7.4 Hz, 3H).

Example 12: 2-(3-(4-(7H-pyrrolo[2,3-d]pyrimidin-4-yl)-1H-pyrazol-1-yl)-1-(ethylsulfonyl)azetidin-3-yl)propanenitrile (12)

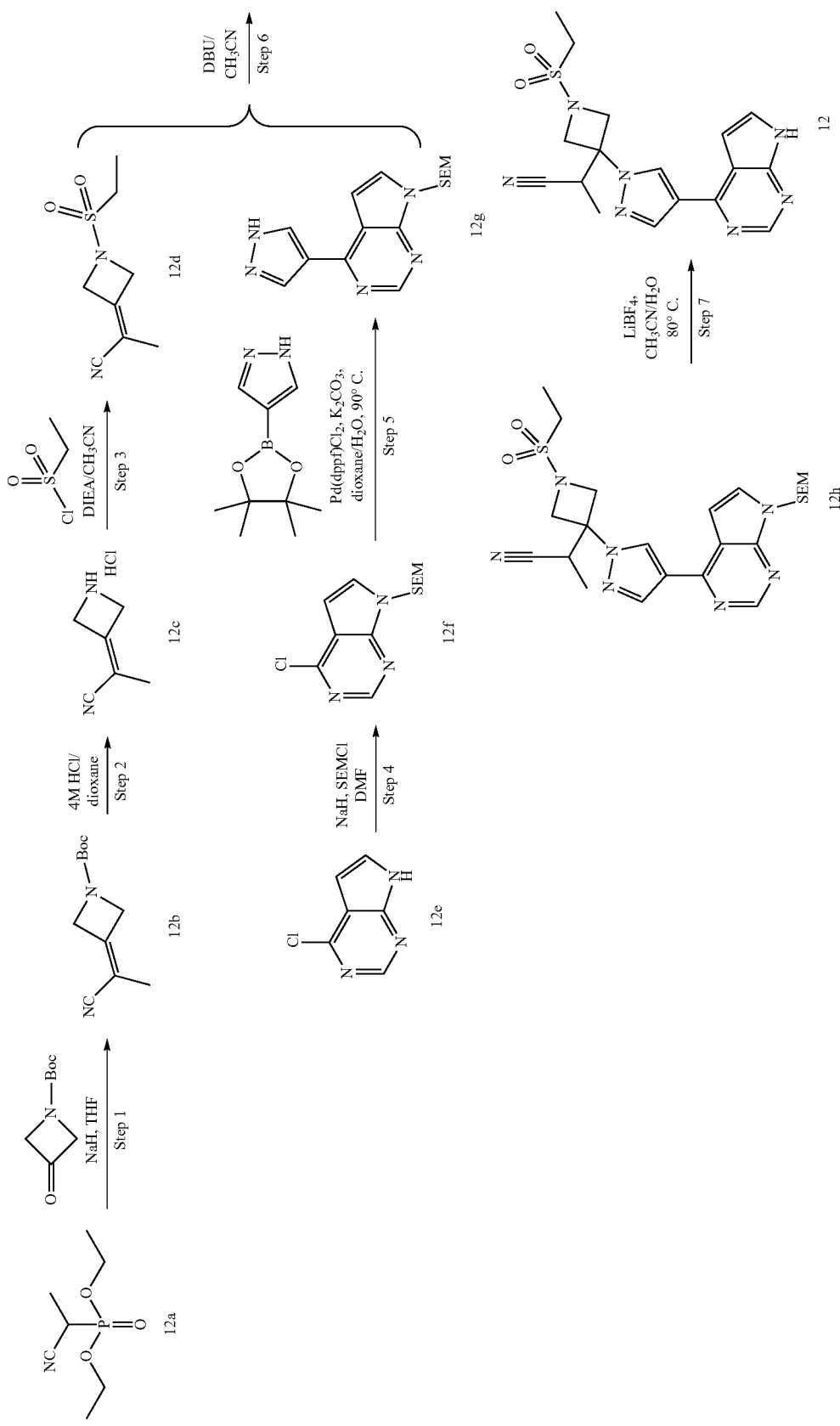

Step 1: tert-butyl 3-(1-cyanoethylidene)azetidine-1-carboxylate (12b)

Under cooling with an ice bath, sodium hydride (70 mg, 60%) was added to a solution of diethyl (1-cyanoethyl) phosphonate (12a) (220 mg, 1.15 mmol) in tetrahydrofuran (10 mL), and after being stirred for 40 min, the reaction became pink. Tert-butyl 3-oxoazetidine-1-carboxylate (394 mg, 2.30 mmol) was added to the reaction, and the reaction became clear slowly. The reaction was slowly warmed to room temperature, and stirred overnight. The reaction was quenched with water, extracted with ethyl acetate, and dried over anhydrous sodium sulfate. The organic phase was concentrated, and purified on a preparative silica gel plate, to afford tert-butyl 3-(1-cyanoethylidene)azetidine-1-carboxylate (12b) (180 mg, oil product), yield: 75%. MS (ESI, m/z): 153 [M+H]$^+$.

Step 2: 2-(azetidin-3-ylidene)propanenitrile hydrochloride salt (12c)

At room temperature, a solution of 4M hydrochloric acid in dioxane (5 mL) was added to tert-butyl 3-(1-cyanoethylidene)azetidine-1-carboxylate (12b) (180 mg, 0.87 mmol), and the reaction dissolved with stirring. The reaction was stirred at room temperature for 1 h, and LC-MS indicated the substrate completely disappeared. The stirring was stopped, and the solvent in the reaction system was rotary evaporated off. The residue was triturated with ether, and filtered, to afford 2-(azetidin-3-ylidene)propanenitrile hydrochloride salt (12c) (115 mg, solid), yield: 92%. MS (ESI, m/z): 109 [M+H]$^+$.

Step 3: 2-(1-(ethylsulfonyl)azetidin-3-ylidene)propanenitrile (12d)

In an ice bath, 2-(azetidin-3-ylidene)propanenitrile hydrochloride salt (12c) (108 mg, 0.75 mmol) was dissolved in acetonitrile (10 mL), DIEA (340 mg) was then added, and the reaction was stirred in the ice bath for 15 min. Ethanesulfonyl chloride (145 mg, 1.12 mmol) was slowly added to the reaction while keeping the temperature of the reaction no higher than 5° C. After the addition of ethanesulfonyl chloride, the reaction was slowly warmed to room temperature, and stirred overnight. LC-MS indicated the substrate substantially disappeared. The reaction was purified on a preparative silica gel plate (PE:EA=2:1), to afford 2-(1-(ethylsulfonyl)azetidin-3-ylidene)propanenitrile (12d) (92 mg, oil product), yield: 61%. MS (ESI, m/z): 201 [M+H]$^+$.

Step 4: 4-chloro-7-((2-(trimethylsilyl)ethoxy)methyl)-7H-pyrrolo[2,3-d]pyrimidine (12f)

Under cooling with an ice-salt bath, sodium hydride (203 mg, 60%) was added in two portions to a solution of 4-chloropyrrolopyrimidine (12e) (600 mg, 3.9 mmol) in DMF (4 mL) while keeping the temperature of the reactants no higher than 10° C., and the reaction was stirred under nitrogen atmosphere protection for 1 h. SEMCl (846 mg, 5.07 mmol) was slowly added via a syringe while keeping the temperature of the reaction no higher than 10° C. The reaction was warmed to room temperature, and stirred overnight. The reaction was quenched with water, extracted with EA, dried over anhydrous sodium sulfate, and the organic phase was concentrated, and purified by preparative flash chromatography (PE:EA=19:1), to afford 4-chloro-7-((2-(trimethylsilyl)ethoxy)methyl)-7H-pyrrolo[2,3-d]pyrimidine (12f) (800 mg, yellow oil), yield: 72%. MS (ESI, m/z): 284 [M+H]$^+$.

Step 5: 4-(1H-pyrazol-4-yl)-7-((2-(trimethylsilyl)ethoxy)methyl)-7H-pyrrolo[2,3-d]pyrimidine (12g)

At room temperature, 4-chloro-7-((2-(trimethylsilyl)ethoxy)methyl)-7H-pyrrolo[2,3-d]pyrimidine (12f) (800 mg, 2.82 mmol) and 4-pyrazoleboronic acid pinacol ester (842 mg, 4.34 mmol) were dissolved in dioxane (10 mL), water (2 mL) and potassium carbonate (857 mg, 6.2 mmol) were then added, nitrogen atmosphere protection was applied, and the reaction was stirred at room temperature for 10 min. Under protection of nitrogen, Pd(dppf)Cl$_2$ (227 mg, 0.31 mmol) was added. The reaction was placed in an oil bath at 95° C., and stirred overnight. TLC indicated starting materials substantially disappeared. The reaction was quenched with water, extracted with EA, and the organic phase was dried over anhydrous sodium sulfate, and purified by preparative flash chromatography (PE:EA=2:3), to afford 4-(1H-pyrazol-4-yl)-7-((2-(trimethylsilyl)ethoxy)methyl)-7H-pyrrolo[2,3-d]pyrimidine (12g) (240 mg, brown solid), yield: 27%. MS (ESI, m/z): 316 [M+H]$^+$.

Step 6: 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)propanenitrile (12h)

At room temperature, acetonitrile (10 mL) was added to a mixture of 4-(1H-pyrazol-4-yl)-7-((2-(trimethylsilyl)ethoxy)methyl)-7H-pyrrolo[2,3-d]pyrimidine (12g) (159 mg, 0.51 mmol) and 2-(1-(ethylsulfonyl)azetidin-3-ylidene)propanenitrile (12d) (102 mg, 0.51 mmol) to obtain a cloudy reaction solution. DBU (100 mg) was then added, and the reaction was stirred at room temperature overnight. The reaction was concentrated, and purified on a preparative silica gel plate, to afford 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)propanenitrile (12h) (160 mg, brown solid), yield: 67.5%. MS (ESI, m/z): 516 [M+H]$^+$.

Step 7: 2-(3-(4-(7H-pyrrolo[2,3-d]pyrimidin-4-yl)-1H-pyrazol-1-yl)-1-(ethylsulfonyl)azetidin-3-yl)propanenitrile (12)

At room temperature, 2-(1-(ethylsulfonyl)-3-(4-(7-((2-(trimethylsilyl)ethoxy)methyl)-7H-pyrrolo[2,3-d]pyrimidin-4-yl)-1H-pyrazol-1-yl)azetidin-3-yl)propanenitrile (12h) (160 mg, 0.31 mmol) was dissolved in acetonitrile (9 mL), water (1 mL) and lithium tetrafluoroborate (583 mg, 6.21 mmol) were added, and then the reaction was placed in an oil bath at 80° C. and stirred overnight. The reaction was quenched with water, extracted with EA, and dried over anhydrous sodium sulfate. The organic phase was concentrated, and purified on a preparative silica gel plate, to afford 2-(3-(4-(7H-pyrrolo[2,3-d]pyrimidin-4-yl)-1H-pyrazol-1-yl)-1-(ethylsulfonyl)azetidin-3-yl)propanenitrile (12) (80 mg, white solid), yield: 66%. MS (ESI, m/z): 386 [M+H]$^+$.
$^1$H NMR (DMSO-d6, 400 MHz) δ 12.16 (s, 1H), 8.94 (s, 1H), 8.71 (s, 1H), 8.47 (s, 1H), 7.62-7.64 (m, 1H), 7.08-7.09 (m, 1H), 4.56-4.62 (m, 2H), 4.33-4.37 (m, 2H), 3.92-3.97 (m, 1H), 3.19-3.25 (m, 2H), 1.19-1.25 (m, 3H), 1.17-1.18 (m, 3H).

The synthesized compound (12) was subjected to chiral separation to obtain two isomers (retention time was 6.9 min (compound 12-1) and 8.4 min (compound 12-2), respectively), and the structures thereof are respectively:

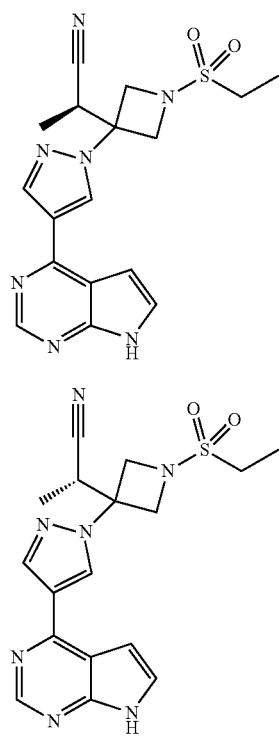

(R)-2-(3-(4-(7H-pyrrolo[2,3-d]pyrimidin-4-yl)-1H-pyrazol-1-yl)-1-(ethylsulfonyl)azetidin-3-yl)propanenitrile (12-1) MS (ESI, m/z): 386 [M+H]⁺. ¹H NMR (DMSO-d6, 400 MHz) δ 12.16 (s, 1H), 8.94 (s, 1H), 8.71 (s, 1H), 8.47 (s, 1H), 7.62-7.64 (m, 1H), 7.08-7.09 (m, 1H), 4.56-4.62 (m, 2H), 4.33-4.37 (m, 2H), 3.92-3.97 (m, 1H), 3.19-3.25 (m, 2H), 1.19-1.25 (m, 3H), 1.17-1.18 (m, 3H); and (S)-2-(3-(4-(7H-pyrrolo[2,3-d]pyrimidin-4-yl)-1H-pyrazol-1-yl)-1-(ethylsulfonyl)azetidin-3-yl)propanenitrile (12-2) MS (ESI, m/z): 386 [M+H]⁺. ¹H NMR (DMSO-d6, 400 MHz) δ 12.16 (s, 1H), 8.94 (s, 1H), 8.71 (s, 1H), 8.47 (s, 1H), 7.62-7.64 (m, 1H), 7.08-7.09 (m, 1H), 4.56-4.62 (m, 2H), 4.33-4.37 (m, 2H), 3.92-3.97 (m, 1H), 3.19-3.25 (m, 2H), 1.19-1.25 (m, 3H), 1.17-1.18 (m, 3H).

Example 13: 2-(1-(ethylsulfonyl)-3-(3-methyl-4-(1H-pyrrolo[2,3-b]pyridin-4-yl)-1H-pyrazol-1-yl)azetidin-3-yl)acetonitrile (13)

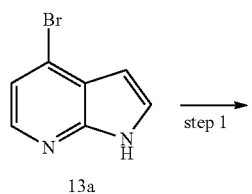

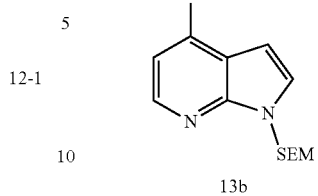
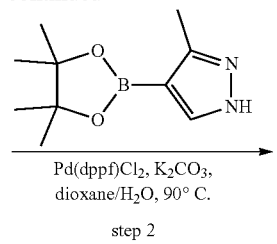

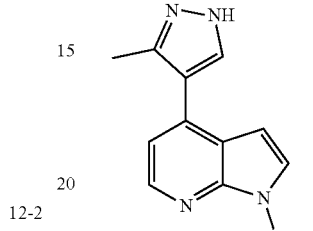
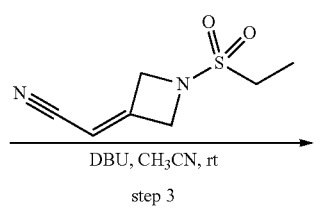

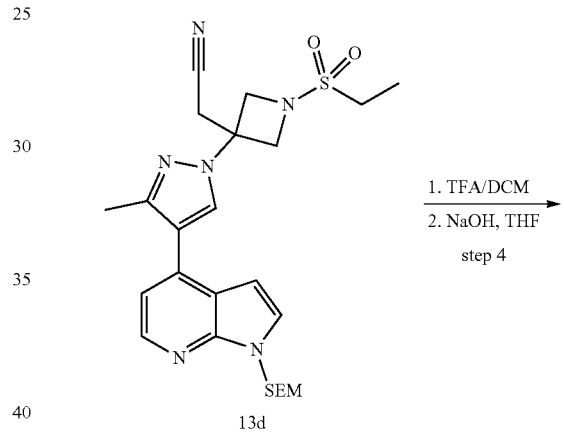

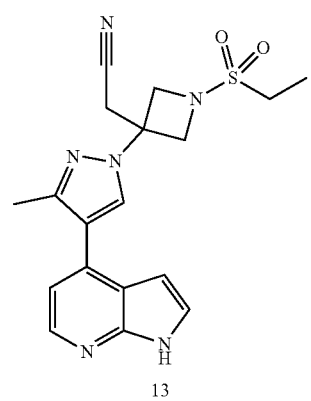

According to the above synthetic route, employing procedures similar to those in Example 8, compound (13) (100 mg, oil product) was prepared, yield: 30%. MS m/z: 385 [M+1]⁺.

¹H NMR (400 MHz, DMSO-d₆) δ 11.72 (s, 1H), 8.46 (s, 1H), 8.23 (d, J=4.9 Hz, 1H), 7.50 (t, J=2.8, 1H), 7.10 (d, J=4.9 Hz, 1H), 6.64 (dd, J=3.2, 1.6 Hz, 1H), 4.56 (d, J=9.0 Hz, 2H), 4.20 (d, J=9.0 Hz, 2H), 3.63 (s, 2H), 3.24 (q, J=7.3 Hz, 2H), 2.39 (s, 3H), 1.25 (t, J=7.3 Hz, 3H).

Example 14: 3-(4-(1H-pyrrolo[2,3-b]pyridin-4-yl)-1H-pyrazol-1-yl)-3-(cyanomethyl)-N,N-dimethyl-azetidine-1-sulfonamide (14)

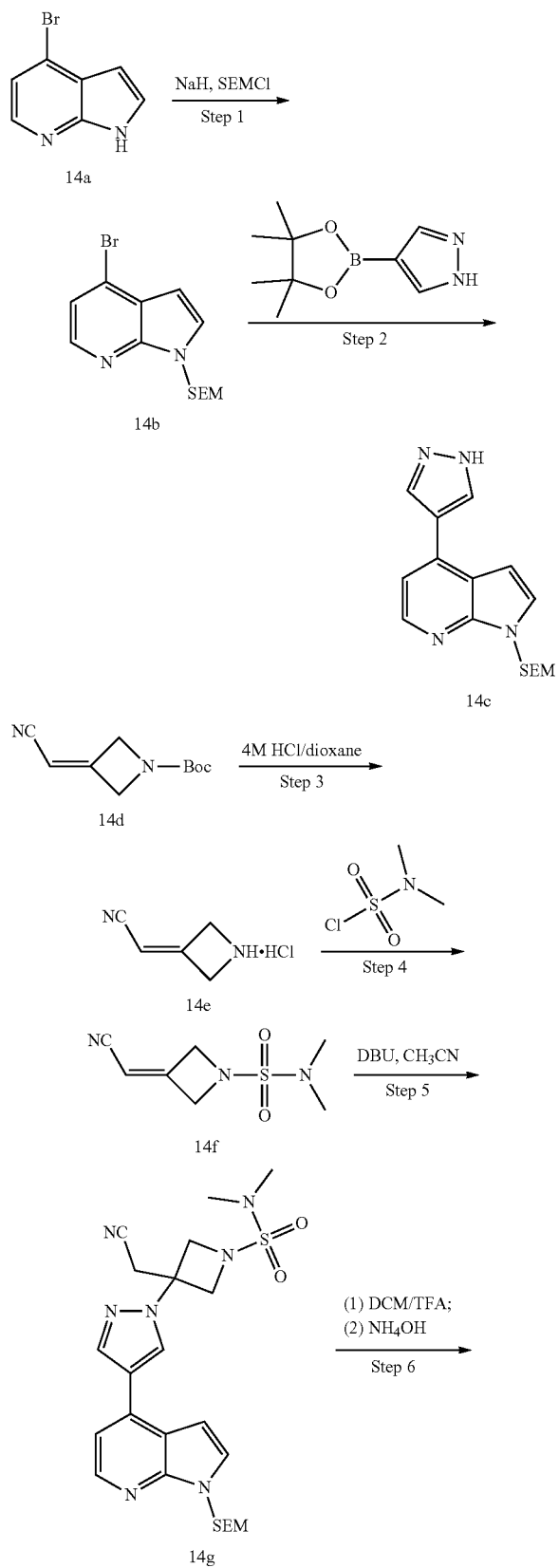

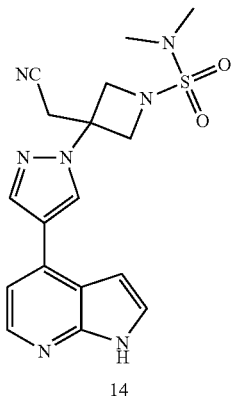 [SMILES: CN(C)S(=O)(=O)N1CC(CC#N)(n2cc(-c3ccnc4[nH]ccc34)cn2)C1]

Step 1: 4-bromo-1-((2-(trimethylsilyl)ethoxy)methyl)-1H-pyrrolo[2,3-b]pyridine (14b)

4-bromo-7-azaindole (14a) (10 g, 50.7 mmol) and DMF (100 mL) were added to a 250 mL three-necked flask, the reaction was cooled to below −10° C. in an ice-salt bath, and nitrogen atmosphere protection was applied. After the reaction solution was stirred until homogeneous, sodium hydride (60%, 2.64 g, 54.4 mmol) was added to the reaction solution in portions within 1 h while keeping the temperature of the reaction no higher than −5° C. After being stirred for 1 h, the system was added with 2-(trimethylsilyl)ethoxymethyl chloride dropwise while keeping the temperature of the reaction no higher than 10° C. The addition was complete within about 1.5 h, and the reaction was stirred for 1 h. The reaction was monitored by thin layer chromatography. After the starting material substantially disappeared, the reaction solution was quenched with water, extracted with ethyl acetate, dried over anhydrous sodium sulfate, concentrated under reduced pressure, and purified by column chromatography on silica gel, to afford compound 4-bromo-1-((2-(trimethylsilyl)ethoxy)methyl)-1H-pyrrolo[2,3-b]pyridine (14b) (14.57 g, yield: 88.0%, yellow oil). MS (ESI, m/z): 326.1 [M+H]$^+$.

Step 2: 4-(1H-pyrazol-4-yl)-1-((2-(trimethylsilyl)ethoxy)methyl)-1H-pyrrolo[2,3-b]pyridine (14c)

Compound 14b (4 g, 12.3 mmol), 4-pyrazoleboronic acid pinacol ester (3.86 g, 19.9 mmol) and dioxane (300 mL) were sequentially added to a 500 mL reaction flask, a potassium carbonate (4.58 g, 33.1 mmol) solution (60 mL) was then added, and the reaction solution was stirred until homogeneous. Pd(dppf)Cl$_2$ (0.97 g, 1.33 mmol) was added, and nitrogen atmosphere protection was applied. The reaction system was heated to 95° C., and refluxed overnight. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford compound 4-(1H-pyrazol-4-yl)-1-((2-(trimethylsilyl)ethoxy)methyl)-1H-pyrrolo[2,3-b]pyridine (14c) (1.67 g, yield: 43.5%, yellow solid). MS (ESI, m/z): 314.2 [M+H]$^+$.

Step 3: 2-(azetidin-3-ylidene)acetonitrile hydrochloride salt (14e)

Compound 14d (1.0 g, 5.15 mmol) and a 4M solution of HCl in dioxane (10 mL) were added to a 50 mL reaction flask, argon atmosphere protection was applied, and the reaction was stirred in an ice bath for 2.5 h, while white solid gradually precipitated. The reaction was monitored by thin layer chromatography. After the starting material substantially disappeared, the reaction solution was filtered with suction, and the filter cake was washed with anhydrous ether and dried, to afford 2-(azetidin-3-ylidene)acetonitrile hydrochloride salt (14e) (600 mg, yield: 90.0%, white solid), which was used directly in the next step.

Step 4: 3-(cyanomethylene)-N,N-dimethylazetidine-1-sulfonamide (14f)

Under cooling with an ice bath, compound 14e (300 mg, 2.31 mmol), dichloromethane (15 mL), triethylamine (1.6 mL, 11.55 mmol) and DMAP (5.7 mg, 0.05 mmol) were sequentially added to a 50 mL reaction flask, and after the reaction was stirred until homogeneous, a solution of dimethylsulfamoyl chloride (431 mg, 3.00 mmol) in dichloromethane (15 mL) was slowly added dropwise to the reaction system. After the addition, the reaction was stirred for 1 h, quenched with water, and extracted with dichloromethane. The organic phase was washed with water, a solution of citric acid and saturated brine, dried over anhydrous sodium sulfate, and concentrated under reduced pressure, to afford 3-(cyanomethylene)-N,N-dimethylazetidine-1-sulfonamide (14f) (311 mg, yield: 67.0%, brown solid). MS (ESI, m/z): 201.1 [M+H]$^+$.

Step 5: 3-(cyanomethyl)-N,N-dimethyl-3-(4-(1-((2-(trimethylsilyl)ethoxy)methyl)-1H-pyrrolo[2,3-b]pyridin-4-yl)-1H-pyrazol-1-yl)azetidine-1-sulfonamide (14g)

Compound 14f (192 mg, 0.96 mmol), compound 14c (300 mg, 0.96 mmol) and acetonitrile (22 mL) were added to a 50 mL reaction flask, DBU (174 mg, 1.15 mmol) was added after the reaction solution was stirred until homogeneous. The reaction solution was stirred at room temperature for 1 h, and monitored by thin layer chromatography. After the reaction was complete, the reaction solution was quenched with water, concentrated under reduced pressure, and purified by column chromatography on silica gel, to afford 3-(cyanomethyl)-N,N-dimethyl-3-(4-(1-((2-(trimethylsilyl)ethoxy)methyl)-1H-pyrrolo[2,3-b]pyridin-4-yl)-1H-pyrazol-1-yl)azetidine-1-sulfonamide (14g) (387 mg, yield: 78.5%, yellow solid). MS (ESI, m/z): 515.2 [M+H]$^+$.

Step 6: 3-(4-(1H-pyrrolo[2,3-b]pyridin-4-yl)-1H-pyrazol-1-yl)-3-(cyanomethyl)-N,N-dimethylazetidine-1-sulfonamide (14)

At room temperature, compound 14g (242 mg, 0.75 mmol) and a mixed solution of TFA/DCM (V:V=1:1.5) (14.4 mL) were added to a 50 mL reaction flask, argon atmosphere protection was applied, and the reaction was stirred at room temperature for 1 h. After LC-MS indicated the reaction was complete, the reaction was adjusted to basic (pH=9-10) with concentrated aqueous ammonia in an ice bath, and stirred overnight. After LC-MS indicated the reaction was complete, the reaction was extracted with dichloromethane, dried over anhydrous sodium sulfate, concentrated under reduced pressure, and purified by TLC, to afford 3-(4-(1H-pyrrolo[2,3-b]pyridin-4-yl)-1H-pyrazol-1-yl)-3-(cyanomethyl)-N,N-dimethylazetidine-1-sulfonamide (14) (87 mg, yield: 15.7%, yellow solid). $^1$H NMR (400 MHz, DMSO-d$_6$) δ: 11.72 (s, 1H), 8.77 (s, 1H), 8.34 (s, 1H), 8.21 (d, J=4.92 Hz, 1H), 7.54 (t, J=2.60 Hz, 1H), 7.34 (d, J=4.96 Hz, 1H), 6.90 (dd, J$_1$=3.64 Hz, J$_2$=1.88 Hz, 1H), 4.52 (d, J=8.84 Hz, 2H), 4.18 (d, J=8.88 Hz, 2H), 3.66 (s, 2H), 2.79 (s, 6H). MS (ESI, m/z): 385.1 [M+H]$^+$.

Example 15: 2-(3-(4-(1H-pyrrolo[2,3-b]pyridin-4-yl)-1H-pyrazol-1-yl)-1-propionylazetidin-3-yl)acetonitrile (15)

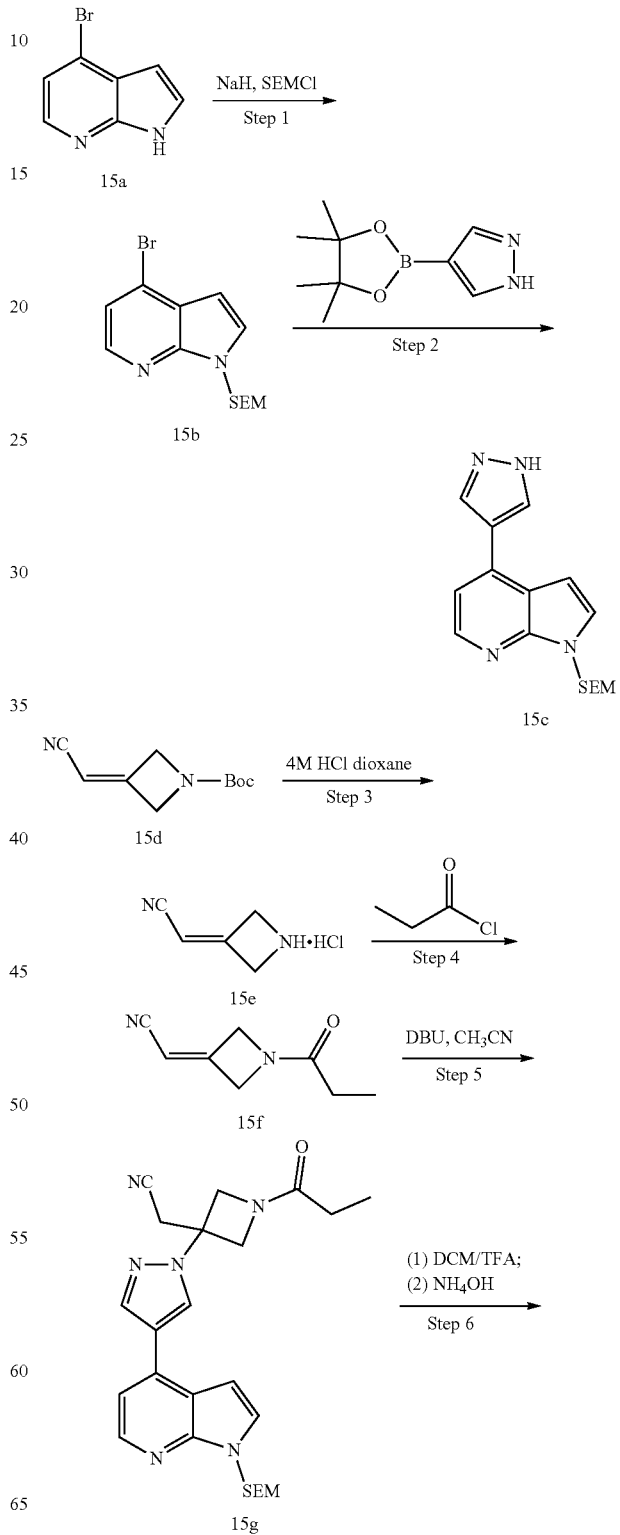

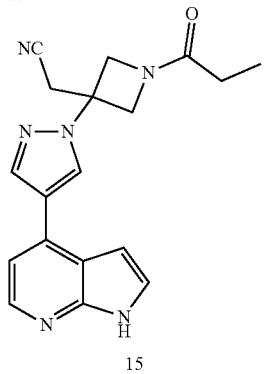 [SMILES: CCC(=O)N1CC(CC#N)(n2cc(-c3ccnc4[nH]ccc34)cn2)C1]

15

Step 1: 4-bromo-1-((2-(trimethylsilyl)ethoxy) methyl)-1H-pyrrolo[2,3-b]pyridine (15b)

4-bromo-7-azaindole (15a) (10 g, 50.7 mmol) and DMF (100 mL) were added to a 250 mL three-necked flask, the reaction was cooled to below −10° C. in an ice-salt bath, and nitrogen atmosphere protection was applied. After the reaction solution was stirred until homogeneous, sodium hydride (60%, 2.64 g, 54.4 mmol) was added to the flask in portions while keeping the temperature of the reaction no higher than −5° C., and the addition was complete after 1 h. After being stirred for 1 h, the reaction was added with 2-(trimethylsilyl) ethoxymethyl chloride dropwise while keeping the temperature of the system no higher than 10° C. The addition was complete within about 1.5 h, and the reaction was stirred for 1 h. The reaction was monitored by thin layer chromatography. After the starting material substantially disappeared, the reaction solution was quenched with water, extracted with ethyl acetate, dried over anhydrous sodium sulfate, concentrated under reduced pressure, and purified by column chromatography on silica gel, to afford compound 4-bromo-1-((2-(trimethylsilyl)ethoxy)methyl)-1H-pyrrolo [2,3-b]pyridine (15b) (14.57 g, yield: 88.0%, yellow oil). MS (ESI, m/z): 326.1 [M+H]$^+$.

Step 2: 4-(1H-pyrazol-4-yl)-1-((2-(trimethylsilyl) ethoxy)methyl)-1H-pyrrolo[2,3-b]pyridine (15c)

Compound 15b (4 g, 12.3 mmol), 4-pyrazoleboronic acid pinacol ester (3.86 g, 19.9 mmol) and dioxane (300 mL) were sequentially added to a 500 mL reaction flask, a potassium carbonate (4.58 g, 33.1 mmol) solution (60 mL) was then added, and the reaction solution was stirred until homogeneous. Pd(dppf)Cl$_2$ (0.97 g, 1.33 mmol) was added, and nitrogen atmosphere protection was applied. The reaction was heated to 95° C., and refluxed overnight. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford compound 4-(1H-pyrazol-4-yl)-1-((2-(trimethylsilyl)ethoxy)methyl)-1H-pyrrolo[2,3-b]pyridine (15c) (1.67 g, yield: 43.5%, yellow solid). MS (ESI, m/z): 314.2 [M+H]$^+$.

Step 3: 2-(azetidin-3-ylidene)acetonitrile hydrochloride salt (15e)

Compound 15d (1.0 g, 5.15 mmol) and a 4M solution of HCl in dioxane (10 mL) were added to a 50 mL reaction flask, argon atmosphere protection was applied, and the reaction was stirred in an ice bath for 2.5 h, while white solid gradually precipitated. The reaction was monitored by thin layer chromatography. After the starting material substantially disappeared, the reaction was filtered with suction, and the filter cake was washed with anhydrous ether and dried, to afford 2-(azetidin-3-ylidene)acetonitrile hydrochloride salt (15e) (600 mg, yield: 90.0%, white solid), which was used directly in the next step.

Step 4: 2-(1-propionylazetidin-3-ylidene)acetonitrile (15f)

Under cooling with an ice bath, compound 15e (160 mg, 1.23 mmol), dichloromethane (8 mL), triethylamine (0.8 mL, 5.78 mmol) and DMAP (2.5 mg, 0.02 mmol) were sequentially added to a 50 mL reaction flask, and after the reaction was stirred until homogeneous, a solution of propionyl chloride (134 mg, 1.45 mmol) in dichloromethane (8 mL) was dropwise added slowly to the reaction system. After the addition, the reaction solution was stirred for 1 h, quenched with water, and extracted with dichloromethane. The organic phase was washed with water, a solution of citric acid and saturated brine, dried over anhydrous sodium sulfate, and concentrated under reduced pressure, to afford 2-(1-propionylazetidin-3-ylidene)acetonitrile (15f) (116 mg, yield: 80.2%, yellow oil). MS (ESI, m/z): 150.1 [M+H]$^+$.

Step 5: 2-(1-propionyl-3-(4-(1-((2-(trimethylsilyl) ethoxy)methyl)-1H-pyrrolo[2,3-b]pyridin-4-yl)-1H-pyrazol-1-yl)azetidin-3-yl)acetonitrile (15g)

Compound 15f (116 mg, 0.77 mmol), compound 15c (243 mg, 0.77 mmol) and acetonitrile (18 mL) were added to a 50 mL reaction flask, DBU (141 mg, 0.93 mmol) was added after the reaction solution was stirred until homogeneous. The reaction solution was stirred at room temperature for 1 h, and monitored by thin layer chromatography. After the reaction was complete, the reaction solution was quenched with water, concentrated under reduced pressure, and purified by column chromatography on silica gel, to afford 2-(1-propionyl-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (15g) (230 mg, yield: 64.4%, yellow solid). MS (ESI, m/z): 464.2 [M+H]$^+$.

Step 6: 2-(3-(4-(1H-pyrrolo[2,3-b]pyridin-4-yl)-1H-pyrazol-1-yl)-1-propionylazetidin-3-yl)acetonitrile (15)

At room temperature, compound 15g (230 mg, 0.50 mmol) and a mixed solution of TFA/DCM (V:V=1:1.5) (15.0 mL) were added to a 50 mL reaction flask, argon atmosphere protection was applied, and the reaction was stirred at room temperature for 1 h. After LC-MS indicated the reaction was complete, the reaction was adjusted to basic (pH=9-10) with concentrated aqueous ammonia in an ice bath, and stirred overnight. After LC-MS indicated the reaction was complete, the reaction was extracted with dichloromethane, dried over anhydrous sodium sulfate, concentrated under reduced pressure, and purified by TLC, to afford 2-(3-(4-(1H-pyrrolo[2,3-b]pyridin-4-yl)-1H-pyrazol-1-yl)-1-propionylazetidin-3-yl)acetonitrile (15) (38 mg, yield: 23.0%, light yellow solid). $^1$H NMR (400 MHz, DMSO-d$_6$) δ: 11.71 (s, 1H), 8.77 (s, 1H), 8.32 (s, 1H), 8.20

(d, J=5.00 Hz, 1H), 7.53 (t, J=2.48 Hz, 1H), 7.33 (d, J=5.00 Hz, 1H), 6.89 (dd, J$_1$=3.56 Hz, J$_2$=1.88 Hz, 1H), 4.77 (d, J=9.32 Hz, 1H), 4.77 (d, J=9.88 Hz, 2H), 4.21 (d, J=10.32 Hz, 1H), 3.67 (s, 2H), 2.15 (q, 2H), 0.99 (t, J=7.48 Hz, 3H). MS (ESI, m/z): 334.1 [M+H]$^+$.

Example 16: 2-(3-(4-(1H-pyrrolo[2,3-b]pyridin-4-yl)-1H-pyrazol-1-yl)-1-(cyclopropanecarbonyl)azetidin-3-yl)acetonitrile (16)

16a

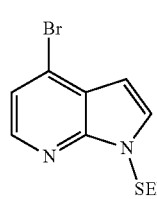

16b

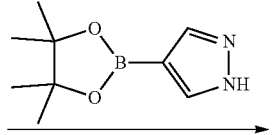

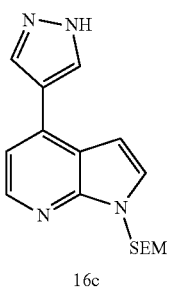

16c

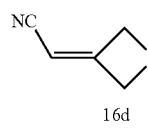

16d

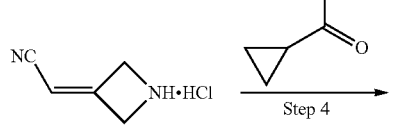

16e

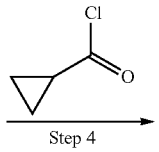

16f

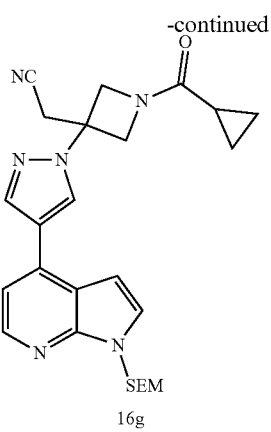

16g

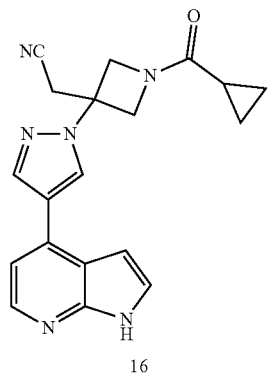 [SMILES: N#CCC1(n2cc(-c3ccnc4[nH]ccc34)cn2)CN(C(=O)C2CC2)C1]

16

Step 1: 4-bromo-1-((2-(trimethylsilyl)ethoxy)methyl)-1H-pyrrolo[2,3-b]pyridine (16b)

4-Bromo-7-azaindole (16a) (10 g, 50.7 mmol) and DMF (100 mL) were added to a 250 mL three-necked flask, the reaction was cooled to below −10° C. in an ice-salt bath, and nitrogen atmosphere protection was applied. After the reaction solution was stirred until homogeneous, sodium hydride (60%, 2.64 g, 54.4 mmol) was added to the reaction in portions within 1 h while keeping the temperature of the reaction no higher than −5° C. After stirred for 1 h, 2-(trimethylsilyl)ethoxymethyl chloride was slowly added to the system dropwise while keeping the temperature of the reaction no higher than 10° C., and the dropwise addition continued for about 1.5 h. The reaction was stirred for 1 h. The reaction was monitored by thin layer chromatography. After the starting material substantially disappeared, the reaction solution was quenched with water, extracted with ethyl acetate, dried over anhydrous sodium sulfate, concentrated under reduced pressure, and purified by column chromatography on silica gel, to afford compound 4-bromo-1-((2-(trimethylsilyl)ethoxy)methyl)-1H-pyrrolo[2,3-b]pyridine (16b) (14.57 g, yield: 88.0%, yellow oil). MS (ESI, m/z): 326.1 [M+H]$^+$.

Step 2: 4-(1H-pyrazol-4-yl)-1-((2-(trimethylsilyl)ethoxy)methyl)-1H-pyrrolo[2,3-b]pyridine (16c)

Compound 16b (4 g, 12.3 mmol), 4-pyrazoleboronic acid pinacol ester (3.86 g, 19.9 mmol) and dioxane (300 mL) were sequentially added to a 500 mL reaction flask, a potassium carbonate (4.58 g, 33.1 mmol) solution (60 mL) was then added, and the reaction solution was stirred until homogeneous. Pd(dppf)Cl$_2$ (0.97 g, 1.33 mmol) was added, and nitrogen atmosphere protection was applied. The reaction system was heated to 95° C., and refluxed overnight. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford compound 4-(1H-pyrazol-4-yl)-1-((2-(trimethylsilyl)ethoxy)methyl)-1H-pyrrolo[2,3-b]pyridine (16c) (1.67 g, yield: 43.5%, yellow solid). MS (ESI, m/z): 314.2 [M+H]$^+$.

Step 3: 2-(azetidin-3-ylidene)acetonitrile hydrochloride salt (16e)

Compound 16d (1.0g, 5.15 mmol) and a 4M solution of HCl in dioxane (10 mL) were added to a 50 mL reaction flask, argon atmosphere protection was applied, and the reaction was stirred in an ice bath for 2.5 h, while white solid gradually precipitated. The reaction was monitored by thin layer chromatography. After the reaction was complete, the reaction solution was filtered with suction, and the filter cake was washed with anhydrous ether and dried, to afford 2-(azetidin-3-ylidene)acetonitrile hydrochloride salt (16e) (600 mg, yield: 90.0%, white solid), which was used directly in the next step.

Step 4: 2-(1-(cyclopropanecarbonyl)azetidin-3-ylidene)acetonitrile (16f)

Under cooling with an ice bath, compound 16e (160 mg, 1.23 mmol), dichloromethane (8 mL), triethylamine (0.8 mL, 5.78 mmol) and DMAP (2.5 mg, 0.02 mmol) were sequentially added to a 50 mL reaction flask, and after the reaction was stirred until homogeneous, a solution of cyclopropanecarbonyl chloride (151 mg, 1.45 mmol) in dichloromethane (8 mL) was dropwise added slowly to the reaction system. After the addition, the reaction solution was stirred for 1 h, quenched with water, and extracted with dichloromethane. The organic phase was washed with water, a solution of citric acid and saturated brine, dried over anhydrous sodium sulfate, and concentrated under reduced pressure, to afford 2-(1-(cyclopropanecarbonyl)azetidin-3-ylidene)acetonitrile (16f) (130 mg, yield: 83.2%, off-white solid). MS (ESI, m/z): 162.1 [M+H]$^+$.

Step 5: 2-(1-(cyclopropanecarbonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (16g)

Compound 16f (130 mg, 0.80 mmol), compound 16c (250 mg, 0.80 mmol) and acetonitrile (19 mL) were added to a 50 mL reaction flask, DBU (183 mg, 1.20 mmol) was added after the reaction solution was stirred until homogeneous. The reaction was stirred at room temperature for 1 h, and monitored by thin layer chromatography. After the reaction was complete, the reaction solution was quenched with water, concentrated under reduced pressure, and purified by column chromatography on silica gel, to afford 2-(1-(cyclopropanecarbonyl)-3-(4-(1-((2-(trimethylsilyl)ethoxy)methyl)-1H-pyrrolo[2,3-b]pyridin-4-yl)-1H-pyrazol-1-yl) azetidin-3-yl)acetonitrile (16g) (243 mg, yield: 63.8%, yellow solid). MS (ESI, m/z): 476.2 [M+H]$^+$.

Step 6: 2-(3-(4-(1H-pyrrolo[2,3-b]pyridin-4-yl)-1H-pyrazol-1-yl)-1-(cyclopropanecarbonyl)azetidin-3-yl)acetonitrile (16)

At room temperature, compound 16g (243 mg, 0.51 mmol) and a mixed solution of TFA/DCM (V:V=1:1.5) (17.3 mL) were added to a 50 mL reaction flask, argon atmosphere protection was applied, and the reaction was stirred at room temperature for 1 h. After LC-MS indicated the reaction was complete, the reaction was adjusted to basic (pH=9-10) with concentrated aqueous ammonia in an ice bath, and stirred overnight. After LC-MS indicated the reaction was complete, the reaction was extracted with dichloromethane, dried over anhydrous sodium sulfate, concentrated under reduced pressure, and purified by TLC, to afford 2-(3-(4-(1H-pyrrolo[2,3-b]pyridin-4-yl)-1H-pyrazol-1-yl)-1-(cyclopropanecarbonyl)azetidin-3-yl)acetonitrile (16) (39 mg, yield: 22.2%, off-white solid). $^1$H NMR (400 MHz, DMSO-d6) δ: 11.71 (s, 1H), 8.79 (s, 1H), 8.34 (s, 1H), 8.20 (d, J=4.96 Hz, 1H), 7.53 (t, J=2.96 Hz, 1H), 7.34 (d, J=5.04 Hz, 1H), 6.89 (dd, J$_1$=3.60 Hz, J$_2$=1.84 Hz, 1H), 4.90 (d, J=9.40 Hz, 1H), 4.63 (d, J=9.40 Hz, 1H), 4.50 (d, J=10.36 Hz, 1H), 4.23 (d, J=10.40 Hz, 1H), 3.72 (s, 2H), 1.63 (q, 1H), 0.76 (t, J=7.20 Hz, 4H). MS (ESI, m/z): 346.2 [M+H]$^+$.

Example 17: 4-(1-(3-(cyanomethyl)-1-(ethylsulfonyl)azetidin-3-yl)-1H-pyrrol-3-yl)-1H-pyrrolo[2,3-b]pyridine-5-carbonitrile (17)

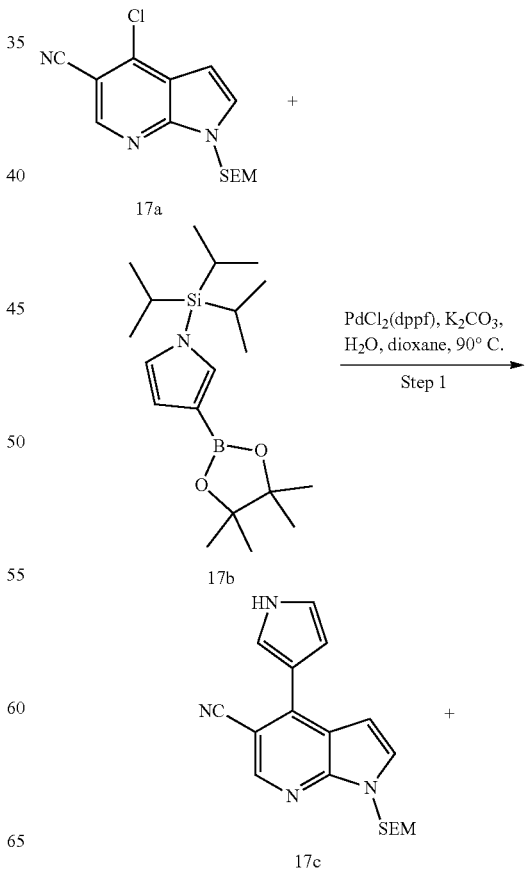

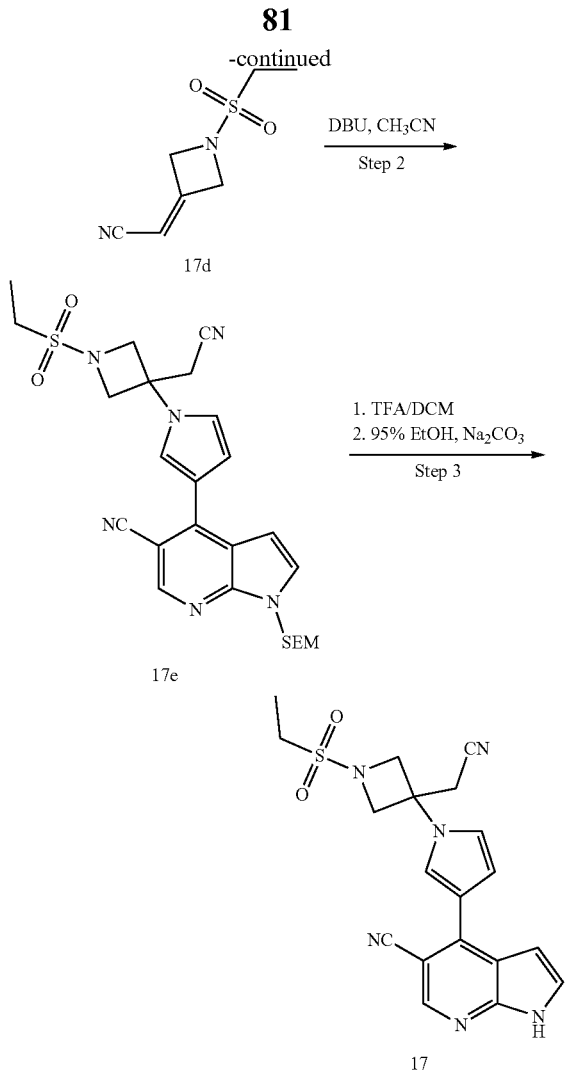

0.42 mmol) and 2-[1-(ethylsulfonyl)azetidin-3-ylidene]acetonitrile (17d) (85 mg, 0.46 mmol) were dissolved in acetonitrile (5 mL), DBU (0.12 mL) was then added, and the reaction was stirred at room temperature. After TLC indicated the reaction was complete, the reaction was rotary evaporated to dryness, and purified by column chromatography, to afford 4-(1-(3-(cyanomethyl)-1-(ethylsulfonyl)azetidin-3-yl)-1H-pyrrol-3-yl)-1-((2-(trimethylsilyl)ethoxy)methyl)-1H-pyrrolo[2,3-b]pyridine-5-carbonitrile (17e) (200 mg, milk white oil, yield: 91%). MS (ESI, m/z): 525 [M+H]$^+$.

Step 3: 4-(1-(3-(cyanomethyl)-1-(ethylsulfonyl)azetidin-3-yl)-1H-pyrrol-3-yl)-1H-pyrrolo[2,3-b]pyridine-5-carbonitrile (17)

4-(1-(3-(cyanomethyl)-1-(ethylsulfonyl)azetidin-3-yl)-1H-pyrrol-3-yl)-1-((2-(trimethylsilyl)ethoxy)methyl)-1H-pyrrolo[2,3-b]pyridine-5-carbonitrile (17e) (110 mg, 0.21 mmol) was dissolved in dichloromethane (2.6 mL), the reaction was placed in an ice bath, and added with trifluoroacetic acid (2.6 mL). The temperature was kept below 10° C. during the whole reaction process. After TLC indicated the reaction was complete, the pH was adjusted to 9 with an aqueous solution of sodium carbonate, and the reaction was extracted with ethyl acetate, and rotary evaporated to dryness to obtain a pale solid, which was dissolved in 95% ethanol, and added with sodium carbonate (334 mg, 3.15 mmol). The reaction was stirred at room temperature, and after its completion, the reaction was rotary evaporated to dryness, and water was added to dissolve the sodium carbonate therein. A solid was obtain by suction filtration, and was triturated with n-hexane, to afford 4-(1-(3-(cyanomethyl)-1-(ethylsulfonyl)azetidin-3-yl)-1H-pyrrol-3-yl)-1H-pyrrolo[2,3-b]pyridine-5-carbonitrile (17) (53 mg, white solid, yield: 64%). $^1$H NMR (400 MHz, DMSO-d6) δ: 12.27 (s, 1H), 8.54 (s, 1H), 7.74 (s, 1H), 7.67 (s, 1H), 7.28 (s, 1H), 6.89 (s, 1H), 6.85 (s, 1H), 4.45 (d, 2H, J=8.4 Hz), 4.24 (d, 2H, J=8.8 Hz), 3.59 (s, 2H), 3.23 (q, 2H, J=6.4 Hz), 1.24 (t, 3H, J=6.4 Hz). MS (ESI, m/z): 395 [M+H]$^+$.

Example 18: 2-(3-(4-(1H-pyrrolo[2,3-b]pyridin-4-yl)-1H-pyrazol-1-yl)-1-(isopropylsulfonyl)azetidin-3-yl)acetonitrile (18)

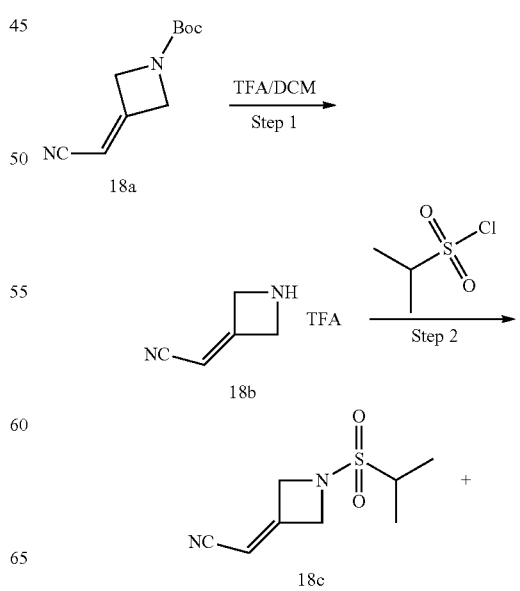

Step 1: 4-(1H-pyrrol-3-yl)-1-((2-(trimethylsilyl)ethoxy)methyl)-1H-pyrrolo[2,3-b]pyridine-5-carbonitrile (17c)

4-chloro-1-((2-(trimethylsilyl)ethoxy)methyl)-1H-pyrrolo[2,3-b]pyridine-5-carbonitrile (17a) (154 mg, 0.5 mmol), 3-(4,4,5,5-tetramethyl-1,3,2-dioxaborolan-2-yl)-1-(triisopropylsilyl)-1H-pyrrole (17b) (262 mg, 0.75 mmol), PdCl$_2$(dppf) (37 mg, 0.05 mmol) and potassium carbonate (173 mg, 1.25 mmol) were added to a 50 mL three-necked flask, dioxane (5 mL) and water (1 mL) were added, argon atmosphere protection was applied, and the reaction solution was heated to 90° C. for 18 h. After TLC indicated the reaction was complete, the reaction was filtered with suction through Celite, and the filtrate was rotary evaporated to dryness, and purified by column chromatography, to afford 4-(1H-pyrrol-3-yl)-1-((2-(trimethylsilyl)ethoxy)methyl)-1H-pyrrolo[2,3-b]pyridine-5-carbonitrile (17c) (142 mg, white solid, yield: 84%). MS (ESI, m/z): 339 [M+H]$^+$.

Step 2: 4-(1-(3-(cyanomethyl)-1-(ethylsulfonyl)azetidin-3-yl)-1H-pyrrol-3-yl)-1-((2-(trimethylsilyl)ethoxy)methyl)-1H-pyrrolo[2,3-b]pyridine-5-carbonitrile (17e)

4-(1H-pyrrol-3-yl)-1-((2-(trimethylsilyl)ethoxy)methyl)-1H-pyrrolo[2,3-b]pyridine-5-carbonitrile (17c) (142 mg,

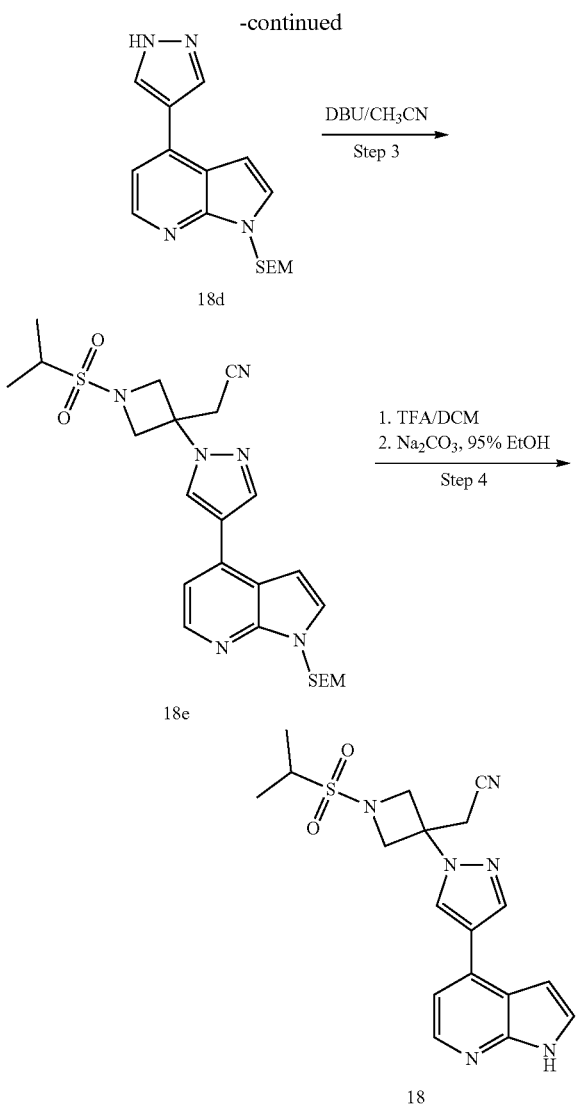

Step 1: 2-(azetidin-3-ylidene)acetonitrile trifluoroacetate salt (18b)

Tert-butyl 3-(cyanomethylene)azetidine-1-carboxylate (18a) (583 mg, 3 mmol) was dissolved in a mixed solution of DCM (18 mL) and trifluoroacetic acid (6 mL), the solution was stirred at room temperature for 30 min, and then rotary evaporated to dryness, to afford a transparent oil, which was used directly in the next step.

Step 2: 2-(1-(isopropylsulfonyl)azetidin-3-ylidene)acetonitrile (18c)

The transparent oil obtained in step 1 was dissolved in dichloromethane (10 mL), the reaction was placed in an ice bath, and triethylamine was slowly added until the pH reached 9. DMAP (8 mg, 0.06 mmol) was then added, and the reaction solution was stirred in an ice bath for 5 min. isopropylsulfonyl chloride (0.44 mL, 3.9 mmol) was dissolved in dichloromethane (2 mL), and then slowly added to the reaction system. The reaction solution was stirred in an ice bath for 30 min, extracted with ethyl acetate, and the organic phase was washed with an aqueous solution of citric acid, dried over anhydrous sodium sulfate, and rotary evaporated to dryness, to afford a solid, which was triturated in petroleum ether, to afford 2-(1-(isopropylsulfonyl)azetidin-3-ylidene)acetonitrile (18c) (450 mg, white solid, yield: 75%), MS (ESI, m/z): 201 [M+H]$^+$.

Step 3: 2-(1-(isopropylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (18e)

4-(1H-pyrazol-4-yl)-1-((2-(trimethylsilyl)ethoxy)methyl)-1H-pyrrolo[2,3-b]pyridine (18d) (200 mg, 0.64 mmol) and 2-(1-(isopropylsulfonyl)azetidin-3-ylidene)acetonitrile (18c) (192 mg, 0.96 mmol) were dissolved in acetonitrile (10 mL), the reaction system was added with DBU (0.16 mL), and then stirred at room temperature overnight. After TLC indicated the reaction was complete, the reaction was rotary evaporated to dryness, and purified by column chromatography on silica gel, to afford 2-(1-(isopropylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (18e) (310 mg, milk white oil, yield: 94%). MS (ESI, m/z): 515 [M+H]$^+$.

Step 4: 2-(3-(4-(1H-pyrrolo[2,3-b]pyridin-4-yl)-1H-pyrazol-1-yl)-1-(isopropylsulfonyl)azetidin-3-yl)acetonitrile (18)

2-(1-(isopropylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (18e) (310 mg, 0.6 mmol) was dissolved in dichloromethane (7 mL), the reaction was placed in an ice bath, and added with trifluoroacetic acid (7 mL). The temperature was kept below 10° C. during the whole reaction process. After TLC indicated the reaction was complete, the pH of the reaction was adjusted to 9 with an aqueous solution of sodium carbonate, and the reaction was extracted with ethyl acetate, and rotary evaporated to dryness. Then the solid was dissolved in 95% ethanol, and added with sodium carbonate (954 mg, 9 mmol). The reaction was stirred at room temperature overnight, rotary evaporated to dryness, and purified by column chromatography on silica gel, to afford 2-(3-(4-(1H-pyrrolo[2,3-b]pyridin-4-yl)-1H-pyrazol-1-yl)-1-(isopropylsulfonyl)azetidin-3-yl)acetonitrile (18) (190 mg, light yellow solid, yield: 82%), $^1$H NMR (400 MHz, DMSO-d$_6$) δ: 11.77 (s, 1H), 8.78 (s, 1H), 8.35 (s, 1H), 8.21 (d, 1H, J=5.2 Hz), 7.55 (t, 1H, J=3.2 Hz), 7.35 (d, 1H, J=4.8 Hz), 6.91 (dd, 1H, J=3.2 Hz, J=2.0 Hz), 4.58 (d, 2H, J=8.8 Hz), 4.21 (d, 2H, J=8.8 Hz), 3.68 (s, 2H), 3.38-3.31 (m, 1H), 1.28 (s, 3H), 1.26 (s, 3H). MS (ESI, m/z): 385 [M+H]$^+$.

Example 19: 2-(3-(4-(1H-pyrrolo[2,3-b]pyridin-4-yl)-1H-pyrazol-1-yl)-1-(methylsulfonyl)azetidin-3-yl)acetonitrile (19)

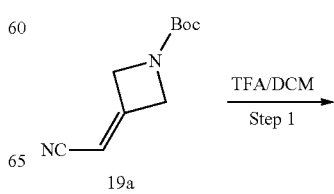

Step 2: 2-(1-(methylsulfonyl)azetidin-3-ylidene)acetonitrile (19c)

The transparent oil obtained in step 1 was dissolved in dichloromethane (10 mL), the reaction was placed in an ice bath, and triethylamine was slowly added until the pH of the reaction reached 9. DMAP (8 mg, 0.06 mmol) was then added, and the reaction was stirred in an ice bath for 5 min. Methanesulfonyl chloride (0.3 mL, 3.9 mmol) was dissolved in dichloromethane (2 mL), and then slowly added to the reaction system. The reaction was performed in an ice bath for 30 min, extracted with ethyl acetate, and the organic phase was washed with an aqueous solution of citric acid, dried over anhydrous sodium sulfate, and rotary evaporated to dryness, to afford a solid, which was triturated in petroleum ether, to afford 2-(1-(methylsulfonyl)azetidin-3-ylidene)acetonitrile (19c) (423 mg, white solid, yield: 82%), MS (ESI, m/z): 173 [M+H]+.

Step 3: 2-(1-(methylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (19e)

4-(1H-pyrazol-4-yl)-1-((2-(trimethylsilyl)ethoxy)methyl)-1H-pyrrolo[2,3-b]pyridine (19d) (252 mg, 0.8 mmol), 2-(1-(methylsulfonyl)azetidin-3-ylidene)acetonitrile (19c) (207 mg, 1.2 mmol) were dissolved in acetonitrile (10 mL), the reaction system was added with DBU (0.16 mL), and then stirred at room temperature overnight. After TLC indicated the reaction was complete, the reaction was rotary evaporated to dryness, and purified by column chromatography on silica gel, to afford 2-(1-(methylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (19e) (320 mg, milk white oil, yield: 82%). MS (ESI, m/z): 487 [M+H]+.

Step 4: 2-(3-(4-(1H-pyrrolo[2,3-b]pyridin-4-yl)-1H-pyrazol-1-yl)-1-(methylsulfonyl)azetidin-3-yl)acetonitrile (19)

2-(1-(methylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (19e) (150 mg, 0.3 mmol) was dissolved in dichloromethane (3 mL), the reaction was placed in an ice bath, and added with trifluoroacetic acid (3 mL). The temperature was kept below 10° C. during the whole reaction process. After TLC indicated the reaction was complete, the reaction was placed in an ice bath, and the pH of the reaction was adjusted to 10 with aqueous ammonia. After proceeded for 22 h, the reaction was extracted with ethyl acetate, rotary evaporated to dryness, and purified on a preparative silica gel plate, to afford 2-(3-(4-(1H-pyrrolo[2,3-b]pyridin-4-yl)-1H-pyrazol-1-yl)-1-(methylsulfonyl)azetidin-3-yl)acetonitrile (19) (40 mg, light yellow solid, yield: 36.6%). $^1$H NMR (400 MHz, DMSO-$d_6$) δ: 11.72 (s, 1H), 8.78 (s, 1H), 8.35 (s, 1H), 8.21 (d, 1H, J=4.8 Hz), 7.54 (t, 1H, J=3.2 Hz), 7.34 (d, 1H, J=5.2 Hz), 6.90 (dd, 1H, J=3.2 Hz, J=2.0 Hz), 4.60 (d, 2H, J=9.2 Hz), 4.27 (d, 2H, J=9.6 Hz), 3.67 (s, 2H), 3.14 (s, 3H). MS (ESI, m/z): 357 [M+H]+.

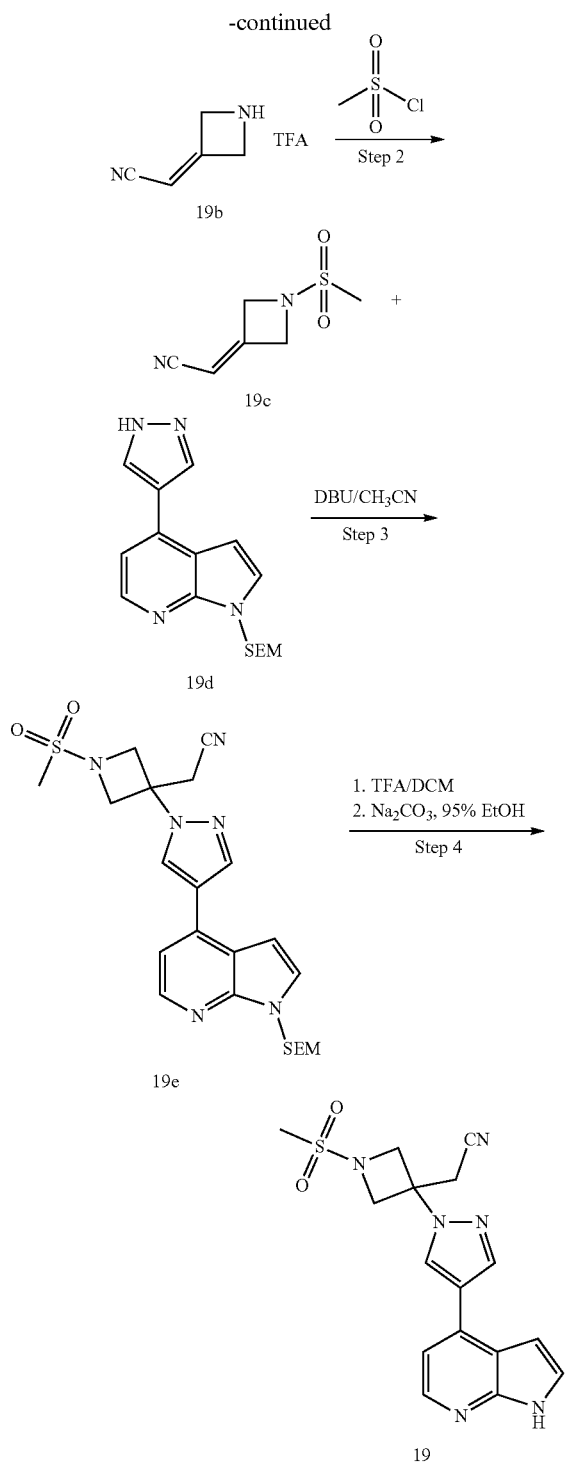

Step 1: 2-(azetidin-3-ylidene)acetonitrile trifluoroacetate salt (19b)

Tert-butyl 3-(cyanomethylene)azetidine-1-carboxylate (19a) (583 mg, 3 mmol) was dissolved in a mixed solution of dichloromethane (18 mL) and trifluoroacetic acid (6 mL), the solution was stirred at room temperature for 30 min, and then rotary evaporated to dryness, to afford a transparent oil, which was used directly in the next step.

Example 20: 4-(1-(3-(cyanomethyl)-1-(ethylsulfonyl)azetidin-3-yl)-1H-pyrazol-4-yl)-7H-pyrrolo[2,3-d]pyrimidine-2-carbonitrile (20)

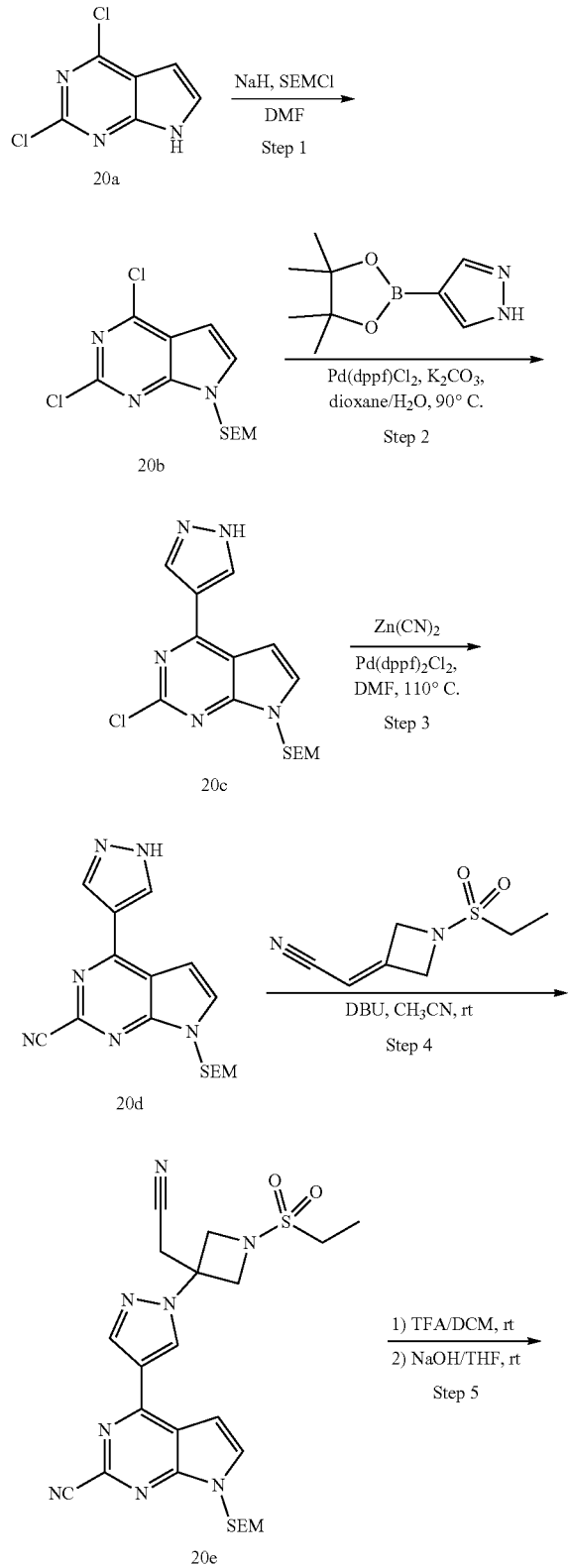

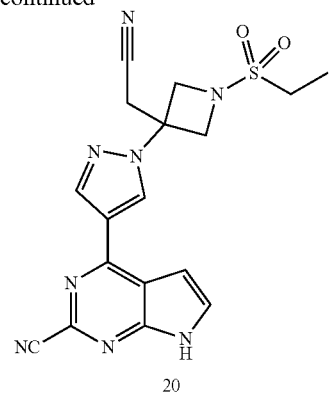

Step 1: 2,4-dichloro-7-((2-(trimethylsilyl)ethoxy)methyl)-7H-pyrrolo[2,3-d]pyrimidine (20b)

At room temperature, 2,4-dichloro-7H-pyrrolo[2,3-d]pyrimidine (20a) (500 mg, 2.66 mmol) and DMF (5 mL) were added to a 50 mL three-necked flask, and nitrogen atmosphere protection was applied. The mixture was cooled to below 5° C. in an ice-salt bath, and after the reaction solution was stirred until homogeneous, sodium hydride (60 wt %, 138 mg, 3.46 mmol) was added to the reaction in portions while keeping the temperature thereof no higher than 10° C. After stirred for 1 h, 2-(trimethylsilyl)ethoxymethyl chloride (577 mg, 3.46 mmol) was slowly added to the reaction dropwise while keeping the temperature thereof no higher than 5° C. and the stir was continued for 2 h. The reaction was monitored by thin layer chromatography. After the starting material substantially disappeared, the reaction solution was quenched with water, extracted with ethyl acetate, dried over anhydrous sodium sulfate, concentrated under reduced pressure, and purified by column chromatography on silica gel, to afford 2,4-dichloro-7-((2-(trimethylsilyl)ethoxy)methyl)-7H-pyrrolo[2,3-d]pyrimidine (20b) (823 mg, yield: 97%, light yellow oil). MS (ESI, m/z): 318 [M+H]$^+$.

Step 2: 2-chloro-4-(1H-pyrazol-4-yl)-7-((2-(trimethylsilyl)ethoxy)methyl)-7H-pyrrolo[2,3-d]pyrimidine (20c)

At room temperature, 2,4-dichloro-7-((2-(trimethylsilyl)ethoxy)methyl)-7H-pyrrolo[2,3-d]pyrimidine (20b) (823 mg, 2.58 mmol), 4-pyrazoleboronic acid pinacol ester (752 mg, 3.88 mmol), a potassium carbonate (891 mg, 6.45 mmol) solution (4 mL) and dioxane (24 mL) were sequentially added to a 100 mL reaction flask, and nitrogen atmosphere protection was applied. After the reaction solution was stirred until homogeneous, Pd(dppf)Cl$_2$ (189 mg, 0.26 mmol) was added under nitrogen atmosphere protection. The reaction was heated to 95° C., and refluxed overnight. The reaction was monitored by thin layer chromatography. After the starting material disappeared, the reaction solution was quenched with water, extracted with ethyl acetate, dried over anhydrous sodium sulfate, concentrated under reduced pressure, and purified by column chromatography on silica gel, to afford 2-chloro-4-(1H-pyrazol-4-yl)-7-((2-(trimethylsilyl)ethoxy)methyl)-7H-pyrrolo[2,3-d]pyrimidine (20c) (500 mg, yield: 55%, yellow solid). MS (ESI, m/z): 350 [M+H]$^+$.

Step 3: 2-cyano-4-(1H-pyrazol-4-yl)-7-((2-(trimethylsilyl)ethoxy)methyl)-7H-pyrrolo[2,3-d]pyrimidine (20d)

2-chloro-4-(1H-pyrazol-4-yl)-7-((2-(trimethylsilyl)ethoxy)methyl)-7H-pyrrolo[2,3-d]pyrimidine (20c) (320 mg, 0.91 mmol), zinc cyanide (53 mg, 0.46 mmol), Pd(dppf)Cl$_2$ (168 mg, 0.23 mmol) and DMF (15 mL) were added to a 50 mL sealed tube, argon atmosphere protection was applied, and the reaction was heated to 110° C. for 24 h. The reaction was monitored by thin layer chromatography. After the starting material was completely consumed, the reaction solution was quenched with water, extracted with ethyl acetate, dried over anhydrous sodium sulfate, concentrated under reduced pressure, and purified by column chromatography on silica gel, to afford 2-cyano-4-(1H-pyrazol-4-yl)-7-((2-(trimethylsilyl)ethoxy)methyl)-7H-pyrrolo[2,3-d]pyrimidine (20d) (219 mg, yield: 71%, light yellow solid). MS (ESI, m/z): 341 [M+H]$^+$.

Step 4: 4-(1-(3-(cyanomethyl)-1-(ethylsulfonyl)azetidin-3-yl)-1H-pyrazol-4-yl)-7-((2-(trimethylsilyl)ethoxy)methyl)-7H-pyrrolo[2,3-d]pyrimidine-2-carbonitrile (20e)

2-cyano-4-(1H-pyrazol-4-yl)-7-((2-(trimethylsilyl)ethoxy)methyl)-7H-pyrrolo[2,3-d]pyrimidine (20d) (219 mg, 0.64 mmol), 2-[1-(ethylsulfonyl)-3-azetidinylidene]acetonitrile (131 mg, 0.71 mmol) and acetonitrile (10 mL) were sequentially added to a 50 mL reaction flask, DBU (108 mg, 0.76 mmol) was added, and the reaction was performed at room temperature for 2 h. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford 4-(1-(3-(cyanomethyl)-1-(ethylsulfonyl)azetidin-3-yl)-1H-pyrazol-4-yl)-7-((2-(trimethylsilyl)ethoxy)methyl)-7H-pyrrolo[2,3-d]pyrimidine-2-carbonitrile (20e) (280 mg, yield: 83%, white solid). MS (ESI, m/z): 527 [M+H]$^+$.

Step 5: 4-(1-(3-(cyanomethyl)-1-(ethylsulfonyl)azetidin-3-yl)-1H-pyrazol-4-yl)-7H-pyrrolo[2,3-d]pyrimidine-2-carbonitrile (20)

At room temperature, 4-(1-(3-(cyanomethyl)-1-(ethylsulfonyl)azetidin-3-yl)-1H-pyrazol-4-yl)-7-((2-(trimethylsilyl)ethoxy)methyl)-7H-pyrrolo[2,3-d]pyrimidine-2-carbonitrile (20e) (218 mg, 0.41 mmol) and a mixed solution of TFA/DCM (1:1) (8 mL) were added to a 50 mL reaction flask, argon atmosphere protection was applied, and the reaction was performed for 2.5 h. After thin layer chromatography indicated the reaction was complete, the reaction was concentrated under reduced pressure to obtain a yellow oil, which was then directly dissolved in tetrahydrofuran (10 mL), and stirred until homogenous. A 1M solution of sodium hydroxide was added to adjust the pH of the reaction to about 10, and the reaction was performed for 0.5 h. After thin lay chromatography indicated the reaction was complete, the reaction was extracted with ethyl acetate, dried over anhydrous sodium sulfate, concentrated under reduced pressure, and purified by column chromatography on silica gel, to afford 4-(1-(3-(cyanomethyl)-1-(ethylsulfonyl)azetidin-3-yl)-1H-pyrazol-4-yl)-7H-pyrrolo[2,3-d]pyrimidine-2-carbonitrile (20) (106 mg, yield: 65%, white solid).

$^1$H NMR (400 MHz, DMSO-d$_6$) δ 12.83 (s, 1H), 9.04 (s, 1H), 8.57 (s, 1H), 7.98 (d, J=3.5 Hz, 1H), 7.30 (d, J=3.5 Hz, 1H), 4.61 (d, J=9.2 Hz, 2H), 4.25 (d, J=9.1 Hz, 2H), 3.70 (s, 2H), 3.24 (q, J=7.3 Hz, 2H), 1.24 (t, J=7.3 Hz, 3H) ppm. MS (ESI, m/z): 397 [M+H]$^+$.

Example 21: 2-(3-(4-(1H-pyrrolo[2,3-b]pyridin-4-yl)-1H-pyrazol-1-yl)-1-(phenylsulfonyl)azetidin-3-yl)acetonitrile (21)

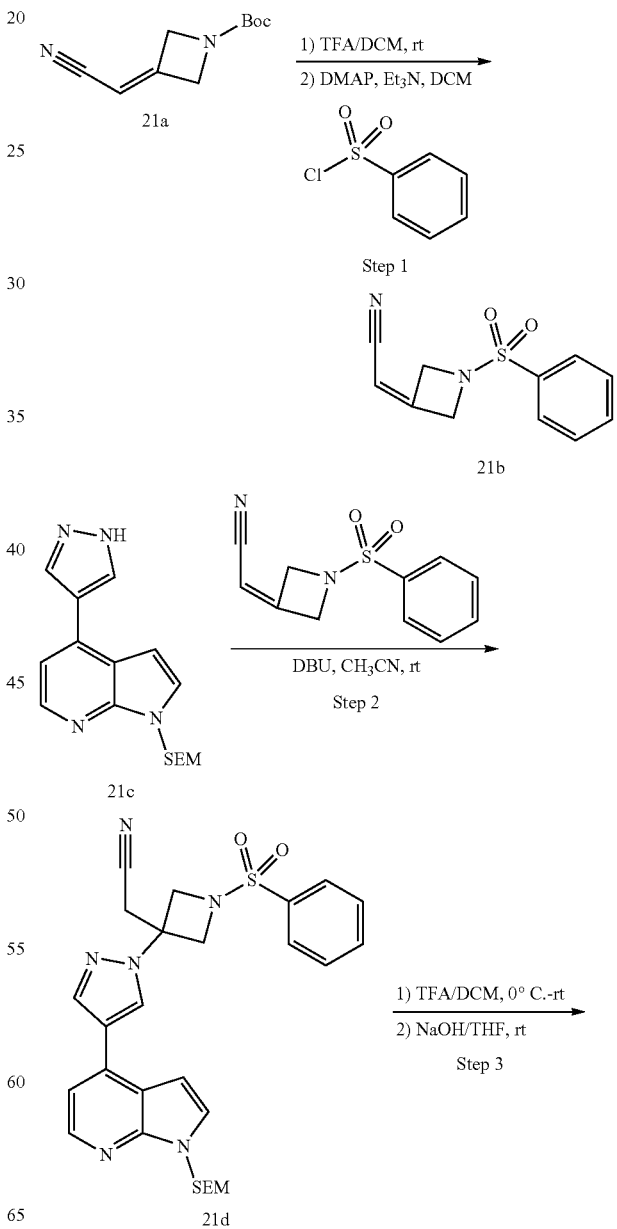

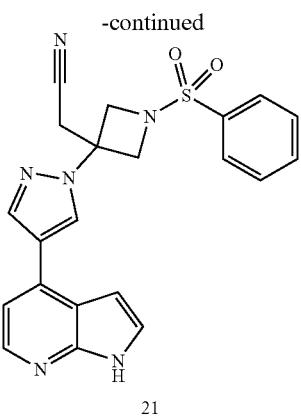

21

Step 1: 2-(1-(phenylsulfonyl)azetidin-3-ylidene)acetonitrile (21b)

Tert-butyl 3-(cyanomethylene)azetidine-1-carboxylate (21a) (583 mg, 3.00 mmol) and TFA/DCM (1/3) (8 mL) were added to a 50 mL reaction flask, and the reaction was stirred at room temperature for half an hour. After thin layer chromatography indicated all the starting materials substantially disappeared, the reaction mixture was concentrated under reduced pressure to dryness. Then, the obtained crude product was dissolved in DCM (5 mL). Under cooling with an ice bath, triethylamine was slowly dropwise added to adjust the pH of the system to about 8, and then DMAP (7 mg, 0.06 mmol) was added, followed by slow dropwise addition of benzenesulfonyl chloride (795 mg, 4.5 mmol). The resulting reaction mixture was gradually warmed to room temperature, and was stirred at room temperature for half an hour. After LC-MS indicated the reaction was complete, the reaction solution was quenched with water, extracted with dichloromethane, and the organic phase was washed with water, a solution of citric acid and saturated brine, dried over anhydrous sodium sulfate, and concentrated under reduced pressure, to afford 2-(1-(phenylsulfonyl)azetidin-3-ylidene)acetonitrile (21b) (650 mg, yield: 90%, brown solid). MS (ESI, m/z): 235 [M+H]$^+$.

Step 2: 2-(1-(phenylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (21 d)

2-(1-(phenylsulfonyl)azetidin-3-ylidene)acetonitrile (21b) (164 mg, 0.70 mmol), 4-(1H-pyrazol-4-yl)-1-((2-(trimethylsilyl)ethoxy)methyl)-1H-pyrrolo[2,3-b]pyridine (21c) (200 mg, 0.64 mmol) and acetonitrile (8 mL) were added to a 50 mL reaction flask, DBU (106 mg, 0.70 mmol) was added, and the reaction was performed at room temperature for 2 h. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford 2-(1-(phenylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (21d) (317 mg, yield: 89%, white solid). MS (ESI, m/z): 549 [M+H]$^+$.

Step 3: 2-(3-(4-(1H-pyrrolo[2,3-b]pyridin-4-yl)-1H-pyrazol-1-yl)-1-(phenylsulfonyl)azetidin-3-yl)acetonitrile (21)

Under cooling with an ice bath, 2-(1-(phenylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (21d) (317 mg, 0.58 mmol) and a mixed solution of TFA/DCM (1:1) (8 mL) were added to a 50 mL reaction flask, argon atmosphere protection was applied, and the reaction was performed for 2.5 h. After thin layer chromatography indicated the reaction was complete, the reaction was concentrated under reduced pressure to obtain a yellow oil, which was then directly dissolved in tetrahydrofuran (10 mL), and stirred until homogenous. A 1M solution of sodium hydroxide was added to adjust the pH of the reaction to about 10, and the reaction was performed for 2 h. After thin lay chromatography indicated the reaction was complete, the reaction was extracted with ethyl acetate, dried over anhydrous sodium sulfate, concentrated under reduced pressure, and purified by thin lay chromatography, to afford the target product, 2-(3-(4-(1H-pyrrolo[2,3-b]pyridin-4-yl)-1H-pyrazol-1-yl)-1-(phenylsulfonyl)azetidin-3-yl)acetonitrile (21) (58 mg, yield: 24%, white solid). $^1$H NMR (400 MHz, DMSO-d$_6$) δ 11.71 (s, 1H), 8.48 (s, 1H), 8.18 (d, J=5.0 Hz, 1H), 8.14 (s, 1H), 7.89-7.84 (m, 2H), 7.68-7.58 (m, 3H), 7.53 (dd, J=3.5, 2.5 Hz, 1H), 7.23 (d, J=5.0 Hz, 1H), 6.79 (dd, J=3.5, 1.9 Hz, 1H), 4.37 (d, J=9.6 Hz, 2H), 4.21 (d, J=9.6 Hz, 2H), 3.52 (s, 2H) ppm. MS (ESI, m/z): 419 [M+H]$^+$.

Example 22: 2-(3-(4-(1H-pyrrolo[2,3-b]pyridin-4-yl)-1H-pyrazol-1-yl)-1-(benzoyl)azetidin-3-yl)acetonitrile (22)

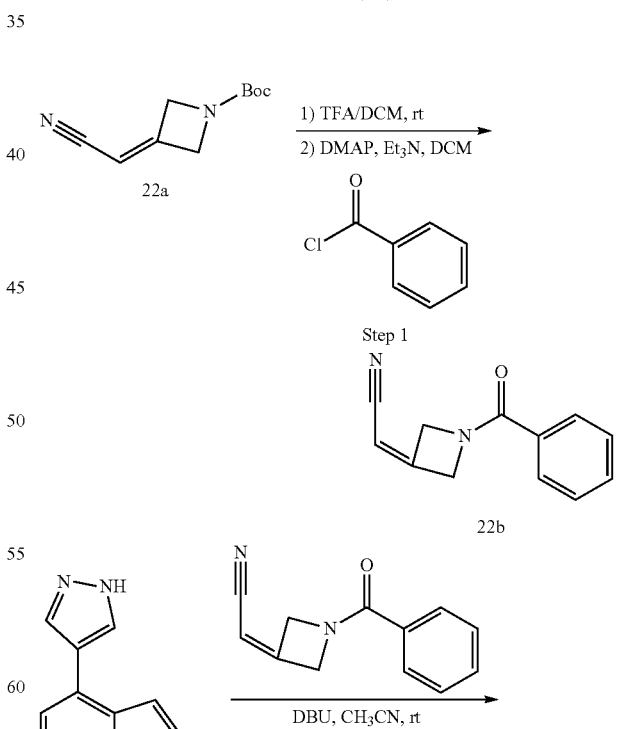

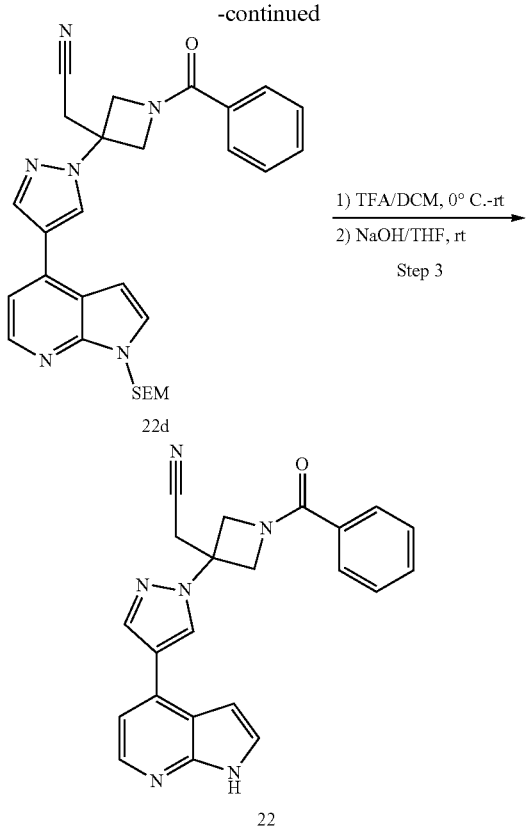

22d

22

Step 1: 2-(1-(benzoyl)azetidin-3-ylidene)acetonitrile (22b)

Tert-butyl 3-(cyanomethylene)azetidine-1-carboxylate (22a) (583 mg, 3.00 mmol) and TFA/DCM (1/3) (8 mL) were added to a 50 mL reaction flask, and the reaction was stirred at room temperature for half an hour. After thin layer chromatography indicated all the starting materials substantially disappeared, the reaction mixture was concentrated under reduced pressure to dryness. Then, the obtained crude product was dissolved in DCM (5 mL). Under cooling with an ice bath, triethylamine was slowly dropwise added to adjust the pH of the reaction to about 8, and then DMAP (7 mg, 0.06 mmol) was added, followed by slow dropwise addition of benzoyl chloride (633 mg, 4.5 mmol). The resulting reaction mixture was gradually warmed to room temperature, and was stirred at room temperature for half an hour. After LC-MS indicated the reaction was complete, the reaction solution was quenched with water, extracted with dichloromethane, and the organic phase was washed with water, a solution of citric acid and saturated brine, dried over anhydrous sodium sulfate, and concentrated under reduced pressure, to afford 2-(1-(benzoyl)azetidin-3-ylidene)acetonitrile (22b) (560 mg, yield: 91%, brown solid). MS (ESI, m/z): 199 [M+H]$^+$.

Step 2: 2-(1-benzoyl-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (22d)

2-(1-(benzoyl)azetidin-3-ylidene)acetonitrile (22b) (139 mg, 0.70 mmol), 4-(1H-pyrazol-4-yl)-1-((2-(trimethylsilyl)ethoxy)methyl)-1H-pyrrolo[2,3-b]pyridine (22c) (200 mg, 0.64 mmol) and acetonitrile (8 mL) were added to a 50 mL reaction flask, DBU (106 mg, 0.70 mmol) was added, and the reaction was performed at room temperature for 2 h. The reaction was monitored by thin layer chromatography. After the reaction was complete, the reaction solution was quenched with water, extracted with ethyl acetate, dried over anhydrous sodium sulfate, concentrated under reduced pressure, and purified by column chromatography on silica gel, to afford 2-(1-benzoyl-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (22d) (311 mg, yield: 93%, white solid). MS (ESI, m/z): 513 [M+H]$^+$.

Step 3: 2-(3-(4-(1H-pyrrolo[2,3-b]pyridin-4-yl)-1H-pyrazol-1-yl)-1-(benzoyl)azetidin-3-yl)acetonitrile (22)

Under cooling with an ice bath, 2-(1-benzoyl-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (22d) (311 mg, 0.58 mmol) and a mixed solution of TFA/DCM (1:1) (8 mL) were added to a 50 mL reaction flask, argon atmosphere protection was applied, and the reaction was performed for 2.5 h. After thin layer chromatography indicated the reaction was complete, the reaction was concentrated under reduced pressure to obtain a yellow oil, which was then directly dissolved in tetrahydrofuran (10 mL), and stirred until homogenous. A 1M solution of sodium hydroxide was added to adjust the pH of the reaction to about 10, and the reaction was performed for 2 h. After thin lay chromatography indicated the reaction was complete, the reaction was extracted with ethyl acetate, dried over anhydrous sodium sulfate, concentrated under reduced pressure, and purified by thin lay chromatography, to afford the target product, 2-(3-(4-(1H-pyrrolo[2,3-b]pyridin-4-yl)-1H-pyrazol-1-yl)-1-(benzoyl)azetidin-3-yl)acetonitrile (22) (104 mg, yield: 47%, white solid). $^1$H NMR (400 MHz, DMSO-d$_6$) δ 11.72 (s, 1H), 8.82 (s, 1H), 8.34 (s, 1H), 8.20 (d, J=5.0 Hz, 1H), 7.77-7.66 (m, 2H), 7.65-7.47 (m, 4H), 7.34 (d, J=5.0 Hz, 1H), 6.91 (dd, J=3.5, 1.8 Hz, 1H), 5.04 (d, J=9.7 Hz, 1H), 4.67 (dd, J=10.5, 4.8 Hz, 2H), 4.45 (d, J=10.9 Hz, 1H), 3.71 (s, 2H) ppm. MS (ESI, m/z): 383 [M+H]$^+$.

Example 23: 2-(3-(4-(1H-pyrrolo[2,3-b]pyridin-4-yl)-1H-pyrazol-1-yl)-1-(propylsulfonyl)azetidin-3-yl)acetonitrile (23)

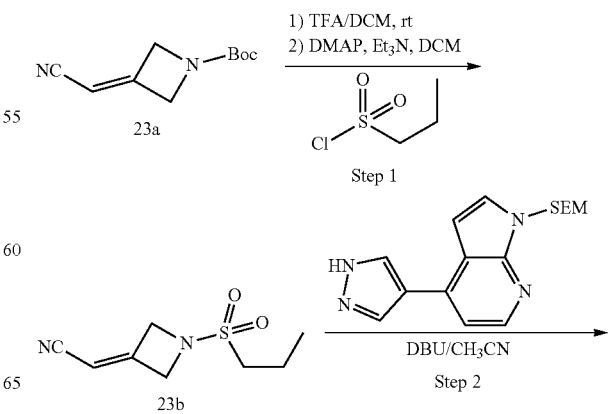

-continued

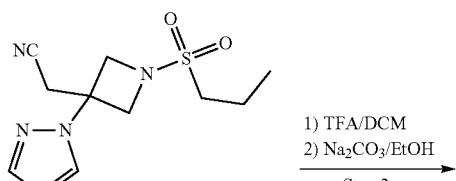

23c

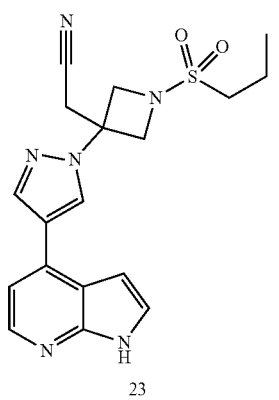

23

Step 1: 2-(1-(propylsulfonyl)azetidin-3-ylidene)acetonitrile (23b)

TFA/DCM (1/2, 8 mL) were added to tert-butyl 3-(cyanomethylene)azetidine-1-carboxylate (23a) (600 mg), and the reaction was stirred at room temperature for half an hour. After TLC indicated all the starting materials substantially disappeared, the reaction mixture was concentrated under reduced pressure to dryness. Then, DCM (10 mL) was added to the crude product. Under cooling with an ice bath, triethylamine was slowly dropwise added to adjust the pH of the reaction to 8, and then DMAP (29 mg) was added, followed by slow dropwise addition of propanesulfonyl chloride (1.02 g). The resulting reaction mixture was gradually warmed to room temperature, and was stirred at room temperature for half an hour. After LC-MS indicated the reaction was complete, the reaction was quenched with water, extracted with dichloromethane, and the organic phase was washed with water, a solution of citric acid and saturated brine, dried over anhydrous sodium sulfate, and concentrated under reduced pressure, to afford a crude product, 2-(1-(propylsulfonyl)azetidin-3-ylidene)acetonitrile (23b) (930 mg, brown solid). MS m/z: 201 [M+1]$^+$.

Step 2: 2-(1-(propylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (23c)

At room temperature, acetonitrile (10 mL) was added to 4-(1H-pyrazol-4-yl)-1-((2-(trimethylsilyl)ethoxy)methyl)-1H-pyrrolo[2,3-b]pyridine (200 mg) and 2-(1-(propylsulfo-nyl)azetidin-3-ylidene)acetonitrile (23b) (153 mg) to obtain a cloudy reaction solution. DBU (194 mg) was then added, and the reaction was stirred at room temperature overnight. The reaction solution was concentrated, and purified on a preparative silica gel plate (DCM:EA=1:3), to afford 2-(1-(propylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (23c) (328 mg, white solid). Yield: 98%. MS m/z: 515 [M+1]$^+$.

Step 3: 2-(3-(4-(1H-pyrrolo[2,3-b]pyridin-4-yl)-1H-pyrazol-1-yl)-1-(propylsulfonyl)azetidin-3-yl)acetonitrile (23)

Under cooling with an ice bath, TFA/DCM (1:2, 12 mL) was added to 2-(1-(propylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (23c) (312 mg), and the reaction was performed for 2.5 h. After TLC indicated the reaction was complete, the reaction was concentrated under reduced pressure to obtain a yellow oil, which was directly dissolved in 95% ethanol (20 mL) under cooling with an ice bath. A suitable amount of sodium carbonate was added to adjust the pH to 8, and a large amount of solid precipitated. After TLC indicated the reaction was complete, the reaction was added with water and ethyl acetate to completely dissolve the solid, then extracted with EA, dried over anhydrous sodium sulfate, concentrated under reduced pressure, and purified on a preparative silica gel plate (DCM:EA=1:5), to afford 2-(3-(4-(1H-pyrrolo[2,3-b]pyridin-4-yl)-1H-pyrazol-1-yl)-1-(propylsulfonyl)azetidin-3-yl)acetonitrile (23) (90 mg, white solid), yield: 39%. MS m/z: 385 [M+1]$^+$. $^1$H NMR (DMSO-d$_6$, 400 MHz) δ 11.72 (s, 1H), 8.78 (s, 1H), 8.35 (s, 1H), 8.20 (d, J=4.0 Hz, 1H), 7.53-7.55 (m, 1H), 7.33 (d, J=4.0 Hz, 1H), 6.89-6.91 (m, 1H), 4.58 (d, J=8.0 Hz, 2H), 4.24 (d, J=4.0 Hz, 2H), 3.67 (s, 2H), 3.22-3.25 (m, 2H), 1.68-1.78 (m, 2H), 1.00 (t, J=8.0 Hz, 3H).

Example 24: 2-(3-(4-(1H-pyrrolo[2,3-b]pyridin-4-yl)-1H-pyrazol-1-yl)-1-(butylsulfonyl)azetidin-3-yl)acetonitrile (24)

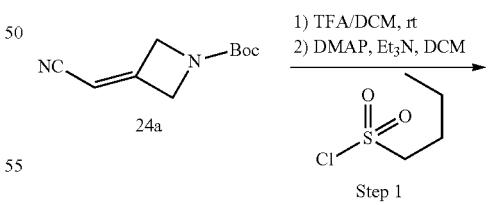

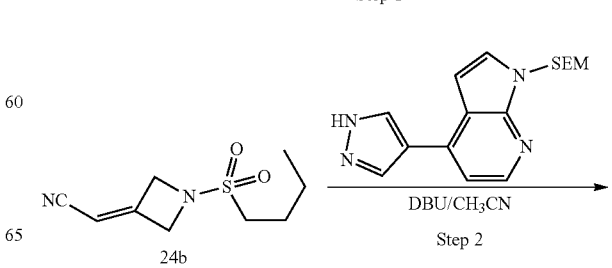

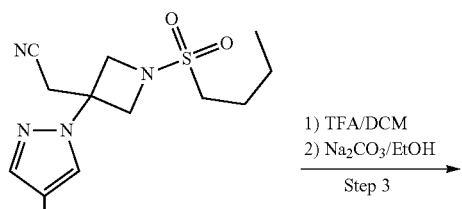

24c

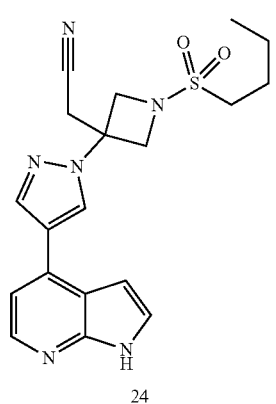

24

Step 1: 2-(1-(butylsulfonyl)azetidin-3-ylidene)acetonitrile (24b)

TFA/DCM (1/2, 8 mL) was added to tert-butyl 3-(cyanomethylene)azetidine-1-carboxylate (24a) (600 mg), and the reaction was stirred at room temperature for half an hour. After TLC indicated all the starting materials substantially disappeared, the reaction mixture was concentrated under reduced pressure to dryness. Then, dichloromethane (10 mL) was added to the crude product. Under cooling with an ice bath, triethylamine was slowly dropwise added to adjust the pH of the reaction to 8, and then DMAP (29 mg) was added, followed by slow dropwise addition of butanesulfonyl chloride (1.02 g). The resulting reaction mixture was gradually warmed to room temperature, and was stirred at room temperature for half an hour. After LC-MS indicated the reaction was complete, the reaction solution was quenched with water, extracted with DCM, and the organic phase was washed with water, a solution of citric acid and saturated brine, dried over anhydrous sodium sulfate, and concentrated under reduced pressure, to afford a crude product, 2-(1-(butylsulfonyl)azetidin-3-ylidene)acetonitrile (24b) (930 mg, brown solid). MS m/z: 215 [M+1]$^+$.

Step 2: 2-(1-(butylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (24c)

At room temperature, acetonitrile (10 mL) was added to 4-(1H-pyrazol-4-yl)-1-((2-(trimethylsilyl)ethoxy)methyl)-1H-pyrrolo[2,3-b]pyridine (200 mg) and 2-(1-(butylsulfonyl)azetidin-3-ylidene)acetonitrile (24b) (300 mg) to obtain a cloudy reaction solution. DBU (194 mg) was then added, and the reaction was stirred at room temperature overnight. The reaction was concentrated, and purified on a preparative silica gel plate (DCM:EA=1:4), to afford 2-(1-(butylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (24c) (329 mg, white solid). Yield: 98%. MS m/z: 529 [M+1]$^+$.

Step 3: 2-(3-(4-(1H-pyrrolo[2,3-b]pyridin-4-yl)-1H-pyrazol-1-yl)-1-(butylsulfonyl)azetidin-3-yl)acetonitrile (24)

Under cooling with an ice bath, TFA/DCM (1:2, 12 mL) was added to 2-(1-(butylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (24c) (328 mg), and the reaction was performed for 2.5 h. After TLC indicated the reaction was complete, the reaction was concentrated under reduced pressure to obtain a yellow oil, which was directly dissolved in 95% ethanol (20 mL) under cooling with an ice bath. A suitable amount of sodium carbonate was added to adjust the pH to 8, and a large amount of solid precipitated after reaction for 2 h. After TLC indicated the reaction was complete, the reaction was added with water and ethyl acetate to completely dissolve the solid, then extracted with EA, dried over anhydrous sodium sulfate, concentrated under reduced pressure, and purified on a preparative silica gel plate (DCM:EA=1:5), to afford 2-(3-(4-(1H-pyrrolo[2,3-b]pyridin-4-yl)-1H-pyrazol-1-yl)-1-(butylsulfonyl)azetidin-3-yl)acetonitrile (24) (100 mg, white solid), yield: 40%. MS m/z: 399 [M+1]$^+$. $^1$H NMR (DMSO-$d_6$, 400 MHz) δ 11.72 (s, 1H), 8.78 (s, 1H), 8.34 (s, 1H), 8.20 (d, J=4.0 Hz, 1H), 7.53-7.54 (m, 1H), 7.33 (d, J=4.0 Hz, 1H), 6.89-6.90 (m, 1H), 4.58 (d, J=12.0 Hz, 2H), 4.24 (d, J=12.0 Hz, 2H), 3.66 (s, 2H), 3.22-3.26 (m, 2H), 1.63-1.71 (m, 2H), 1.35-1.45 (m, 2H), 0.89 (t, J=8.0 Hz, 3H).

Example 25: 2-(3-(4-(1H-pyrrolo[2,3-b]pyridin-4-yl)-1H-pyrazol-1-yl)-1-(isobutylsulfonyl)azetidin-3-yl)acetonitrile (25)

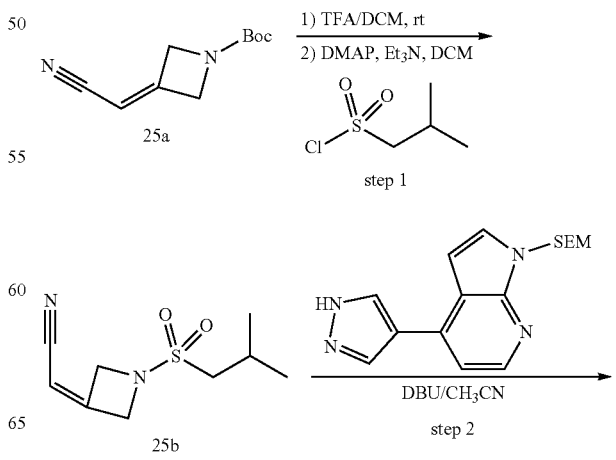

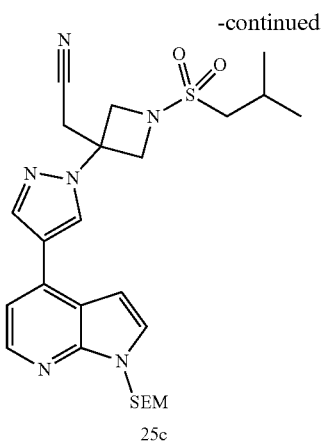

1) TFA/DCM, 0° C.-rt
2) NaCO₃/THF, rt
step 3

25c

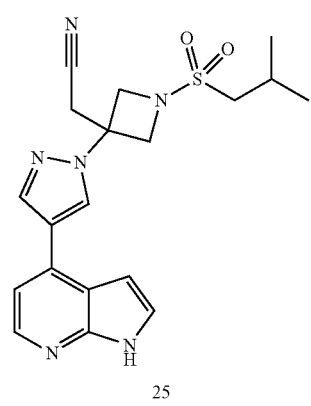

25

Step 1: 2-(1-(isobutylsulfonyl)azetidin-3-ylidene)acetonitrile (25b)

At room temperature, TFA/DCM (1:2, 8 mL) was added to tert-butyl 3-(cyanomethylene)azetidine-1-carboxylate (25a) (583 mg, 3.00 mmol), and the reaction was stirred at room temperature for half an hour. After the reaction was complete, the reaction mixture was concentrated under reduced pressure to obtain a crude product, which was dissolved in DCM (10 mL). Under cooling with an ice bath, triethylamine was slowly dropwise added to adjust the pH of the system to 8, and then DMAP (7 mg, 0.06 mmol) and isobutylsulfonyl chloride (633 mg, 4.5 mmol) were sequentially added. The reaction solution was stirred at room temperature for half an hour. After the reaction was complete, the reaction was quenched with water, extracted with dichloromethane, and the organic phase was washed with water, a solution of citric acid and saturated brine, dried over anhydrous sodium sulfate, and concentrated under reduced pressure, to afford a crude product, 2-(1-(isobutylsulfonyl)azetidin-3-ylidene)acetonitrile (25b) (600 mg, white solid), yield: 93%. MS m/z: 215 [M+1]⁺.

Step 2: 2-(1-(isobutylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (25c)

At room temperature, acetonitrile (10 mL) and DBU (80 mg, 0.53 mmol) were added to a system of 4-(1H-pyrazol-4-yl)-1-((2-(trimethylsilyl)ethoxy)methyl)-1H-pyrrolo[2,3-b]pyridine (150 mg, 0.48 mmol) and 2-(1-(isobutylsulfonyl)azetidin-3-ylidene)acetonitrile (25b) (113 mg, 0.53 mmol), and the reaction solution was stirred at room temperature overnight. After the reaction was complete, the reaction was concentrated, and the residue after concentration was purified by column chromatography, to afford 2-(1-(isobutylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (25c) (242 mg, white solid). Yield: 98%. MS m/z: 529 [M+1]⁺.

Step 3: 2-(3-(4-(1H-pyrrolo[2,3-b]pyridin-4-yl)-1H-pyrazol-1-yl)-1-(isobutylsulfonyl)azetidin-3-yl)acetonitrile (25)

Under cooling with an ice bath, TFA/DCM (1:2, 12 mL) was added to 2-(1-(isobutylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (25c) (242 mg, 0.46 mmol), and the reaction was performed for 2.5 h. After the reaction was complete, the reaction was concentrated under reduced pressure to obtain a crude product as a yellow oil, which was directly dissolved in 95% ethanol (20 mL) under cooling with an ice bath. A suitable amount of sodium carbonate was added to adjust the pH to 8, and the reaction solution was stirred for 2 h. After the reaction was complete, the reaction was added with water and ethyl acetate, and extracted with EA. The organic phase was collected, dried over anhydrous sodium sulfate, filtered, concentrated under reduced pressure, and purified by column chromatography, to afford 2-(3-(4-(1H-pyrrolo[2,3-b]pyridin-4-yl)-1H-pyrazol-1-yl)-1-(isobutylsulfonyl)azetidin-3-yl)acetonitrile (25) (90 mg, white solid), yield: 49%. MS m/z: 399 [M+1]⁺. H NMR (400 MHz, DMSO) δ 11.72 (s, 1H), 8.78 (s, 1H), 8.35 (s, 1H), 8.21 (d, J=5.0 Hz, 1H), 7.56-7.53 (m, 1H), 7.34 (d, J=5.0 Hz, 1H), 6.90 (dd, J=3.5, 1.8 Hz, 1H), 4.58 (d, J=9.2 Hz, 2H), 4.25 (d, J=9.2 Hz, 2H), 3.66 (s, 2H), 3.16 (d, J=6.6 Hz, 2H), 2.20-2.10 (m, 1H), 1.04 (d, J=6.7 Hz, 6H).

Example 26: 2-(3-(4-(1H-pyrrolo[2,3-b]pyridin-4-yl)-1H-pyrazol-1-yl)-1-(cyclopropylsulfonyl)azetidin-3-yl)acetonitrile (26)

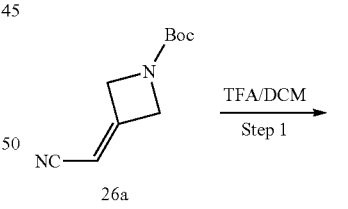

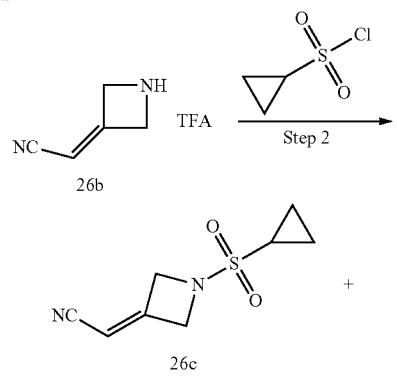

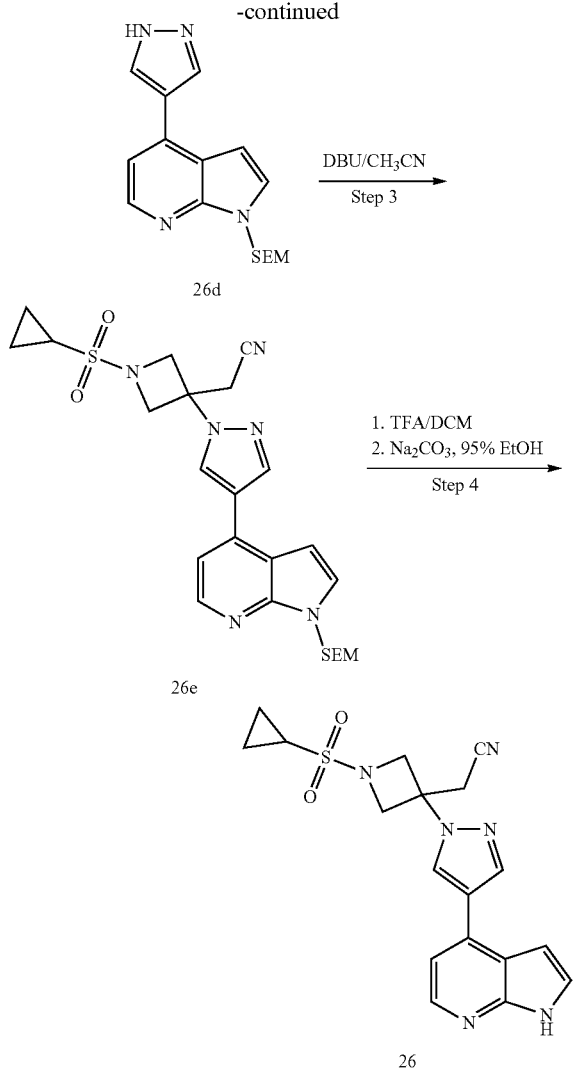

Step 1: 2-(azetidin-3-ylidene)acetonitrile trifluoroacetate salt (26b)

Tert-butyl 3-(cyanomethylene)azetidine-1-carboxylate (26a) (583 mg, 3 mmol) was dissolved in a mixed solution of dichloromethane (18 mL) and trifluoroacetic acid (6 mL), and stirred at room temperature for 30 min. The reaction was rotary evaporated to dryness, to afford a transparent oil, which was used directly in the next step.

Step 2: 2-(1-(cyclopropylsulfonyl)azetidin-3-ylidene)acetonitrile (26c)

Under cooling with an ice bath, the transparent oil obtained in step 1 was dissolved in dichloromethane (10 mL), triethylamine was added until the pH of the system reached 9, followed by addition of a solution of DMAP (8 mg, 0.06 mmol) and cyclopropanesulfonyl chloride (0.44 mL, 3.9 mmol) in dichloromethane (2 mL). The reaction solution was stirred for 30 min. After the reaction was complete, the reaction solution was extracted with ethyl acetate, and the organic phase was washed with an aqueous solution of citric acid, dried over anhydrous sodium sulfate, filtered, and concentrated, to afford 2-(1-(cyclopropylsulfonyl)azetidin-3-ylidene)acetonitrile (26c) (450 mg, white solid, yield: 79%), MS (ESI, m/z): 199 [M+H]$^+$.

Step 3: 2-(1-(cyclopropylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (26e)

4-(1H-pyrazol-4-yl)-1-((2-(trimethylsilyl)ethoxy)methyl)-1H-pyrrolo[2,3-b]pyridine (26d) (200 mg, 0.64 mmol) and 2-(1-(cyclopropylsulfonyl)azetidin-3-ylidene)acetonitrile (26c) (192 mg, 0.96 mmol) were dissolved in acetonitrile (10 mL), the reaction system was added with DBU (0.16 mL), and then stirred at room temperature overnight. After the reaction was complete, the reaction solution was concentrated, and the residue after concentration was purified by column chromatography, to afford 2-(1-(cyclopropylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (26e) (293 mg, milk white oil, yield: 90%). MS (ESI, m/z): 513 [M+H]$^+$.

Step 4: 2-(3-(4-(1H-pyrrolo[2,3-b]pyridin-4-yl)-1H-pyrazol-1-yl)-1-(cyclopropylsulfonyl)azetidin-3-yl)acetonitrile (26)

Under cooling with an ice bath, 2-(1-(cyclopropylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (26e) (293 mg, 0.57 mmol) was dissolved in dichloromethane (6 mL), trifluoroacetic acid (6 mL) was added, and the reaction solution was stirred for 1 h. After the reaction was complete, the pH of the system was adjusted to 9 with an aqueous solution of sodium carbonate, and the reaction was extracted with ethyl acetate. The organic phase was collected, dried, filtered, and concentrated to obtain a solid, which was dissolved in 95% ethanol, and sodium carbonate (907 mg, 8.55 mmol) was then added. The reaction solution was stirred at room temperature overnight, and then purified by column chromatography, to afford 2-(3-(4-(1H-pyrrolo[2,3-b]pyridin-4-yl)-1H-pyrazol-1-yl)-1-(cyclopropylsulfonyl)azetidin-3-yl)acetonitrile (26) (133 mg, white solid, yield: 61%). $^1$H NMR (400 MHz, DMSO-d6) δ: 11.72 (s, 1H), 8.79 (s, 1H), 8.34 (s, 1H), 8.20 (d, 1H, J=4.8 Hz), 7.54 (d, 1H, J=3.6 Hz), 7.34 (d, 1H, J=5.2 Hz), 6.89 (d, 1H, J=3.6 Hz), 4.64 (d, 2H, J=9.2 Hz), 4.28 (d, 2H, J=9.2 Hz), 3.67 (s, 2H), 2.88-2.81 (m, 1H), 1.07-1.02 (m, 2H), 1.01-0.97 (m, 2H). MS (ESI, m/z): 383 [M+H]$^+$.

Example 27: 4-(1-(3-(cyanomethyl)-1-(phenylsulfonyl)azetidin-3-yl)-1H-pyrazol-4-yl)-1H-pyrrolo[2,3-b]pyridine-5-carbonitrile (27)

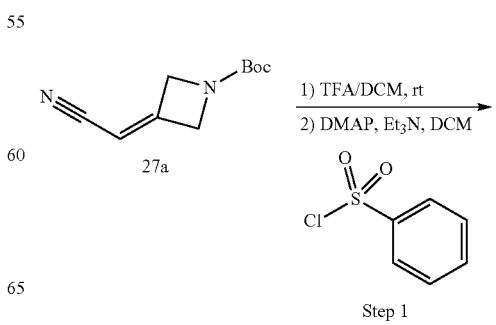

Step 1

-continued

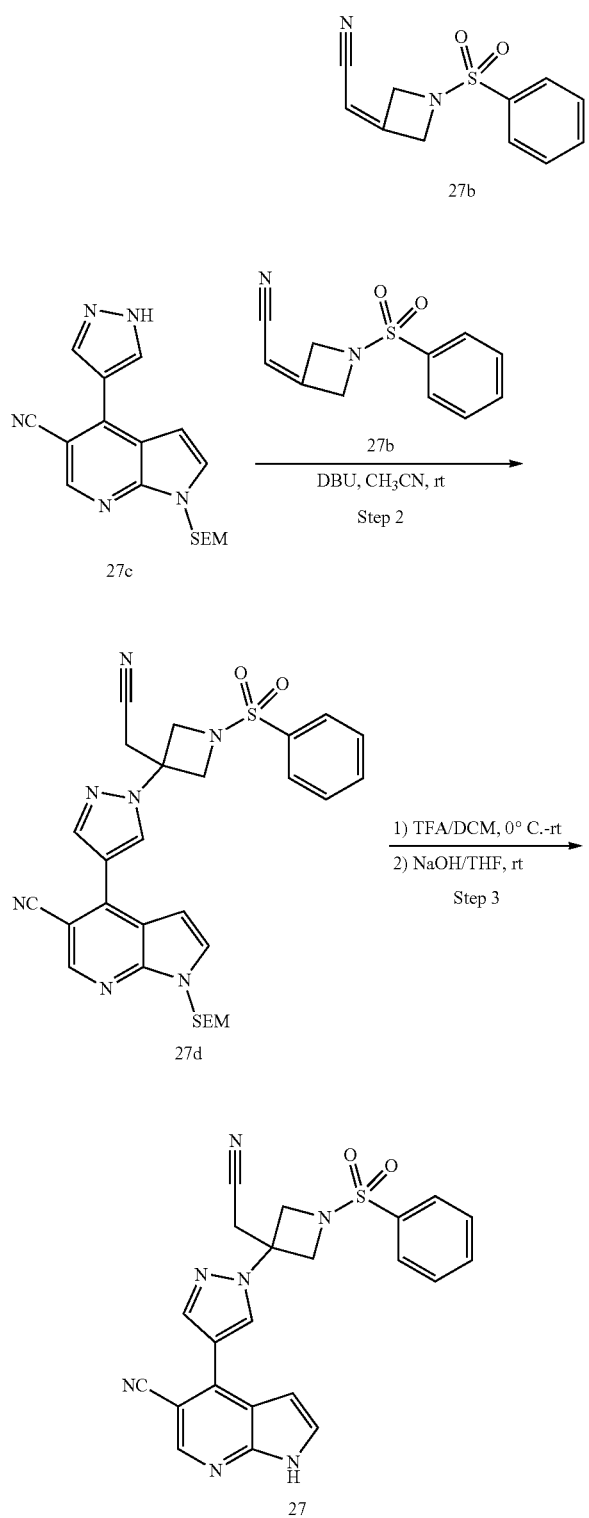

Step 1: 2-(1-(phenylsulfonyl)azetidin-3-ylidene)acetonitrile (27b)

Tert-butyl 3-(cyanomethylene)azetidine-1-carboxylate (27a) (583 mg, 3.00 mmol) and TFA/DCM (1:3, 8 mL) were added to a reaction flask, and the reaction was stirred at room temperature for half an hour. After the reaction was complete, the reaction mixture was concentrated under reduced pressure to obtain a crude product, which was then dissolved in DCM (10 mL). Under cooling with an ice bath, triethylamine was slowly dropwise added to adjust the pH of the system to about 8, and then DMAP (7 mg, 0.06 mmol) and benzenesulfonyl chloride (795 mg, 4.5 mmol) were sequentially added. The reaction was stirred at room temperature for half an hour. After the reaction was complete, the reaction was quenched with water, extracted with dichloromethane, and the organic phase was collected, washed with water, a solution of citric acid and saturated brine, dried over anhydrous sodium sulfate, filtered, and concentrated under reduced pressure, to afford 2-(1-(phenylsulfonyl)azetidin-3-ylidene)acetonitrile (27b) (650 mg, yield: 90%, brown solid). MS (ESI, m/z): 235 [M+H]$^+$.

Step 2: 4-(1-(3-(cyanomethyl)-1-(phenylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (27d)

At room temperature, 2-(1-(phenylsulfonyl)azetidin-3-ylidene)acetonitrile (27b) (114 mg, 0.48 mmol), 4-(1H-pyrazol-4-yl)-5-cyano-1-((2-(trimethylsilyl)ethoxy)methyl)-1H-pyrrolo[2,3-b]pyridine (27c) (150 mg, 0.44 mmol) and acetonitrile (8 mL) were added to a reaction flask, DBU (73 mg, 0.48 mmol) was added, and the reaction was stirred for 2 h. After the reaction was complete, the reaction was quenched with water, extracted with ethyl acetate. The organic phase was collected, dried over anhydrous sodium sulfate, filtered, and concentrated under reduced pressure. The residue obtained after the concentration was purified by column chromatography, to afford 4-(1-(3-(cyanomethyl)-1-(phenylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (27d) (223 mg, yield: 89%, white solid). MS (ESI, m/z): 574 [M+H]$^+$.

Step 3: 4-(1-(3-(cyanomethyl)-1-(phenylsulfonyl)azetidin-3-yl)-1H-pyrazol-4-yl)-1H-pyrrolo[2,3-b]pyridine-5-carbonitrile (27)

Under cooling with an ice bath, 2-(1-(phenylsulfonyl)-3-(5-cyano-4-(1-((2-(trimethylsilyl)ethoxy)methyl)-1H-pyrrolo[2,3-b]pyridin-4-yl)-1H-pyrazol-1-yl)azetidin-3-yl)acetonitrile (27d) (223 mg, 0.39 mmol) and a mixture of TFA/DCM (1:1, 6 mL) were added to a reaction flask, argon atmosphere protection was applied, and the reaction was stirred for 2.5 h. After the reaction was complete, the reaction was concentrated under reduced pressure to obtain a crude product as a yellow oil, which was then dissolved in tetrahydrofuran (10 mL), and stirred until homogenous. A 1M solution of sodium hydroxide was added to adjust the pH of the system to 10, and the reaction solution was stirred for 0.5 h. After the reaction was complete, the reaction was extracted with ethyl acetate. The organic phase was collected, dried over anhydrous sodium sulfate, filtered, and concentrated under reduced pressure. The residue obtained after the concentration was purified by column chromatography, to afford the target product, 4-(1-(3-(cyanomethyl)-1-(phenylsulfonyl)azetidin-3-yl)-1H-pyrazol-4-yl)-1H-pyrrolo[2,3-b]pyridine-5-carbonitrile (27) (100 mg, yield: 58%, white solid). $^1$H NMR (400 MHz, DMSO) δ 12.40 (s, 1H), 8.61 (s, 1H), 8.53 (s, 1H), 8.10 (s, 1H), 7.89-7.82 (m, 2H), 7.76 (d, J=3.5 Hz, 1H), 7.70-7.56 (m, 3H), 6.75 (d, J=3.5 Hz, 1H), 4.40 (d, J=9.8 Hz, 2H), 4.25 (d, J=9.8 Hz, 2H), 3.54 (s, 2H). MS (ESI, m/z): 444 [M+H]$^+$.

Example 28: 2-(3-(3-(1H-pyrrolo[2,3-b]pyridin-4-yl)-1H-pyrrol-1-yl)-1-(ethylsulfonyl)azetidin-3-yl)acetonitrile (28)

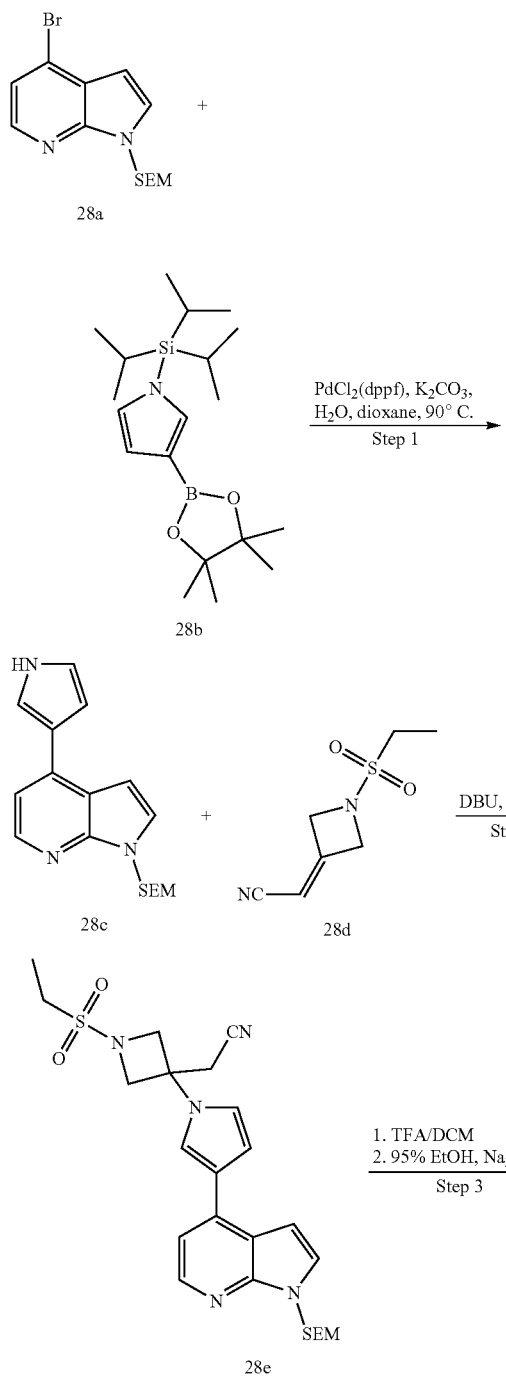

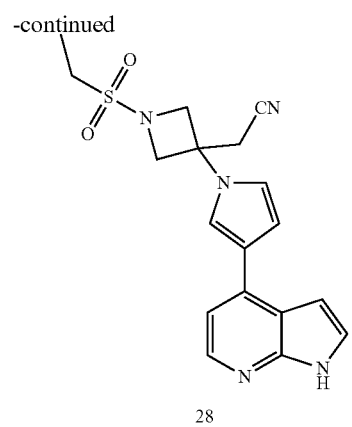

Step 1: 4-(1H-pyrrol-3-yl)-1-((2-(trimethylsilyl)ethoxy)methyl)-1H-pyrrolo[2,3-b]pyridine (28c)

4-bromo-1-((2-(trimethylsilyl)ethoxy)methyl)-1H-pyrrolo[2,3-b]pyridine (28a) (326 mg, 1 mmol), 3-(4,4,5,5-tetramethyl-1,3,2-dioxaborolan-2-yl)-1-(triisopropylsilyl)-1H-pyrrole (28b) (524 mg, 1.5 mmol), Pd(dppf)Cl$_2$ (74 mg, 0.1 mmol) and potassium carbonate (346 mg, 2.5 mmol) were placed in a reaction flask, dioxane (10 mL) and water (2 mL) were added, and the reaction solution was heated to 90° C. and stirred 22 h after argon atmosphere protection was applied. After the reaction was complete, the reaction solution was filtered with suction, and the filtrate was concentrated and purified by column chromatography, to afford 4-(1-(triisopropylsilyl)-1H-pyrrol-3-yl)-1-((2-(2-(trimethylsilyl)ethoxy)methyl)-1H-pyrrolo[2,3-b]pyridine and 4-(1H-pyrrol-3-yl)-1-((2-(trimethylsilyl)ethoxy)methyl)-1H-pyrrolo[2,3-b]pyridine (28c), respectively. Deprotection of the silyl protecting group in 4-(1-(triisopropylsilyl)-1H-pyrrol-3-yl)-1-((2-(2-(trimethylsilyl)ethoxy)methyl)-1H-pyrrolo[2,3-b]pyridine was performed in a 1M solution of tetrabutylammonium fluoride in tetrahydrofuran, to afford 4-(1H-pyrrol-3-yl)-1-((2-(trimethylsilyl)ethoxy)methyl)-1H-pyrrolo[2,3-b]pyridine (28c) (283 mg in total, white solid), yield: 90%, MS (ESI, m/z): 314 [M+H]$^+$.

Step 2: 2-(1-(ethylsulfonyl)-3-(3-(1-((2-(trimethylsilyl)ethoxy)methyl)-1H-pyrrolo[2,3-b]pyridin-4-yl)-1H-pyrrol-1-yl)azetidin-3-yl)acetonitrile (28e)

4-(1H-pyrrol-3-yl)-1-((2-(trimethylsilyl)ethoxy)methyl)-1H-pyrrolo[2,3-b]pyridine (28c) (283 mg, 0.9 mmol) and 2-(1-(ethylsulfonyl)azetidin-3-ylidene)acetonitrile (28d) (183 mg, 0.99 mmol) were dissolved in acetonitrile (10 mL), the reaction system was added with DBU (0.3 mL), and then stirred at room temperature overnight. The reaction solution was concentrated, and purified by column chromatography, to afford 2-(1-(ethylsulfonyl)-3-(3-(1-((2-(trimethylsilyl)ethoxy)methyl)-1H-pyrrolo[2,3-b]pyridin-4-yl)-1H-pyrrol-1-yl)azetidin-3-yl)acetonitrile (28e) (240 mg, milk white oil, yield: 53%). MS (ESI, m/z): 500 [M+H]$^+$.

Step 3: 2-(3-(3-(1H-pyrrolo[2,3-b]pyridin-4-yl)-1H-pyrrol-1-yl)-1-(ethylsulfonyl)azetidin-3-yl)acetonitrile (28)

Under cooling with an ice bath, 2-(1-(ethylsulfonyl)-3-(3-(1-((2-(trimethylsilyl)ethoxy)methyl)-1H-pyrrolo[2,3-b]

pyridin-4-yl)-1H-pyrrol-1-yl)azetidin-3-yl)acetonitrile (28e) (240 mg, 0.48 mmol) was dissolved in dichloromethane (5 mL), trifluoroacetic acid (5 mL) was added, and the reaction solution was stirred for 1 h. After the reaction was complete, an aqueous solution of $Na_2CO_3$ was added to adjust the pH to 9, and the reaction was extracted with ethyl acetate. The organic phase was collected and rotary evaporated to dryness to obtain a light yellow solid, which was dissolved in 95% ethanol, and added with sodium carbonate (763 mg, 7.2 mmol). The reaction was stirred at room temperature. After the reaction was complete, it was concentrated, and purified by column chromatography, to afford 2-(3-(3-(1H-pyrrolo[2,3-b]pyridin-4-yl)-1H-pyrrol-1-yl)-1-(ethylsulfonyl)azetidin-3-yl)acetonitrile (28) (83 mg, light yellow solid, yield: 46%.). $^1$H NMR (400 MHz, DMSO-$d_6$) δ: 11.56 (s, 1H), 8.13 (d, 1H, J=5.2 Hz), 7.70 (s, 1H), 7.45 (t, 1H, J=2.8 Hz), 7.20 (d, 1H, J=4.8 Hz), 7.16 (t, 1H, J=2.4 Hz), 6.84-6.83 (m, 1H), 6.78-6.77 (m, 1H), 4.44 (d, 2H, J=9.2 Hz), 4.20 (d, 2H, J=8.8 Hz), 3.56 (s, 2H), 3.22 (q, 2H, J=7.2 Hz), 1.23 (t, 3H, J=7.2 Hz). MS (ESI, m/z): 370 [M+H]$^+$.

Example 29: 4-(1-(1-(ethylsulfonyl)-3-(fluoromethyl)azetidin-3-yl)-1H-pyrazol-4-yl)-1H-pyrrolo[2,3-b]pyridine-5-carbonitrile (29)

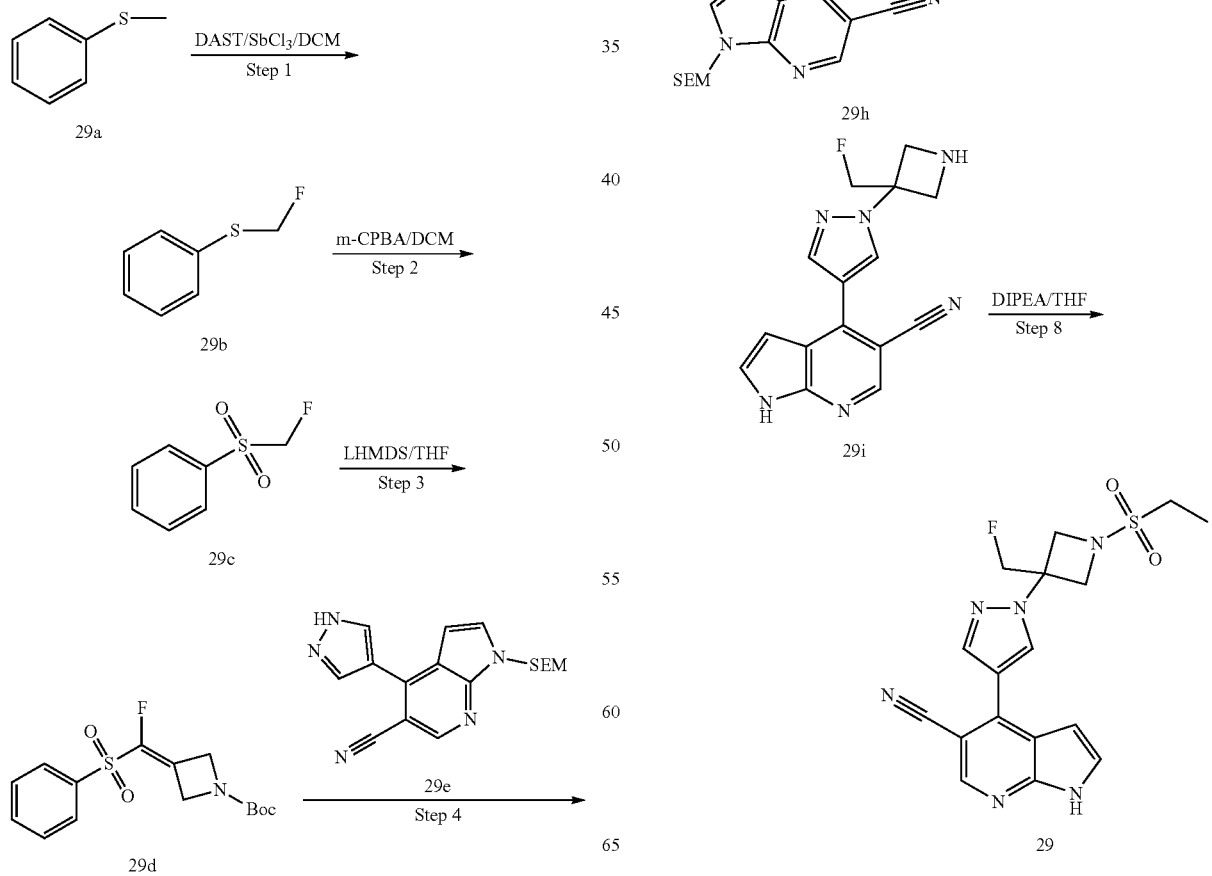

Step 1: fluoromethylphenylsulfane (29b)

Under cooling with an ice-water bath, DCM (50 mL), trichlorostibane (0.9 g), methyl(phenyl)sulfane (29a) (5.0 mL) and DAST (13.0 g) were sequentially added to a reaction flask, and the reaction solution was stirred for 6 h. After the reaction was complete, the reaction solution was concentrated, and the residue obtained after the concentration was purified by flash column chromatography, to afford a yellow oil (4.6 g), purity: 94%, yield: 80%. MS (ESI, m/z): 143 [M+H]$^+$.

Step 2: fluoromethylphenylsulphone (29c)

Under cooling with an ice-water bath, fluoromethylphenylsulfane (29b) (4.0 g) obtained in step 1 was dissolved in DCM (160 mL), 3-chloroperbenzoic acid (16.5 g) was added in portions, and the reaction solution was stirred overnight. After the reaction was complete, a 10% potassium carbonate solution (100 mL) and DCM (100 mL) were added, and the reaction was filtered through Celite, and extracted with DCM. The organic phase was combined, washed with saturated NaCl, dried over anhydrous sodium sulfate, filtered, and concentrated. The residue obtained after the concentration was purified by column chromatography, to afford a colorless oil (3.3 g), purity: 91%, yield: 67%. MS (ESI, m/z): 175 [M+H]$^+$.

Step 3: tert-butyl 3-(fluoro(phenylsulfonyl)methylene)azetidine-1-carboxylate (29d)

Under protection of nitrogen, THF (10 mL), fluoromethylphenylsulphone (29c) (0.5 g), and diethyl chlorophosphate (0.5 g) were added to a reaction flask. The reaction system was cooled to −78° C., LHMDS (6.2 mL) was added dropwise, and the reaction was performed for 1 h while keeping the temperature of the system below −78° C. Tert-butyl 3-oxoazetidine-1-carboxylate (0.378 g) was dissolved in THF (2 mL), and was then added dropwise to the reaction system. The reaction solution was warmed to room temperature, and allowed to proceed for 2 h. After the reaction was complete, the reaction solution was poured into a saturated ammonium chloride solution (50 mL), and extracted with EA. The organic phase was combined, washed with saturated brine, dried over anhydrous sodium sulfate, and filtered. The filtrate was concentrated, and the residue obtained after the concentration was purified by column chromatography, to afford tert-butyl 3-(fluoro(phenylsulfonyl)methylene)azetidine-1-carboxylate (29d) (colorless oil, 565 mg), purity: 91.6%. MS (ESI, m/z): 328 [M+H]$^+$.

Step 4: tert-butyl 3-(4-(5-cyano-1-((2-(trimethylsilyl)ethoxy)methyl)-1H-pyrrolo[2,3-b]pyridin-4-yl)-1H-pyrazol-1-yl)-3-(fluoro(phenylsulfonyl)methyl)azetidine-1-carboxylate (29f)

Acetonitrile (6 mL), tert-butyl 3-(fluoro(phenylsulfonyl)methylene)azetidine-1-carboxylate (29d) (550 mg), 4-(1H-pyrazol-4-yl)-1-((2-(trimethylsilyl)ethoxy)methyl)-1H-pyrrolo[2,3-b]pyridine-5-carbonitrile (29e) (439 mg), and DBU (196 mg) were added to a reaction flask, and the reaction was stirred for 2.5 h. After the reaction was complete, the reaction solution was concentrated, and the residue obtained after the concentration was purified by column chromatography, to afford the title product (29f) (off-white solid, 730 mg, purity: 95%, yield: 85%). MS (ESI, m/z): 667 [M+H]$^+$.

Step 5: tert-butyl 3-(4-(5-cyano-1-((2-(trimethylsilyl)ethoxy)methyl)-1H-pyrrolo[2,3-b]pyridin-4-yl)-1H-pyrazol-1-yl)-3-(fluoromethyl)azetidine-1-carboxylate (29g)

Under protection of nitrogen, tert-butyl 3-(4-(5-cyano-1-((2-(trimethylsilyl)ethoxy)methyl)-1H-pyrrolo[2,3-b]pyridin-4-yl)-1H-pyrazol-1-yl)-3-(fluoro(phenylsulfonyl)methyl)azetidine-1-carboxylate (29f) (500 mg), methanol (12.5 mL) and anhydrous disodium hydrogen phosphate (2.13 g) were added to a reaction flask. The system was cooled to −20° C., sodium amalgam (3.35 g) was added, and the system was stirred for 1.5 h while keeping the reaction temperature between −20° C.–0° C. After the reaction was complete, the reaction system was added with EA (100 mL), filtered through Celite, and the filtrate was poured into a saturated solution of ammonium chloride (150 mL). The organic phase was separated, washed with saturated brine, dried over anhydrous sodium sulfate, filtered, concentrated, and purified on a preparative TLC plate, to afford the title product (29g, 61 mg, yellow solid, yield: 15%). MS (ESI, m/z): 527 [M+H]$^+$.

Step 6: 4-(1-(3-(fluoromethyl)azetidin-3-yl)-1H-pyrazol-4-yl)-1-((2-(trimethylsilyl)ethoxy)methyl)-1H-pyrrolo[2,3-b]pyridine-5-carbonitrile hydrochloride salt (29h)

Tert-butyl 3-(4-(5-cyano-1-((2-(trimethylsilyl)ethoxy)methyl)-1H-pyrrolo[2,3-b]pyridin-4-yl)-1H-pyrazol-1-yl)-3-(fluoromethyl)azetidine-1-carboxylate (29g) (20 mg), 1,4-dioxane (2 mL), and 1,4-dioxane/HCl (1 mL) were added to a reaction flask, and the reaction solution was stirred at room temperature for 1 h. Then the reaction solution was concentrated to remove the solvent to obtain a crude product, which was used directly in the next step. MS (ESI, m/z): 427 [M+H]$^+$.

Step 7: 4-(1-(3-(fluoromethyl)azetidin-3-yl)-1H-pyrazol-4-yl)-1H-pyrrolo[2,3-b]pyridine-5-carbonitrile (29i)

The crude product obtained in step 6, DCM (4 mL) and TFA (1.5 mL) were added to a reaction flask, and the reaction solution was stirred for 1.5 h. After the reaction was complete, the reaction solution was concentrated, the residue was added with aqueous ammonia to adjust the pH to 9-10, and stirred for 2 h. 2N HCl was then added to adjust the pH to 1-2. The solution was extracted with DCM to remove impurities. The aqueous phase was added with a solution of sodium carbonate to adjust the pH to 9-10, and extracted with DCM. The organic phase was combined, dried over sodium sulfate, filtered, and the filtrate was concentrated to obtain the title product (29i, 6 mg), which was used directly in the next step. MS (ESI, m/z): 297 [M+H]$^+$.

Step 8: 4-(1-(1-(ethylsulfonyl)-3-(fluoromethyl)azetidin-3-yl)-1H-pyrazol-4-yl)-1H-pyrrolo[2,3-b]pyridine-5-carbonitrile (29)

At room temperature, THF (3 mL), 29i (6 mg), DIPEA (13 mg), and ethanesulfonyl chloride (9 mg) were added to a reaction flask, and the reaction solution was stirred for 1 h. After the reaction was complete, the reaction solution was concentrated, and purified on a preparative TLC plate to afford the title compound as a yellow solid (7 mg).

$^1$H NMR (400 MHz, CDCl3) δ: 9.69 (s, 1H), 8.58 (s, 1H), 8.30 (s, 1H), 8.23 (s, 1H), 7.48 (s, 1H), 6.76 (s, 1H), 5.06 (s, 1H), 4.94 (s, 1H), 4.64 (d, J=9.76 Hz, 2H), 4.28 (d, J=9.00 Hz, 2H), 3.08-3.14 (m, 2H), 1.41-1.45 (t, J=7.08 Hz, 3H). MS (ESI, m/z): 389 [M+H]$^+$.

Example 30: 2-(3-(4-(1H-pyrrolo[2,3-b]pyridin-4-yl)-1H-pyrazol-1-yl)-1-((3,3,3-trifluoropropyl)sulfonyl)azetidin-3-yl)acetonitrile (30)

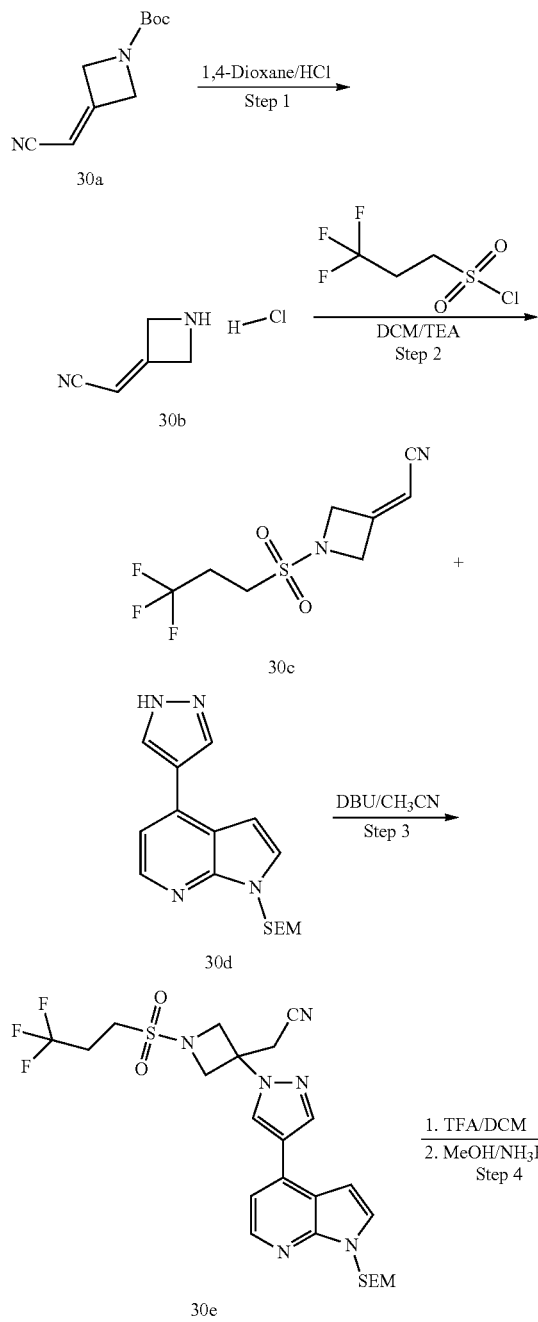

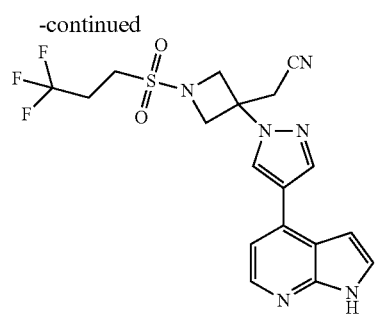

Step 1: 2-(azetidin-3-ylidene)acetonitrile hydrochloride salt (30b)

In an ice-water bath, tert-butyl 3-(cyanomethylene)azetidine-1-carboxylate (2.0 g) and 1,4-dioxane/HCl (20 mL) were added to a reaction flask, the reaction solution was warmed to room temperature, and stirred for 2 h. After the reaction was complete, the reaction solution was filtrated, the filter cake was washed with methyl tert-butyl ether, and dried, to afford 2-(azetidin-3-ylidene)acetonitrile hydrochloride salt (30b) as a white solid, (1.11 g, yield: 82.4%). MS (ESI, m/z): 95 [M+H]$^+$.

Step 2: 2-(1-((3,3,3-trifluoropropyl)sulfonyl)azetidin-3-ylidene)acetonitrile (30c)

In an ice-water bath, the white solid obtained in step 1 (30b) (500 mg) was added to dichloromethane (20 mL), a solution of (3,3,3-trifluoropropane)sulfonyl chloride (1.126 g) and TEA (1.16 g) in DCM (15 mL) was added, and the reaction solution was stirred for 5 h. After the reaction was complete, the reaction was added with water (10 mL), and stirred for 10 min. The organic phase was separated, concentrated, and the residue was used directly in the next reaction. MS (ESI, m/z): 255 [M+H]$^+$.

Step 3: 2-(1-(3,3,3-trifluoropropyl)sulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (30e)

4-(1H-pyrazol-4-yl)-1-((2-(trimethylsilyl)ethoxy)methyl)-1H-pyrrolo[2,3-b]pyridine (30d) (600 mg), 2-(1-((3,3,3-trifluoropropyl)sulfonyl)azetidin-3-ylidene)acetonitrile (30c) (485 mg, crude) were dissolved in acetonitrile (50 mL), the reaction system was added with DBU (1 mL), and then stirred at room temperature overnight. After the reaction was complete, the reaction solution was concentrated, and the residue obtained after the concentration was purified by column chromatography, to afford 2-(1-(3,3,3-trifluoropropyl)sulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (30e), yellow solid, 165 mg. MS (ESI, m/z): 569 [M+H]$^+$.

Step 4: 2-(3-(4-(1H-pyrrolo[2,3-b]pyridin-4-yl)-1H-pyrazol-1-yl)-1-(3,3,3-trifluoropropylsulfonyl)azetidin-3-yl)acetonitrile (30)

Under cooling with an ice bath, 2-(1-(3,3,3-trifluoropropyl)sulfonyl)-3-(4-(1-((2-(trimethylsilyl)ethoxy)methyl)-

1H-pyrrolo[2,3-b]pyridin-4-yl)-1H-pyrazol-1-yl)azetidin-3-yl)acetonitrile (30e) (120 mg) was dissolved in dichloromethane (8 mL), trifluoroacetic acid (4.8 mL) was added, and the reaction solution was stirred for 3 h. After the reaction was complete, the pH of the system was adjusted to 10 with an aqueous ammonia, and the reaction was stirred overnight. The reaction solution was extracted with DCM/MeOH=10:1, the organic phase was combined, dried over anhydrous sodium sulfate, filtered, concentrated, and purified on a preparative TLC plate, to afford 2-(3-(4-(1H-pyrrolo[2,3-b]pyridin-4-yl)-1H-pyrazol-1-yl)-1-(3,3,3-trifluoropropylsulfonyl)azetidin-3-yl)acetonitrile (30) (70 mg, light yellow solid, yield: 60.5%), $^1$H NMR (400 MHz, CDCl$_3$) δ 9.34 (s, 1H), 8.31 (d, J=5.24 Hz, 1H), 8.11 (d, J=3.72 Hz, 2H), 7.39 (d, J=2.84 Hz, 1H), 7.18 (d, J=5.04 Hz, 1H), 6.70 (d, J=3.56 Hz, 1H), 4.71 (d, J=9.52 Hz, 2H), 4.30 (d, J=9.20 Hz, 2H), 3.39 (s, 2H), 3.29 (m, 2H), 2.68 (m, 2H). MS (ESI, m/z): 439 [M+H]$^+$.

Example 31: 2-(3-(4-(1H-pyrrolo[2,3-b]pyridin-4-yl)-1H-pyrazol-1-yl)-1-((1-methylcyclopropyl)sulfonyl)azetidin-3-yl)acetonitrile (31)

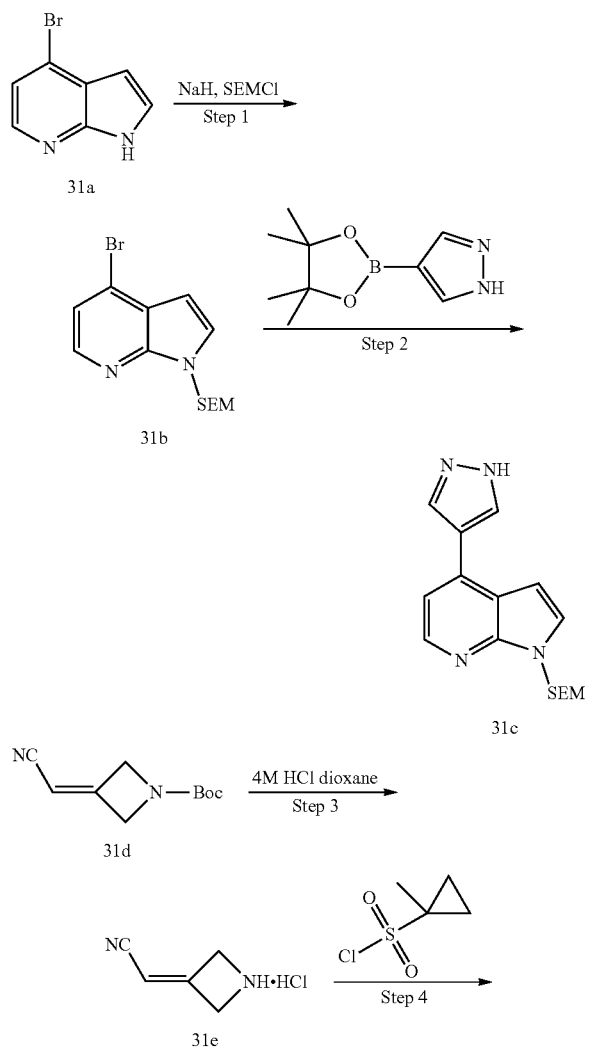

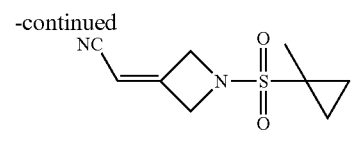

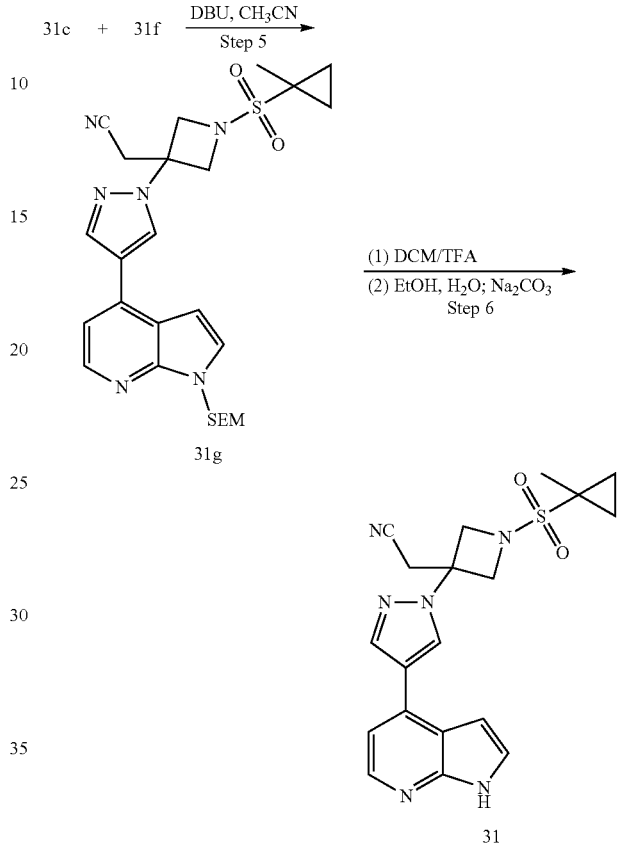

Step 1: 4-bromo-1-((2-(trimethylsilyl)ethoxy)methyl)-1H-pyrrolo[2,3-b]pyridine (31b)

Under cooling with an ice-salt bath, 4-bromo-7-azaindole (31a) (10 g, 50.7 mmol) and DMF (100 mL) were added to a reaction flask, sodium hydride (60%, 2.64 g, 54.4 mmol) and [2-(trimethylsilyl)ethoxy]methyl chloride were added in portions after argon atmosphere protection was applied, and the reaction solution was stirred for 1 h. After the reaction was complete, the reaction was quenched with water, and extracted with ethyl acetate. The organic phase was collected, dried over anhydrous sodium sulfate, filtered, concentrated under reduced pressure, and the residue obtained after the concentration was purified by column chromatography, to afford compound 4-bromo-1-((2-(trimethylsilyl)ethoxy)methyl)-1H-pyrrolo[2,3-b]pyridine (31b) (14.57 g, yield: 88.0%, yellow oil). MS (ESI, m/z): 326.1 [M+H]$^+$.

Step 2: 4-(1H-pyrazol-4-yl)-1-((2-(trimethylsilyl)ethoxy)methyl)-1H-pyrrolo[2,3-b]pyridine (31c)

Compound 31b (4 g, 12.3 mmol), 4-pyrazoleboronic acid pinacol ester (3.86 g, 19.9 mmol) and 1,4-dioxane (300 mL) were sequentially added to a reaction flask, a potassium carbonate (4.58 g, 33.1 mmol) solution (60 mL) and Pd(dppf)Cl$_2$ (0.97 g, 1.33 mmol) were added, and the reaction solution was heated to 95° C. and stirred overnight after argon atmosphere protection was applied. After the reaction was complete, the reaction was quenched with water, and extracted with ethyl acetate. The organic phase was collected, dried over anhydrous sodium sulfate, filtered, concentrated under reduced pressure, and the residue obtained after the concentration was purified by column chromatography, to afford compound 4-(1H-pyrazol-4-yl)-1-((2-(trimethylsilyl)ethoxy)methyl)-1H-pyrrolo[2,3-b]pyridine (31c) (1.67 g, yield: 43.5%, yellow solid). MS (ESI, m/z): 314.2 [M+H]$^+$.

Step 3: 2-(azetidin-3-ylidene)acetonitrile hydrochloride salt (31e)

In an ice bath, compound 31d (1.0 g, 5.15 mmol) and a 4M solution of HCl in dioxane (10 mL) were added to a reaction flask, and the reaction was stirred for 2.5 h after argon atmosphere protection was applied. After the reaction was complete, the reaction solution was filtrated, and the filter cake was washed with anhydrous ether and dried, to afford 2-(azetidin-3-ylidene)acetonitrile hydrochloride salt (31e) (600 mg, yield: 90.0%, white solid), which was used directly in the next step.

Step 4: 2-(1-((1-methylcyclopropyl)sulfonyl)azetidin-3-ylidene)acetonitrile (31f)

Under cooling with an ice bath, compound 31e (200 mg, 1.54 mmol), dichloromethane (10 mL), triethylamine (1.3 mL, 9.24 mmol) and DMAP (3.8 mg, 0.03 mmol) were added to a reaction flask, a solution of 1-methylcyclopropane-1-sulfonyl chloride (357 mg, 2.31 mmol) in dichloromethane (10 mL) was slowly added dropwise, and the reaction solution was stirred for 1 h. After the reaction was complete, the reaction was quenched with water, and extracted with dichloromethane. The organic phase was collected, washed with water, a solution of citric acid and saturated brine, dried over anhydrous sodium sulfate, filtered, and concentrated under reduced pressure, to afford 2-(1-((1-methylcyclopropyl)sulfonyl)azetidin-3-ylidene)acetonitrile (31f) (272 mg, yield: 83.4%, brown solid). MS (ESI, m/z): 213.1 [M+H]$^+$.

Step 5: 2-(1-((1-methylcyclopropyl)sulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (31g)

Compound 31f (140 mg, 0.66 mmol), compound 31c (197 mg, 0.63 mmol) and acetonitrile (20 mL) were added to a reaction flask, DBU (115 mg, 0.76 mmol) was added, and the reaction solution was stirred at room temperature for 1 h. After the reaction was complete, the reaction solution was quenched with water, concentrated under reduced pressure, and the residue obtained after the concentration was purified by column chromatography, to afford 2-(1-((1-methylcyclopropyl)sulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (31g) (233 mg, yield: 70.4%, yellow foamy solid). MS (ESI, m/z): 526.2 [M+H]$^+$.

Step 6: 2-(3-(4-(1H-pyrrolo[2,3-b]pyridin-4-yl)-1H-pyrazol-1-yl)-1-((1-methylcyclopropyl)sulfonyl)azetidin-3-yl)acetonitrile (31)

At room temperature, compound 31g (233 mg, 0.44 mmol) and a mixture of TFA/DCM (V:V=1:2) (11.2 mL) were added to a reaction flask, argon atmosphere protection was applied, and the reaction was stirred at room temperature for 1.5 h. After the reaction was complete, the reaction solution was quenched with water, and extracted with dichloromethane. The organic phase was collected, dried over anhydrous sodium sulfate, filtered, concentrated under reduced pressure, and the residue obtained after the concentration was purified by column chromatography, to afford a hydroxymethyl intermediate (145 mg), which was then placed in a reaction flask. Absolute ethyl alcohol (35 mL), distilled water (4 mL) and anhydrous sodium carbonate (721 mg, 6.8 mmol) were sequentially added, the pH was adjusted to 9, and the reaction was stirred at room temperature overnight. The reaction solution was filtered with suction, the filter cake was washed with water, and dried to obtain a crude product, which was purified by column chromatography, to afford 2-(3-(4-(1H-pyrrolo[2,3-b]pyridin-4-yl)-1H-pyrazol-1-yl)-1-((1-methylcyclopropyl)sulfonyl)azetidin-3-yl)acetonitrile (31) (70 mg, yield: 40.1%, off-white solid). $^1$H NMR (400 MHz, DMSO-d$_6$) δ: 11.70 (s, 1H), 8.76 (s, 1H), 8.33 (s, 1H), 8.19 (d, J=5.00 Hz, 1H), 7.52 (t, J=2.84 Hz, 1H), 7.32 (d, J=5.00 Hz, 1H), 6.88 (dd, J$_1$=3.64 Hz, J$_2$=1.88 Hz, 1H), 4.56 (d, J=8.80 Hz, 2H), 4.20 (d, J=8.84 Hz, 2H), 3.66 (s, 2H), 1.45 (s, 3H), 1.18 (t, 2H), 0.89 (t, 2H). MS (ESI, m/z): 396.1 [M+H]$^+$.

Example 32: 2-(3-(4-(1H-pyrrolo[2,3-b]pyridin-4-yl)-1H-pyrazol-1-yl)-1-(tert-butylsulfonyl)azetidin-3-yl)acetonitrile (32)

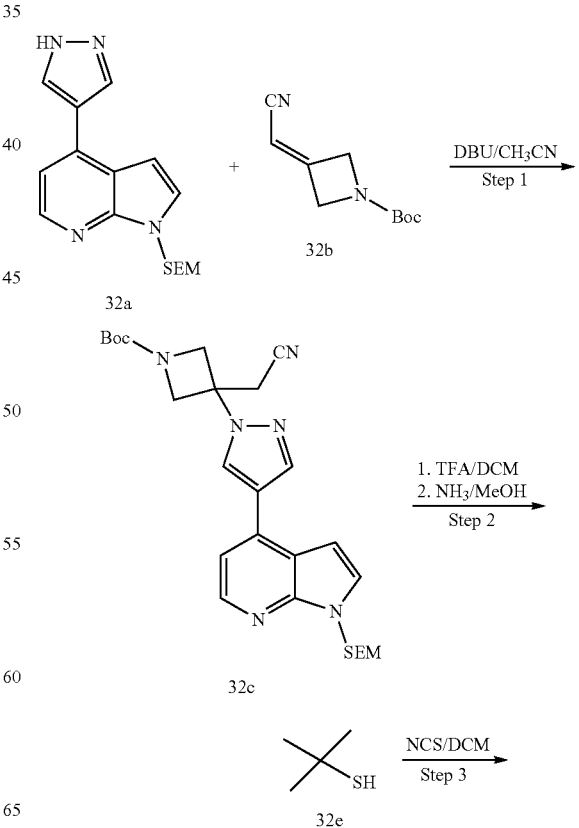

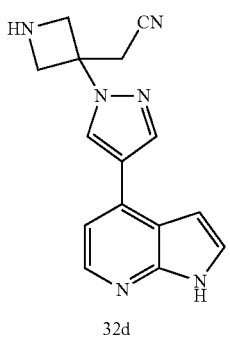

32d

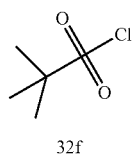

32f

Et₃N/Dioxane
Step 4

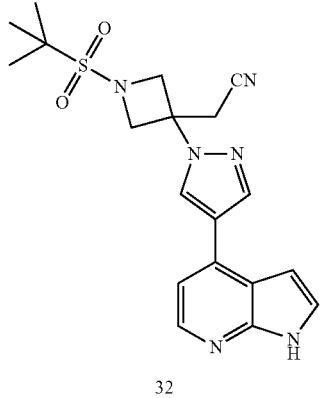

32

Step 1: tert-butyl 3-(cyanomethyl)-3-(4-(1-((2-(trimethylsilyl)ethoxy)methyl)-1H-pyrrolo[2,3-b]pyridin-4-yl)-1H-pyrazol-1-yl)azetidine-1-carboxylate (32c)

At room temperature, 4-(1H-pyrazol-4-yl)-1-((2-(trimethylsilyl)ethoxy)methyl)-1H-pyrrolo[2,3-b]pyridine (32a) (500 mg, 1.6 mmol), tert-butyl 3-(cyanomethylene)azetidine-1-carboxylate (32b) (464 mg, 2.38 mmol) were dissolved in acetonitrile (15 mL), the reaction solution was added with DBU (0.4 mL), and then stirred overnight. After the reaction was complete, the reaction solution was concentrated, and the residue obtained after concentration was purified by column chromatography, to afford tert-butyl 3-(cyanomethyl)-3-(4-(1-((2-(trimethylsilyl)ethoxy)methyl)-1H-pyrrolo[2,3-b]pyridin-4-yl)-1H-pyrazol-1-yl)azetidine-1-carboxylate (32c) (680 mg, light yellow oil, yield: 84%). MS (ESI, m/z): 509 [M+H]⁺.

Step 2: 2-(3-(4-(1H-pyrrolo[2,3-b]pyridin-4-yl)-1H-pyrazol-1-yl)azetidin-3-yl)acetonitrile (32d)

Under cooling with an ice bath, the oil obtained in step 1 was dissolved in dichloromethane (14 mL), trifluoroacetic acid (14 mL) was added, and the reaction solution was warmed to room temperature, and stirred for 1 h. After the reaction was complete, the reaction was added with ice water (20 mL), extracted with dichloromethane, and the pH of the aqueous phase was adjusted to 10 with aqueous ammonia. After the solution was stirred overnight, it was extracted with dichloromethane/methanol (10:1). The organic phase was collected, filtered, and concentrated, to afford a crude product of 2-(3-(4-(1H-pyrrolo[2,3-b]pyridin-4-yl)-1H-pyrazol-1-yl)azetidin-3-yl)acetonitrile, MS (ESI, m/z): 279 [M+H]⁺.

Step 3: tert-butylsulfonyl chloride (32f)

Under cooling with an ice-salt bath, NCS (1.2 g, 9 mmol) was dissolved in dichloromethane (15 mL), tert-butylthiol (1 mL) diluted in dichloromethane (5 mL) was slowly added dropwise to the reaction system, and the reaction solution was stirred for 3 h. The reaction solution was diluted with dichloromethane to a volume of 30 mL, and the reaction solution was used directly in the next step.

Step 4: 2-(3-(4-(1H-pyrrolo[2,3-b]pyridin-4-yl)-1H-pyrazol-1-yl)-1-(tert-butylsulfonyl)azetidin-3-yl)acetonitrile (32)

Under cooling with an ice bath, the crude product of 2-(3-(4-(1H-pyrrolo[2,3-b]pyridin-4-yl)-1H-pyrazol-1-yl)azetidin-3-yl)acetonitrile (32d) (273 mg) obtained in step 2 was dissolved in 1,4-dioxane (15 mL), triethylamine (0.7 mL) was added, and the reaction solution was stirred for 10 min. Then, a solution of tert-butylsulfonyl chloride (32f) in dichloromethane (5 mL) obtained in step 3 was dropwise added to the reaction system, the reaction solution was warmed to room temperature, and stirred for 2 h. After the reaction was complete, the reaction solution was concentrated, and purified on a preparative TLC plate, to afford 2-(3-(4-(1H-pyrrolo[2,3-b]pyridin-4-yl)-1H-pyrazol-1-yl)-1-(tert-butylsulfonyl)azetidin-3-yl)acetonitrile (32) (64 mg, light yellow solid), ¹H NMR (400 MHz, CDCl₃) δ: 10.67 (s, 1H), 8.35 (d, 1H, J=4.8 Hz), 8.18 (s, 1H), 8.13 (s, 1H), 7.47 (d, 1H, J=4.4 Hz), 7.24 (d, 1H, J=5.2 Hz), 6.76 (d, 1H, J=3.6 Hz), 4.12 (d, 2H, J=9.2 Hz), 3.88 (d, 2H, J=9.2 Hz), 3.41 (s, 2H), 1.42 (s, 9H). MS (ESI, m/z): 399 [M+H]⁺.

Example 33: 2-(3-(4-(1H-pyrrolo[2,3-b]pyridin-4-yl)-1H-pyrazol-1-yl)-1-(ethylsulfonyl)azetidin-3-yl)propanenitrile (33)

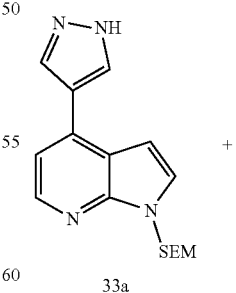

33a

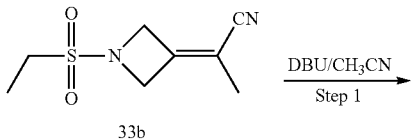

33b

DBU/CH₃CN
Step 1

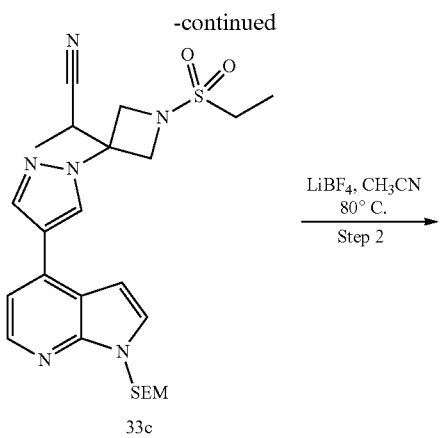

chromatography, to afford 2-(3-(4-(1H-pyrrolo[2,3-b]pyridin-4-yl)-1H-pyrazol-1-yl)-1-(ethylsulfonyl)azetidin-3-yl)propanenitrile (33) (50 mg, grey solid), yield: 40%. MS m/z: 385 [M+1]$^+$. $^1$H NMR (400 MHz, DMSO-d$_6$) δ 11.71 (s, 1H), 8.76 (s, 1H), 8.33 (s, 1H), 8.20 (d, J=5.00 Hz, 1H), 7.65-7.49 (m, 1H), 7.34 (d, J=4.99 Hz, 1H), 6.89 (dd, J=3.58, 1.85 Hz, 1H), 4.57 (dd, J=14.48, 9.37 Hz, 2H), 4.35 (dd, J=9.36, 6.46 Hz, 2H), 3.92 (q, J=6.99 Hz, 1H), 3.22 (q, J=7.32 Hz, 2H), 1.23 (t, J=7.33 Hz, 3H), 1.15 (d, J=6.96 Hz, 3H).

Example 34: 3-(4-(5-cyano-1H-pyrrolo[2,3-b]pyridin-4-yl)-1H-pyrazol-1-yl)-3-(cyanomethyl)-N,N-dimethylazetidine-1-sulfonamide (34)

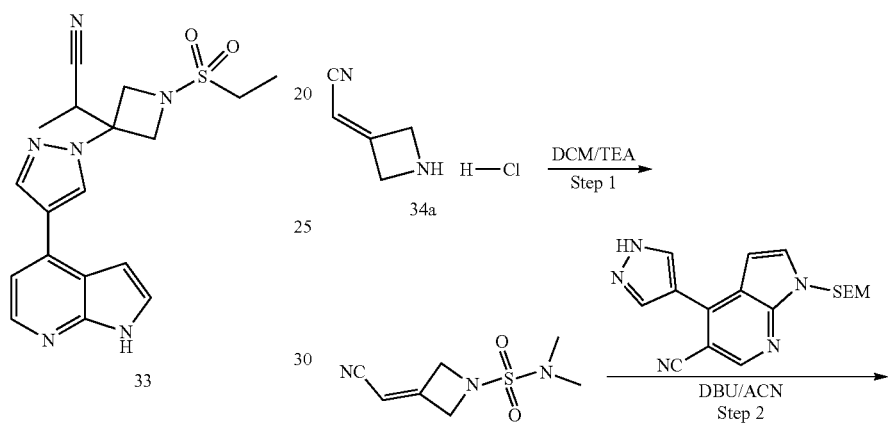

Step 1: 2-(1-(ethylsulfonyl)-3-(4-(1-((2-(trimethylsilyl)ethoxy)methyl)-1H-pyrrolo[2,3-b]pyridinyl)-1H-pyrazolyl)azetidin-3-yl)propanenitrile (33c)

At room temperature, acetonitrile (10 mL) and DBU (100 mg) were added to 4-(1H-pyrazol-4-yl)-1-((2-(trimethylsilyl)ethoxy)methyl)-1H-pyrrolo[2,3-b]pyridine (33a) (160 mg, 0.51 mmol) and 2-(1-(ethylsulfonyl)azetidin-3-ylidene)propanenitrile (33b) (102 mg, 0.51 mmol), and the reaction solution was stirred at room temperature overnight. After the reaction was complete, the reaction solution was concentrated, and the residue obtained after concentration was purified by column chromatography, to afford 2-(1-(ethylsulfonyl)-3-(4-(1-((2-(trimethylsilyl)ethoxy)methyl)-1H-pyrrolo[2,3-b]pyridinyl)-1H-pyrazolyl)azetidin-3-yl)propanenitrile (33c) (170 mg, brown oil), yield: 65%. MS m/z: 515 [M+1]$^+$.

Step 2: 2-(3-(4-(1H-pyrrolo[2,3-b]pyridin-4-yl)-1H-pyrazol-1-yl)-1-(ethylsulfonyl)azetidin-3-yl)propanenitrile (33)

At room temperature, 2-(1-(ethylsulfonyl)-3-(4-(1-((2-(trimethylsilyl)ethoxy)methyl)-1H-pyrrolo[2,3-b]pyridinyl)-1H-pyrazol-1-yl)azetidin-3-yl)propanenitrile (33c) (170 mg, 0.33 mmol) was dissolved in acetonitrile (9 mL), water (1 mL) and lithium tetrafluoroborate (583 mg, 6.21 mmol) were added, and the reaction solution was warmed to 80° C. and stirred overnight. After the reaction was complete, the reaction was quenched with water, and extracted with EA. The organic phase was collected, dried over anhydrous sodium sulfate, filtrated, concentrated, and the residue obtained after concentration was purified by column -continued

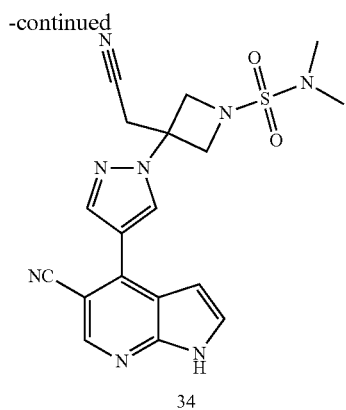

34

Step 1: 3-(cyanomethylene)-N,N-dimethylazetidine-1-sulfonamide (34b)

In an ice-water bath, 2-(azetidin-3-ylidene)acetonitrile hydrochloride salt (34a) (400 mg) and DCM (20 mL) were added to a reaction flask, DMAP (8 mg) and TEA (1548 mg) were added, and the reaction was stirred until homogenous. N,N-dimethylsulfonyl chloride (571 mg) diluted in DCM (20 mL) was slowly added dropwise to the reaction system, and the reaction solution was stirred for 5 h. After the reaction was complete, it was added with water (20 mL) and DCM (20 mL). The organic phase was separated, washed with an aqueous solution of citric acid and saturated brine, dried over anhydrous sodium sulfate, filtered, and concentrated, to afford a crude product (34b, 596 mg), which was used directly in the next reaction without purification. MS (ESI, m/z): 202 [M+H]$^+$.

Step 2: 3-(4-(5-cyano-1-((2-(trimethylsilyl)ethoxy)methyl)-1H-pyrrolo[2,3-b]pyridin-4-yl)-1H-pyrazol-1-yl)-3-(cyanomethyl)-N,N-dimethylazetidine-1-sulfonamide (34c)

The crude product of 3-(cyanomethylene)-N,N-dimethylazetidine-1-sulfonamide (34b) (240 mg) obtained in step 1 was dissolved in acetonitrile (150 mL), 4-(1H-pyrazol-4-yl)-1-((2-(trimethylsilyl)ethoxy)methyl)-1H-pyrrolo[2,3-b]pyridine-5-carbonitrile (200 mg) and DBU (0.5 mL) were added, and the reaction solution was stirred for 2 h. After the reaction was complete, the reaction solution was concentrated, and the residue obtained after the concentration was purified on a preparative TLC plate, to afford a white viscous oil (34c, 200 mg), yield: 63%. MS (ESI, m/z): 541 [M+H]$^+$.

Step 3: 3-(4-(5-cyano-1-(hydroxymethyl)-1H-pyrrolo[2,3-b]pyridin-4-yl)-1H-pyrazol-1-yl)-3-(cyanomethyl)-N,N-dimethylazetidine-1-sulfonamide (34d)

3-(4-(5-cyano-1-((2-(trimethylsilyl)ethoxy)methyl)-1H-pyrrolo[2,3-b]pyridin-4-yl)-1H-pyrazol-1-yl)-3-(cyanomethyl)-N,N-dimethylazetidine-1-sulfonamide (34c) (200 mg) was dissolved in dichloromethane (6 mL), TFA (2 mL) was added to the reaction system, and the reaction solution was stirred for 3 h. After the reaction was complete, the reaction solution was concentrated, and the residue obtained after the concentration was purified on a preparative TLC plate, to afford a white solid (34d, 84 mg). MS (ESI, m/z): 441 [M+H]$^+$.

Step 4: 3-(4-(5-cyano-1H-pyrrolo[2,3-b]pyridin-4-yl)-1H-pyrazol-1-yl)-3-(cyanomethyl)-N,N-dimethylazetidine-1-sulfonamide (34)

3-(4-(5-cyano-1-(hydroxymethyl)-1H-pyrrolo[2,3-b]pyridin-4-yl)-1H-pyrazol-1-yl)-3-(cyanomethyl)-N,N-dimethylazetidine-1-sulfonamide (34d) (84 mg) was dissolved in ethanol (150 mL), water (15 mL) and sodium carbonate (403 mg) were added, and the reaction solution was stirred overnight. After the reaction was complete, the reaction solution was concentrated to obtain a white solid, to which water (30 mL) was added, and the filter cake was dissolved in DCM/MeOH=1:1 (80 mL), dried over anhydrous sodium sulfate, filtered, concentrated, and dried, to afford an off-white solid (34) (53 mg, yield: 68%).

$^1$H NMR (400 MHz, DMSO) δ 12.40 (s, 1H), 8.81 (s, 1H), 8.63 (s, 1H), 8.32 (s, 1H), 7.75 (d, J=3.36 Hz, 1H), 6.88 (d, J=3.40 Hz, 1H), 4.52 (d, J=8.96 Hz, 2H), 4.22 (d, J=8.96 Hz, 2H), 3.69 (s, 2H), 2.79 (s, 6H). MS (ESI, m/z): 411 [M+H]$^+$.

Example 35: 2-(3-(4-(1H-pyrrolo[2,3-b]pyridin-4-yl)-1H-pyrazol-1-yl)-1-(pyrrolidin-1-ylsulfonyl)azetidin-3-yl)acetonitrile (35)

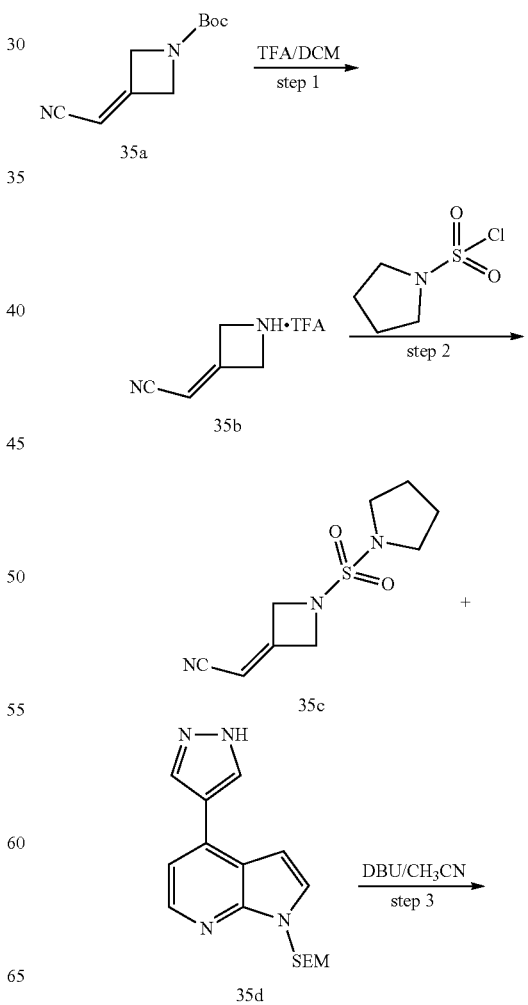

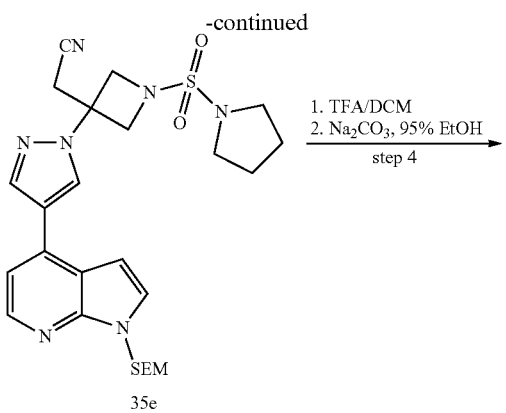

Step 1: 2-(azetidin-3-ylidene)acetonitrile trifluoroacetate salt (35b)

Compound (35b) (crude product, transparent oil) was prepared according to step 1 in Example 2, and it was used directly in the next reaction.

Step 2: 2-(1-(pyrrolidin-1-ylsulfonyl)azetidin-3-ylidene)acetonitrile (35c)

Compound (35b) (780 mg, 4 mmol) was dissolved in dichloromethane (10 mL), the reaction was placed in an ice bath, triethylamine was then slowly added until the pH of the reaction reached 9. DMAP (8 mg, 0.06 mmol) was then added, and the reaction was stirred in an ice bath for 5 min. Pyrrolidine-1-sulfonyl chloride (0.44 mL, 3.90 mmol) was then dissolved in dichloromethane (2 mL), it was slowly added dropwise to the reaction system, and the reaction was performed in an ice bath for 30 min. The reaction solution was extracted with ethyl acetate, the organic phase was washed with an aqueous solution of citric acid, the organic phase was dried over anhydrous sodium sulfate, and then rotary evaporated to dryness, to obtained a solid, which was triturated with petroleum ether, and filtered, to afford compound (35c) (505 mg, white solid), yield: 74%, MS (ESI, m/z): 228 [M+H]$^+$.

Step 3: 2-(1-(pyrrolidin-1-ylsulfonyl)-3-(4-(1-((2-(trimethylsilyl)ethoxy)methyl)-1H-pyrrolo[2,3-b]pyridin-4-yl)-1H-pyrazol-1-yl)azetidin-3-yl)acetonitrile (35e)

Compound (35d) (200 mg, 0.64 mmol) and compound (35c) (218 mg, 0.96 mmol) were dissolved in acetonitrile (10 mL), and DBU (0.16 mL) was added to the reaction, which was stirred at room temperature overnight. After TLC indicated the reaction was complete, the reaction was rotary evaporated to dryness, and purified by column chromatography, to afford compound (35e) (329 mg, milky white oil), yield: 95%. MS (ESI, m/z): 542 [M+H]$^+$.

Step 4: 2-(3-(4-(1H-pyrrolo[2,3-b]pyridin-4-yl)-1H-pyrazol-1-yl)-1-(pyrrolidin-1-ylsulfonyl)azetidin-3-yl)acetonitrile (35)

Compound (35e) (329 mg, 0.61 mmol) was dissolved in dichloromethane (7 mL), the reaction was placed in an ice bath, and added with trifluoroacetic acid (7 mL). The temperature was kept below 10° C. during the whole reaction process. After TLC indicated the reaction was complete, the pH of the reaction was adjusted to 9 with an aqueous solution of sodium carbonate, and the reaction was extracted with ethyl acetate, and rotary evaporated to dryness. The solid was dissolved in 95% ethanol, the reaction was added with sodium carbonate (954 mg, 9 mmol), stirred at room temperature overnight, rotary evaporated to dryness, and purified by column chromatography on silica gel, to afford compound (35) (188 mg, white solid), yield: 75%. MS (ESI, m/z): 412 [M+H]$^+$.

$^1$H NMR (400 MHz, DMSO-d) δ 11.73 (s, 1H), 8.76 (s, 1H), 8.34 (s, 1H), 8.21 (d, 1H, J=5.2 Hz), 7.54 (s, 1H), 7.34 (d, 1H, J=4.8 Hz), 6.89 (s, 1H), 4.52 (d, 2H, J=8.8 Hz), 4.17 (d, 2H, J=8.8 Hz), 3.65 (s, 2H), 3.26 (s, 4H), 1.84 (s, 4H).

Example 36: 1-(3-(cyanomethyl)-1-(ethylsulfonyl)azetidin-3-yl)-4-(1H-pyrrolo[2,3-b]pyridin-4-yl)-1H-pyrazole-3-carbonitrile (36)

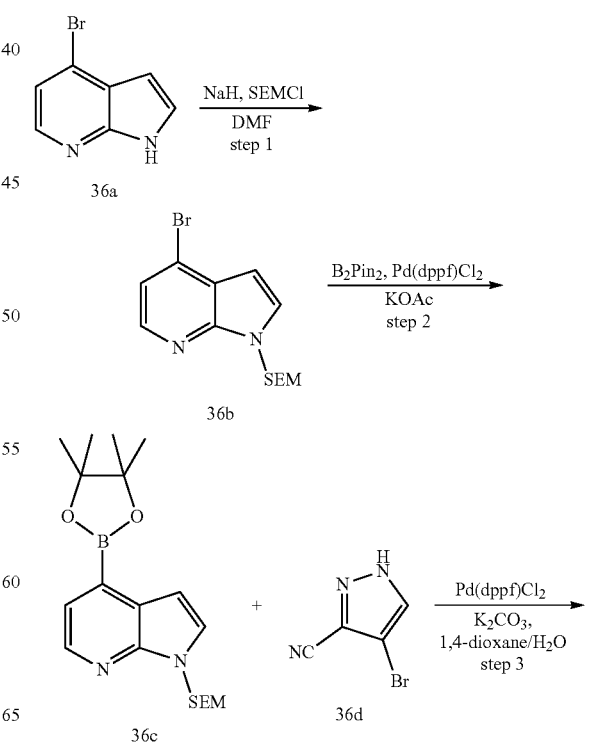

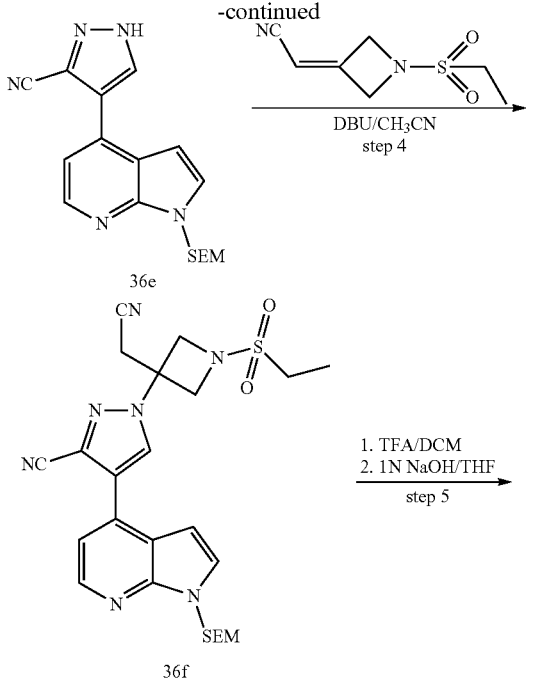

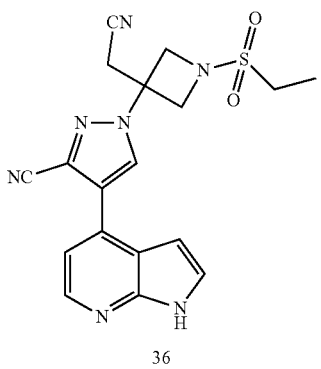 [SMILES: CCS(=O)(=O)N1CC(CC#N)(n2cc(-c3ccnc4[nH]ccc34)c(C#N)n2)C1]

Step 1: 4-bromo-1-((2-(trimethylsilyl)ethoxy)methyl)-1H-pyrrolo[2,3-b]pyridine (36b)

According to step 1 in Example 8, compound (36b) was prepared (14.57 g, yellow liquid), yield: 88%. MS (ESI, m/z): 326 [M+H]$^+$.

Step 2: 4-(4,4,5,5-tetramethyl-1,3,2-dioxaborolan-2-yl)-1-((2-(trimethylsilyl)ethoxy)methyl)-1H-pyrrolo[2,3-b]pyridine (36c)

At room temperature, compound (36b) (10 g, 27.60 mmol), bis(pinacolato)diboron (8.41 g, 33.10 mmol), potassium acetate (2.70 g, 82.80 mmol) and dioxane (200 mL) were sequentially added to a 500 mL reaction flask, and nitrogen atmosphere protection was applied. After the reaction solution was stirred until homogenous, Pd(dppf)Cl$_2$ (1.00 g, 1.38 mmol) was added under protection of nitrogen. The system was heated to 90° C., and allowed to proceed for 3 h. After thin layer chromatography indicated the reaction was complete, the reaction solution was quenched with water, extracted with ethyl acetate, dried over anhydrous sodium sulfate, and concentrated under reduced pressure, to afford compound (36c) as a crude product, which was used directly in the next reaction. MS (ESI, m/z): 375 [M+H]$^+$.

Step 3: 4-(1-((2-(trimethylsilyl)ethoxy)methyl)-1H-pyrrolo[2,3-b]pyridin-4-yl)-1H-pyrazole-3-carbonitrile (36e)

At room temperature, compound (36c) (1.63 g, 4.36 mmol), 4-bromo-1H-pyrazole-3-carbonitrile (36d) (500 mg, 2.91 mmol), a potassium carbonate (1.00 g, 7.28 mmol) solution (10 mL) and 1,4-dioxane (50 mL) were sequentially added to a 150 mL reaction flask, and nitrogen atmosphere protection was applied. After the reaction solution was stirred until homogenous, Pd(dppf)Cl$_2$ (213 mg, 0.29 mmol) was added under protection of nitrogen. The system was heated to 100° C., and the reaction was allowed to proceed overnight. After thin layer chromatography indicated the reaction was complete, the reaction solution was quenched with water, extracted with ethyl acetate, dried over anhydrous sodium sulfate, concentrated under reduced pressure, and purified by column chromatography on silica gel, to afford compound (36e) (255 mg, white solid), yield: 26%. MS (ESI, m/z): 340 [M+H]$^+$.

Step 4: 4-(1-(3-(cyanomethyl)-1-(ethylsulfonyl)azetidin-3-yl)-1H-(3-cynaopyrazole)-4-yl)-1-((2-(trimethylsilyl)ethoxy)methyl)-1H-pyrrolo[2,3-b]pyridine (36f)

At room temperature, 2-[1-(ethylsulfonyl)azetidin-3-ylidene]acetonitrile (521 mg, 2.80 mmoL) and DBU (127 mg, 0.84 mmol) were sequentially added to a solution of a compound (36e) (189 mg, 0.56 mmol) in acetonitrile (2 mL), and the reaction was allowed to proceed overnight. After thin layer chromatography indicated the reaction was complete, the reaction solution was quenched with water, extracted with ethyl acetate, dried over anhydrous sodium sulfate, concentrated under reduced pressure, and purified by column chromatography on silica gel, to afford compound (36f) (140 mg, light yellow solid), yield: 48%. MS (ESI, m/z): 526 [M+H]$^+$.

Step 5: 1-(3-(cyanomethyl)-1-(ethylsulfonyl)azetidin-3-yl)-4-(1H-pyrrolo[2,3-b]pyridin-4-yl)-1H-pyrazole-3-carbonitrile (36)

At room temperature, a solution of compound (36f) (147 mg, 0.28 mmol) in TFA/DCM (1:1) (4 mL) was added to a 25 mL reaction flask, argon atmosphere protection was applied, and the reaction was stirred at room temperature for 1 h. After LC-MS indicated the reaction was complete, the reaction was extracted with ethyl acetate, dried over anhydrous sodium sulfate, and concentrated under reduced pressure, to afford a yellow oil; tetrahydrofuran (5 mL) was added thereto at room temperature, after stirred until homogeneous, 1M sodium hydroxide solution was added to adjust the pH value of the system to about 10, and the reaction was stirred at room temperature for 2 h. After thin layer chromatography indicated the reaction was complete, the reaction was extracted with ethyl acetate, dried over anhydrous sodium sulfate, concentrated under reduced pressure, and purified by column chromatography on silica gel, to afford compound (36) (10 mg, white solid), yield: 10%. MS (ESI, m/z): 396 [M+H]$^+$.

$^1$H NMR (400 MHz, DMSO-d$_6$) δ 11.95 (s, 1H), 8.96 (s, 1H), 8.35 (s, 1H), 7.64 (s, 1H), 7.35 (s, 1H), 6.77 (s, 1H), 4.62 (d, J=9.2 Hz, 2H), 4.29 (d, J=9.2 Hz, 2H), 3.74 (s, 2H), 3.25 (q, J=7.3 Hz, 2H), 1.23 (t, J=7.3 Hz, 3H).

Example 37: 4-(1-(3-(cyanomethyl)-1-propionylazetidin-3-yl)-1H-pyrazol-4-yl)-1H-pyrrolo[2,3-b]pyridine-5-carbonitrile (37)

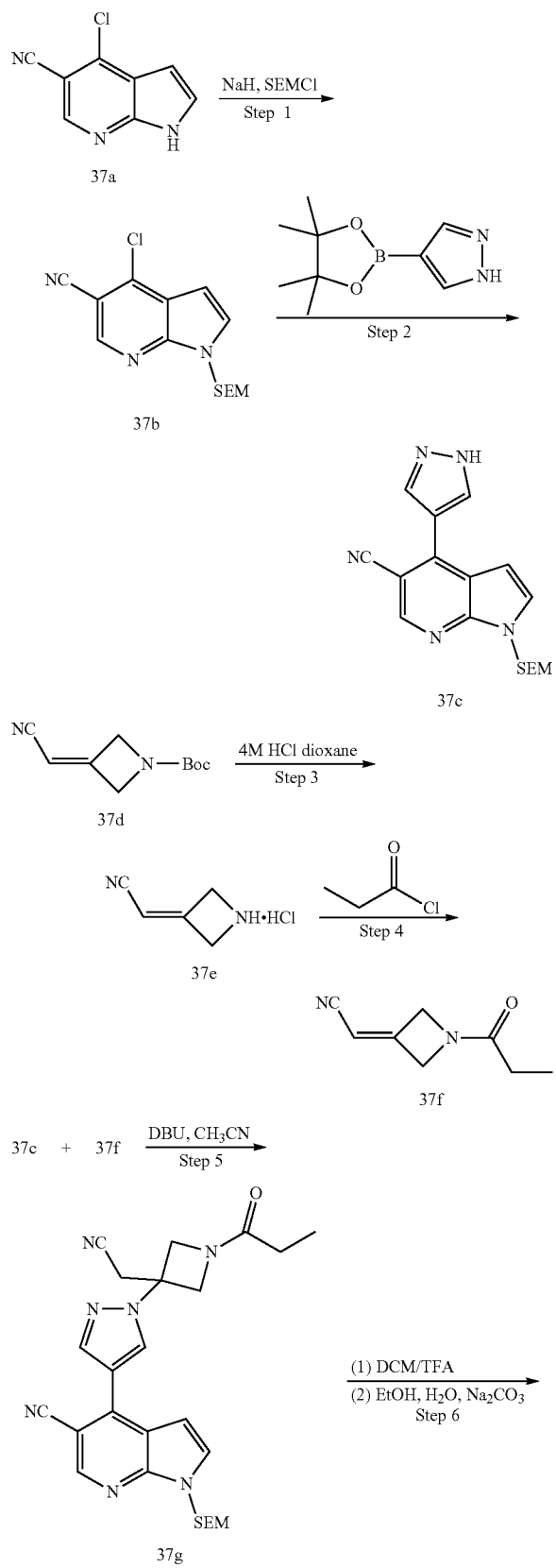

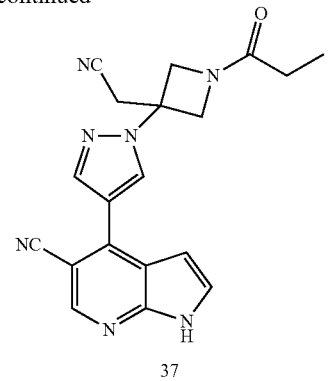

Step 1: 4-chloro-5-cyano-1-((2-(trimethylsilyl)ethoxy)methyl)-1H-pyrrolo[2,3-b]pyridine (37b)

At room temperature, 4-chloro-5-cyano-7-azaindole (37a) (1.92 g, 10.76 mmol) and DMF (22 mL) were added to a reaction flask, sodium hydride (60 wt %, 560 mg, 13.98 mmol) and [2-(trimethylsilyl)ethoxy]methyl chloride (2.33 g, 13.98 mmol) were added in portions after nitrogen atmosphere protection was applied, and the reaction solution was stirred for 2 h. After the reaction was complete, the reaction was quenched with water, and extracted with ethyl acetate. The organic phase was collected, dried over anhydrous sodium sulfate, filtered, concentrated under reduced pressure, and the residue obtained after concentration was purified by column chromatography, to afford 4-chloro-5-cyano-1-((2-(trimethylsilyl)ethoxy)methyl)-1H-pyrrolo[2,3-b]pyridine (37b) (4.30 g, yield: 86%, white solid). MS (ESI, m/z): 307.1 [M+H]$^+$.

Step 2: 4-(1H-pyrazol-4-yl)-5-cyano-1-((2-(trimethylsilyl)ethoxy)methyl)-1H-pyrrolo[2,3-b]pyridine (37c)

At room temperature, compound 37b (200 mg, 0.65 mmol), 4-pyrazoleboronic acid pinacol ester (189 mg, 0.98 mmol), a potassium carbonate (225 mg, 1.63 mmol) solution (2 mL) and 1,4-dioxane (8 mL) were added to a reaction flask, Pd(dppf)Cl$_2$ (50 mg, 0.065 mmol) was added after nitrogen atmosphere protection was applied. The reaction solution was heated to 95° C., and stirred overnight. After the reaction was complete, the reaction was quenched with water, and extracted with ethyl acetate. The organic phase was collected, dried over anhydrous sodium sulfate, filtered, concentrated under reduced pressure, and the residue obtained after concentration was purified by column chromatography, to afford 4-(1H-pyrazol-4-yl)-5-cyano-1-((2-(trimethylsilyl)ethoxy)methyl)-1H-pyrrolo[2,3-b]pyridine (37c) (134 mg, yield: 61%, yellow solid). MS (ESI, m/z): 339.2 [M+H]$^+$.

Step 3: 2-(azetidin-3-ylidene)acetonitrile hydrochloride salt (37e)

Compound 37d (1.0 g, 5.15 mmol) and a 4M solution of HCl in dioxane (10 mL) were added to a reaction flask, argon atmosphere protection was applied, and the reaction solution was stirred for 2.5 h. After the reaction was complete, the reaction solution was filtered, and the filter cake was washed with anhydrous ether and dried, to afford 2-(azetidin-3-ylidene)acetonitrile hydrochloride salt (37e) (600 mg, yield: 90.0%, white solid), which was used directly in the next step.

Step 4: 2-(1-propionylazetidin-3-ylidene)acetonitrile (37f)

Under cooling with an ice bath, compound 37e (200 mg, 1.54 mmol), dichloromethane (10 mL), triethylamine (1.3 mL, 9.24 mmol) and DMAP (3.8 mg, 0.03 mmol) were added to a reaction flask, and after the reaction was stirred until homogeneous, a solution of propionylsulfonyl chloride (212 mg, 2.3 mmol) in dichloromethane (10 mL) was slowly added dropwise to the reaction system, and the reaction solution was stirred for 1 h. After the reaction was complete, the reaction was quenched with water, and extracted with dichloromethane. The organic phase was collected, washed with water, a solution of citric acid and saturated brine, dried over anhydrous sodium sulfate, filtered, and concentrated under reduced pressure, to afford 2-(1-propionylazetidin-3-ylidene)acetonitrile (37f) (140 mg, yield: 60.6%, brown solid). MS (ESI, m/z): 150.1 [M+H]+.

Step 5: 4-(1-(3-(cyanomethyl)-1-propionylazetidin-3-yl)-1H-pyrazol-4-yl)-1-((2-(trimethylsilyl)ethoxy)methyl)-1H-pyrrolo[2,3-b]pyridine-5-carbonitrile (37g)

Compound 37f (107 mg, 0.71 mmol), compound 37c (200 mg, 0.59 mmol) and acetonitrile (15 mL) were added to a reaction flask, and DBU (183 mg, 0.71 mmol) was added. The reaction solution was stirred at room temperature for 1 h. After the reaction was complete, the reaction solution was quenched with water, concentrated under reduced pressure, and the residue obtained after concentration was purified by column chromatography, to afford 4-(1-(3-(cyanomethyl)-1-propionylazetidin-3-yl)-1H-pyrazol-4-yl)-1-((2-(trimethylsilyl)ethoxy)methyl)-11H-pyrrolo[2,3-b]pyridine-5-carbonitrile (37g) (202 mg, yield: 70.0%, white foamy solid). MS (ESI, m/z): 489.2 [M+H]+.

Step 6: 4-(1-(3-(cyanomethyl)-1-propionylazetidin-3-yl)-1H-pyrazol-4-yl)-1H-pyrrolo[2,3-b]pyridine-5-carbonitrile (37)

At room temperature, compound 37g (202 mg, 0.44 mmol) and a mixed solution of TFA/DCM (V:V=1:2) (9.75 mL) were added to a reaction flask, argon atmosphere protection was applied, and the reaction was stirred at room temperature for 2 h. After the reaction was complete, the reaction solution was quenched with water, and extracted with dichloromethane. The organic phase was collected, dried over anhydrous sodium sulfate, filtered, concentrated under reduced pressure, and the residue obtained after concentration was purified by column chromatography, to afford a hydroxymethyl intermediate (137 mg, yield: 85.3%, white solid), which was placed in a reaction flask. Absolute ethyl alcohol (90 mL), distilled water (10 mL) and anhydrous sodium carbonate (746 mg, 7.04 mmol) were sequentially added, and the reaction was stirred at room temperature overnight. After the reaction was complete, the reaction solution was concentrated, filtered with suction, the filter cake was washed with water, and dried, to afford compound 37 (73 mg, yield: 57.6%, white solid). 1H NMR (400 MHz, DMSO-d) δ: 12.40 (s, 1H), 8.79 (s, 1H), 8.62 (s, 1H), 8.29 (s, 1H), 7.75 (d, J=3.32 Hz, 1H), 6.88 (d, J=3.40 Hz, 1H), 4.79 (d, J=9.88 Hz, 1H), 4.49 (m, 2H), 4.24 (d, J=9.80 Hz, 1H), 3.69 (s, 2H), 2.15 (q, 2H), 0.99 (t, J=7.44 Hz, 3H). MS (ESI, m/z): 359.1 [M+H]+.

Example 38: 4-(1-(3-(cyanomethyl)-1-(cyclopropanecarbonyl)azetidin-3-yl)-1H-pyrazol-4-yl)-1H-pyrrolo[2,3-b]pyridine-5-carbonitrile (38)

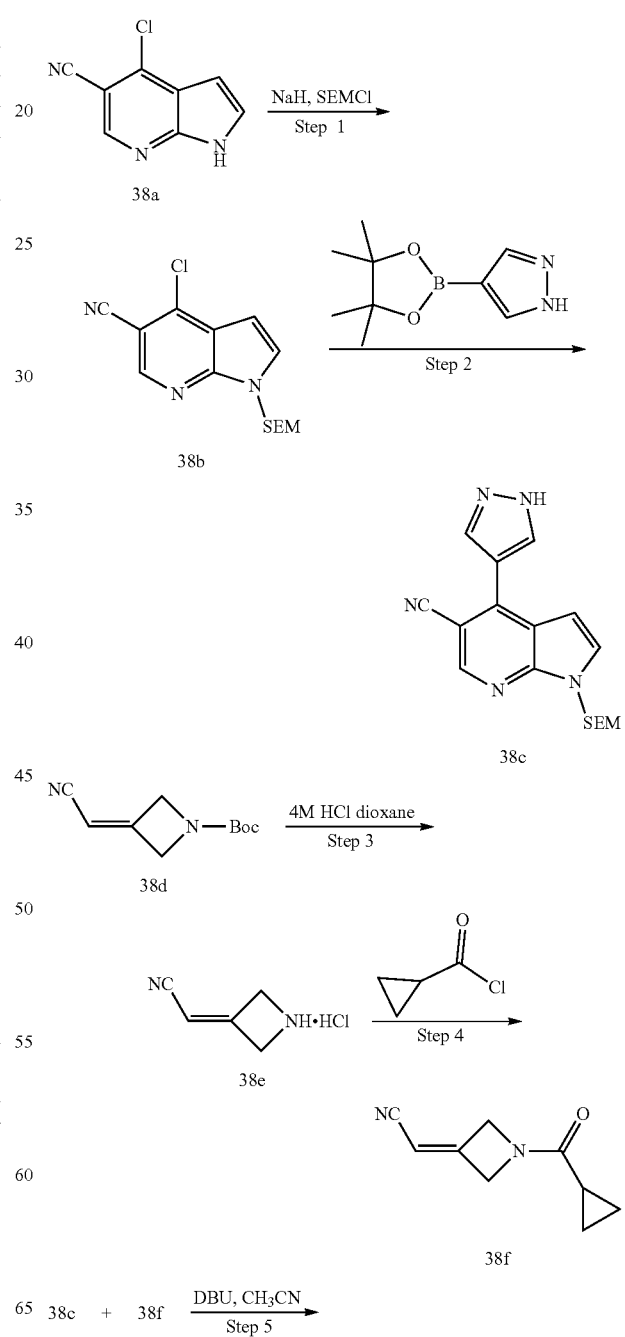

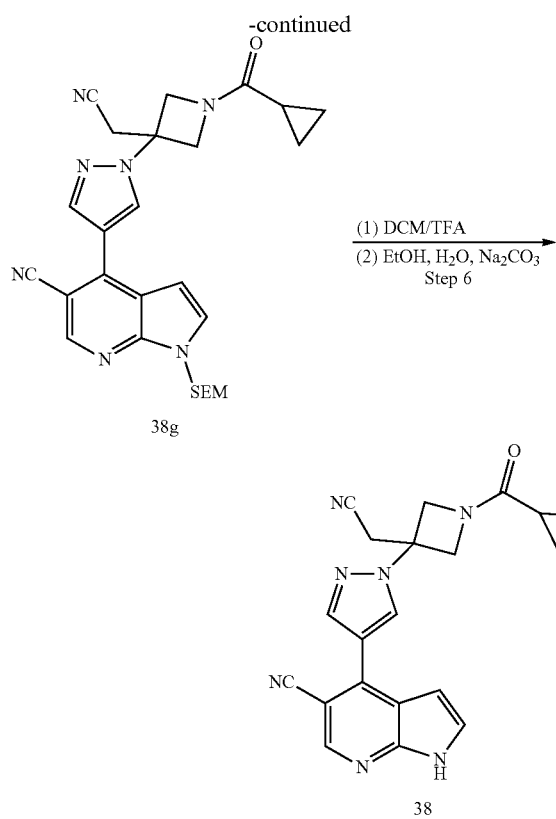

Step 1: 4-chloro-5-cyano-1-((2-(trimethylsilyl)ethoxy)methyl)-1H-pyrrolo[2,3-b]pyridine (38b)

At room temperature, 4-chloro-5-cyano-7-azaindole (38a) (1.92 g, 10.76 mmol) and DMF (22 mL) were added to a reaction flask, the mixture was cooled to below 5° C. after nitrogen atmosphere protection was applied, sodium hydride (60 wt %, 560 mg, 13.98 mmol) and [2-(trimethylsilyl)ethoxy]methyl chloride (2.33 g, 13.98 mmol) were added in portions, and the reaction solution was stirred for 2 h. After the reaction was complete, the reaction was quenched with water, and extracted with ethyl acetate. The organic phase was collected, dried over anhydrous sodium sulfate, filtered, concentrated under reduced pressure, and purified by column chromatography, to afford 4-chloro-5-cyano-1-((2-(trimethylsilyl)ethoxy)methyl)-1H-pyrrolo[2,3-b]pyridine (38b) (4.30 g, yield: 86%, white solid). MS (ESI, m/z): 307.1 $[M+H]^+$.

Step 2: 4-(1H-pyrazol-4-yl)-5-cyano-1-((2-(trimethylsilyl)ethoxy)methyl)-1H-pyrrolo[2,3-b]pyridine (38c)

At room temperature, compound 38b (200 mg, 0.65 mmol), 4-pyrazoleboronic acid pinacol ester (189 mg, 0.98 mmol), a potassium carbonate (225 mg, 1.63 mmol) solution (2 mL) and 1,4-dioxane (8 mL) were added to a reaction flask, Pd(dppf)Cl$_2$ (50 mg, 0.065 mmol) was added after nitrogen atmosphere protection was applied, and the reaction solution was heated to 95° C. and stirred overnight. After the reaction was complete, the reaction was quenched with water, and extracted with ethyl acetate. The organic phase was collected, dried over anhydrous sodium sulfate, filtered, concentrated under reduced pressure, and the residue obtained after the concentration was purified by column chromatography, to afford 4-(1H-pyrazol-4-yl)-5-cyano-1-((2-(trimethylsilyl)ethoxy)methyl)-1H-pyrrolo[2,3-b]pyridine (38c) (134 mg, yield: 61%, yellow solid). MS (ESI, m/z): 339.2 $[M+H]^+$.

Step 3: 2-(azetidin-3-ylidene)acetonitrile hydrochloride salt (38e)

In an ice bath, compound 38d (1.0 g, 5.15 mmol) and a 4M solution of HCl in dioxane (10 mL) were added to a reaction flask, and the reaction was stirred for 2.5 h after argon atmosphere protection was applied. After the reaction was complete, the reaction solution was filtrated, the filter cake was washed with anhydrous ether, and dried, to afford 2-(azetidin-3-ylidene)acetonitrile hydrochloride salt (38e) (600 mg, yield: 90.0%, white solid), which was used directly in the next step.

Step 4: 2-(1-(cyclopropanecarbonyl)azetidin-3-ylidene)acetonitrile (38f)

In an ice bath, compound 38e (200 mg, 1.54 mmol), dichloromethane (10 mL), triethylamine (1.3 mL, 9.24 mmol) and DMAP (3.8 mg, 0.03 mmol) were added to a reaction flask, a solution of cyclopropanecarbonyl chloride (240 mg, 2.30 mmol) in dichloromethane (10 mL) was slowly added dropwise to the reaction system, and the reaction solution was stirred for 1 h. After the reaction was complete, the reaction was quenched with water, and extracted with dichloromethane. The organic phase was collected, washed with water, a solution of citric acid and saturated brine, dried over anhydrous sodium sulfate, filtered, and concentrated under reduced pressure, to afford 2-(1-(cyclopropanecarbonyl)azetidin-3-ylidene)acetonitrile (38f) (223 mg, yield: 89.9%, brown solid). MS (ESI, m/z): 162.1 $[M+H]^+$.

Step 5: 4-(1-(3-(cyanomethyl)-1-(cyclopropanecarbonyl)azetidin-3-yl)-1H-pyrazol-4-yl)-1-((2-(trimethylsilyl)ethoxy)methyl)-1H-pyrrolo[2,3-b]pyridine-5-carbonitrile (38g)

Compound 38f (115 mg, 0.71 mmol), compound 38c (200 mg, 0.59 mmol) and acetonitrile (15 mL) were added to a reaction flask, DBU (183 mg, 0.71 mmol) was added, and the reaction solution was stirred at room temperature for 1 h. After the reaction was complete, the reaction solution was quenched with water, concentrated under reduced pressure, and the residue obtained after the concentration was purified by column chromatography, to afford 4-(1-(3-(cyanomethyl)-1-(cyclopropanecarbonyl)azetidin-3-yl)-1H-pyrazol-4-yl)-1-((2-(trimethylsilyl)ethoxy)methyl)-1H-pyrrolo[2,3-b]pyridine-5-carbonitrile (38g) (236 mg, yield: 79.8%, white solid). MS (ESI, m/z): 501.2 $[M+H]^+$.

Step 6: 4-(1-(3-(cyanomethyl)-1-(cyclopropanecarbonyl)azetidin-3-yl)-1H-pyrazol-4-yl)-1H-pyrrolo[2,3-b]pyridine-5-carbonitrile (38)

At room temperature, compound 38g (236 mg, 0.47 mmol) and a mixture of TFA/DCM (V:V=1:2) (11.38 mL) were added to a reaction flask, argon atmosphere protection was applied, and the reaction was stirred at room temperature for 2 h. After the reaction was complete, the reaction solution was quenched with water, and extracted with dichloromethane. The organic phase was collected, dried over anhydrous sodium sulfate, filtered, concentrated under reduced pressure, and the residue obtained after the concentration was purified by column chromatography, to afford a hydroxymethyl intermediate (157 mg, yield: 83.1%, white solid), which was then placed in a reaction flask. Absolute ethyl alcohol (100 mL), distilled water (11 mL) and anhydrous sodium carbonate (830 mg, 7.83 mmol) were added, and the reaction was stirred at room temperature overnight. After the reaction was complete, the reaction solution was filtered, the filter cake was washed with water, and dried, to afford compound 38 (101 mg, yield: 70.0%, white solid). $^1$H NMR (400 MHz, DMSO-$d_6$) δ: 12.40 (s, 1H), 8.81 (s, 1H), 8.63 (s, 1H), 8.31 (s, 1H), 7.75 (d, J=3.60 Hz, 1H), 6.88 (d, J=3.52 Hz, 1H), 4.92 (d, J=9.04 Hz, 1H), 4.66 (d, J=9.20 Hz, 1H), 4.49 (d, J=10.76 Hz, 1H), 4.66 (d, J=10.32 Hz, 1H), 3.73 (s, 2H), 1.63 (m, 1H), 0.75 (s, 4H). MS (ESI, m/z): 371.1 [M+H]$^+$.

Example 39: 1-(3-(cyanomethyl)-1-(ethylsulfonyl)azetidin-3-yl)-4-(7H-pyrrolo[2,3-d]pyrimidin-4-yl)-1H-pyrrole-2-carbonitrile (39)

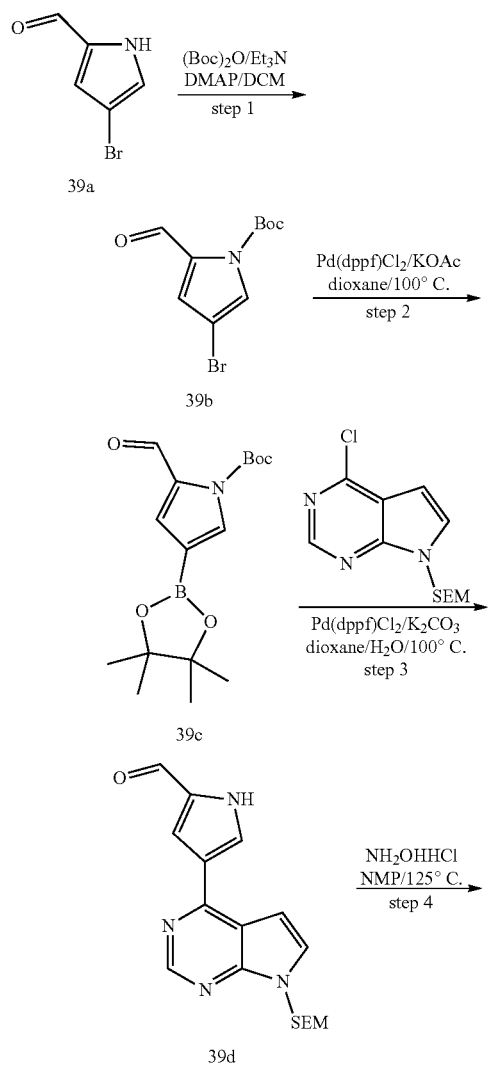

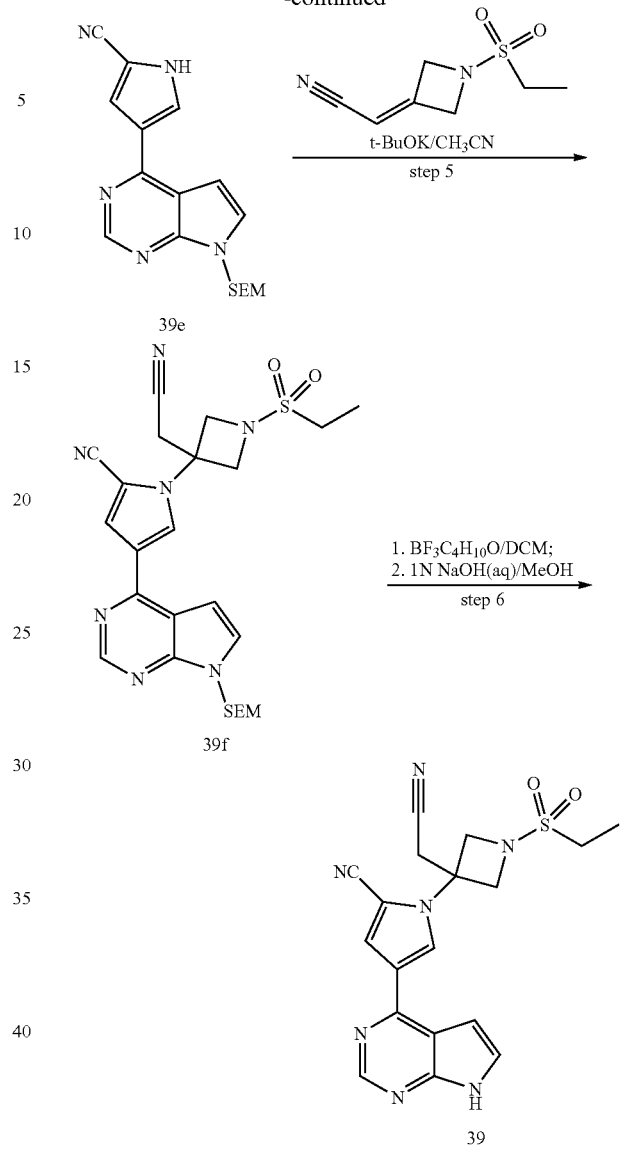

Step 1: tert-butyl 4-bromo-2-formyl-1H-pyrrole-1-carboxylate (39b)

At room temperature, 4-bromo-1H-pyrrole-2-carbaldehyde (39a) (7.40 g, 43 mmol) and di-tert-butyl dicarbonate (9.40 g) were dissolved in dichloromethane (100 mL), Et$_3$N (8.80 mL) and 4-dimethylaminopyridine (263 mg) were then added, and the reaction was stirred at room temperature for 4 h. After TLC (PE:EA=5:1) indicated the substrate disappeared, the reaction system was poured into an aqueous solution of citric acid, and extracted with DCM. The organic phase was combined, dried over anhydrous sodium sulfate, and the solvent was rotary evaporated off, to afford compound (39b) (11.58 g, brown solid), yield: 99%. MS m/z: 274 [M+1]$^+$.

Step 2: tert-butyl 2-formyl-4-(4,4,5,5-tetramethyl-1,3,2-dioxaborolan-2-yl)-1H-pyrrole-1-carboxylate (39c)

Compound (39b) (11.58 g, 0.04 mol), bis(pinacolato)diboron (21.54 g, 0.08 mol), potassium acetate (12.47 g, 0.12 mol) and Pd(dppf)Cl₂ (2.08 g) were placed in a 250 mL single-necked flask, nitrogen replacement was performed, dioxane (120 mL) was added lastly, and nitrogen atmosphere protection was applied. The reaction system was placed in an oil bath at 100° C., and stirred for 5 h. After TLC (PE:EA=6:1) indicated the substrate disappeared, insolubles were filtered off, and the filtrate was concentrated, dissolved in EA, and purified by preparative flash chromatography (PE:EA=10:1), to afford compound (39c) (8.70 g, yellow oil), yield: 67%. MS m/z: 266 [M−55]⁺.

Step 3: 4-(7-((2-(trimethylsilyl)ethoxy)methyl)-7H-pyrrolo[2,3-d]pyrimidin-4-yl)-1H-pyrrole-2-carbaldehyde (39d)

4-chloro-7-((2-(trimethylsilyl)ethoxy)methyl)-7H-pyrrolo[2,3-d]pyrimidine (2.50 g, 8.80 mmol), compound (39c) (4.60 g) and potassium carbonate (3.10 g, 22.08 mmol) were placed in a 100 mL flask, dioxane (50 mL) and water (6 mL) were added, the reaction was stirred until homogeneous, Pd(dppf)Cl₂ (370 mg) was then added, nitrogen replacement was performed for 2-3 times, and the flask was placed in an oil bath at 100° C. The reaction was allowed to proceed overnight. After LC-MS indicated the substrate disappeared, insolubles were filtered off through Celite, the solvent was rotary evaporated off, and the residue was dissolved in EA, washed with water to obtain the organic phase, which was dried over anhydrous sodium sulfate, and purified by preparative flash chromatography (PE:EA=3:2), to afford compound (39d) (1.67 g, yellow solid), yield: 56%. MS m/z: 243 [M+1]⁺.

Step 4: 4-(7-((2-(trimethylsilyl)ethoxy)methyl)-7H-pyrrolo[2,3-d]pyrimidin-4-yl)-1H-pyrrole-2-carbonitrile (39e)

Compound (39d) (1.67 g, 5 mmol) and hydroxylamine hydrochloride salt (520 mg, 7 mmol) were dissolved in NMP (15 mL), and the reaction was stirred in an oil bath at 125° C. for 18 h. After LC-MS indicated the reaction was complete, the reaction system was cooled to room temperature, poured into an aqueous solution of citric acid, extracted with EA, and the organic phase was combined, dried over anhydrous sodium sulfate, and purified by preparative flash chromatography (PE:EA=3:2), to afford compound (39e) (1.65 g, oil), yield: 97%. MS m/z: 340 [M+1]⁺.

Step 5: 1-(3-(cyanomethyl)-1-(ethylsulfonyl)azetidin-3-yl)-4-(7-((2-(trimethylsilyl)ethoxy)methyl)-7H-pyrrolo[2,3-d]pyrimidin-4-yl)-1H-pyrrole-2-carbonitrile (39f)

Compound (39e) (1.65 g, 4.86 mmol) and 2-[1-(ethylsulfonyl)azetidin-3-ylidene]acetonitrile (1.36 g, 7.30 mmol) were added to acetonitrile (50 mL), the reactants were dispersed in the solvent, potassium tert-butoxide (1.37 g, 12.17 mmol) was added, and the reaction was stirred at room temperature for 24 h. After TLC (PE:EA=1:1) indicated the reaction was complete, the reaction was quenched with water, extracted with EA, the organic phase was dried over anhydrous sodium sulfate, concentrated, and purified by preparative flash chromatography (PE:EA=1:1), to afford compound (39f) (1.30 g, yellow oil), yield: 51%. MS m/z: 526 [M+1]⁺.

Step 6: 1-(3-(cyanomethyl)-1-(ethylsulfonyl)azetidin-3-yl)-4-(7H-pyrrolo[2,3-d]pyrimidin-4-yl)-1H-pyrrole-2-carbonitrile (39)

At room temperature, compound (39f) (1.3 g, 2.48 mmol) was dissolved in dichloromethane (20 mL), the system was stirred until clear, a boron trifluoride etherate solution was added, and stirred for 3 h. After LC-MS indicated the substrate disappeared, the solvent was rotary evaporated off, 20 mL methanol was added, and an aqueous solution of 1N NaOH was slowly dropwise added, to adjust the pH value to about 10. The reaction was stirred at room temperature overnight, and then separated and purified, to afford compound (39) (120 mg, white solid), yield: 55%. MS m/z: 410 [M+1]⁺.

¹H NMR (400 MHz, DMSO-d₆) δ 12.17 (s, 1H), 8.71 (s, 1H), 8.22 (d, J=1.7 Hz, 1H), 7.96 (d, J=1.7 Hz, 1H), 7.63 (d, J=3.6 Hz, 1H), 7.10 (d, J=3.6 Hz, 1H), 4.71 (d, J=9.2 Hz, 2H), 4.25 (d, J=9.3 Hz, 2H), 3.66 (s, 2H), 3.27 (q, J=7.3 Hz, 2H), 1.25 (t, J=7.3 Hz, 3H).

Example 40: 4-(1-(3-(cyanomethyl)-1-(propylsulfonyl)azetidin-3-yl)-1H-pyrazol-4-yl)-1H-pyrrolo[2,3-b]pyridine-5-carbonitrile (40)

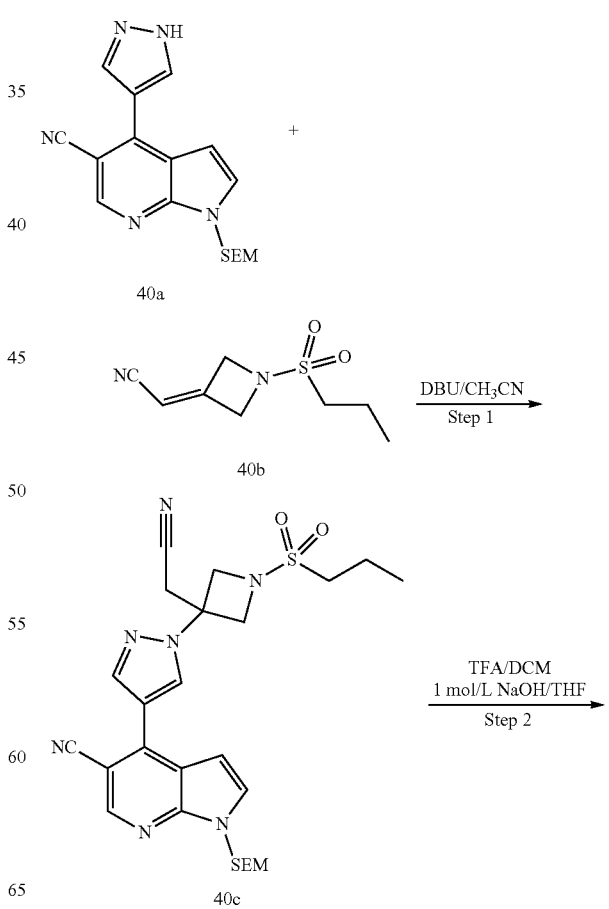

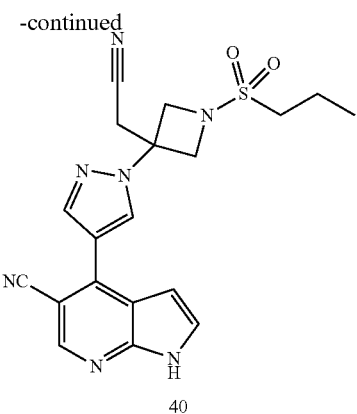

40

Step 1: 4-(1-(3-(cyanomethyl)-1-(propylsulfonyl) azetidin-3-yl)-1H-pyrazol-4-yl)-1-((2-(trimethylsilyl) ethoxy)methyl)-1H-pyrrolo[2,3-b]pyridine-5-carbonitrile (40c)

At room temperature, acetonitrile (20 mL) and DBU (200 mg) were added to a mixture of 4-(1H-pyrazol-4-yl)-1-((2-(trimethylsilyl)ethoxy)methyl)-1H-pyrrolo[2,3-b]pyridine-5-carbonitrile (40a) (220 mg, 0.64 mmol) and 2-(1-(propylsulfonyl)azetidin-3-ylidene)acetonitrile (40b) (192 mg, 0.96 mmol), the reaction solution was stirred at room temperature overnight. After the reaction was complete, the reaction was concentrated, and the residue obtained after concentration was purified on a preparative TLC plate, to afford 4-(1-(3-(cyanomethyl)-1-(propylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (40c) (290 mg, brown solid), yield: 83%. MS m/z: 540 [M+1]$^+$.

Step 2: 4-(1-(3-(cyanomethyl)-1-(propylsulfonyl) azetidin-3-yl)-1H-pyrazol-4-yl)-1H-pyrrolo[2,3-b]pyridine-5-carbonitrile (40)

At room temperature, 4-(1-(3-(cyanomethyl)-1-(propylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (40c) (290 mg, 0.54 mmol) was dissolved in DCM (12 mL), TFA (6 mL) was added under cooling with an ice bath, the reaction solution was slowly warmed to room temperature, and stirred overnight. After the reaction was complete, the pH value was adjusted to about 7 with saturated sodium carbonate, and the reaction was extracted with EA. The organic phase was collected, dried over anhydrous sodium sulfate, filtered, concentrated under reduced pressure, and the residue obtained after the concentration was purified by column chromatography, to afford an intermediate as a solid (200 mg), which was dissolved in THF (20 mL), a 1 mol/L sodium hydroxide solution was added dropwise to adjust the pH of the reaction system to about 10. The reaction solution was stirred at room temperature. After the reaction was complete, the reaction solution was extracted with EA. The organic phase was collected, dried over anhydrous sodium sulfate, filtered, and concentrated, to afford 4-(1-(3-(cyanomethyl)-1-(propylsulfonyl)azetidin-3-yl)-1H-pyrazol-4-yl)-1H-pyrrolo[2,3-b]pyridine-5-carbonitrile (40) (120 mg, white solid), yield: 55%. MS m/z: 410 [M+1]$^+$.

$^1$H NMR (400 MHz, DMSO-d$_6$) δ 12.40 (s, 1H), 8.81 (s, 1H), 8.63 (s, 1H), 8.32 (s, 1H), 7.75 (d, J=3.48 Hz, 1H), 6.88 (d, J=3.56 Hz, 1H), 4.58 (d, J=9.28 Hz, 2H), 4.27 (d, J=9.28 Hz, 2H), 3.69 (s, 2H), 3.22 (t, J=7.66 Hz, 2H), 1.68-1.77 (m, 2H), 0.99 (t, J=7.40 Hz, 3H).

Example 41 1-(3-(cyanomethyl)-1-(ethylsulfonyl) azetidin-3-yl)-4-(7H-pyrrolo[2,3-d]pyrimidin-4-yl)-1H-pyrrole-3-carbonitrile (60)

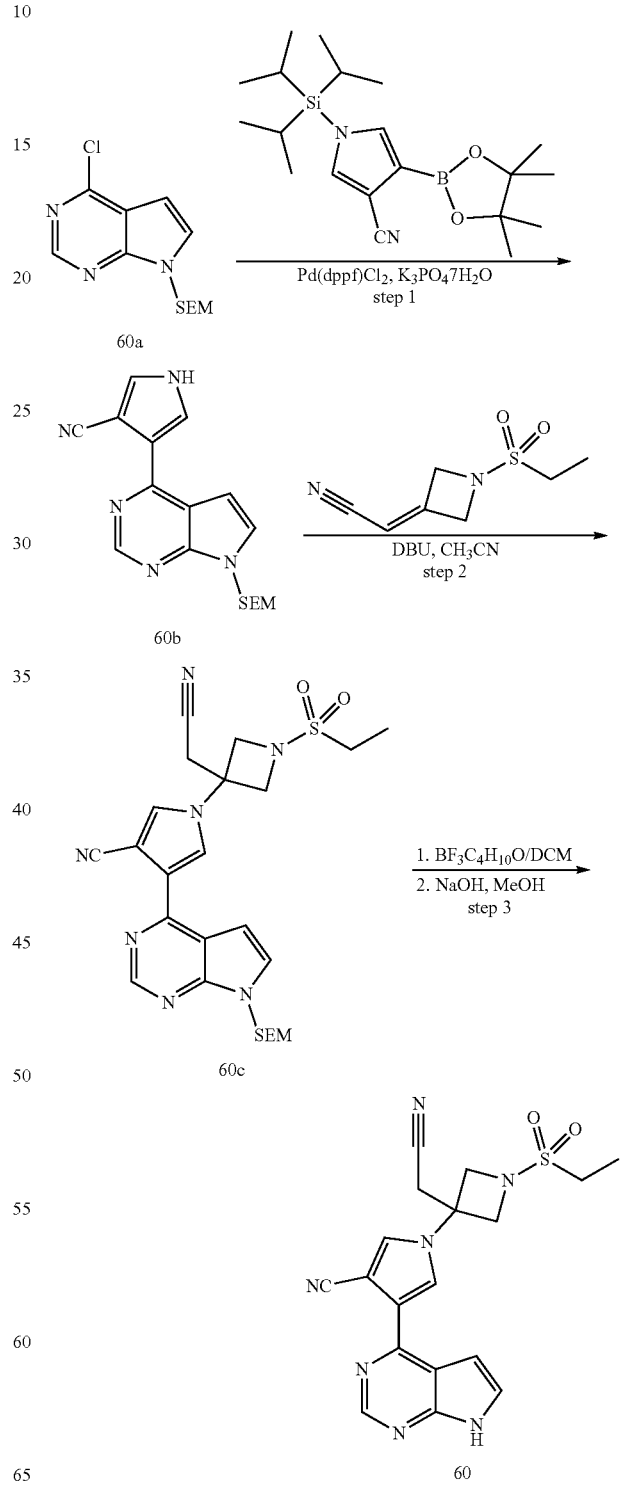

Step 1: 4-(7-((2-(trimethylsilyl)ethoxy)methyl)-7H-pyrrolo[2,3-d]pyrimidin-4-yl)-1H-pyrrole-3-carbonitrile (60b)

At room temperature, 4-chloro-7-((2-(trimethylsilyl)ethoxy)methyl)-7H-pyrrolo[2,3-d]pyrimidine (60a) (268 mg, 0.95 mmol) and 4-(4,4,5,5-tetramethyl-1,3,2-dioxaborolan-2-yl)-1-(triisopropylsilyl)-1H-pyrrole-3-carbonitrile (532 mg, 1.50 mmol) were dissolved in dioxane (6 mL), water (0.6 mL) and tribasic potassium phosphate heptahydrate (801 mg) were added, nitrogen replacement was performed, and the reaction was stirred at room temperature for 10 min. Pd(dppf)Cl$_2$ (77 mg) was added under protection of nitrogen. The reaction system was placed in an oil bath at 90° C., and stirred overnight. TLC indicated the substrate disappeared, the reaction solution was quenched by slowly pouring to ice-water, extracted with EA, and the organic phase was dried over sodium sulfate, purified on a preparative silica gel plate (PE:EA=1:1), to afford compound (60b) (235 mg, white solid), yield: 73%. MS m/z: 340 [M+1]$^+$.

Step 2: 1-(3-(cyanomethyl)-1-(ethylsulfonyl)azetidin-3-yl)-4-(7-((2-(trimethylsilyl)ethoxy)methyl)-7H-pyrrolo[2,3-d]pyrimidin-4-yl)-1H-pyrrole-3-carbonitrile (60c)

At room temperature, acetonitrile (10 mL) was added to a system of compound (60b) (200 mg, 0.59 mmol) and 2-[1-(ethylsulfonyl)azetidin-3-ylidene]acetonitrile (164 mg), and a cloudy reaction solution was obtained. DBU (269 mg) was added, the reaction solution became clear, and was stirred at room temperature overnight. The reaction solution was concentrated, the residue was dissolved in DCM, and purified on a preparative silica gel plate (PE:EA=1:2), to afford compound (60c) (232 mg, light yellow solid), yield: 75%. MS m/z: 526 [M+1]$^+$.

Step 3: 1-(3-(cyanomethyl)-1-(ethylsulfonyl)azetidin-3-yl)-4-(7H-pyrrolo[2,3-d]pyrimidin-4-yl)-1H-pyrrole-3-carbonitrile (60)

DCM (10 mL) and boron trifluoride etherate (188 mg) were added to compound (60c) (232 mg, 0.44 mmol), and the reaction was stirred at room temperature for 2 h. After LC-MS indicated the substrate disappeared, the solvent was rotary evaporated off to afford an oil, which was completely dissolved in MeOH (10 mg) followed by dropwise addition of a 1 mol/L sodium hydroxide solution, to adjust the pH value to about 10. The reaction solution was stirred at room temperature for 4 h. After LC-MS indicated the reaction was complete, the reaction was concentrated under reduced pressure to remove most of MeOH. After addition of water, solid precipitated, and was collected by filtration, and it was purified by preparative reverse-phase chromatography, to afford compound (60) (80 mg, white solid). Yield: 46%. MS m/z: 396 [M+1]$^+$.

$^1$H NMR (400 MHz, DMSO-d$_6$) δ 12.20 (s, 1H), 8.76 (s, 1H), 8.18 (d, J=2.4 Hz, 1H), 8.06 (d, J=2.4 Hz, 1H), 7.65 (t, J=2.9 Hz, 1H), 7.05-6.98 (m, 1H), 4.54 (d, J=9.4 Hz, 2H), 4.25 (d, J=9.4 Hz, 2H), 3.65 (s, 2H), 3.23 (q, J=7.3 Hz, 2H), 1.24 (t, J=7.3 Hz, 3H).

Example 42: 1-(3-(cyanomethyl)-1-(ethylsulfonyl)azetidin-3-yl)-4-(1H-pyrrolo[2,3-b]pyridin-4-yl)-1H-pyrrole-2-carbonitrile (61)

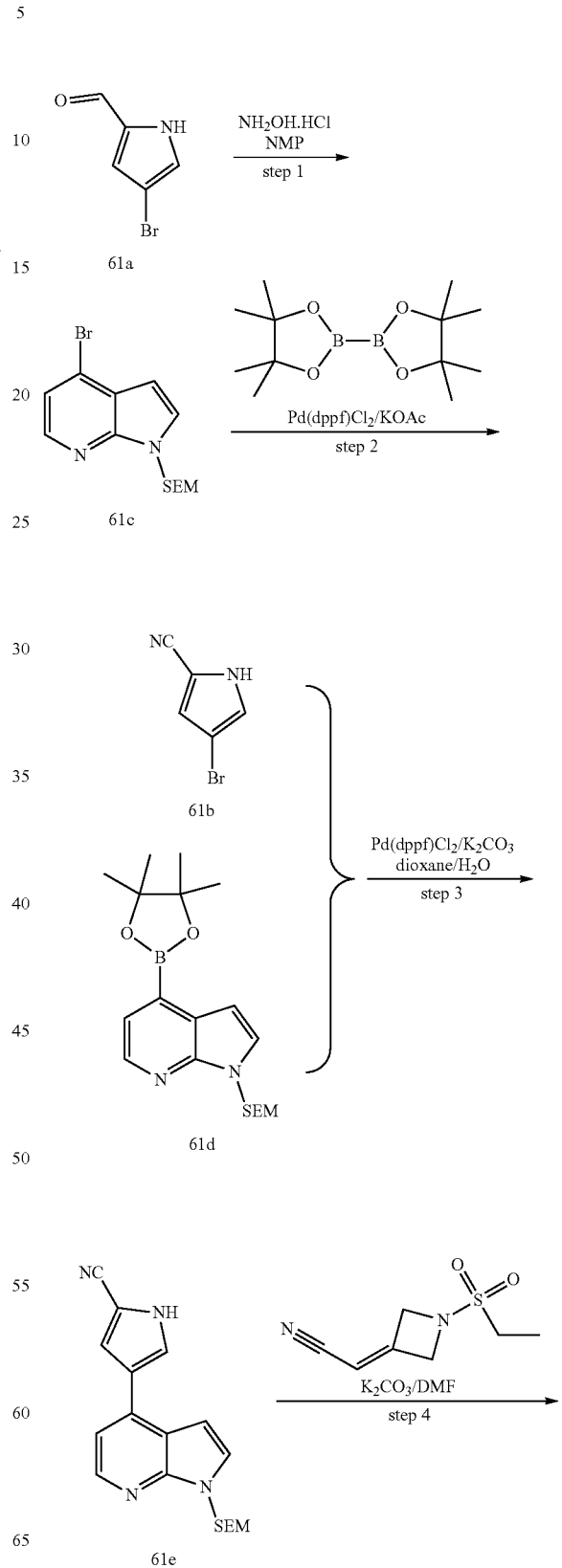

-continued

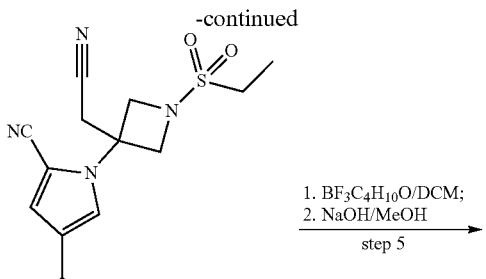

61f

1. BF₃C₄H₁₀O/DCM;
2. NaOH/MeOH
step 5

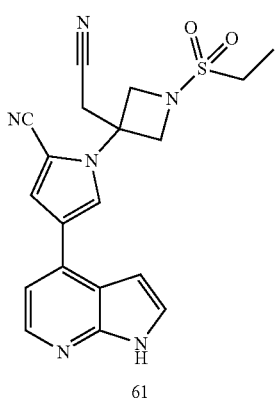 [SMILES: CCS(=O)(=O)N1CC(CC#N)(n2cc(-c3ccnc4[nH]ccc34)cc2C#N)C1]

61

Step 1: 4-bromo-1H-pyrrole-2-carbonitrile (61b)

4-bromo-1H-pyrrole-2-carbaldehyde (61a) (2.00 g, 11.49 mmol) and hydroxylamine hydrochloride (1.30 g, 18.39 mmol) were dissolved in NMP (10 mL), and the reaction was stirred in an oil bath at 125° C. for 18 h. After LC-MS indicated the reaction was complete, the reaction system was cooled to room temperature, poured into an aqueous solution of citric acid, and extracted with EA. The organic phase was combined, dried over anhydrous sodium sulfate, and purified by preparative flash chromatography (PE:EA=9:1), to afford compound (61b) (1.18 g, brown solid), yield: 60%. MS m/z: 170 [M+1]⁺.

Step 2: 4-(4,4,5,5-tetramethyl-1,3,2-dioxaborolan-2-yl)-1-((2-(trimethylsilyl)ethoxy)methyl)-1H-pyrrolo[2,3-b]pyridine (61d)

4-bromo-1-((2-(trimethylsilyl)ethoxy)methyl)-1H-pyrrolo[2,3-b]pyridine (61c) (1.00 g, 3.06 mmol), bis(pinacolato)diboron (1.50 g, 6.11 mmol), potassium acetate (898 mg, 9.17 mmol) and Pd(dppf)Cl₂ (125 mg) were placed in a 100 mL single-necked flask, nitrogen replacement was performed, and dioxane (12 mL) was added. The reaction system was placed in an oil bath at 100° C., and stirred for 3 h. After TLC (PE:EA=10:1) indicated the substrate disappeared, insolubles were filtered off, the reaction was concentrated, dissolved in EA, and purified by preparative flash chromatography (PE:EA=9:1), to afford compound (61d) (1.58 g, yellow oil), which contained a small amount of the solvent. MS m/z: 375 [M+1]⁺.

Step 3: 4-(1-((2-(trimethylsilyl)ethoxy)methyl)-1H-pyrrolo[2,3-b]pyridin-4-yl)-1H-pyrrole-2-carbonitrile (61e)

Compound (61b) (500 mg, 2.94 mmol), compound (61d) (1.60 g) and potassium carbonate (1.1 g) were placed in a 100 mL flask, dioxane (20 mL) and water (3 mL) were added, the reaction was stirred until homogeneous, Pd(dppf)Cl₂ (241 mg) was then added, nitrogen replacement was performed for 2-3 times, and the flask was placed in an oil bath at 100° C. The reaction was allowed to proceed overnight. After LC-MS indicated the substrate disappeared, insolubles were filtered off through Celite, the solvent was rotary evaporated off, the residue was dissolved in EA and washed with water to obtain an organic phase, which was dried over anhydrous sodium sulfate, and purified by preparative flash chromatography (PE:EA=2:1), to afford compound (61e) (260 mg, solid), yield: 26%. MS m/z: 339 [M+1]⁺.

Step 4: 1-(3-(cyanomethyl)-1-(ethylsulfonyl)azetidin-3-yl)-4-(1-((2-(trimethylsilyl)ethoxy)methyl)-1H-pyrrolo[2,3-b]pyridin-4-yl)-1H-pyrrole-2-carbonitrile (61f)

DMF (20 mL) was added to compound (61e) (260 mg, 0.77 mmol) and 2-[1-(ethylsulfonyl)azetidin-3-ylidene]acetonitrile (215 mg, 1.15 mmol), the reactants were dispersed in the solvent, potassium carbonate (319 mg, 2.31 mmol) was then added, and the reaction was stirred overnight at room temperature. After LC-MS indicated the substrate disappeared, the reaction solution was poured into water, extracted with EA, the organic phase was dried over anhydrous sodium sulfate, concentrated, and purified on a preparative silica gel plate (PE:EA=1:1), to afford compound (61f) (159 mg, oil), yield: 39%. MS m/z: 525 [M+1]⁺.

Step 5: 1-(3-(cyanomethyl)-1-(ethylsulfonyl)azetidin-3-yl)-4-(1H-pyrrolo[2,3-b]pyridin-4-yl)-1H-pyrrole-2-carbonitrile (61)

At room temperature, compound (61f) (159 mg, 0.30 mmol) was dissolved in dichloromethane (5 mL), after the reaction solution was stirred to clear, a boron trifluoride etherate (130 mg) solution was added, and the reaction was stirred for 2 h. After LC-MS indicated the substrate disappeared, the solvent was rotary evaporated off, 5 mL methanol was added, 1 N sodium hydroxide solution was slowly added dropwise to adjust the pH value to about 10. The reaction solution was stirred at room temperature overnight. After LC-MS indicated the reaction was complete, most of methanol was removed by concentration, the solid was dispersed in water, filtered, and purified by preparative reverse-phase chromatography, to afford compound (61) (20 mg, white solid), yield: 17%. MS m/z: 395 [M+1]⁺.

¹H NMR (400 MHz, DMSO-d₆) δ 11.72 (s, 1H), 8.20 (d, J=5.0 Hz, 1H), 8.04 (d, J=1.8 Hz, 1H), 7.81 (d, J=1.8 Hz, 1H), 7.53 (t, J=3.0 Hz, 1H), 7.29 (d, J=5.0 Hz, 1H), 6.89 (dd, J=3.6, 1.8 Hz, 1H), 4.70 (d, J=8.9 Hz, 2H), 4.25 (d, J=8.8 Hz, 2H), 3.65 (s, 2H), 3.28 (q, J=7.4 Hz, 2H), 1.25 (t, J=7.3 Hz, 3H).

Example 43: 4-(1-(3-(cyanomethyl)-1-(isopropylsulfonyl)azetidin-3-yl)-1H-pyrazol-4-yl)-1H-pyrrolo[2,3-b]pyridine-5-carbonitrile (43)

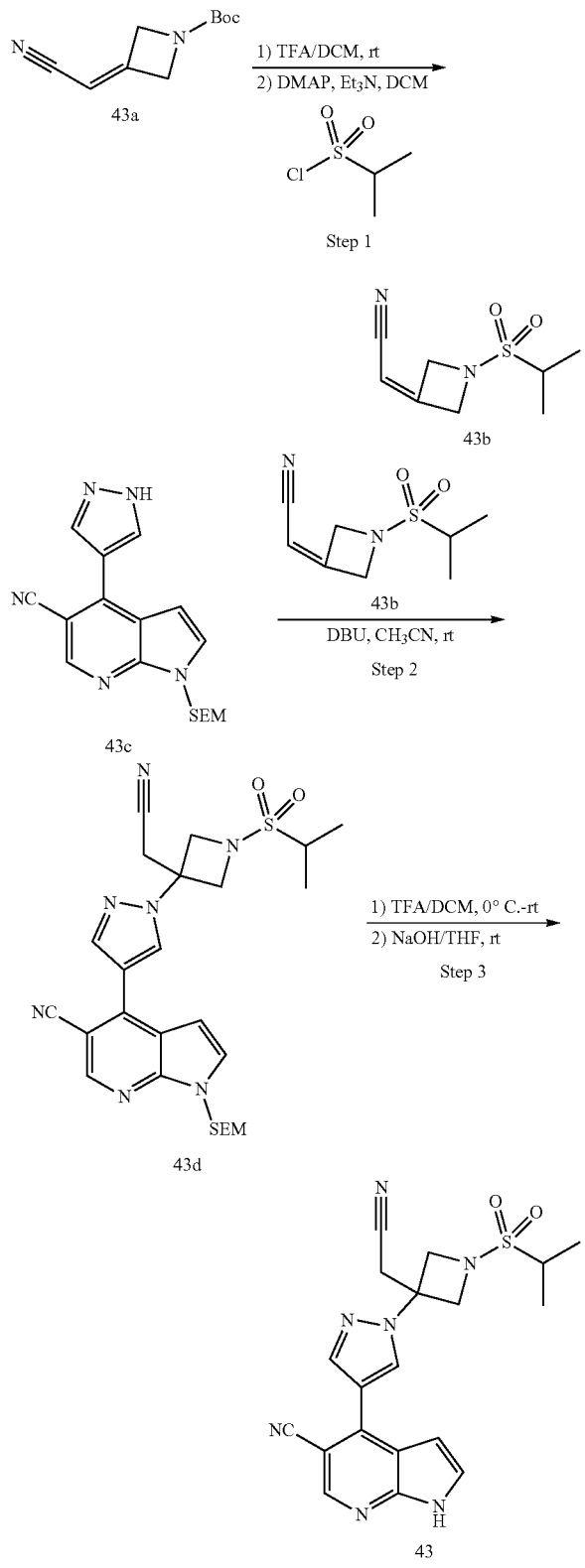

Step 1: 2-(1-(isopropylsulfonyl)azetidin-3-ylidene)acetonitrile (43b)

Tert-butyl 3-(cyanomethylene)azetidine-1-carboxylate (43a) (583 mg, 3.00 mmol) and TFA/DCM (1/3, 8 mL) were added to a 50 mL reaction flask, and the reaction was stirred at room temperature for half an hour. After thin layer chromatography indicated all the starting materials substantially disappeared, the reaction mixture was concentrated under reduced pressure to dryness. Then, the crude product thus obtained was dissolved in DCM (10 mL), triethylamine was slowly dropwise added to adjust the pH value of the system to about 8 in an ice bath. DMAP (7 mg, 0.06 mmol) was added, and then isopropylsulfonyl chloride (705 mg, 4.5 mmol) was slowly dropwise added. The resulting reaction mixture was gradually warmed to room temperature, and was stirred at room temperature for half an hour. After LC-MS indicated the reaction was complete, the reaction solution was quenched with water, extracted with dichloromethane, and the organic phase was washed with water, citric acid, and saturated brine, dried over anhydrous sodium sulfate, and concentrated under reduced pressure, to afford 2-(1-(isopropylsulfonyl)azetidin-3-ylidene)acetonitrile (43b) (600 mg, yield: 93%, brown solid). MS (ESI, m/z): 201 [M+H]$^+$.

Step 2: 4-(1-(3-(cyanomethyl)-1-(isopropylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (43d)

2-(1-(isopropylsulfonyl)azetidin-3-ylidene)acetonitrile (43b) (220 mg, 0.65 mmol), 4-(1H-pyrazol-4-yl)-5-cyano-1-((2-(trimethylsilyl)ethoxy)methyl)-1H-pyrrolo[2,3-b]pyridine (43c) (220 mg, 0.59 mmol) and acetonitrile (8 mL) were added to a 50 mL reaction flask, DBU (99 mg, 0.65 mmol) was added. The reaction was performed at room temperature for 2 h. After thin layer chromatography indicated the reaction was complete, the reaction solution was quenched with water, extracted with ethyl acetate, dried over anhydrous sodium sulfate, concentrated under reduced pressure, and purified by column chromatography on silica gel, to afford 4-(1-(3-(cyanomethyl)-1-(isopropylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (43d) (290 mg, yield: 91%, light yellow solid). MS (ESI, m/z): 540 [M+H]$^+$.

Step 3: 4-(1-(3-(cyanomethyl)-1-(isopropylsulfonyl)azetidin-3-yl)-1H-pyrazol-4-yl)-1H-pyrrolo[2,3-b]pyridine-5-carbonitrile (43)

In an ice bath, 4-(1-(3-(cyanomethyl)-1-(isopropylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (43d) (290 mg, 0.54 mmol) and a mixed solution of TFA/DCM (V:V=1:1, 6 mL) were added to a 25 mL reaction flask, argon atmosphere protection was applied, and the reaction was performed for 2.5 h. After thin layer chromatography indicated the reaction was complete, the reaction was concentrated under reduced pressure to obtain a yellow oil, which was then directly dissolved in tetrahydrofuran, and stirred until homogenous. A 1M solution of sodium hydroxide was added to adjust the pH of the system to about 10, and the reaction was performed for 0.5 h. After thin lay chromatography indicated the reaction was complete, the reaction was extracted with ethyl acetate, dried over anhydrous sodium sulfate, concentrated under reduced pressure, and purified by thin layer chromatography, to afford the target product, 4-(1-(3-(cyanomethyl)-1-(isopropylsulfonyl) azetidin-3-yl)-1H-pyrazol-4-yl)-1H-pyrrolo[2,3-b]pyridine-5-carbonitrile (43) (105 mg, yield: 48%, white solid).

$^1$H NMR (1 MHz, DMSO-$d_6$) δ 12.41 (s, 1H), 8.80 (s, 1H), 8.63 (s, 1H), 8.31 (s, 1H), 7.75 (s, 1H), 6.88 (s, 1H), 4.57 (d, J=8.8 Hz, 2H), 4.25 (d, J=8.8 Hz, 2H), 3.70 (s, 2H), 1.28 (s, 3H), 1.26 (s, 3H). MS (ESI, m/z): 410 [M+H]$^+$.

Example 44: 4-(1-(3-(cyanomethyl)-1-((3,3,3-trifluoropropyl)sulfonyl)azetidin-3-yl)-1H-pyrazol-4-yl)-1H-pyrrolo[2,3-b]pyridine-5-carbonitrile (44)

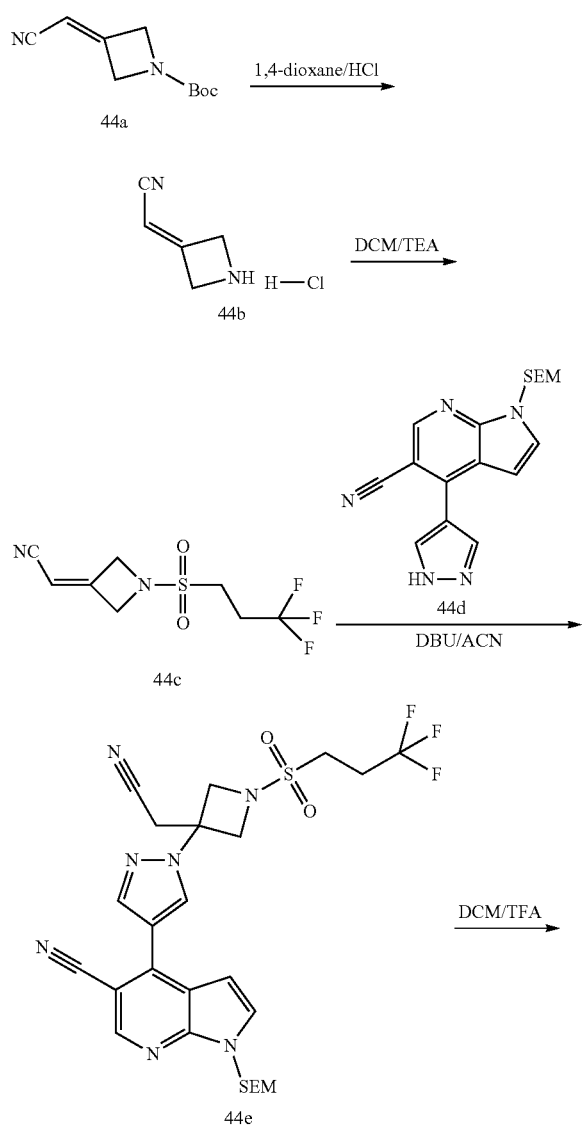

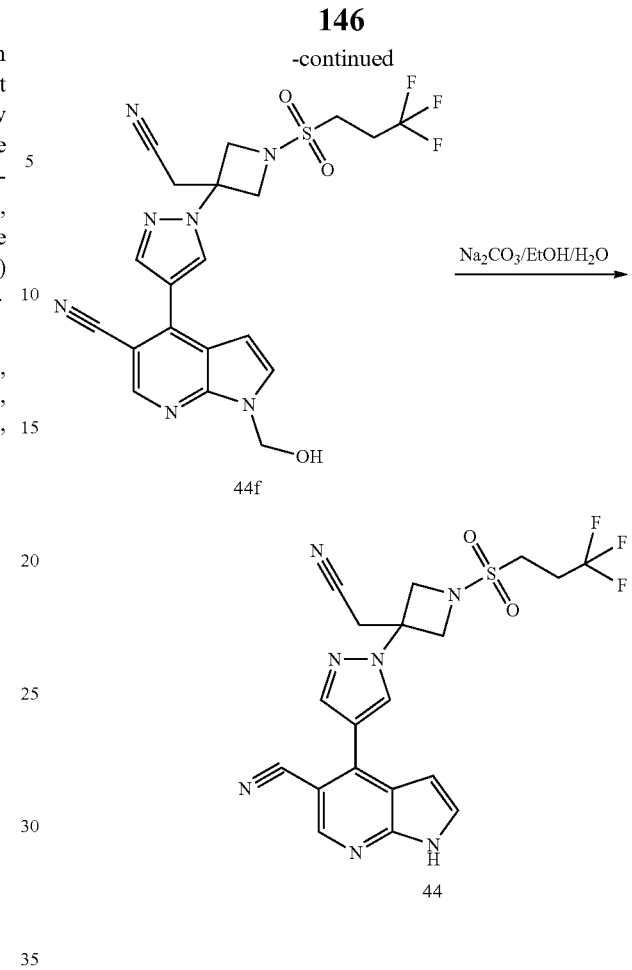

Step 1: 2-(azetidin-3-ylidene)acetonitrile hydrochloride salt (44b)

Tert-butyl 3-(cyanomethylene)azetidine-1-carboxylate (2.0 g) was added to a reaction flask. Under cooling with an ice-water bath, 1,4-dioxane/HCl (20 mL) was slowly dropwise added to the reaction system, and the bath was removed after the addition. The reaction was stirred for 2 h, and a large amount of white solid precipitated from the system. The reaction system was filtered, and the filter cake was washed with methyl tert-butyl ether, and dried, to afford 2-(azetidin-3-ylidene)acetonitrile hydrochloride salt (44b) (1.15 g, yield: 85.4%) as a white solid. MS (ESI, m/z): 95 [M+H]$^+$.

Step 2: 2-(1-((3,3,3-trifluoropropyl)sulfonyl)azetidin-3-ylidene)acetonitrile (44c)

The white solid (44b) (500 mg) obtained in step 1 was added to dichloromethane (20 mL), and (3,3,3-trifluoropropane)sulfonyl chloride (1.126 g) was added. The system was placed in an ice-water bath, to which TEA (1.16 g) diluted in DCM (15 mL) was slowly dropwise added, and the reaction was stirred for 5 h after the addition. The reaction system was added with water (10 mL), stirred for 10 min, and the organic phase was separated. The aqueous phase was back extracted with DCM (30 mL), the organic phase was combined, concentrated to dryness, and directly used in the next step. MS (ESI, m/z): 255 [M+H]$^+$.

Step 3: 4-(1-(3-(cyanomethyl)-1-((3,3,3-trifluoropropyl)sulfonyl)azetidin-3-yl)-1H-pyrazol-4-yl)-1-((2-(trimethylsilyl)ethoxy)methyl)-1H-pyrrolo[2,3-b]pyridine-5-carbonitrile (44e)

4-(1H-pyrazol-4-yl)-1-((2-(trimethylsilyl)ethoxy)methyl)-1H-pyrrolo[2,3-b]pyridine-5-carbonitrile (44d) (350 mg) and 2-(1-((3,3,3-trifluoropropyl)sulfonyl)azetidin-3-ylidene)acetonitrile (44c) (940 mg, crude) were dissolved in acetonitrile (15 mL), and DBU (1 mL) was added to the reaction system. The reaction was stirred at room temperature overnight. After TLC indicated the reaction was complete, the reaction was rotary evaporated to dryness, and purified by column chromatography on silica gel, to afford a yellow solid (44e, 380 mg). MS (ESI, m/z): 594 [M+H]$^+$.

Step 4: 4-(1-(3-(cyanomethyl)-1-((3,3,3-trifluoropropyl)sulfonyl)azetidin-3-yl)-1H-pyrazol-4-yl)-1-(hydroxymethyl)-1H-pyrrolo[2,3-b]pyridine-5-carbonitrile (44f)

4-(1-(3-(cyanomethyl)-1-((3,3,3-trifluoropropyl)sulfonyl)azetidin-3-yl)-1H-pyrazol-4-yl)-1-((2-(trimethylsilyl)ethoxy)methyl)-1H-pyrrolo[2,3-b]pyridine-5-carbonitrile (44e) (350 g) was dissolved in dichloromethane (8 mL). The reaction system was placed in an ice bath, trifluoroacetic acid was added, and the reaction was performed for about 3 h. After TLC indicated the reaction was complete, the reaction solution was concentrated, and purified by TLC, to afford a white solid (44f, 160 mg). MS (ESI, m/z): 494 [M+H]$^+$.

Step 5: 4-(1-(3-(cyanomethyl)-1-((3,3,3-trifluoropropyl)sulfonyl)azetidin-3-yl)-1H-pyrazol-4-yl)-1H-pyrrolo[2,3-b]pyridine-5-carbonitrile (44)

4-(1-(3-(cyanomethyl)-1-((3,3,3-trifluoropropyl)sulfonyl)azetidin-3-yl)-1H-pyrazol-4-yl)-1-(hydroxymethyl)-1H-pyrrolo[2,3-b]pyridine-5-carbonitrile (44f) (160 mg) and ethanol (200 mL) were added to a reaction flask, and the dissolving process was aided by ultrasound. Water (20 mL) and sodium carbonate (678 mg) were added, and the mixture was stirred overnight. The reaction solution was concentrate, a large amount of solid precipitated, and was filtered, washed with water, dried under vacuum, to obtain a white solid (44, 65 mg). $^1$H NMR (400 MHz, DMSO) δ 12.42 (s, 1H), 8.81 (s, 1H), 8.63 (s, 1H), 8.32 (s, 1H), 7.75 (s, 1H), 6.88 (s, 1H), 4.66 (m, J=8.92 Hz, 2H), 4.35 (m, J=8.96 Hz, 2H), 3.72 (s, 2H), 3.59 (m, 3H), 2.76 (m, 2H). MS (ESI, m/z): 464 [M+H]$^+$.

Example 45: 4-(1-(3-(1-cyanoethyl)-1-(ethylsulfonyl)azetidin-3-yl)-1H-pyrazol-4-yl)-1H-pyrrolo[2,3-b]pyridine-5-carbonitrile (45)

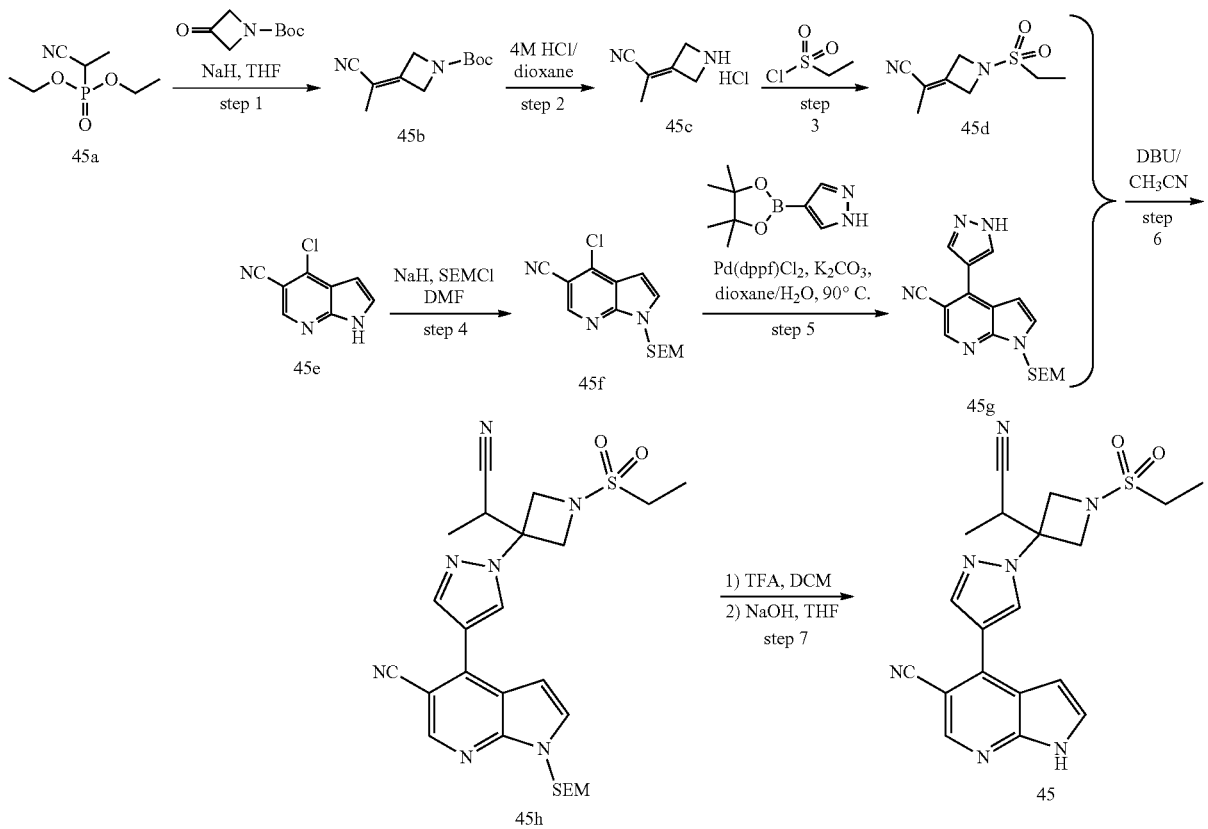

Step 1: tert-butyl 3-(1-cyanoethylidene)azetidine-1-carboxylate (45b)

In an ice bath, sodium hydride (880 mg, 60%) was added to a solution of diethyl (1-cyanoethyl)phosphonate (45a) (2 g, 11 mmol) in tetrahydrofuran (100 mL), and after being stirred for 40 min, the system became pink. Tert-butyl 3-oxoazetidine-1-carboxylate (3.8 g, 22 mmol) was added to the reaction system, and the reaction became clear slowly.

The system was slowly warmed to room temperature, and stirred overnight. The reaction was quenched with water, extracted with ethyl acetate, and dried over anhydrous sodium sulfate. The organic phase was concentrated, to afford tert-butyl 3-(1-cyanoethylidene)azetidine-1-carboxylate (45b) (3.95 g, light yellow oil), which was used directly in the next step. MS (ESI, m/z): 209 [M+H]$^+$.

Step 2: 2-(azetidin-3-ylidene)propanenitrile hydrochloride salt (45c)

At room temperature, a solution of 4M hydrochloric acid in dioxane (40 mL) was added to tert-butyl 3-(1-cyanoethylidene)azetidine-1-carboxylate (45b) (3.8 g, 18.3 mmol), and the reactants dissolved with stirring. The reaction was stirred at room temperature for 1 h. LC-MS indicated the substrate disappeared. The stirring was stopped, and the solvent in the reaction system was rotary evaporated. The residue was triturated with ether, and filtered, to afford 2-(azetidin-3-ylidene)propanenitrile hydrochloride salt (45c) (2.24 g, yield: 85%, white solid). MS (ESI, m/z): 109 [M+H]$^+$.

Step 3: 2-(1-(ethylsulfonyl)azetidin-3-ylidene)propanenitrile (45d)

In an ice bath, 2-(azetidin-3-ylidene)propanenitrile hydrochloride salt (45c) (2.24 g, 15.5 mmol) was dissolved in acetonitrile (100 mL), DIEA (7.0 g) was then added, and the reaction was stirred in the ice bath for 15 min. Ethanesulfonyl chloride (3.98 g, 31 mmol) was slowly added to the system while keeping the temperature no higher than 5° C. After the addition of the substrate, the reaction was slowly warmed to room temperature, and stirred overnight. LC-MS indicated the substrate disappeared. The reaction was purified by column chromatography (PE:EA=2:1), to afford 2-(1-(ethylsulfonyl)azetidin-3-ylidene)propanenitrile (45d) (1.2 g, yield: 65%, yellow oil). MS (ESI, m/z): 201 [M+H]$^+$.

Step 4: 4-chloro-5-cyano-1-((2-(trimethylsilyl)ethoxy)methyl)-1H-pyrrolo[2,3-b]pyridine (45f)

At room temperature, 4-chloro-5-cyano-7-azaindole (45e) (1.92 g, 10.76 mmol) and DMF (22 mL) were added to a 100 mL three-necked flask, and nitrogen atmosphere protection was applied. The mixture was cooled to below 5° C. in an ice-salt bath, and after the reaction solution was stirred until homogeneous, sodium hydride (60 wt %, 560 mg, 13.98 mmol) was added to the flask in portions while keeping the temperature of the system no higher than 10° C. After stirred for 1 h, 2-(trimethylsilyl)ethoxymethyl chloride (2.33 g, 13.98 mmol) was slowly added to the system dropwise while keeping the temperature no higher than 5° C., and the stir was continued for 2 h. The reaction was monitored by thin layer chromatography. After the starting material substantially disappeared, the reaction solution was quenched with water, extracted with ethyl acetate, dried over anhydrous sodium sulfate, concentrated under reduced pressure, and purified by column chromatography on silica gel, to afford 4-chloro-5-cyano-1-((2-(trimethylsilyl)ethoxy)methyl)-1H-pyrrolo[2,3-b]pyridine (45f) (4.30 g, yield: 86%, white solid). MS (ESI, m/z): 308 [M+H]$^+$.

Step 5: 4-(1H-pyrazol-4-yl)-1-((2-(trimethylsilyl)ethoxy)methyl)-1H-pyrrolo[2,3-b]pyridine-5-carbonitrile (45g)

At room temperature, 4-chloro-5-cyano-1-((2-(trimethylsilyl)ethoxy)methyl)-1H-pyrrolo[2,3-b]pyridine (45f) (200 mg, 0.65 mmol), 4-pyrazoleboronic acid pinacol ester (189 mg, 0.98 mmol), a potassium carbonate (225 mg, 1.63 mmol) solution (2 mL) and 1,4-dioxane (8 mL) were sequentially added to a 50 mL reaction flask, and nitrogen atmosphere protection was applied. After the reaction solution was stirred until homogeneous, Pd(dppf)Cl$_2$ (50 mg, 0.065 mmol) was added under nitrogen atmosphere protection. The reaction system was heated to 95° C., and refluxed overnight. The reaction was monitored by thin layer chromatography. After the starting material was consumed, the reaction solution was quenched with water, extracted with ethyl acetate, dried over anhydrous sodium sulfate, concentrated under reduced pressure, and purified by column chromatography on silica gel, to afford 4-(1H-pyrazol-4-yl)-1-((2-(trimethylsilyl)ethoxy)methyl)-1H-pyrrolo[2,3-b]pyridine-5-carbonitrile (45g) (134 mg, yield: 61%, yellow solid). MS (ESI, m/z): 340 [M+H]$^+$.

Step 6: 4-(1-(3-(1-cyanoethyl)-1-(ethylsulfonyl) azetidin-3-yl)-1H-pyrazol-4-yl)-1-((2-(trimethylsilyl)ethoxy)methyl)-1H-pyrrolo[2,3-b]pyridine-5-carbonitrile (45h)

4-(1H-pyrazol-4-yl)-1-((2-(trimethylsilyl)ethoxy)methyl)-1H-pyrrolo[2,3-b]pyridine-5-carbonitrile (45g) (600 mg, 1.77 mmol), 2-(1-(ethylsulfonyl)azetidin-3-ylidene)propanenitrile (45d) (388 mg, 1.94 mmol) and acetonitrile (20 mL) were sequentially added to a 50 mL reaction flask, and then DBU (277 mg, 1.94 mmol) was added. The reaction was performed at room temperature for 2 h. After thin layer chromatography indicated the reaction was complete, the reaction solution was quenched with water, extracted with ethyl acetate, dried over anhydrous sodium sulfate, concentrated under reduced pressure, and purified by column chromatography on silica gel, to afford 4-(1-(3-(1-cyanoethyl)-1-(ethylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (45h) (851 mg, yield: 89%, light yellow solid). MS (ESI, m/z): 540 [M+H]$^+$.

Step 7: 4-(1-(3-(1-cyanoethyl)-1-(ethylsulfonyl) azetidin-3-yl)-1H-pyrazol-4-yl)-1H-pyrrolo[2,3-b] pyridine-5-carbonitrile (45)

At room temperature, 4-(1-(3-(1-cyanoethyl)-1-(ethylsulfonyl)azetidin-3-yl)-1H-pyrazol-4-yl)-1-((2-(trimethylsilyl)ethoxy)methyl)-1H-pyrrolo[2,3-b]pyridine-5-carbonitrile (45h) (851 mg, 1.58 mmol) and a mixed solution of TFA/DCM (V:V=1:1, 20 mL) were added to a 50 mL reaction flask, argon atmosphere protection was applied, and the reaction was performed for 2.5 h. After thin layer chromatography indicated the reaction was complete, the reaction solution was concentrated under reduced pressure to obtain a yellow oil, which was then directly dissolved in tetrahydrofuran (20 mL), and stirred until homogenous. A 1M solution of sodium hydroxide was added to adjust the pH of the system to about 10, and the reaction was performed for 0.5 h. After thin lay chromatography indicated the reaction was complete, the reaction was extracted with ethyl acetate, dried over anhydrous sodium sulfate, concentrated under reduced pressure, and purified by column chromatography on silica gel, to afford 4-(1-(3-(1-cyanoethyl)-1-(ethylsulfonyl)azetidin-3-yl)-1H-pyrazol-4-yl)-1H-pyrrolo[2,3-b]pyridine-5-carbonitrile (45) (305 mg, yield: 48%, white solid).

¹H NMR (400 MHz, DMSO-d₆) δ 12.44 (s, 1H), 8.82 (s, 1H), 8.66 (s, 1H), 8.32 (s, 1H), 7.78 (d, J=5.00 Hz, 1H), 6.87 (d, J=5.00 Hz, 1H), 4.59 (dd, J=14.48, 9.37 Hz, 2H), 4.40 (dd, J=9.36, 6.46 Hz, 2H), 3.98 (q, J=6.99 Hz, 1H), 3.25 (q, J=7.32 Hz, 2H), 1.26 (t, J=7.33 Hz, 3H), 1.20 (d, J=6.96 Hz, 3H). MS (ESI, m/z): 410 [M+H]⁺.

Compound (45h) synthesized in step 6 was separated by chiral chromatography to obtain stereoisomer (45h-1) (retention time: 2.7 min) and stereoisomer (45h-2) (retention time: 3.2 min), and compound (45-1) and compound (45-2) were obtained by removing the protecting group in stereoisomer (45h-1) and stereoisomer (45h-2), respectively:

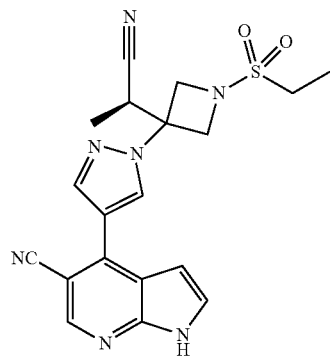

45-1

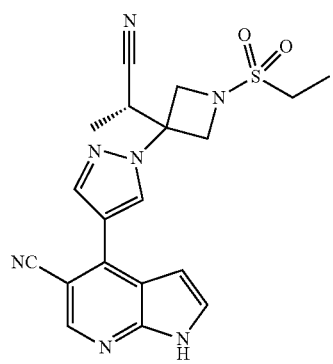

45-2

(R)-4-(1-(3-(1-cyanoethyl)-1-(ethylsulfonyl)azetidin-3-yl)-1H-pyrazol-4-yl)-1H-pyrrolo[2,3-b]pyridine-5-carbonitrile (45-1): MS (ESI, m/z): 410 [M+H]⁺. ¹H NMR (400 MHz, DMSO-d₆) δ 12.44 (s, 1H), 8.82 (s, 1H), 8.66 (s, 1H), 8.32 (s, 1H), 7.78 (d, J=5.00 Hz, 1H), 6.87 (d, J=5.00 Hz, 1H), 4.59 (dd, J=14.48, 9.37 Hz, 2H), 4.40 (dd, J=9.36, 6.46 Hz, 2H), 3.98 (q, J=6.99 Hz, 1H), 3.25 (q, J=7.32 Hz, 2H), 1.26 (t, J=7.33 Hz, 3H), 1.20 (d, J=6.96 Hz, 3H); and (S)-4-(1-(3-(1-cyanoethyl)-1-(ethylsulfonyl)azetidin-3-yl)-1H-pyrazol-4-yl)-1H-pyrrolo[2,3-b]pyridine-5-carbonitrile (45-2): MS (ESI, m/z): 410 [M+H]⁺. ¹H NMR (400 MHz, DMSO-d₆) δ 12.44 (s, 1H), 8.82 (s, 1H), 8.66 (s, 1H), 8.32 (s, 1H), 7.78 (d, J=5.00 Hz, 1H), 6.87 (d, J=5.00 Hz, 1H), 4.59 (dd, J=14.48, 9.37 Hz, 2H), 4.40 (dd, J=9.36, 6.46 Hz, 2H), 3.98 (q, J=6.99 Hz, 1H), 3.25 (q, J=7.32 Hz, 2H), 1.26 (t, J=7.33 Hz, 3H), 1.20 (d, J=6.96 Hz, 3H).

Example 46: 2-(1-(ethylsulfonyl)-3-(4-(5-fluoro-1H-pyrrolo[2,3-b]pyridin-4-yl)-1H-pyrazol-1-yl)azetidin-3-yl)acetonitrile hydrochloride salt (52-HCl)

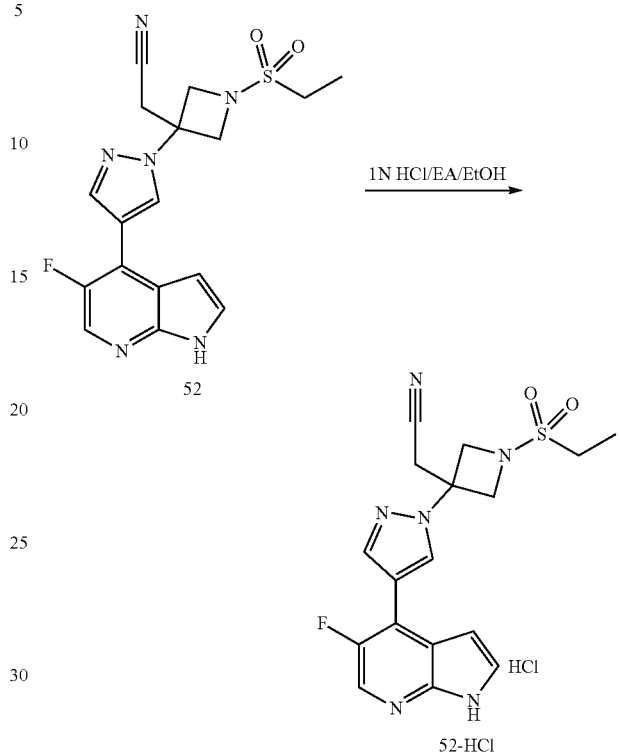

Compound (52) (60 mg) obtained in Example 52 was dispersed in a mixed solvent (EA/EtOH=1, 15 mL), a 1 mol/L solution of hydrochloric acid in ethyl acetate was slowly dropwise added. After the reaction solution became clear, the dropwise addition was stopped, and the reaction was stirred at room temperature for 10 min. The organic solvent was rotary evaporated off, water (30 mL) was added to disperse the solid, and the hydrochloride salt of compound (52) (52-HCl) (65 mg, white solid) was obtained after lyophilization. MS m/z: 389 [M+1]⁺.

¹H NMR (400 MHz, DMSO-d₆) δ 11.90 (s, 1H), 8.73 (s, 1H), 8.27 (t, J=3.2 Hz, 2H), 7.64 (t, J=3.0 Hz, 1H), 6.90 (dd, J=3.6, 1.8 Hz, 1H), 4.60 (d, J=9.1 Hz, 2H), 4.25 (d, J=9.1 Hz, 2H), 3.69 (s, 2H), 3.24 (q, J=7.3 Hz, 2H), 1.24 (t, J=7.3 Hz, 3H).

Example 47: 2-(3-(3-chloro-4-(7H-pyrrolo[2,3-d]pyrimidin-4-yl)-1H-pyrrol-1-yl)-1-(ethylsulfonyl)azetidin-3-yl)acetonitrile (59)

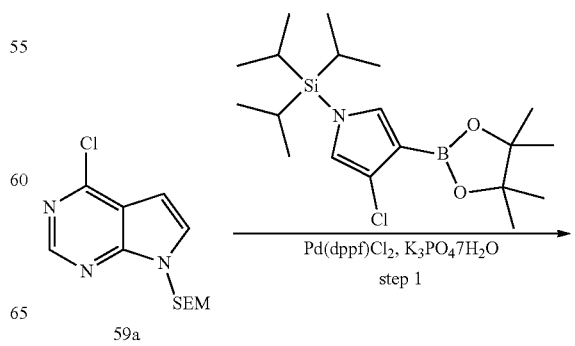

-continued
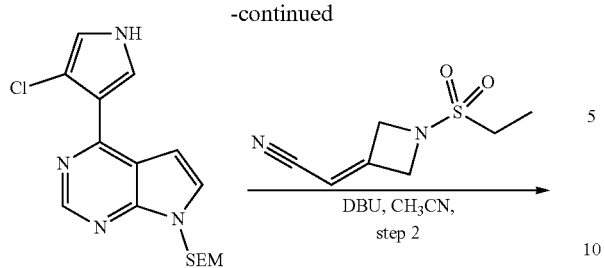
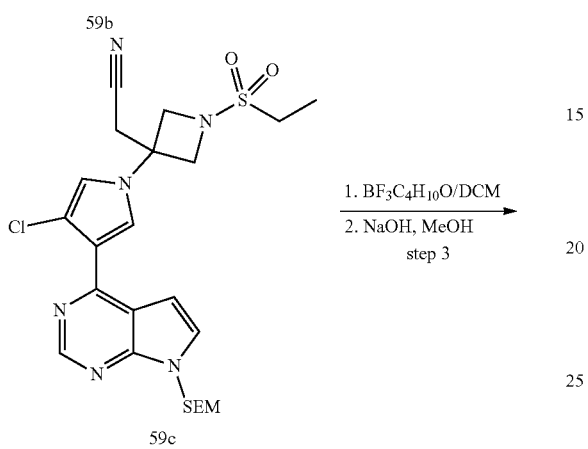
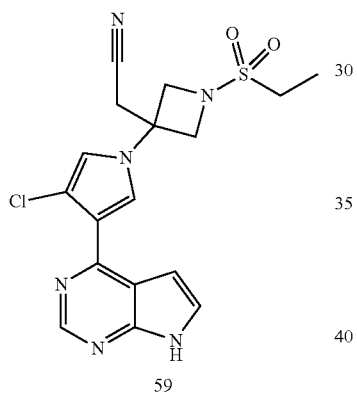
Compound (59) (98 mg, white solid) was prepared according to the above synthetic route, employing procedures similar to those in Example 41. Yield: 59%. MS m/z: 405 [M+1]⁺.
¹H NMR (400 MHz, DMSO-d₆) δ 12.10 (s, 1H), 8.73 (s, 1H), 7.74 (d, J=2.7 Hz, 1H), 7.57 (t, J=2.9 Hz, 1H), 7.42 (d, J=2.7 Hz, 1H), 6.82 (dd, J=3.6, 1.8 Hz, 1H), 4.47 (d, J=9.2 Hz, 2H), 4.20 (d, J=9.2 Hz, 2H), 3.59 (s, 2H), 3.23 (q, J=7.3 Hz, 2H), 1.24 (t, J=7.3 Hz, 3H).
Example 48: 2-(3-(3-chloro-4-(1H-pyrrolo[2,3-b]pyridin-4-yl)-1H-pyrazol-1-yl)-1-(ethylsulfonyl)azetidin-3-yl)acetonitrile (48)
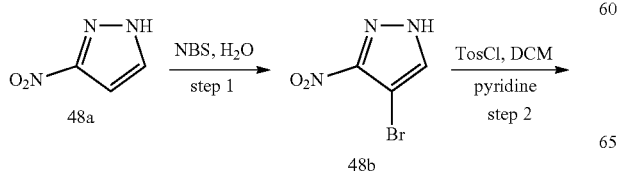
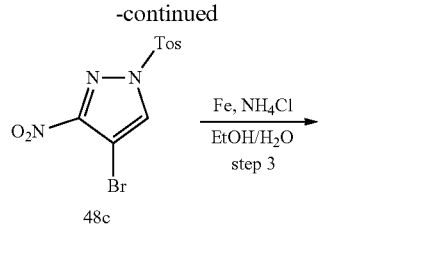
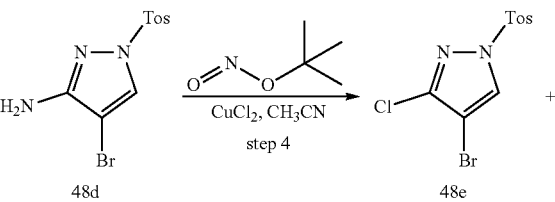
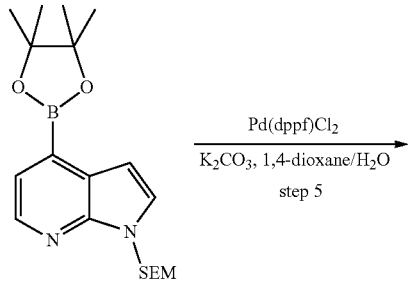
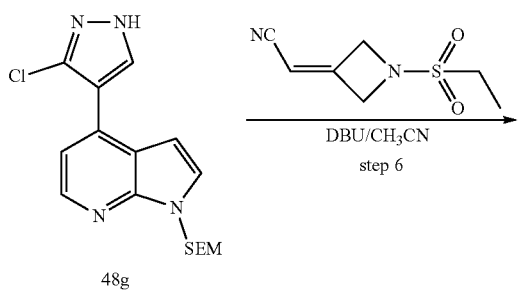
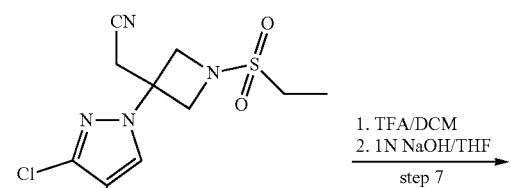

-continued

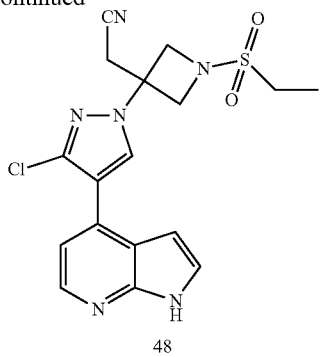

48

Step 1: 4-bromo-3-nitro-1H-pyrazole (48b)

At room temperature, water (15 mL) was added to a mixture of 3-nitro-1H-pyrazole (48a) (1 g, 8.90 mmol) and NBS (1.73 g, 9.70 mmol), and the reaction was stirred overnight. After thin layer chromatography indicated the reaction was complete, the reaction solution was diluted with water, extracted with ethyl acetate, washed with saturated brine, dried over anhydrous sodium sulfate, concentrated under reduced pressure, and rotary evaporated to dryness, to afford compound (48b) (1.66 g, yield: 93%, white solid). MS (ESI, m/z): 192 [M+H]$^+$.

Step 2: 4-bromo-3-nitro-1-tosyl-1H-pyrazole (48c)

At room temperature, compound (48b) (500 mg, 2.60 mmol), p-toluene sulfonyl chloride (595 mg, 3.10 mmol) and dichloromethane (10 mL) were added to a round bottom flask, pyridine (1.3 mL) was then dropwise added, and the reaction was performed for 3 h. After thin layer chromatography indicated the reaction was complete, the reaction solution was quenched with a saturated solution of sodium bicarbonate, extracted with dichloromethane, washed with an aqueous solution of sodium chloride, dried over anhydrous sodium sulfate, concentrated under reduced pressure, and rotary evaporated to dryness, to afford compound (48c) (652 mg, yield: 73%, white solid). MS (ESI, m/z): 346 [M+H]$^+$.

Step 3: 4-bromo-1-tosyl-1H-pyrazol-3-amine (48d)

At room temperature, compound (48c) (650 mg, 1.90 mmol), iron powder (526 mg, 9.40 mmol), ammonium chloride (502 mg, 9.40 mmol), ethanol (20 mL) and water (20 mL) were sequentially added to a 100 mL round bottom flask, and the reaction was heated to 55° C., and allowed to proceed for 2 h. After thin layer chromatography indicated the reaction was complete, iron powder was filtered off through Celite, the reaction solution was rotary evaporated to remove part of ethanol, extracted with ethyl acetate, washed with saturated brine, dried over anhydrous sodium sulfate, concentrated under reduced pressure, and purified by column chromatography on silica gel, to afford compound (48d) (526 mg, yield: 89%, light yellow solid). MS (ESI, m/z): 316 [M+H]$^+$.

Step 4: 4-bromo-3-chloro-1-tosyl-1H-pyrazole (48e)

Tert-butyl nitrite (255 mg, 2.50 mmol), cupric chloride (338 mg, 2.00 mmol) and acetonitrile (10 mL) were placed in a 50 mL three-necked flask, and the reaction was stirred under protection of nitrogen in an ice bath. Compound (48d) (521 mg, 1.70 mmol) dissolved in acetonitrile (5 mL) was then dropwise added to the flask, and the reaction was continued for 3 h. After thin layer chromatography indicated the reaction was complete, cupric chloride was filtered off through Celite. The reaction solution was rotary evaporated to remove part of acetonitrile, extracted with ethyl acetate, washed with saturated brine, dried over anhydrous sodium sulfate, concentrated under reduced pressure, and purified by column chromatography on silica gel, to afford compound (48e) (280 mg, light yellow solid), yield: 51%. MS (ESI, m/z): 335 [M+H]$^+$.

Step 5: 4-(3-chloro-1H-pyrazol-4-yl)-1-((2-(trimethylsilyl)ethoxy)methyl)-1H-pyrrolo[2,3-b]pyridine (48g)

At room temperature, under protection of nitrogen, compound (48e) (260 mg, 0.80 mmol), 4-(4,4,5,5-tetramethyl-1,3,2-dioxaborolan-2-yl)-1-((2-(trimethylsilyl)ethoxy)methyl)-1H-pyrrolo[2,3-b]pyridine (435 mg, 1.20 mmol), a potassium carbonate (268 mg, 1.90 mmol) solution (3 mL) and dioxane (15 mL) were sequentially added to a 50 mL reaction flask. After the reaction solution was stirred until homogenous, Pd(dppf)Cl$_2$ (57 mg, 0.08 mmol) was added under protection of nitrogen. The system was heated to 100° C., and the reaction was allowed to proceed overnight. After thin layer chromatography indicated the reaction was complete, the reaction solution was quenched with water, extracted with ethyl acetate, dried over anhydrous sodium sulfate, concentrated under reduced pressure, and purified by column chromatography on silica gel, to afford compound (48g) (159 mg, white solid), yield: 59%. MS (ESI, m/z): 349 [M+H]$^+$.

Step 6: 2-(3-(3-chloro-4-(1-((2-(trimethylsilyl)ethoxy)methyl)-1H-pyrrolo[2,3-b]pyridin-4-yl)-1H-pyrazol-1-yl)-1-(ethylsulfonyl)azetidin-3-yl)acetonitrile (48h)

At room temperature, 2-[1-(ethylsulfonyl)azetidin-3-ylidene]acetonitrile (169 mg, 0.91 mmoL) and DBU (105 mg, 0.69 mmol) were sequentially added to a solution of compound (48g) (159 mg, 0.46 mmol) in acetonitrile (5 mL), and the reaction was performed for 3 h. After thin layer chromatography indicated the reaction was complete, the reaction solution was quenched with water, extracted with ethyl acetate, dried over anhydrous sodium sulfate, concentrated under reduced pressure, and purified by column chromatography on silica gel, to afford compound (48h) (177 mg, white solid), yield: 73%. MS (ESI, m/z): 535 [M+H]$^+$.

Step 7: 2-(3-(3-chloro-4-(1H-pyrrolo[2,3-b]pyridin-4-yl)-1H-pyrazol-1-yl)-1-(ethylsulfonyl)azetidin-3-yl)acetonitrile (48)

At room temperature, a solution of compound (48h) (110 mg, 0.21 mmol) in TFA/DCM (1:1) (4 mL) was added to a 25 mL reaction flask, and the reaction was stirred for 1 h under protection of argon in an ice bath. After LC-MS indicated the reaction was complete, the reaction was extracted with ethyl acetate, dried over anhydrous sodium sulfate, and concentrated under reduced pressure, to afford a yellow oil; to which tetrahydrofuran (3 mL) was added at room temperature, after stirred until homogeneous, 1M sodium hydroxide solution was added to adjust the pH value of the reaction solution to about 10, and the reaction was stirred for 2 h. After thin layer chromatography indicated the reaction was complete, the reaction was extracted with ethyl acetate, dried over anhydrous sodium sulfate, concentrated under reduced pressure, and purified by column chromatography on silica gel, to afford compound (48) (47 mg, white solid), yield: 55%. MS (ESI, m/z): 405 [M+H]$^+$.

$^1$H NMR (400 MHz, DMSO-d$_6$) δ 11.83 (s, 1H), 8.70 (s, 1H), 8.28 (d, J=5.0 Hz, 1H), 7.58-7.55 (m, 1H), 7.29 (d, J=5.0 Hz, 1H), 6.67 (dd, J=3.3, 1.8 Hz, 1H), 4.57 (d, J=9.2 Hz, 2H), 4.24 (d, J=9.2 Hz, 2H), 3.68 (s, 2H), 3.25 (q, J=7.3 Hz, 2H), 1.24 (t, J=7.3 Hz, 3H).

Example 49: 2-(1-(ethylsulfonyl)-3-(3-methyl-4-(7H-pyrrolo[2,3-d]pyrimidin-4-yl)-1H-pyrazol-1-yl)azetidin-3-yl)acetonitrile (49)

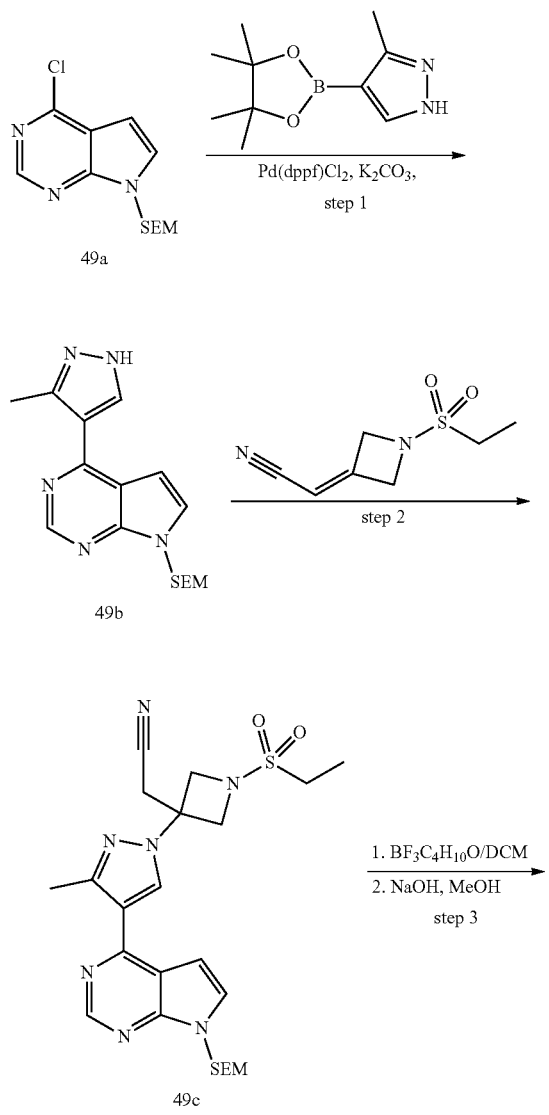

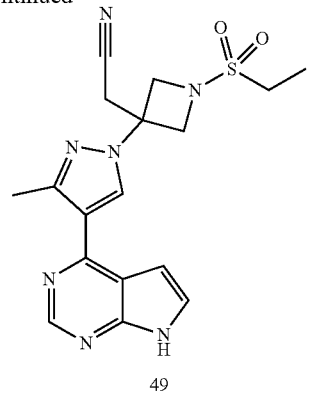

Step 1: 4-(3-methyl-1H-pyrazol-4-yl)-7-((2-(trimethylsilyl)ethoxy)methyl)-7H-pyrrolo[2,3-d]pyrimidine (49b)

At room temperature, 4-chloro-7-((2-(trimethylsilyl)ethoxy)methyl)-7H-pyrrolo[2,3-d]pyrimidine (49a) (1.00 g, 3.52 mmol) and 3-methyl-4-(4,4,5,5-tetramethyl-1,3,2-dioxaborolan-2-yl)-1H-pyrazole (1.10 g, 5.28 mmol) were dissolved in dioxane (30 mL), water (4 mL) and potassium carbonate (1.20 g) were then added, nitrogen replacement was performed, and the reaction was stirred at room temperature for 10 min. Pd(dppf)Cl$_2$ (140 mg) was added under protection of nitrogen. The reaction system was stirred in an oil bath at 90° C. overnight. After TLC indicated the substrate disappeared, the reaction solution was quenched by slowly pouring into ice-water, extracted with EA, the organic phase was dried over anhydrous sodium sulfate, and purified by preparative flash chromatography (PE:EA=1:1), to afford compound (49b) (200 mg, yellow solid), yield: 18%. MS m/z: 330 [M+1]$^+$.

Step 2: 2-(1-(ethylsulfonyl)-3-(3-methyl-4-(7-((2-(trimethylsilyl)ethoxy)methyl)-7H-pyrrolo[2,3-d]pyrimidin-4-yl)-1H-pyrazol-1-yl)azetidin-3-yl)acetonitrile (49c)

At room temperature, acetonitrile (15 mL) was added to compound (49b) (200 mg, 0.59 mmol) and 2-[1-(ethylsulfonyl)azetidin-3-ylidene]acetonitrile (112 mg) to obtain a cloudy reaction solution, DBU (249 mg) was then added, and the reaction was stirred at room temperature overnight. The reaction was concentrated, and purified on a preparative silica gel plate (DCM:EA=2:1), to afford compound (49c) (220 mg, white solid). Yield: 73%. MS m/z: 516 [M+1]$^+$.

Step 3: 2-(1-(ethylsulfonyl)-3-(3-methyl-4-(7H-pyrrolo[2,3-d]pyrimidin-4-yl)-1H-pyrazol-1-yl)azetidin-3-yl)acetonitrile (49)

DCM (10 mL) and boron trifluoride etherate (182 mg) were added to compound (49c) (220 mg, 0.43 mmol), and the reaction was stirred at room temperature for 4 h. After LC-MS indicated the substrate disappeared, the solvent was rotary evaporated off to obtain an oil, which was complete dissolved in MeOH (9 mg), an aqueous solution of 1 mol/L NaOH was added to adjust the pH value to about 10, and the reaction was stirred at room temperature overnight. After LC-MS indicated the reaction was complete, the reaction was concentrated under reduced pressure to remove most of MeOH, solid precipitated after addition of water, it was collected by filtration, and purified by preparative reverse-phase chromatography, to afford compound (49) (114 mg, white solid). Yield: 69%. MS m/z: 386 [M+1]+.

1H NMR (400 MHz, DMSO-d6) δ 12.12 (s, 1H), 8.74 (s, 2H), 7.60 (d, J=3.6 Hz, 1H), 6.96 (d, J=3.6 Hz, 1H), 4.60 (d, J=9.1 Hz, 2H), 4.21 (d, J=9.2 Hz, 2H), 3.65 (s, 2H), 3.24 (q, J=7.3 Hz, 2H), 2.60 (s, 3H), 1.25 (t, J=7.3 Hz, 3H).

Example 50: 2-(3-(4-(5-chloro-1H-pyrrolo[2,3-b]pyridin-4-yl)-1H-pyrazol-1-yl)-1-(ethylsulfonyl)azetidin-3-yl)acetonitrile (50)

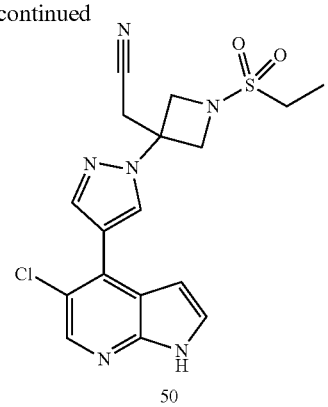

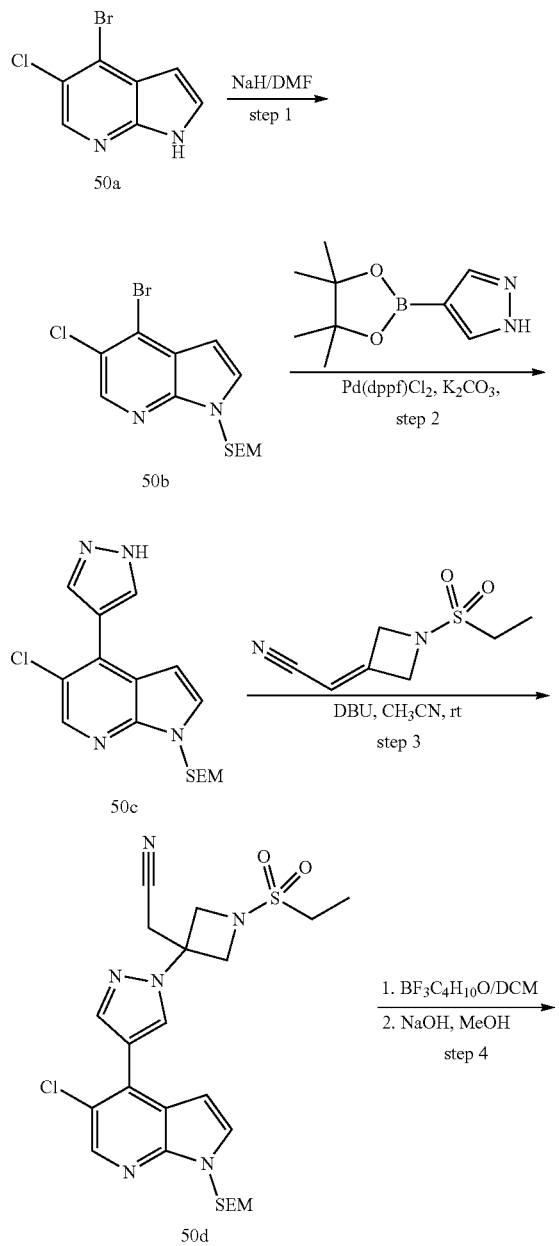

Step 1: 4-bromo-5-chloro-1-((2-(trimethylsilyl)ethoxy)methyl)-1H-pyrrolo[2,3-b]pyridine (50b)

4-bromo-5-chloro-1H-pyrrolo[2,3-b]pyridine (50a) (200 mg, 0.86 mmol) was dissolved in DMF (3 mL), nitrogen replacement was performed, and the reaction was placed in an ice-salt bath to cool the solution to below 0° C. NaH (60%, 80 mg) was then added, and the reaction was stirred for 30 min. Lastly, SEMCl (190 mg, 1.12 mmol) was added. After the temperature was stable, the reaction was placed at room temperature and stirred for 4 h. After TLC indicated (PE:EA=10:1) the substrate disappeared, the reaction system was quenched with ice-water, and extracted with EA. The organic phase was combined, dried over anhydrous sodium sulfate, filtered, concentrated, and purified on a preparative silica gel plate (PA:EA=20:1), to afford compound (50b) (275 mg, oil product), yield: 89%. MS m/z: 361 [M+1]+.

Step 2: 5-chloro-4-(1H-pyrazol-4-yl)-1-((2-(trimethysiyilyl)ethoxy)methyl)-1H-pyrrolo[2,3-b]pyridine (50c)

At room temperature, compound (50b) (275 mg, 0.76 mmol) and 4-(4,4,5,5-tetramethyl-1,3,2-dioxaborolan-2-yl)-1H-pyrazole (296 mg, 1.52 mmol) were dissolved in dioxane (10 mL), water (1.5 mL) and potassium carbonate (316 mg, 2.29 mmol) were added, nitrogen replacement was performed, and the reaction was stirred at room temperature for 10 min. Pd(dppf)Cl2 (80 mg) was added under protection of nitrogen. The reaction system was stirred in an oil bath at 90° C. overnight. TLC indicated the substrate disappeared, the reaction solution was quenched by slowly pouring into ice-water, extracted with EA, the organic phase was dried over anhydrous sodium sulfate, and purified by preparative flash chromatography (PE:EA=2:1), to afford compound (50c) (130 mg, yellow solid), yield: 49%. MS m/z: 349 [M+1]+.

Step 3: 2-(3-(4-(5-chloro-1-((2-(trimethylsilyl)ethoxy)methyl)-1H-pyrrolo[2,3-b]pyridin-4-yl)-1H-pyrazol-1-yl)-1-(ethylsulfonyl)azetidin-3-yl)acetonitrile (50d)

At room temperature, acetonitrile (3 mL) was added to compound (50c) (130 mg, 0.37 mmol) and 2-[1-(ethylsulfonyl)azetidin-3-ylidene]acetonitrile (76 mg, 0.41 mmol) to obtain a cloudy reaction solution. DBU (170 mg) was then added, the system became clear, and was stirred at room temperature overnight. The reaction solution was concentrated under reduced pressure, and purified on a preparative silica gel plate (PE:EA=2:1), to afford compound (50d) (141 mg, oil).

Yield: 71%. MS m/z: 535 [M+1]$^+$.

Step 4: 2-(3-(4-(5-chloro-1H-pyrrolo[2,3-b]pyridin-4-yl)-1H-pyrazol-1-yl)-1-(ethylsulfonyl)azetidin-3-yl)acetonitrile (50)

DCM (3 mL) and boron trifluoride etherate (112 mg) were added to compound (50d) (141 mg, 0.26 mmol), and the reaction was stirred at room temperature for 2 h. After LC-MS indicated the substrate disappeared, the solvent was rotary evaporated off to afford an oil, which was completely dissolved in MeOH (3 mL) followed by dropwise addition of 1 mol/L sodium hydroxide solution, to adjust the pH value to about 10, and the reaction was stirred at room temperature for 4 h. After LC-MS indicated the reaction was complete, the reaction was concentrated under reduced pressure to remove most of MeOH, solid precipitated after addition of water, and it was collected by filtration, and purified by preparative reverse-phase chromatography, to afford compound (50) (54 mg, white solid). Yield: 51%. MS m/z: 405 [M+1]$^+$.

$^1$H NMR (400 MHz, DMSO-d$_6$) δ 11.97 (s, 1H), 8.66 (s, 1H), 8.29 (s, 1H), 8.19 (s, 1H), 7.60 (d, J=2.6 Hz, 1H), 6.68-6.61 (m, 1H), 4.58 (d, J=9.1 Hz, 2H), 4.25 (d, J=9.1 Hz, 2H), 3.68 (s, 2H), 3.24 (q, J=7.3 Hz, 2H), 1.25 (t, J=7.3 Hz, 3H).

Example 51: 2-(1-(ethylsulfonyl)-3-(4-(5-methyl-1H-pyrrolo[2,3-b]pyridin-4-yl)-1H-pyrazol-1-yl)azetidin-3-yl)acetonitrile (51)

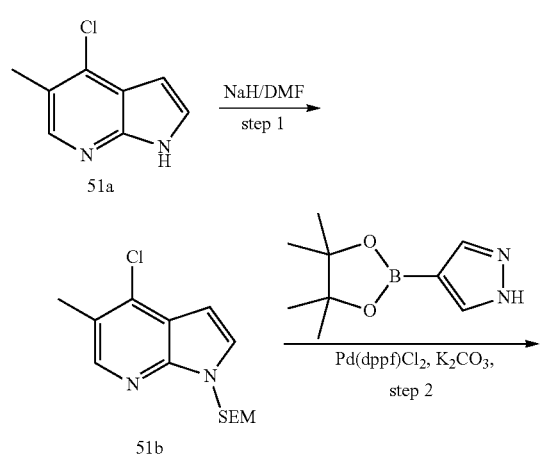

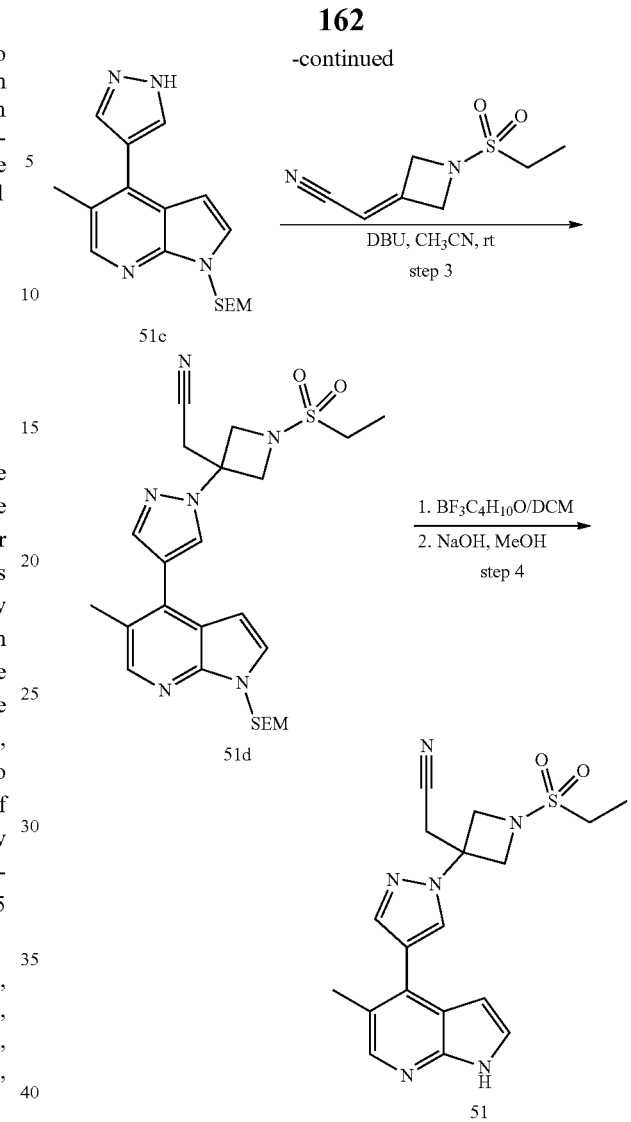

According to the above synthetic route, using 4-chloro-5-methyl-1H-pyrrolo[2,3-b]pyridine (51a) as a starting material, and employing procedures similar to those in Example 50, compound (51) (11 mg, white solid) was prepared. Yield: 32%. MS m/z: 385 [M+1]$^+$.

$^1$H NMR (400 MHz, DMSO-d$_6$) δ 11.54 (s, 1H), 8.49 (s, 1H), 8.12 (s, 1H), 8.05 (s, 1H), 7.42 (t, J=2.4 Hz, 1H), 6.50 (d, J=1.7 Hz, 1H), 4.58 (d, J=9.1 Hz, 2H), 4.24 (d, J=9.1 Hz, 2H), 3.67 (s, 2H), 3.24 (q, J=7.4 Hz, 2H), 2.42 (s, 3H), 1.25 (t, J=7.3 Hz, 3H).

Example 52: 2-(1-(ethylsulfonyl)-3-(4-(5-fluoro-1H-pyrrolo[2,3-b]pyridin-4-yl)-1H-pyrazol-1-yl)azetidin-3-yl)acetonitrile (52)

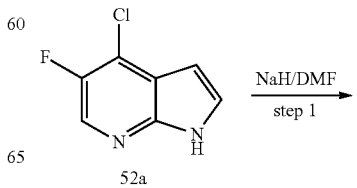

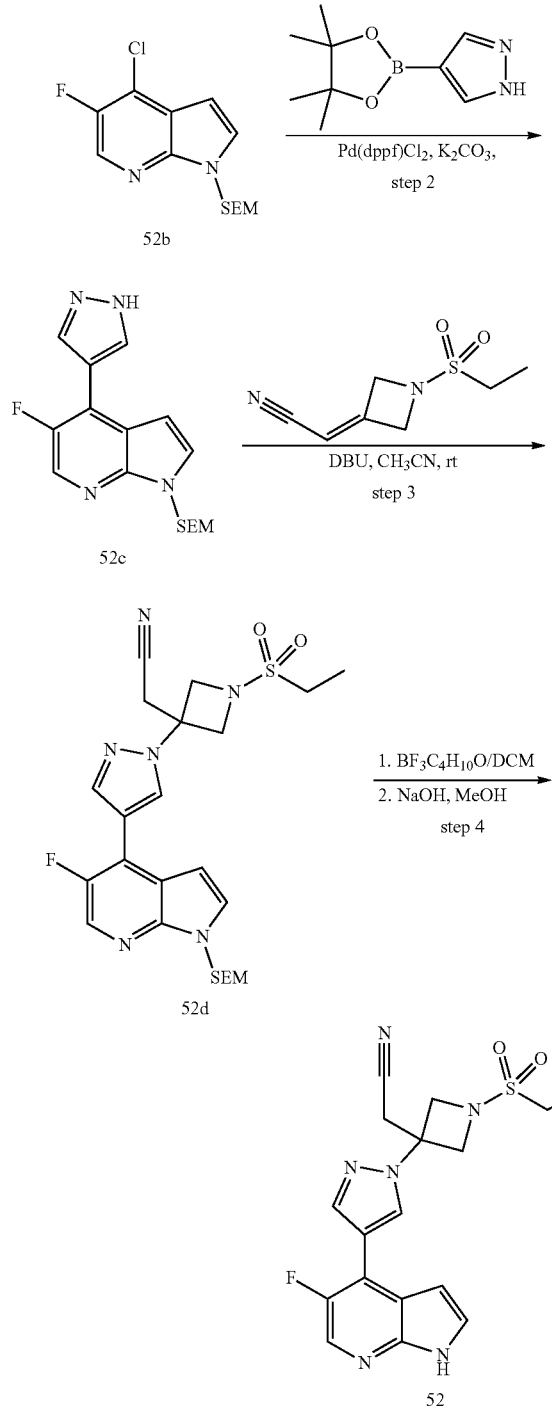

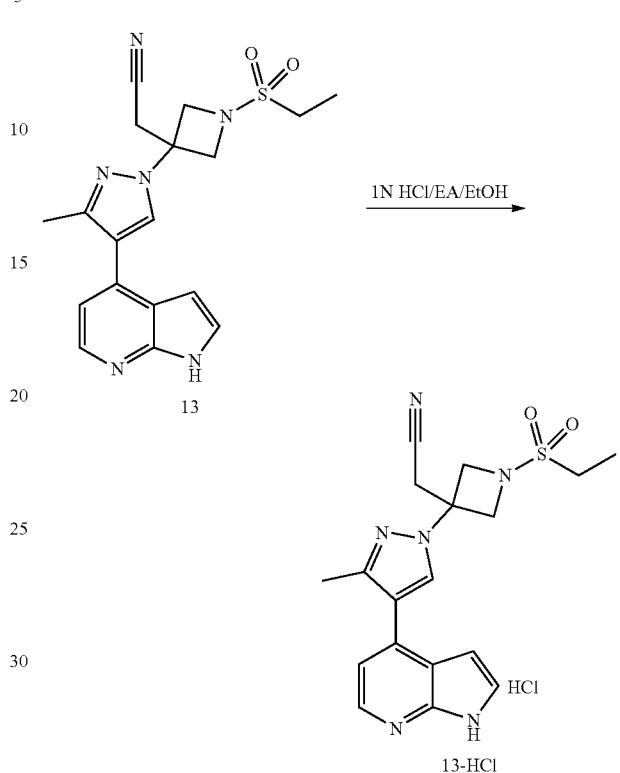

According to the above synthetic route, using 4-chloro-5-fluoro-1H-pyrrolo[2,3-b]pyridine (52a) as a starting material, and employing procedures similar to those in Example 50, compound (52) (90 mg, white solid) was prepared. Yield: 20%. MS m/z: 389 [M+1]⁺.

¹H NMR (400 MHz, DMSO-d₆) δ 11.88 (s, 1H), 8.73 (s, 1H), 8.28-8.25 (m, 2H), 7.64 (d, J=3.4 Hz, 1H), 6.90 (d, J=3.5 Hz, 1H), 4.60 (d, J=9.1 Hz, 2H), 4.25 (d, J=9.1 Hz, 2H), 3.69 (s, 2H), 3.24 (q, J=7.3 Hz, 2H), 1.25 (t, J=7.3 Hz, 3H).

Example 53: 2-(1-(ethylsulfonyl)-3-(3-methyl-4-(1H-pyrrolo[2,3-b]pyridin-4-yl)-1H-pyrazol-1-yl)azetidin-3-yl)acetonitrile hydrochloride salt (13-HCl)

Employing procedures similar to those in Example 46, the hydrochloride salt of compound (13) (13-HCl) (336 mg, white solid) was prepared from compound (13) (300 mg) synthesized in Example 13. MS m/z: 385 [M+1]⁺.

¹H NMR (400 MHz, DMSO-d₆) δ 12.85 (s, 1H), 8.73 (s, 1H), 8.45 (d, J=6.0 Hz, 1H), 7.78 (dd, J=3.6, 2.3 Hz, 1H), 7.52 (d, J=6.0 Hz, 1H), 7.01 (dd, J=3.6, 1.6 Hz, 1H), 4.58 (d, J=9.1 Hz, 2H), 4.23 (d, J=9.1 Hz, 2H), 3.67 (s, 2H), 3.24 (q, J=7.3 Hz, 2H), 2.47 (s, 3H), 1.25 (t, J=7.3 Hz, 3H).

Example 54: 2-(3-(4-(1H-pyrrolo[2,3-b]pyridin-4-yl)-1H-pyrazol-1-yl)-1-(isobutylsulfonyl)azetidin-3-yl)acetonitrile hydrochloride salt (25-HCl)

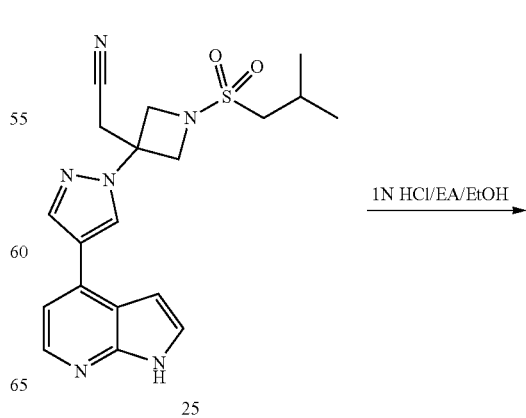

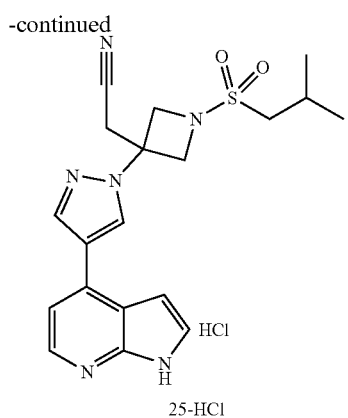

25-HCl

Employing procedures similar to those in Example 46, the hydrochloride salt of compound (25) (25-HCl) (33 mg, white solid) was prepared from compound (25) (30 mg) synthesized in Example 25. MS m/z: 399 [M+1]$^+$.

$^1$H NMR (400 MHz, DMSO-d$_6$) δ 12.61 (s, 1H), 9.04 (s, 1H), 8.55 (s, 1H), 8.40 (d, J=5.8 Hz, 1H), 7.75 (dd, J=3.6, 2.2 Hz, 1H), 7.68 (d, J=5.8 Hz, 1H), 7.21 (dd, J=3.5, 1.5 Hz, 1H), 4.59 (d, J=9.2 Hz, 2H), 4.28 (d, J=9.1 Hz, 2H), 3.69 (s, 2H), 3.16 (d, J=6.8 Hz, 2H), 2.20-2.10 (m, 1H), 1.04 (d, J=6.7 Hz, 6H).

Example 55: 2-(3-(4-(5-chloro-1H-pyrrolo[2,3-b]pyridin-4-yl)-1H-pyrazol-1-yl)-1-(ethylsulfonyl)azetidin-3-yl)acetonitrile hydrochloride salt (50-HCl)

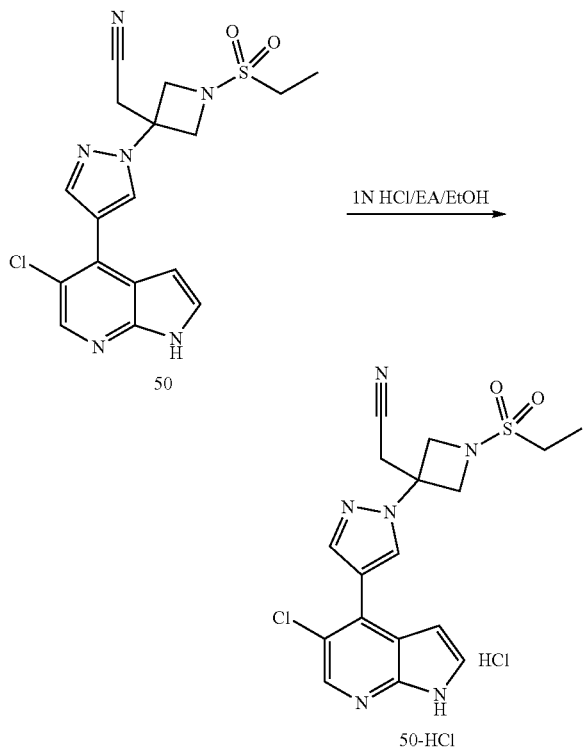

Employing procedures similar to those in Example 46, the hydrochloride salt of compound (50) (50-HCl) (55 mg, white solid) was prepared from compound (50) (50 mg) synthesized in Example 50. MS m/z: 405 [M+1]$^+$.

$^1$H NMR (400 MHz, DMSO-d) δ 11.97 (s, 1H), 8.66 (s, 1H), 8.29 (s, 1H), 8.19 (s, 1H), 7.63-7.57 (m, 1H), 6.64 (dd, J=3.5, 1.9 Hz, 1H), 4.58 (d, J=9.1 Hz, 2H), 4.25 (d, J=9.1 Hz, 2H), 3.69 (s, 2H), 3.25 (q, J=7.3 Hz, 2H), 1.25 (t, J=7.3 Hz, 3H).

Example 56: 2-(1-(ethylsulfonyl)-3-(3-methyl-4-(7H-pyrrolo[2,3-d]pyrimidin-4-yl)-1H-pyrrol-1-yl)azetidin-3-yl)acetonitrile (56)

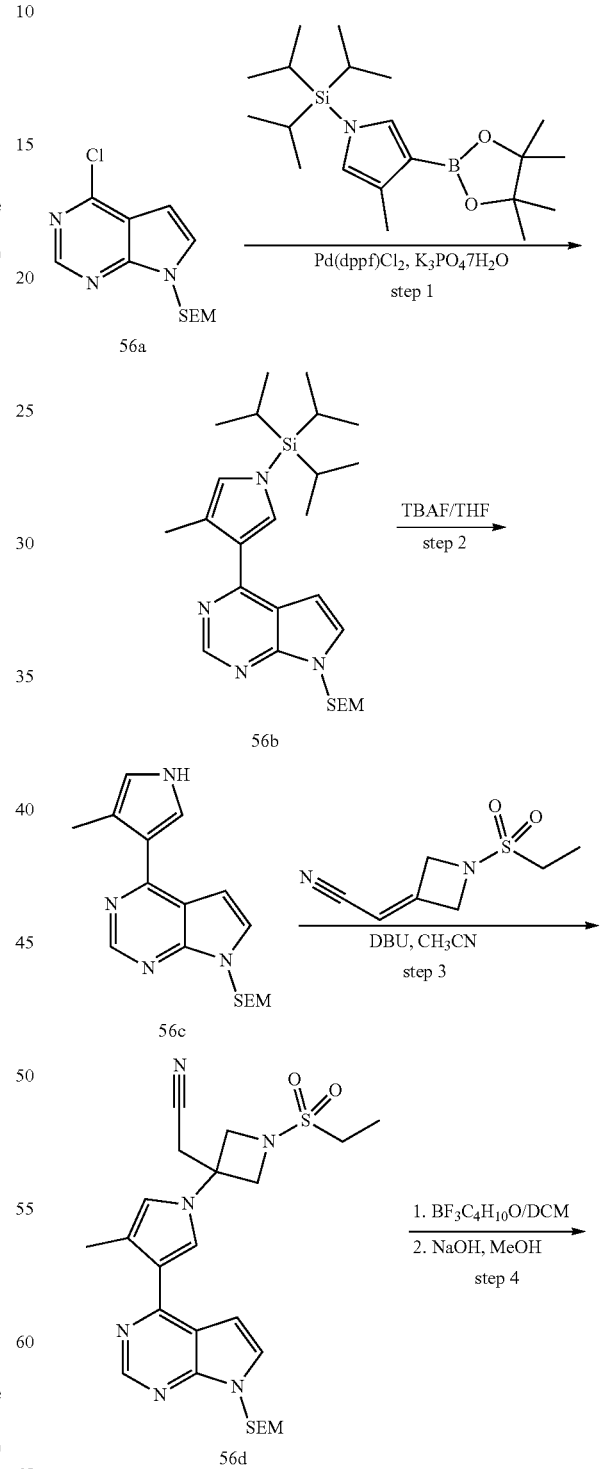

-continued

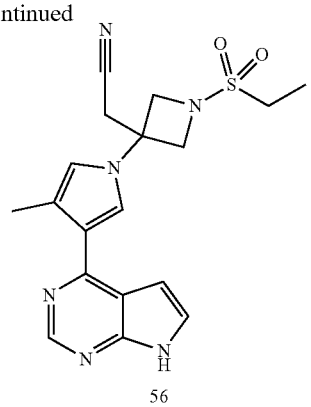

56

Step 1: 4-(4-methyl-1-(triisopropylsilyl)-1H-pyrrol-3-yl)-7-((2-(trimethylsilyl)ethoxy)methyl)-7H-pyrrolo[2,3-d]pyrimidine (56b)

At room temperature, 4-chloro-7-((2-(trimethylsilyl)ethoxy)methyl)-7H-pyrrolo[2,3-d]pyrimidine (56a) (150 mg, 0.53 mmol) and 3-methyl-4-(4,4,5,5-tetramethyl-1,3,2-dioxaborolan-2-yl)-1-(triisopropylsilyl)-1H-pyrrole (289 mg, 0.80 mmol) were dissolved in dioxane (4 mL), water (0.5 mL) and tribasic potassium phosphate heptahydrate (448 mg) were then added, nitrogen replacement was performed, and the reaction was stirred at room temperature for 10 min. Pd(dppf)Cl$_2$ (50 mg) was added under protection of nitrogen. The reaction system was stirred in an oil bath at 90° C., and the reaction was allowed to proceed overnight. After TLC indicated the substrate disappeared, the reaction solution was quenched by slowly pouring into ice-water, extracted with EA, the organic phase was dried over anhydrous sodium sulfate, and purified on a preparative silica gel plate (PE:EA=10:1), to afford compound (56b) (190 mg, oil), yield: 74%. MS m/z: 485 [M+1]$^+$.

Step 2: 4-(4-methyl-1H-pyrrol-3-yl)-7-((2-(trimethylsilyl)ethoxy)methyl)-7H-pyrrolo[2,3-d]pyrimidine (56c)

Compound (56b) (190 mg) was dissolved in tetrahydrofuran (2 mL), tetrabutylammonium fluoride was added, and the reaction was stirred at room temperature for 30 min. After TLC (PE:EA=δ:1) indicated the substrate disappeared, the reaction system was quenched by pouring into water, and extracted with EA. The organic phase was combined, dried over anhydrous sodium sulfate, filtered, concentrated, and purified on a preparative silica gel plate (PE:EA=3:1), to afford compound (56c) (128 mg, light yellow solid), yield: 99%. MS m/z: 329 [M+1]$^+$.

Step 3: 2-(1-(ethylsulfonyl)-3-(3-methyl-4-(7-((2-(trimethylsilyl)ethoxy)methyl)-7H-pyrrolo[2,3-d]pyrimidin-4-yl)-1H-pyrrol-1-yl)azetidin-3-yl)acetonitrile (56d)

At room temperature, acetonitrile (5 mL) was added to compound (56c) (108 mg, 0.33 mmol) and 2-[1-(ethylsulfonyl)azetidin-3-ylidene]acetonitrile (92 mg), to obtain a cloudy reaction solution. DBU (150 mg) was then added, and the reaction was stirred at room temperature overnight. The reaction solution was concentrated, the residue was dissolved in DCM, and purified on a preparative silica gel plate (PE:EA=1:1), to afford compound (56d) (88 mg, yellow solid), yield: 53%. MS m/z: 515 [M+1]$^+$.

Step 4: 2-(1-(ethylsulfonyl)-3-(3-methyl-4-(7H-pyrrolo[2,3-d]pyrimidin-4-yl)-1H-pyrrol-1-yl)azetidin-3-yl)acetonitrile (56)

DCM (3 mL) and boron trifluoride etherate (80 mg) were added to compound (56d) (88 mg, 0.17 mmol), and the reaction was stirred at room temperature for 2 h. After LC-MS indicated the substrate disappeared, the solvent was rotary evaporated off to afford an oil, which was completely dissolved in MeOH (3 mg), followed by dropwise addition of 1 mol/L sodium hydroxide solution, to adjust the pH value to about 10, and the reaction was stirred at room temperature for 4 h. After LC-MS indicated the reaction was complete, the reaction solution was concentrated under reduced pressure to remove most of MeOH, solid precipitated after addition of water, and it was collected by filtration, and purified by preparative reverse-phase chromatography, to afford compound (56) (20 mg, white solid). Yield: 31%. MS m/z: 385 [M+1]$^+$.

$^1$H NMR (400 MHz, DMSO-d$_6$) δ 11.98 (s, 1H), 8.68 (s, 1H), 7.70 (d, J=2.4 Hz, 1H), 7.51 (dd, J=3.6, 2.2 Hz, 1H), 6.95 (dd, J=2.5, 1.2 Hz, 1H), 6.89 (dd, J=3.6, 1.6 Hz, 1H), 4.44 (d, J=9.2 Hz, 2H), 4.19 (d, J=9.0 Hz, 2H), 3.55 (s, 2H), 3.22 (q, J=7.3 Hz, 2H), 2.38 (s, 3H), 1.24 (t, J=7.3 Hz, 3H).

The following compounds were prepared according to corresponding preparation methods in the above Examples:

| Compound No. | Compound Structure | Compound Name | Characterization Data |
|---|---|---|---|
| 62 | 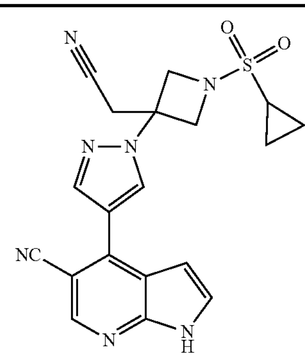 | 4-(1-(3-(cyanomethyl)-1-(cyclopropylsulfonyl)-azetidin-3-yl)-1H-pyrazol-4-yl)-1H-pyrrolo[2,3-b]pyridine-5-carbonitrile | $^1$H NMR (400 MHz, DMSO-d$_6$) δ: 12.40 (s, 1H), 8.81 (s, 1H), 8.63 (s, 1H), 8.31 (s, 1H), 7.75 (d, J = 3.60 Hz, 1H), 6.88 (d, J = 3.60 Hz, 1H), 4.92 (d, J = 9.20 Hz, 1H), 4.66 (d, J = 9.20 Hz, 1H), 4.49 (d, J = 10.60 Hz, 1H), 4.66 (d, J = 10.60 Hz, 1H), 3.73 (s, 2H), 1.75-1.73 (m, 1H), 0.75-0.64 (m, 4H). MS (ESI, m/z): 408.1 [M + H]$^+$. |

| Compound No. | Compound Name | Characterization Data |
|---|---|---|
| 63 | 4-(1-(3-(cyanomethyl)-1-(isobutylsulfonyl)azetidin-3-yl)-1H-pyrazol-4-yl)-1H-pyrrolo[2,3-b]pyridine-5-carbonitrile | $^1$H NMR (400 MHz, DMSO-d$_6$) δ: 12.40 (s, 1H), 8.81 (s, 1H), 8.63 (s, 1H), 8.31 (s, 1H), 7.75 (d, J = 3.60 Hz, 1H), 6.88 (d, J = 3.60 Hz, 1H), 4.92 (d, J = 9.20 Hz, 1H), 4.66 (d, J = 9.20 Hz, 1H), 4.49 (d, J = 10.60 Hz, 1H), 4.66 (d, J = 10.60 Hz, 1H), 3.73 (s, 2H), 3.43 (d, J = 11.60 Hz, 2H), 1.81-1.76 (m, 2H), 0.91 (d, J = 11.60 Hz, 6H). MS (ESI, m/z): 424.2 [M + H]$^+$. |
| 64 | 4-(1-(-3-(cyanomethyl)-1-(tert-butylsulfonyl)azetidin-3-yl)-1H-pyrazol-4-yl)-1H-pyrrolo[2,3-b]pyridine-5-carbonitrile | $^1$H NMR (400 MHz, DMSO-d$_6$) δ: 12.40 (s, 1H), 8.81 (s, 1H), 8.63 (s, 1H), 8.31 (s, 1H), 7.75 (d, J = 3.60 Hz, 1H), 6.88 (d, J = 3.60 Hz, 1H), 4.92 (d, J = 9.20 Hz, 1H), 4.66 (d, J = 9.20 Hz, 1H), 4.49 (d, J = 10.60 Hz, 1H), 4.66 (d, J = 10.60 Hz, 1H), 3.73 (s, 2H), 1.33 (s, 9H). MS (ESI, m/z): 424.2 [M + H]$^+$. |
| 65 | 4-(1-(1-(butylsulfonyl)-3-(cyanomethyl)azetidin-3-yl)-1H-pyrazolo-4-yl)-1H-pyrrolo[2,3-b]pyridine-5-carbonitrile | $^1$H NMR (400 MHz, DMSO-d$_6$) δ: 12.40 (s, 1H), 8.81 (s, 1H), 8.63 (s, 1H), 8.31 (s, 1H), 7.75 (d, J = 3.60 Hz, 1H), 6.88 (d, J = 3.60 Hz, 1H), 4.92 (d, J = 9.20 Hz, 1H), 4.66 (d, J = 9.20 Hz, 1H), 4.49 (d, J = 10.60 Hz, 1H), 4.66 (d, J = 10.60 Hz, 1H), 3.73 (s, 2H), 3.14 (t, J = 11.20 Hz, 2H), 1.61-1.31 (m, 4H), 0.91 (t, J = 11.60 Hz, 3H). MS (ESI, m/z): 424.2 [M + H]$^+$. |
| 66 | 4-(1-(1-benzoyl-3-(cyanomethyl)azetidin-3-yl)-1H-pyrazol-4-yl)-1H-pyrrolo[2,3-b]pyridine-5-carbonitrile | $^1$H NMR (400 MHz, DMSO-d$_6$) δ: 12.40 (s, 1H), 8.81 (s, 1H), 8.63 (s, 1H), 8.31 (s, 1H), 8.09-8.01 (m, 2H), 7.75 (d, J = 3.60 Hz, 1H), 7.55-7.42 (m, 3H), 6.88 (d, J = 3.60 Hz, 1H), 4.92 (d, J = 9.20 Hz, 1H), 4.66 (d, J = 9.20 Hz, 1H), 4.49 (d, J = 10.60 Hz, 1H), 4.66 (d, J = 10.60 Hz, 1H), 3.73 (s, 2H). MS (ESI, m/z): 408.2 [M + H]$^+$. |

| Compound No. | Compound Name | Characterization Data |
|---|---|---|
| 67 | 2-(1-(ethylsulfonyl)-3-(3-methoxy-4-(1H-pyrrolo[2,3-b]pyridin-4-yl)-1H-pyrazol-1-yl)azetidin-3-yl)acetonitrile | $^1$H NMR (400 MHz, DMSO-$d_6$) δ: 12.40 (s, 1H), 8.64 (d, J = 9.60 Hz, 1H), 7.43 (d, J = 9.60 Hz, 1H), 7.34 (d, J = 9.60 Hz, 1H), 7.12 (s, 1H), 6.50 (d, J = 9.60 Hz, 1H), 4.07 (s, 3H), 4.05-3.97 (m, 2H), 3.83-3.76 (m, 2H), 3.45 (q, J = 8.40 Hz, 2H), 2.77 (s, 2H), 1.39 (t, J = 8.40 Hz, 3H). MS (ESI, m/z): 401.1 [M + H]$^+$. |
| 68 | 2-(1-(ethylsulfonyl)-3-(2-methoxy-4-(7H-pyrrolo[2,3-d]pyrimidin-4-yl)-1H-pyrrol-1-yl)azetidin-3-yl)acetonitrile | $^1$H NMR (400 MHz, DMSO-$d_6$) δ: 9.54 (s, 1H), 7.36 (d, J = 9.60 Hz, 1H), 7.20 (s, 1H), 6.50 (d, J = 9.60 Hz, 1H), 6.10 (s, 1H), 4.07 (s, 3H), 3.83-3.76 (m, 2H), 3.63-3.55 (m, 2H), 3.45 (q, J = 8.40 Hz, 2H), 2.56 (s, 2H), 1.39 (t, J = 8.40 Hz, 3H). MS (ESI, m/z): 401.1 [M + H]$^+$. |
| 69 | 2-(1-(ethysulfonyl)-3-(2-methyl-4-(7H-pyrrolo[2,3-d]pyrimidin-4-yl)-1H-pyrrol-1-yl)azetidin-3-yl)acetonitrile | $^1$H NMR (400 MHz, DMSO-$d_6$) δ: 9.54 (s, 1H), 7.36 (d, J = 9.60 Hz, 1H), 6.94 (s, 1H), 6.50 (d, J = 9.60 Hz, 1H), 5.80 (s, 1H), 3.83-3.76 (m, 2H), 3.63-3.55 (m, 2H), 3.45 (q, J = 8.40 Hz, 2H), 2.56 (s, 2H), 2.19 (s, 3H), 1.39 (t, J = 8.40 Hz, 3H). MS (ESI, m/z): 385.1 [M + H]$^+$. |
| 70 | 2-(3-(2-chloro-4-(7H-pyrrolo[2,3-d]pyrimidin-4-yl)-1H-pyrrol-1-yl)-1-(ethylsulfonyl)azetidin-3-yl)acetonitrile | $^1$H NMR (400 MHz, DMSO-$d_6$) δ: 9.54 (s, 1H), 7.36 (d, J = 9.60 Hz, 1H), 7.21 (s, 1H), 6.50 (d, J = 9.60 Hz, 1H), 6.11 (s, 1H), 3.83-3.76 (m, 2H), 3.63-3.55 (m, 2H), 3.45 (q, J = 8.40 Hz, 2H), 2.56 (s, 2H), 1.39 (t, J = 8.40 Hz, 3H). MS (ESI, m/z): 405.1 [M + H]$^+$. |

| Compound No. | Compound Structure | Compound Name | Characterization Data |
|---|---|---|---|
| 71 | 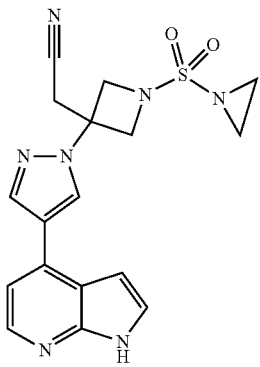 [SMILES: N#CCC1(n2cc(-c3ccnc4[nH]ccc34)cn2)CN(S(=O)(=O)N2CC2)C1] | 2-(3-(4-(1H-pyrrolo[2,3-b]pyridin-4-yl)-1H-pyrazol-1-yl)-1-(aziridin-1-ylsulfonyl)azetidin-3-yl)acetonitrile | $^1$H NMR (400 MHz, DMSO-$d_6$) 8.64 (d, J = 9.60 Hz, 1H), 8.00 (s, 1H), 7.43 (d, J = 9.60 Hz, 1H), 7.36 (d, J = 9.60 Hz, 1H), 7.21 (s, 1H), 6.50 (d, J = 9.60 Hz, 1H), 4.05-3.95 (m, 2H), 3.83-3.76 (m, 2H), 2.77 (s, 2H), 1.61 (s, 4H). MS (ESI, m/z): 384.2 [M + H]$^+$. |

Biological Assays

Experimental Example 1: JAK1, JAK2, JAK3 and TYK2 Enzymatic Inhibition Assay

1. Test Materials

JAK1, JAK2, JAK3 and TYK2 enzymes were purchased from Life Technologies; and substrate GFP-STAT1 was purchased from Life Technologies.

2. Test Method

Test compounds, enzymes, the substrate and ATP were diluted to the desired concentrations with the assay buffer (40 mM Tris-HCl, pH 7.4, 20 mM MgCl$_2$, 0.1% BSA). The former three were added into a multiple well plate, and incubated at room temperature after being mixed homogeneously. ATP was added to initiate the kinase reaction, and incubation at room temperature was performed. ADP-Glo was added, and incubation at room temperature was performed. The kinase detector reagent was then added, and incubation at room temperature was performed. The luminescence intensity of each test group was detected, and the half maximal inhibitory concentration (IC$_{50}$) value was calculated. The results are shown in Table 1-1 and Table 1-2.

As for the TYK2 enzyme, Tb-anti-pSTAT1 was added, and incubation at room temperature was performed. TR-FRET was detected using the method of LanthaScreen, and the half maximal inhibitory concentration (IC$_{50}$) value was calculated. The results are shown in Table 1-3.

TABLE 1-1 the enzymatic inhibitory concentrations (IC$_{50}$) of the exemplified compounds for JAK1 and JAK2

| | IC$_{50}$ (nM) | |
|---|---|---|
| Compound | JAK1 | JAK2 |
| 1 | 0.78 | 1.98 |
| 2 | 0.17 | 0.42 |
| 5 | 0.71 | 1.49 |
| 8 | 1.05 | 0.82 |
| 14 | 1.30 | 0.50 |
| 17 | 1.13 | 0.93 |
| 19 | 0.69 | 0.41 |
| 23 | 2.41 | 0.89 |
| 25 | 2.29 | 0.83 |
| 26 | 0.46 | 0.37 |
| 30 | 2.22 | 2.16 |

TABLE 1-1-continued the enzymatic inhibitory concentrations (IC$_{50}$) of the exemplified compounds for JAK1 and JAK2

| | IC$_{50}$ (nM) | |
|---|---|---|
| Compound | JAK1 | JAK2 |
| 31 | 0.72 | 1.23 |
| 34 | 0.80 | 1.66 |
| 40 | 0.97 | 2.24 |
| 12-2 | 0.86 | 1.81 |
| 43 | 0.55 | 2.54 |
| 44 | 1.95 | 3.93 |
| 45 | 1.66 | 3.22 |
| 13 | 2.89 | 1.44 |
| 35 | 1.46 | 1.40 |
| 45-1 | 1.65 | 1.17 |
| 45-2 | 1.85 | 1.11 |
| 39 | 0.87 | 0.69 |
| 48 | 5.66 | 1.40 |
| 49 | 1.63 | 1.21 |
| 50 | 1.14 | 0.67 |
| 52 | 0.54 | 0.40 |
| 56 | 3.52 | 1.76 |
| 50-HCl | 0.52 | 0.62 |
| 52-HCl | 0.38 | 0.35 |

According to Table 1-1, the compound of the present invention has a good inhibitory effect on JAK1 and JAK2.

TABLE 1-2 the enzymatic inhibitory concentrations (IC$_{50}$) of the exemplified compounds for JAK3

| Compound | IC$_{50}$ (nM) JAK3 |
|---|---|
| 5 | 33.84 |
| 8 | 47.93 |
| 19 | 10.29 |
| 25 | >30 |
| 30 | 36.48 |
| 31 | 23.65 |
| 12-2 | 10-30 |
| 43 | 10-30 |
| 13 | >30 |
| 35 | >30 |
| 45-1 | 10-30 |
| 45-2 | 10-30 |
| 39 | 10-30 |

According to Table 1-1 and Table 1-2, the inhibitory effect of the compound of the present invention on JAK1 and JAK2 is significantly higher than that on JAK3, indicating the compound of the present invention has good JAK1/2 selectivity.

TABLE 1-3 the enzymatic inhibitory concentrations (IC$_{50}$) of the exemplified compounds for TYK2

| Compound | IC$_{50}$ (nM) TYK2 |
|---|---|
| 5 | 27.02 |
| 8 | 27.28 |
| 25 | >30 |
| 30 | 58.21 |
| 12-2 | ~30 |
| 43 | >30 |
| 13 | ~30 |
| 35 | >30 |
| 45-1 | ~30 |
| 45-2 | ~30 |

According to Table 1-1 and Table 1-3, the inhibitory effect of the compound of the present invention on JAK1 and JAK2 is significantly higher than that on TYK2, indicating the compound of the present invention has good JAK1/2 selectivity.

Experimental Example 2: Safety Test

The effect of test compounds on hERG potassium channel were determined using Predictor™ hERG Fluorescence Polarization Assay at concentrations of 3, 10, and 30 μM. The results are shown in Table 2-1.

TABLE 2-1 hERG test results

| Compound | IC$_{50}$ (μM) |
|---|---|
| 5 | >30 |
| 8 | >30 |
| 14 | >30 |
| 17 | >30 |
| 19 | >30 |
| 23 | >30 |
| 25 | >30 |
| 26 | >30 |
| 30 | >30 |
| 31 | >30 |
| 12-2 | >30 |
| 43 | >30 |
| 1 | >30 |
| 2 | >30 |
| 13 | >30 |
| 35 | >30 |
| 45-1 | >30 |
| 45-2 | >30 |
| 39 | >30 |
| 48 | >30 |
| 49 | >30 |
| 50 | >30 |
| 52 | >30 |
| 50-HCl | >30 |
| 52-HCl | >30 |

According to the experimental data in Table 2-1, in this test, the 50% inhibitory concentrations (IC$_{50}$) of the compounds of the present invention are all higher than 30 μM. As such, the compounds of the present invention have no inhibitory effect on hERG, and thus have no safety issue concerning cardiac QT interval prolongation.

CYP450 is the most important enzymatic system in drug metabolism. The enzymes involved in the metabolism interact with a drug, and mainly include CYP1A2, CYP2D6 and CYP3A4. In the CYP450 enzyme test, P450-Glo™ CYP1A2 screening system was employed to determine the inhibitory activity of compounds on CYP1A2 and CYP3A4. The Vivid® CYP2D6 Cyan screening kit was employed to determine the inhibitory activity of test compounds on CYP2D6. The test results are shown in Table 2-2.

TABLE 2-2

Test Results

| Compound | IC$_{50}$ (μM) | | |
|---|---|---|---|
| | CYP1A2 | CYP2D6 | CYP3A4 |
| 5 | >10 | >10 | >10 |
| 19 | >10 | >10 | >10 |
| 25 | >10 | >10 | >10 |
| 43 | >10 | >10 | >10 |
| 39 | >10 | >10 | >10 |
| 48 | >10 | >10 | >10 |
| 49 | >10 | >10 | >10 |
| 50 | >10 | >10 | >10 |
| 52 | >10 | >10 | >10 |

According to the experimental data in Table 2-2, in this test, the 50% inhibitory concentrations (IC$_{50}$) of the test compounds on CYP1A2, CYP3A4 and CYP2D6 are all higher than 10 μM. As such, the compound of the present invention has no significant inhibitory effect on CYP1A2, CYP2D6 and CYP3A4, and thus has no safety issue caused by metabolism interactions among different drugs due to inhibition of the enzymes.

Experimental Example 3: Pharmacokinetic Studies

Rats:

To study the pharmacokinetic characteristics of test compounds, the test compounds were administrated by intravenous (IV) and gavage (PO) routes to male SD rats. The dosage for IV administration was 1 mg/kg, and that for PO administration was 0.5-5 mg/kg. The vehicle is 10% DMSO: 10% solutol:80% physiological saline, or 5% DMSO:5% solutol:90% physiological saline, or 10% DMSO:60% PEG: 30% physiological saline. Blood was collected at various time points after administration. Plasma samples were analyzed by LC-MS/MS after protein precipitation process with acetonitrile.

The results obtained by intravenous (IV) administration are shown in Tables 3-1 and 3-2.

TABLE 3-1 compound exposure (AUC$_{last}$) after IV administration at 1 mg/kg to rats

| Compound No. | AUC$_{last}$ h * ng/mL |
|---|---|
| Baricitinib | 505 |
| 5 | 834 |
| 8 | 2650 |
| 19 | 1390 |
| 30 | 3170 |
| 31 | 540 |

AUC$_{last}$: the area under the curve at all time points (0-24 h).

TABLE 3-2 compound half-life ($T_{1/2}$) after IV administration at 1 mg/kg to rats

| Compound No. | $T_{1/2}$ h |
|---|---|
| Baricitinib | 0.946 |
| 5 | 0.997 |
| 8 | 3.93 |
| 19 | 7.1 |
| 30 | 1.5 |
| 39 | 1.67 |

The results show that with IV administration at a dosage of 1 mg/kg, the compound of the present invention has better exposure ($AUC_{last}$) and longer half-life ($T_{1/2}$), compared with Baricitinib. Therefore, the compound of the present invention has significant pharmacokinetic advantages.

The results obtained after gavage (PO) administration to rats are shown in Table 4-1.

TABLE 4-1 pharmacokinetic parameters obtained after gavage administration at 5 mg/kg to rats

| Compound No. | $AUC_{last}$ h * ng/ml |
|---|---|
| Baricitinib | 3050 |
| 5 | 3150 |
| 8 | 14100 |
| 19 | 5030 |
| 30 | 32200 |

$AUC_{last}$: the area under the curve at all time points (0-24 h).

The results show that with PO administration at a dosage of 5 mg/kg, the compound of the present invention has better exposure ($AUC_{last}$), compared with Baricitinib. With PO administration at a dosage of 0.5-5 mg/kg, the bioavailability (F %) of the compound of the present invention was higher than 70%, and the half-life ($T_{1/2}$) was 2-4 h, which were significantly better than those of Baricitinib (at same conditions, its F % was 55%, and $T_{1/2}$ was 1.58 h). Therefore, the compound of the present invention has significant pharmacokinetic advantages.

Rhesus Monkeys:

To study the pharmacokinetic characteristics of test compounds, the test compounds were administrated by an intravenous (IV) route to male Rhesus monkeys. The dosage for IV administration was 0.5 mg/kg. Blood was collected at various time points after the IV administration. Plasma samples were analyzed by LC-MS/MS after protein precipitation process with acetonitrile. Pharmacokinetic parameters were calculated with a non-compartmental model by using WinNonlin 6.3 software.

The results show that with IV administration at a dosage of 0.5 mg/kg, compound 8 of the present invention has a half-life of 5.29 h, while Baricitinib has a half-life of 1.38 h. As such, the half-life of compound 8 is significantly longer, and thus compound 8 of the present invention has significant pharmacokinetic advantages. Other compounds of the present invention have similar advantages.

To study the pharmacokinetic characteristics of test compounds, the test compounds were administrated by a gavage (PO) route to male Rhesus monkeys. The dosage for PO administration was 1 mg/kg. Blood was collected at various time points after the PO administration. Plasma samples were analyzed by LC-MS/MS after protein precipitation process with acetonitrile. Pharmacokinetic parameters were calculated with a non-compartmental model by using WinNonlin 6.3 software.

The results are as shown below:

| Compound | $AUC_{last}$ h * ng/ml | $T_{1/2}$ h | F % |
|---|---|---|---|
| Baricitinib | 994 | 1.96 | 26.3 |
| 8 | 2600 | 2.68 | 78.6 |

$AUC_{last}$: the area under the curve at all time points (0-24 h).

The results show that with PO administration at a dosage of 1 mg/kg, the compound of the present invention (e.g., compound 8) has better exposure ($AUC_{last}$), longer half-life ($T_{1/2}$), and higher oral bioavailability (F %), compared with Baricitinib. Therefore, the compound of the present invention (e.g., compound 8) has significant pharmacokinetic advantages.

Experimental Example 4: In Vivo Efficacy in Collagen-Induced Arthritis (CIA) Model in Rats A mixed emulsion of bovine type II collagen and incomplete Freund's adjuvant 1:1 was injected at the back and the tail tip (3 sites) in Lewis rats. After 14 days, the paw thickness and paw volume of the rats were measured, and the arthritis development was scored. The day before the administration was set as D0, the animals were grouped based on paw volume, and the test compounds (vehicle: 5% DMSO+5% solutol) were gavage administered once a day for two weeks. The paw thickness and paw volume of the rats were measured, and the arthritis development was scored. The test results are shown in Tables 5-1, 5-2 and 5-3.

TABLE 5-1 change in paw thickness

| Group | Mean paw thickness (mm) | | | | |
|---|---|---|---|---|---|
| | D 0 | D 4 | D 7 | D 11 | D 15 |
| Vehicle group | 7.12 | 7.47 | 7.74 | 7.74 | 7.66 |
| Baricitinib 10 mg/kg | 7.17 | 6.67 | 6.47 | 6.36 | 6.21 |
| Compound 8 10 mg/kg | 7.18 | 6.04 | 5.67 | 5.56 | 5.52 |

According to the above Table, with the increase in the days of administration, at the same dosage of compound 8 and Baricitinib, the decrease in paw thickness of the rats achieved by compound 8 is significantly better than that achieved by Baricitinib.

TABLE 5-2 change in paw volume

| Group | Mean paw volume (mL) | | | | |
|---|---|---|---|---|---|
| | D 0 | D 4 | D 7 | D 11 | D 15 |
| Vehicle group | 1.71 | 1.76 | 1.88 | 1.83 | 1.86 |
| Baricitinib 10 mg/kg | 1.71 | 1.55 | 1.47 | 1.48 | 1.59 |
| Compound 8 10 mg/kg | 1.71 | 1.47 | 1.41 | 1.42 | 1.48 |

According to the above Table, with the increase in the days of administration, at the same dosage of compound 8 and Baricitinib, the decrease in paw volume of the rats achieved by compound 8 is significantly better than that achieved by Baricitinib.

TABLE 5-3

| | arthritis score | | | | |
|---|---|---|---|---|---|
| | Mean arthritis score | | | | |
| Group | D 0 | D 4 | D 7 | D 11 | D 15 |
| Vehicle group | 2.88 | 4.13 | 4.63 | 5.25 | 5.38 |
| Baricitinib 10 mg/kg | 3.00 | 2.25 | 1.38 | 1.75 | 1.88 |
| Compound 8 10 mg/kg | 2.63 | 1.38 | 1.00 | 1.00 | 1.13 |

According to the above Table, with the increase in the days of administration, at the same dosage of compound 8 and Baricitinib, the decrease in mean arthritis score achieved by compound 8 is significantly more than that achieved by Baricitinib (The lower a mean arthritis score is, the more potent a compound is in improving arthritis symptoms in an animal model).

In conclusion, the test results show that compared with the vehicle group, the compound of the present invention at a dosage of 10 mg/kg can effectively improve the symptoms and arthritis score in a model animal. Moreover, at the same dosage, the improvement achieved by compound 8 of the present invention is more significant than that achieved by Baricitinib (control). Other compounds of the present invention achieved similar results.

Formulation Examples

Formulation Example 1. Tablet

As a specific embodiment for an oral pharmaceutical composition, a tablet comprising the following ingredients was prepared.
Ingredient:

| | |
|---|---|
| Compound 5 | 100 mg |
| Microcrystalline cellulose | 268 mg |
| Cross-linked sodium carboxymethyl cellulose | 20 mg |
| Magnesium stearate | 4 mg |
| Total: | 392 mg |

First, compound 5, microcrystalline cellulose and cross-linked sodium carboxymethyl cellulose were mixed, and the mixture was then lubricated with magnesium stearate and compressed into a tablet.

Formulation Example 2. Capsule

A capsule filled with granules of the active ingredient of compound 8 was prepared.
Ingredient:

| | |
|---|---|
| Compound 8 | 15 mg |
| Lactose | 90 mg |
| Corn starch | 42 mg |
| Low viscosity hydroxypropyl cellulose (HPC-L) | 3 mg |
| Total: | 150 mg |

Compound 8 and lactose were sieved through a 60 mesh sieve. Corn starch was sieved through a 120 mesh sieve. They were mixed, added with a HPC-L solution, followed by kneading, granulation and drying. The dry granules (150 mg) were granulated, and filled into No. 4 hard gelatin capsule.

Formulation Example 3. Granule

A granule comprising the following ingredients was prepared.
Ingredient:

| | |
|---|---|
| Compound 31 | 10 mg |
| Lactose | 700 mg |
| Corn starch | 274 mg |
| Low viscosity hydroxypropyl cellulose | 16 mg |
| Total: | 1000 mg |

Compound 31 and lactose were sieved through a 60 mesh sieve. Corn starch was sieved through a 120 mesh sieve. They were mixed in a V-type mixer. To the mixed powder, an aqueous solution of low viscosity hydroxypropyl cellulose was added, and procedures of kneading, granulation (extrusion granulation, pore diameter 0.5~1 mm) and drying were conducted. The resulting dry particles were sieved through an oscillating sieve (12/60 mesh) to obtain the granule.

In addition to those described herein, according to the foregoing description, various modifications to the present invention would be apparent to those skilled in the art. Such modifications are intended to fall within the scope of the appended claims. Each reference cited herein (including all patents, patent applications, journal articles, books and any other disclosures) are incorporated herein by reference in its entirety.

What is claimed is:

1. A compound of Formula I or a pharmaceutically acceptable salt, stereoisomer, polymorph, or solvate thereof:

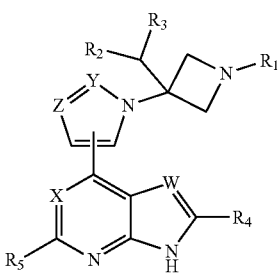

Formula I wherein:
$R_1$ is selected from the group consisting of $C_{1-6}$ alkyl, $C_{3-10}$ cycloalkyl, 3- to 10-membered heterocyclyl, $C_{6-14}$ aryl, 5- to 14-membered heteroaryl, $C_{7-20}$ aralkyl, $C(O)R_{10}$, and $S(O)_2R_{11}$;
$R_2$ and $R_3$ are each independently selected from the group consisting of H, CN, halogen, and $C_{1-6}$ alkyl;
$R_4$ and $R_5$ are each independently selected from group consisting of H, halogen, and CN;
X is $CR_6$;
Y is selected from the group consisting of N and $CR_9$;
Z is selected from the group consisting of N and $CR_7$;
W is selected from the group consisting of N and $CR_8$;
$R_6$, $R_7$, $R_8$ and $R_9$ are each independently selected from the group consisting of H, halogen, CN, $C_{1-6}$ alkyl, $C_{1-6}$ alkoxyl, and $C(O)NR_{12}R_{13}$;
$R_{10}$ and $R_{11}$ are each independently selected from the group consisting of $C_{1-6}$ alkyl, $C_{3-10}$ cycloalkyl, 3- to 10-membered heterocyclyl, $C_{6-14}$ aryl, 5- to 14-membered heteroaryl, $C_{7-20}$ aralkyl, and $NR_{12}R_{13}$;

$R_{12}$ and $R_{13}$ are each independently selected from the group consisting of H and $C_{1-6}$ alkyl;

wherein the above alkyl, cycloalkyl, heterocyclyl, aryl, heteroaryl and aralkyl are each optionally substituted with 1, 2 or 3 substituents independently selected from the group consisting of halogen, CN, and $C_{1-4}$ alkyl.

2. The compound according to claim 1, or a pharmaceutically acceptable salt, stereoisomer, polymorph, or solvate thereof, wherein the compound is a compound of Formula II:

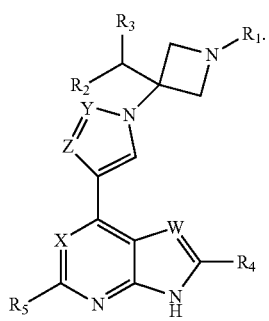

Formula II

3. The compound according to claim 2, or a pharmaceutically acceptable salt, stereoisomer, polymorph, or solvate thereof, wherein the compound is a compound of Formula IV:

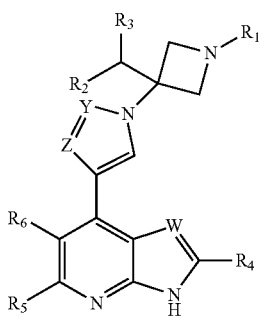

Formula IV wherein:

$R_1$ is selected from the group consisting of $C(O)R_{10}$ and $S(O)_2R_{11}$;

$R_{10}$ and $R_{11}$ are each independently selected from the group consisting of $C_{1-6}$ alkyl, $C_{3-10}$ cycloalkyl, 3- to 10-membered heterocyclyl, $C_{6-14}$ aryl, 5- to 14-membered heteroaryl, $C_{7-20}$ aralkyl, and $NR_{12}R_{13}$, wherein the alkyl, cycloalkyl, heterocyclyl, aryl, heteroaryl and aralkyl are each optionally substituted with 1, 2 or 3 substituents independently selected from the group consisting of halogen, CN, and $C_{1-4}$ alkyl.

4. The compound according to claim 3, or a pharmaceutically acceptable salt, stereoisomer, polymorph, or solvate thereof, wherein the compound is a compound of Formula V:

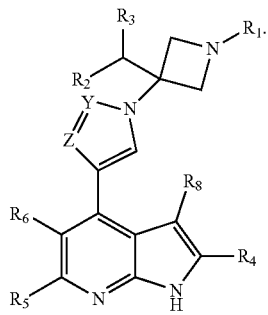

Formula V

5. The compound according to claim 4, or a pharmaceutically acceptable salt, stereoisomer, polymorph, or solvate thereof, wherein the compound is a compound of Formula VI:

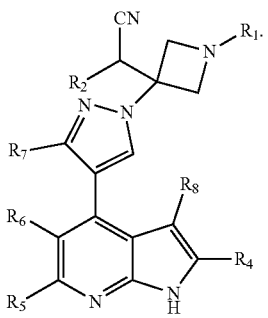

Formula VI

6. A compound or a pharmaceutically acceptable salt, stereoisomer, polymorph, or solvate thereof, wherein the compound is selected from the group consisting of:

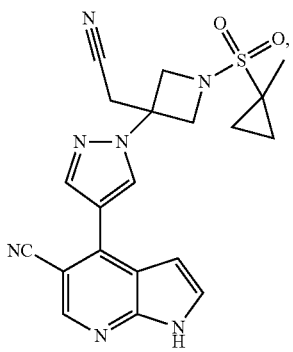

1

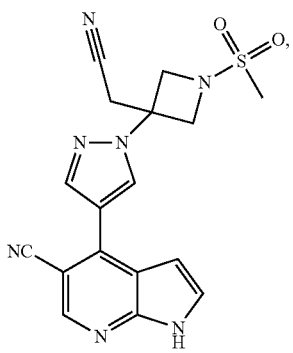

2

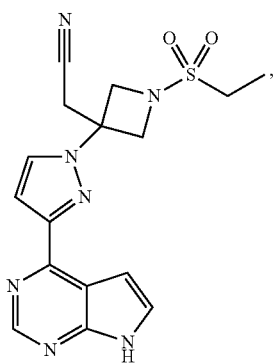
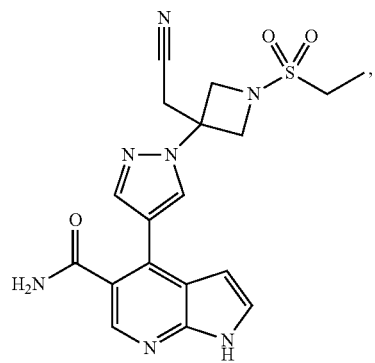
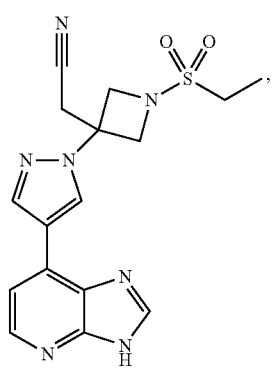
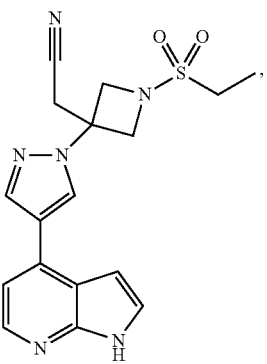
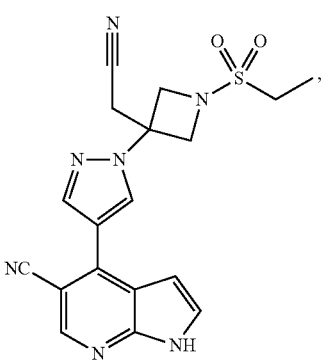
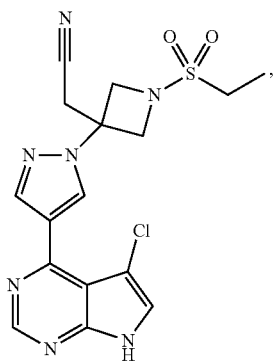
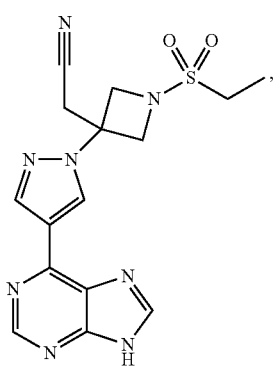
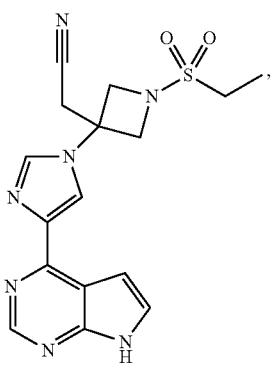

| 11 | 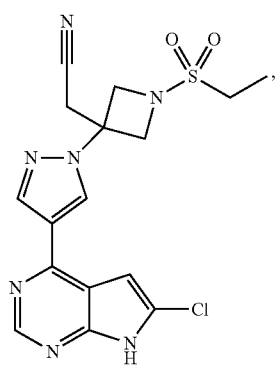 | 15 | 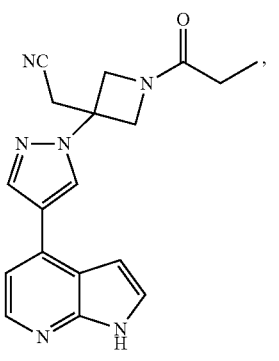 |
| 12 | 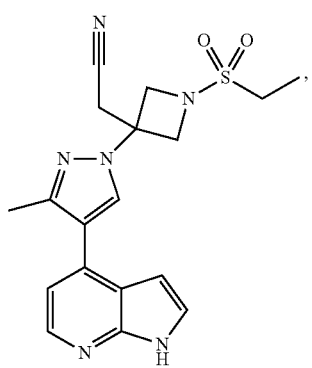 | 16 | 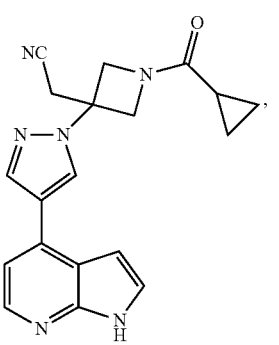 |
| 13 | 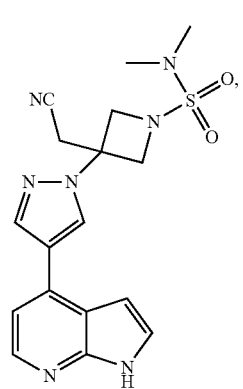 | 17 | 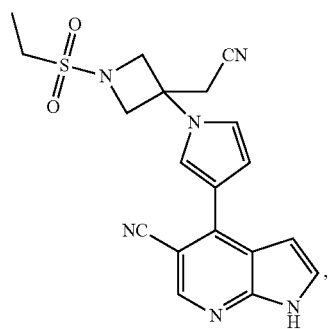 |
| 14 | | 18 | 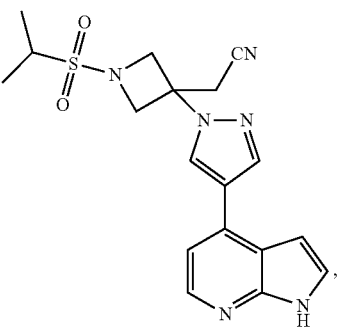 |

187
-continued
19
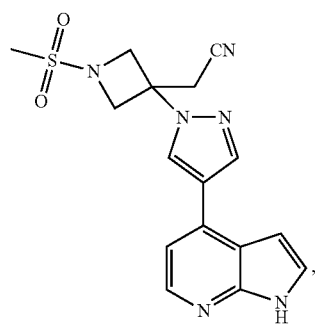
20
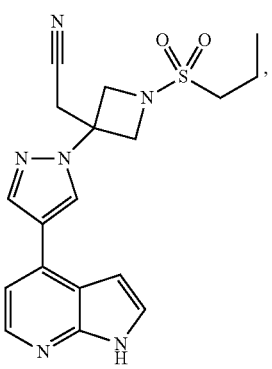
21
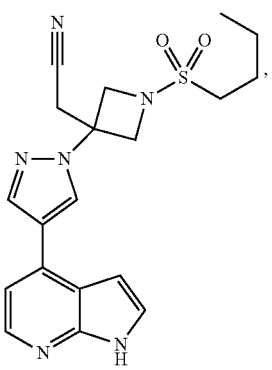
22
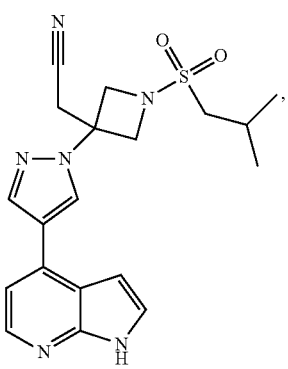
188
-continued
23
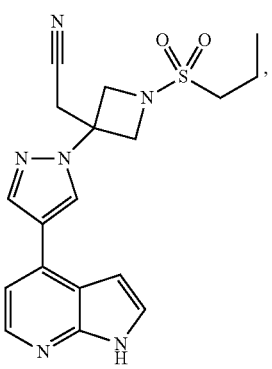
24
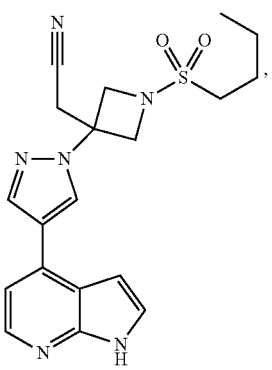
25
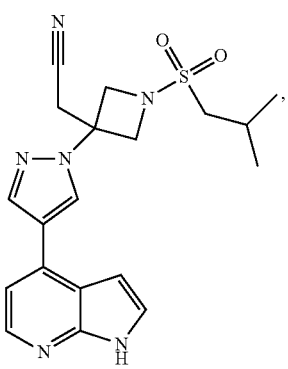
26
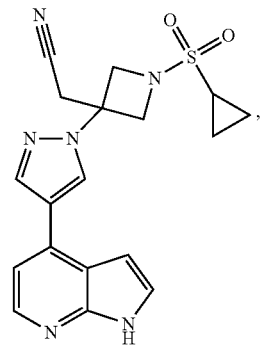

27
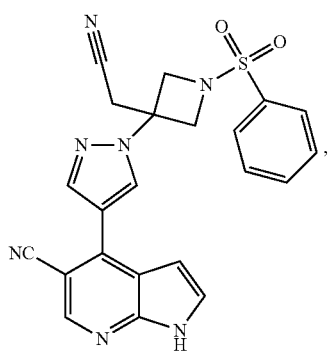
28
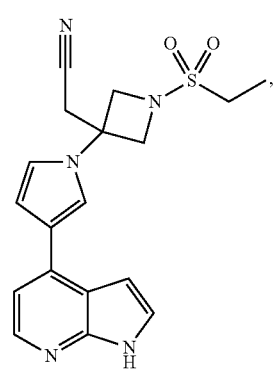
29
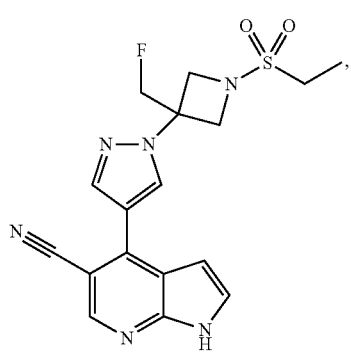
30
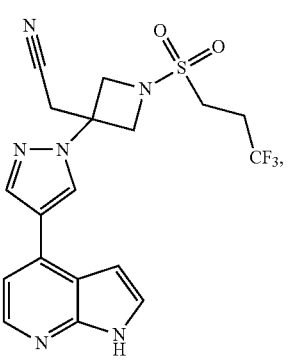
31
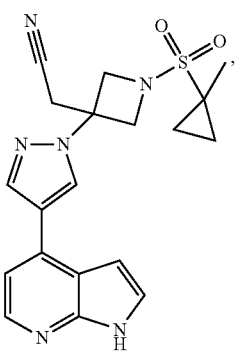
32
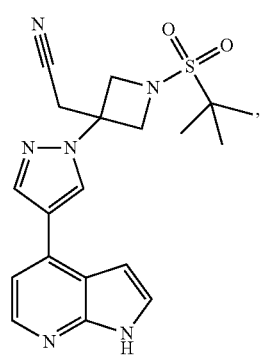
33
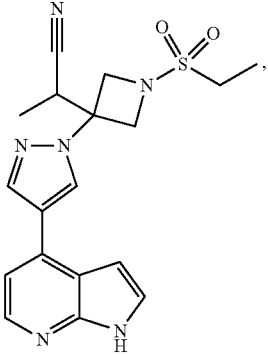
34
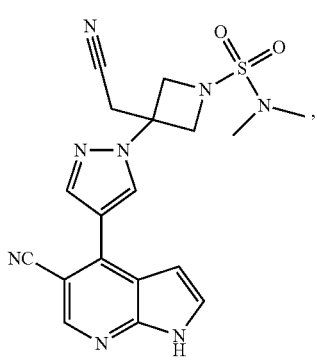

191
-continued
35
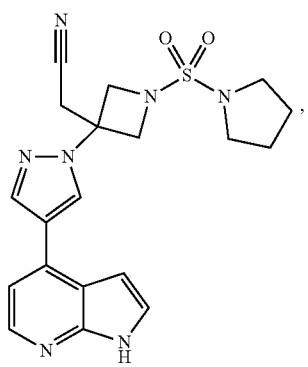
36
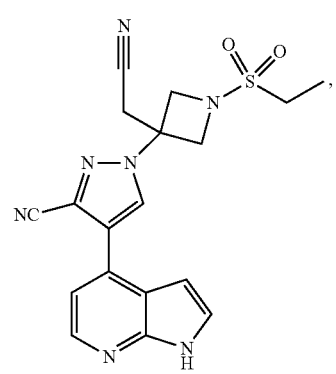
37
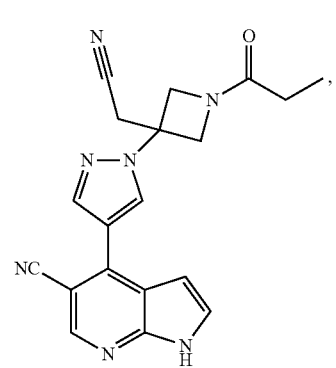
38
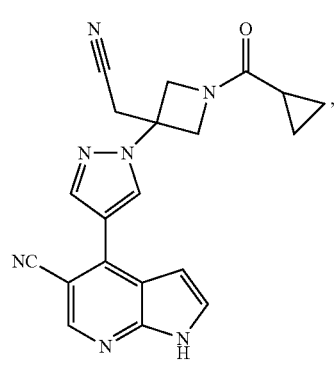
192
-continued
39
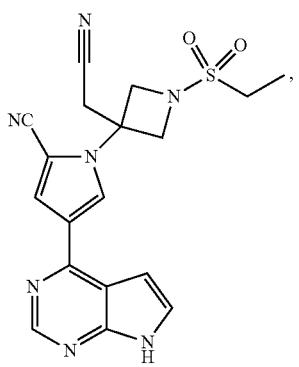
40
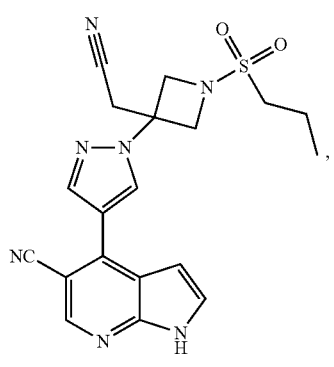
43
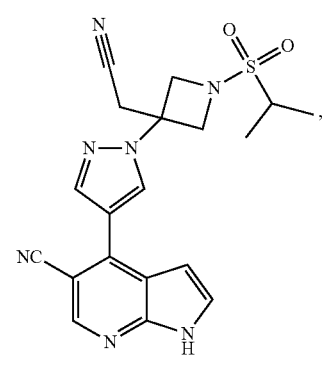
44
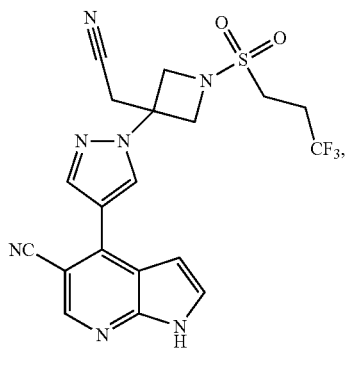

193
-continued
45
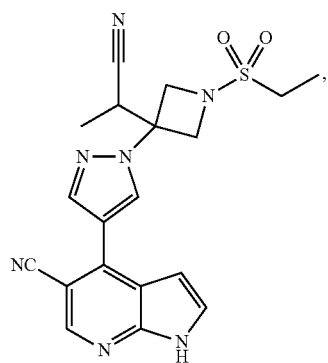
48
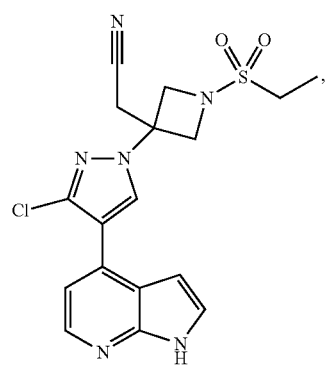
49
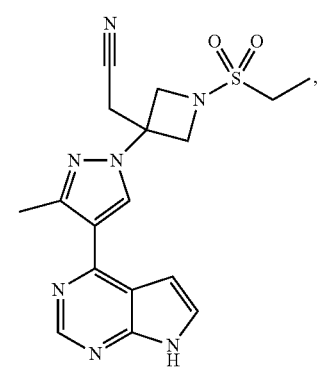
50
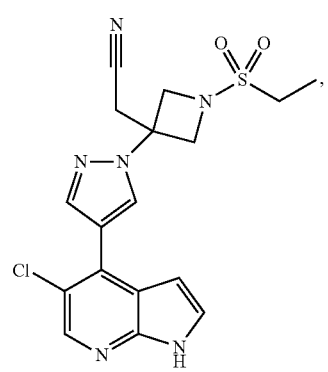
194
-continued
51
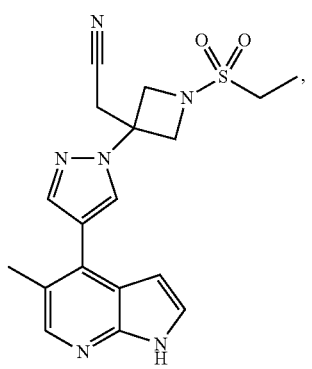
52
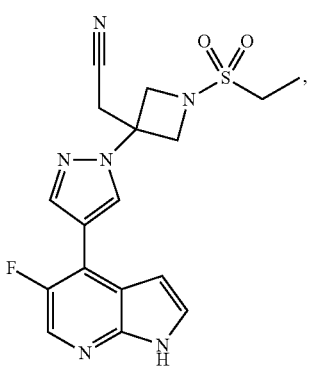
56
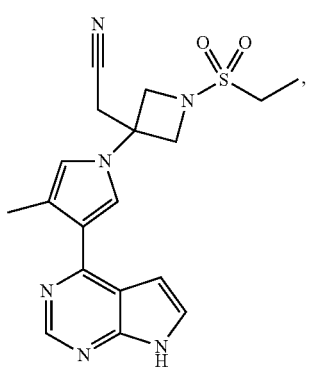
59
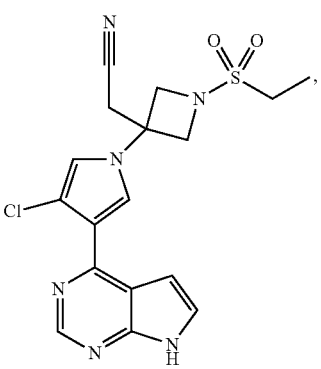

-continued
60
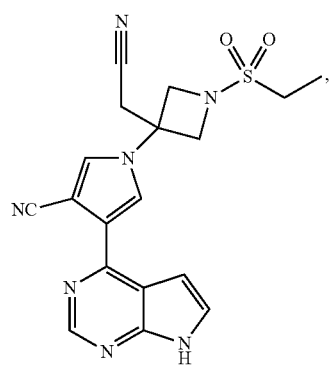
61
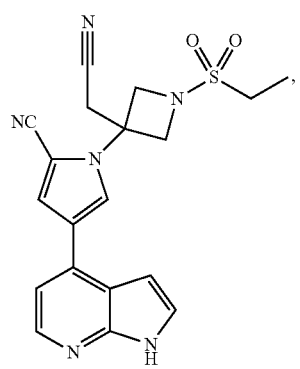
62
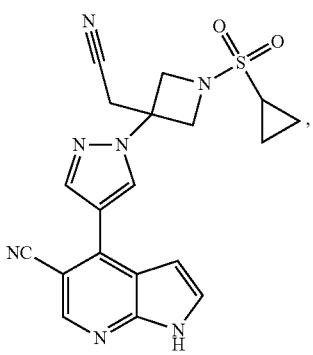
63
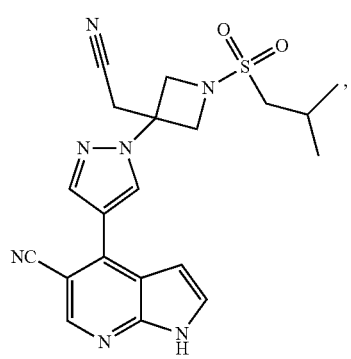
-continued
64
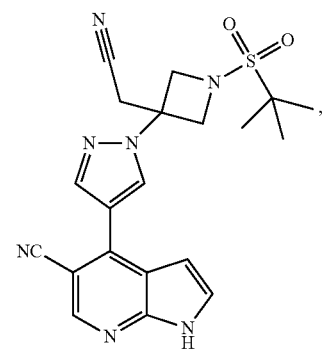
65
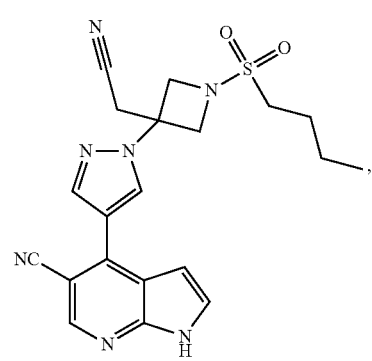
66
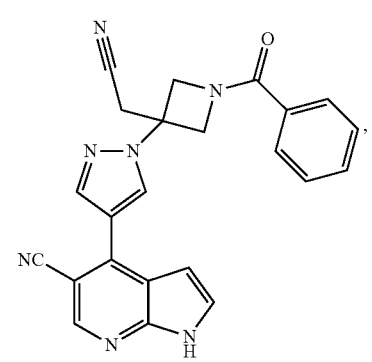
67
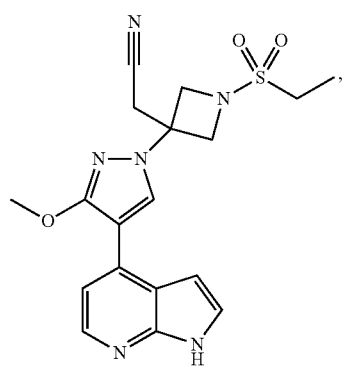

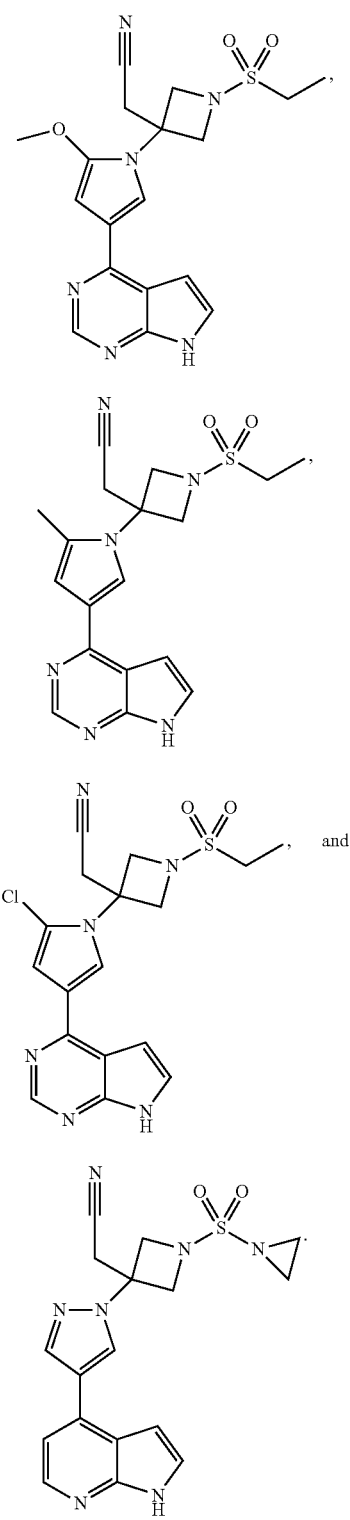

7. A pharmaceutical composition, comprising a therapeutically effective amount of the compound according to claim 1 and one or more pharmaceutically acceptable carriers.

8. The pharmaceutical composition according to claim 7, wherein the therapeutically effective amount is a range of about 0.01 mg to about 1000 mg.

9. The pharmaceutical composition according to claim 7, further comprising one or more additional drugs.

10. The pharmaceutical composition according to claim 9, wherein the additional drug(s) is one or more selected from the group consisting of efalizumab, mycophenolate sodium, etanercept, and methotrexate.

11. A method for the treatment of a JAK-related disease, comprising administering to a subject in need thereof a therapeutically effective amount of the compound according to claim 1, wherein the JAK-related disease is rheumatoid arthritis.

12. A pharmaceutical composition, comprising a therapeutically effective amount of the compound according to claim 3 and one or more pharmaceutically acceptable carriers.

13. The pharmaceutical composition according to claim 12, wherein the therapeutically effective amount is a range of about 0.01 mg to about 1000 mg.

14. The pharmaceutical composition according to claim 12, further comprising one or more additional drugs.

15. The pharmaceutical composition according to claim 14, wherein the additional drug(s) is one or more selected from the group consisting of efalizumab, mycophenolate sodium, etanercept, and methotrexate.

16. A method for the treatment of a JAK-related disease, comprising administering to a subject in need thereof a therapeutically effective amount of the compound according to claim 3, wherein the JAK-related disease is rheumatoid arthritis.

17. A pharmaceutical composition, comprising a therapeutically effective amount of the compound according to claim 6 and one or more pharmaceutically acceptable carriers.

18. The pharmaceutical composition according to claim 17, wherein the therapeutically effective amount is a range of about 0.01 mg to about 1000 mg.

19. The pharmaceutical composition according to claim 17, further comprising one or more additional drugs.

20. The pharmaceutical composition according to claim 19, wherein the additional drug(s) is one or more selected from the group consisting of efalizumab, mycophenolate sodium, etanercept, and methotrexate.

21. A method for the treatment of a JAK-related disease, comprising administering to a subject in need thereof a therapeutically effective amount of the compound according to claim 6, wherein the JAK-related disease is rheumatoid arthritis.

22. A method for the treatment of a JAK-related disease, comprising administering to a subject in need thereof a therapeutically effective amount of the pharmaceutical composition according to claim 7, wherein the JAK-related disease is rheumatoid arthritis.

23. A method for the treatment of a JAK-related disease, comprising administering to a subject in need thereof a therapeutically effective amount of the pharmaceutical composition according to claim 12, wherein the JAK-related disease is rheumatoid arthritis.

24. A method for the treatment of a JAK-related disease, comprising administering to a subject in need thereof a therapeutically effective amount of the pharmaceutical composition according to claim 17, wherein the JAK-related disease is rheumatoid arthritis.

25. The pharmaceutical composition according to any of claim 8, 13 or 18, wherein the therapeutically effective amount is 0.1-500 mg.

26. The pharmaceutical composition according to any of claim 8, 13 or 18, wherein the therapeutically effective amount is 0.5-300 mg.

27. The pharmaceutical composition according to any of claim 8, 13 or 18, wherein the therapeutically effective amount is 1-150 mg.

28. The pharmaceutical composition according to any of claim 8, 13 or 18, wherein the therapeutically effective amount is 1-50 mg.

29. The pharmaceutical composition according to any of claim 8, 13 or 18, wherein the therapeutically effective amount is 1.5 mg.

30. The pharmaceutical composition according to any of claim 8, 13 or 18, wherein the therapeutically effective amount is 2 mg.

31. The pharmaceutical composition according to any of claim 8, 13 or 18, wherein the therapeutically effective amount is 4 mg.

32. The pharmaceutical composition according to any of claim 8, 13 or 18, wherein the therapeutically effective amount is 10 mg.

33. The pharmaceutical composition according to any of claim 8, 13 or 18, wherein the therapeutically effective amount is 25 mg.

* * * * *